(12) United States Patent
Gray et al.

(10) Patent No.: US 11,712,458 B2
(45) Date of Patent: Aug. 1, 2023

(54) DEGRADATION OF BRUTON'S TYROSINE KINASE (BTK) BY CONJUGATION OF BTK INHIBITORS WITH E3 LIGASE LIGAND AND METHODS OF USE

(71) Applicant: DANA-FARBER CANCER INSTITUTE, INC., Boston, MA (US)

(72) Inventors: Nathanael S. Gray, Boston, MA (US); Jinhua Wang, Beijing (CN); Dennis Dobrovolsky, Somerville, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/963,993

(22) PCT Filed: Jan. 29, 2019

(86) PCT No.: PCT/US2019/015505
§ 371 (c)(1),
(2) Date: Jul. 22, 2020

(87) PCT Pub. No.: WO2019/148150
PCT Pub. Date: Aug. 1, 2019

(65) Prior Publication Data
US 2021/0030832 A1     Feb. 4, 2021

Related U.S. Application Data

(60) Provisional application No. 62/674,946, filed on May 22, 2018, provisional application No. 62/623,387, filed on Jan. 29, 2018.

(51) Int. Cl.
*A61K 38/05*      (2006.01)
*A61K 47/62*      (2017.01)
*A61K 47/54*      (2017.01)

(52) U.S. Cl.
CPC .............. *A61K 38/05* (2013.01); *A61K 47/54* (2017.08); *A61K 47/545* (2017.08); *A61K 47/62* (2017.08)

(58) Field of Classification Search
None
See application file for complete search history.

(56) References Cited

FOREIGN PATENT DOCUMENTS

| JP | 2010540452 |    | 12/2010 |
|----|------------|----|---------|
| JP | 2018502097 |    | 1/2018 |
| JP | 2019535744 |    | 12/2019 |
| JP | 2020532552 |    | 11/2020 |
| WO | 2009039397 | A2 | 3/2009 |
| WO | 2016105518 | A1 | 12/2015 |
| WO | 2016145935 | A1 | 9/2016 |
| WO | 2016169989 | A1 | 10/2016 |
| WO | 2016174183 | A1 | 11/2016 |
| WO | 2017185036 | A1 | 10/2017 |
| WO | 2017218844 | A2 | 12/2017 |
| WO | 2018013918 | A2 | 1/2018 |
| WO | 2018098275 | A1 | 5/2018 |
| WO | 2018098288 | A1 | 5/2018 |
| WO | 2019042445 | A1 | 3/2019 |

OTHER PUBLICATIONS

Hematologic Malignancies MEI Pharma, 2022, 6 pages. (Year: 2022).*

* cited by examiner

*Primary Examiner* — Thomas S Heard
(74) *Attorney, Agent, or Firm* — Burns & Levinson, LLP; Daniel W. Clarke; Shawn P. Foley

(57) ABSTRACT

The present application provides bifunctional compounds of Formula X or an enantiomer, diastereomer, or stereoisomer thereof, or pharmaceutically acceptable salt, hydrate, solvate, or prodrug thereof, which act as protein degradation inducing moieties for Bruton's tyrosine kinase (BTK). The present application also relates to methods for the targeted degradation of BTK through the use of bifunctional compounds that link a ubiquitin ligase-binding moiety to a ligand that is capable of binding to BTK which can be utilized in the treatment of disorders modulated by BTK.

20 Claims, 3 Drawing Sheets

MOLM-14, 4 hrs treatment

DEGRADATION OF BRUTON'S TYROSINE KINASE (BTK) BY CONJUGATION OF BTK INHIBITORS WITH E3 LIGASE LIGAND AND METHODS OF USE

CROSS-REFERENCE TO-RELATED APPLICATIONS

This application is a national stage application, filed under 35 U.S.C. § 371, of International Application No. PCT/US2019/015505, filed Jan. 29, 2019, which claims the benefit of priority under 35 U.S.C. § 119(e) to U.S. Provisional Application No. 62/623,387, filed Jan. 29, 2018 and to U.S. Provisional Application No. 62/674,946, filed May 22, 2018, the entire contents of each of which are incorporated herein by reference.

BACKGROUND

Ubiquitin-Proteasome Pathway (UPP) is a critical pathway that regulates proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity. For example, cereblon (CRBN) interacts with damaged DNA binding protein 1 and forms an E3 ubiquitin ligase complex with Cullin 4 in which the proteins recognized by CRBN are ubiquinated and degraded by proteasomes. Various immunomodulatory drugs (IMiDs), e.g., thalidomide and lenalidomide, binds to CRBN and modulates CRBN's role in the ubiquitination and degradation of protein factors involved in maintaining regular cellular function.

Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression, and could be useful as biochemical reagents for the treatment of diseases.

Bruton's tyrosine kinase (BTK) is a member of the Tec family of tyrosine kinases and a key signaling enzyme expressed in B-cells and myeloid cells. BTK plays an essential role in the B-cell signaling pathway linking cell surface B-cell receptor (BCR) stimulation to downstream intracellular responses, and is a key regulator of B-cell development, activation, signaling, and survival. Moreover, BTK plays a role in a number of other hematopoietic cell signaling pathways, including IgE receptor signaling in Mast cells, Toll like receptor (TLR) and cytokine receptor-mediated TNF-α production in macrophages, inhibition of Fas/APO-1 apoptotic signaling in B-lineage lymphoid cells, and collagen-stimulated platelet aggregation.

Inhibition of BTK has been shown to affect cancer development (e.g., B cell malignancies) and cell viability, and improve autoimmune diseases (e.g., rheumatoid arthritis and lupus). Compounds which inhibit BTK via alternative strategies, such as through degradation of BTK, have the potential to be more potent than known inhibitors of BTK and are needed. The present application addresses the need.

SUMMARY

The present application relates to novel bifunctional compounds, which function to recruit targeted proteins (e.g., BTK) to E3 ubiquitin ligase for degradation, and methods of preparation and uses thereof. The bifunctional compound is of Formula X:

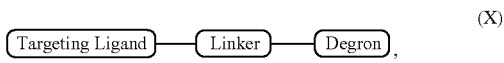

(X)

wherein:

the Targeting Ligand is capable of binding to a targeted protein, such as a protein kinase (e.g., BTK);

the Linker is a group that covalently binds to the Targeting Ligand and the Degron; and the Degron is capable of binding to a ubiquitin ligase, such as an E3 ubiquitin ligase (e.g., cereblon).

The present application relates to targeted degradation of proteins through the use of bifunctional compounds, including bifunctional compounds that link an E3 ubiquitin ligase-binding moiety to a ligand that binds the targeted proteins, such as BTK.

The resent application also relates to a bifunctional compound of Formula I, II, or III:

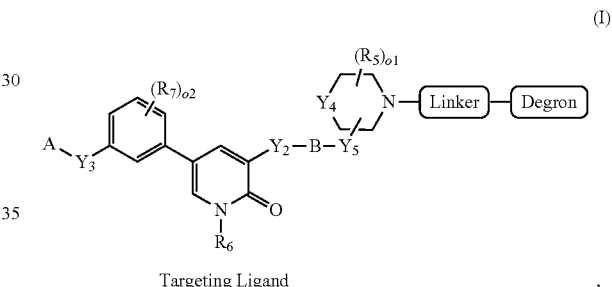

(I)

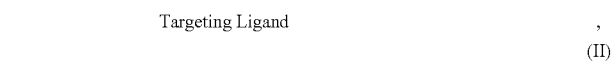

(II)

, or

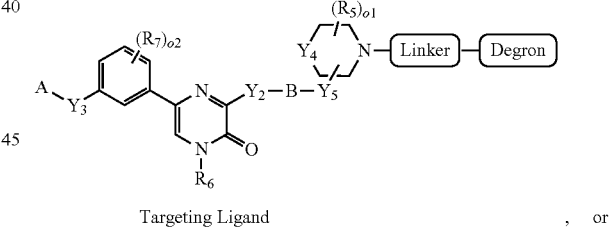

(III)

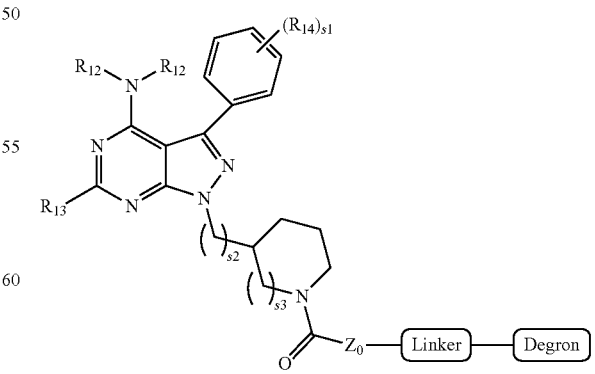

or an enantiomer, diastereomer, stereoisomer, or pharmaceutically acceptable salt thereof, wherein:

$R_5$, $R_6$, $R_7$, $R_{12}$, $R_{13}$, $R_{14}$, $Y_2$, $Y_3$, $Y_4$, $Y_5$, $Z_0$, A, B, o1, o2, s, s2, and s3 are each as defined herein;

the Linker is a group that covalently binds to

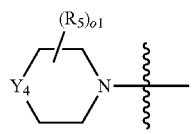

in Formula I,

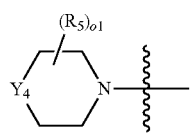

in Formula II, or $Z_0$ in Formula III and the Degron;

the Degron is capable of binding to a ubiquitin ligase, such as an E3 ubiquitin ligase (i.e., cereblon); and the Targeting Ligand is capable of binding to a targeted protein, such as BTK.

The resent application further relates to a Degron of Formula D0, D1, D2, D3, or D4:

(D0)

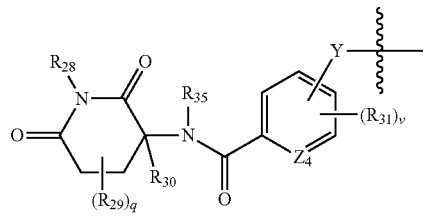

(D1)

(D2)

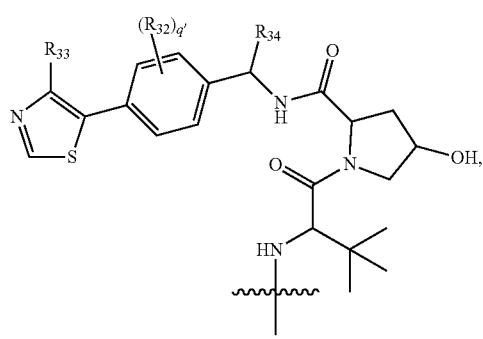

(D3)

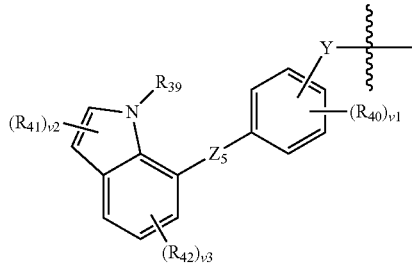

, or (D4)

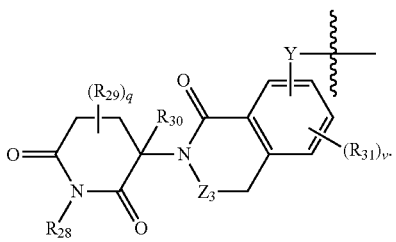

or an enantiomer, diastereomer, or stereoisomer thereof, wherein Y, $Y_1$, $Z_3$, $Z_4$, $Z_5$, $R_2$, $R_{29}$, $R_{30}$, $R_{31}$, $R_{32}$, $R_{33}$, $R_{34}$, $R_{35}$, $R_{39}$, $R_{40}$, $R_{41}$, $R_{42}$, v, v1, v2, v3, q, and q' are each as defined herein, and the Degron covalently binds to a Linker via

.

The present application further relates to a Linker of Formula L1 or L2:

(L1)

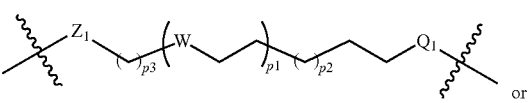

or (L2)

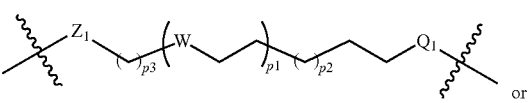

, or an enantiomer, diastereomer, or stereoisomer thereof, wherein p1, p2, p3, p4, p4', p5, p6, W, $W_1$, $W_2$, $W_3$, $Q_1$, $Q_2$, $Z_1$, and $Z_2$ are each as defined herein, the Linker is covalently bonded to a Degron via the

next to $Q_1$ or $Q_2$, and covalently bonded to a Targeting Ligand via the

next to $Z_1$ or $Z_2$.

The present application also relates to a pharmaceutical composition comprising a therapeutically effective amount of a bifunctional compound of the application, or an enantiomer, diastereomer, or stereoismer, or pharmaceutically acceptable salt thereof, and a pharmaceutically acceptable carrier.

Another aspect of the present application relates to a method of inhibiting or degrading BTK. The method comprises administering to a subject in need thereof an effective amount of a bifunctional compound of the application, or an enantiomer, diastereomer, or stereoisomer, or pharmaceutically acceptable salt thereof, or a pharmaceutical composition of the application.

Another aspect of the present application relates to a method of modulating (e.g., decreasing) the amount of BTK. The method comprises administering to a subject in need thereof a therapeutically effective amount of a bifunctional compound of the application, or an enantiomer, diastereomer, or stereoisomer, or pharmaceutically acceptable salt thereof, or a pharmaceutical composition of the application.

Another aspect of the present application relates to a method of treating or preventing a disease (e.g., a disease in which BTK plays a role). The method comprises administering to a subject in need thereof an effective amount of a bifunctional compound of the application, or an enantiomer, diastereomer, or stereoisomer, or pharmaceutically acceptable salt thereof, or a pharmaceutical composition of the application. In one aspect, the disease is BTK mediated disorder. In one aspect, the disease is a proliferative disease (e.g., a proliferative disease in which BTK plays a role).

Another aspect of the present application relates to a method of treating or preventing cancer in a subject, wherein the cancer cell comprises an activated BTK or wherein the subject is identified as being in need of BTK inhibition or degradation for the treatment or prevention of cancer. The method comprises administering to the subject an effective amount of a bifunctional compound of the application, or an enantiomer, diastereomer, or stereoisomer, or pharmaceutically acceptable thereof, or a pharmaceutical composition of the application.

Another aspect of the present application relates to a kit comprising a bifunctional compound capable of inhibiting BTK activity, selected from a bifunctional compound of the application, or an enantiomer, diastereomer, or stereoisomer, or pharmaceutically acceptable salt thereof.

Another aspect of the present application relates to a kit comprising a bifunctional compound capable of modulating (e.g., decreasing) the amount of BTK, selected from a bifunctional compound of the application, or an enantiomer, diastereomer, or stereoisomer, or pharmaceutically acceptable salt thereof.

Another aspect of the present application relates to use of a bifunctional compound of the application, or an enantiomer, diastereomer, or stereoisomer, or pharmaceutically acceptable salt thereof, or a pharmaceutical composition of the application, in the manufacture of a medicament for inhibiting or degrading BTK or for modulating (e.g., decreasing) the amount of BTK.

Another aspect of the present application relates to use of a bifunctional compound of the application, or an enantiomer, diastereomer, or stereoisomer, or pharmaceutically acceptable salt thereof, or a pharmaceutical composition of the application, in the manufacture of a medicament for treating or preventing a disease (e.g., a disease in which BTK plays a role). In one aspect, the disease is a BTK mediated disorder. In one aspect, the disease is a proliferative disease (e.g., a proliferative disease in which BTK plays a role).

Another aspect of the present application relates to use of a bifunctional compound of the application, or an enantiomer, diastereomer, or stereoisomer, or pharmaceutically acceptable salt thereof, or a pharmaceutical composition of the application, in the manufacture of a medicament for treating or preventing cancer in a subject, wherein the cancer cell comprises an activated BTK or wherein the subject is identified as being in need of BTK inhibition or degradation for the treatment or prevention of cancer.

Another aspect of the present application relates to a bifunctional compound of the application, or an enantiomer, diastereomer, or stereoisomer, or pharmaceutically acceptable salt thereof, or a pharmaceutical composition of the application, for inhibiting or degrading BTK or modulating (e.g., decreasing) the amount of BTK.

Another aspect of the present application relates to a bifunctional compound of the application, or an enantiomer, diastereomer, or stereoisomer, or pharmaceutically acceptable salt thereof, or a pharmaceutical composition of the application, for treating or preventing a disease (e.g., a disease in which BTK plays a role). In one aspect, the disease is BTK mediated disorder. In one aspect, the disease is a proliferative disease (e.g., a proliferative disease in which BTK plays a role).

Another aspect of the present application relates to a bifunctional compound of the application, or an enantiomer, diastereomer, or stereoisomer, or pharmaceutically acceptable salt thereof, or a pharmaceutical composition of the application, for treating or preventing cancer in a subject, wherein the cancer cell comprises an activated BTK or wherein the subject is identified as being in need of BTK inhibition or degradation for the treatment or prevention of cancer.

The present application provides inhibitors or degraders of BTK that are therapeutic agents in the treatment or prevention of diseases such as cancer and metastasis.

The present application further provides compounds and compositions with an improved efficacy and/or safety profile relative to known BTK inhibitors. The present application also provides agents with novel mechanisms of action toward BTK proteins in the treatment of various types of diseases including cancer and metastasis.

The compounds and methods of the present application address unmet needs in the treatment of diseases or disorders in which pathogenic or oncogenic endogenous proteins (e.g., BTK) play a role, such as cancer.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

Compounds of the Application

Figure 1:
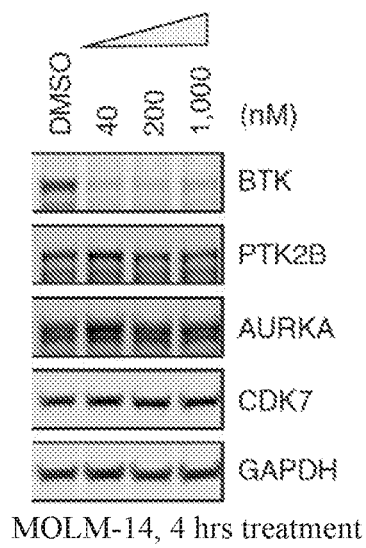
FIG. 1 is a Western blot showing the levels of BTK, PTK2B, AURKA, CDK7, and GAPDH in MOLM-14 cells treated for 4 hours with DMSO or 40 nM, 200 nM, or 1 µM of Compound I-0.

The present application relates to bifunctional compounds having utility as modulators of ubiquination and proteosomal degradation of targeted proteins, especially compounds comprising a moiety capable of binding to a polypeptide or a protein that is degraded and/or otherwise inhibited by the bifunctional compounds of the present application. In particular, the present application is directed to compounds which contain a moiety, e.g., a small molecule moiety (i.e., having a molecular weight of below 2,000, 1,000, 500, or 200 Daltons), such as a thalidomide-like moiety, which is capable of binding to an E3 ubiquitin ligase, such as cereblon, and a ligand that is capable of binding to a target protein, in such a way that the target protein is placed in proximity to the ubiquitin ligase to effect degradation (and/or inhibition) of that protein.

In one embodiment, the present application provides a bifunctional compound of Formula X:

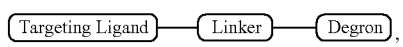 (X)

wherein:

the Targeting Ligand is capable of binding to a targeted protein, such as BTK;

the Linker is a group that covalently binds to the Targeting Ligand and the Degron; and the Degron is capable of binding to a ubiquitin ligase, such as an E3 ubiquitin ligase (e.g., cereblon).

In one embodiment, the present application provides a compound of Formula I or Formula II:

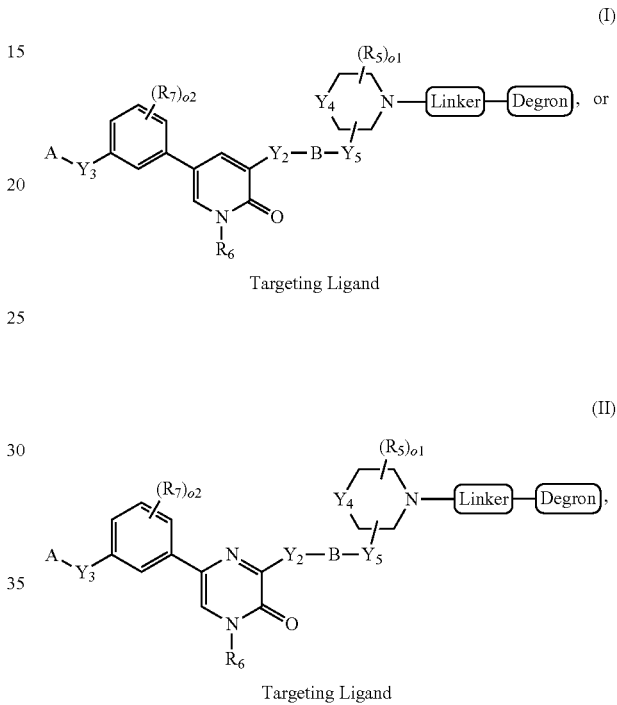

or an enantiomer, diastereomer, stereoisomer, or pharmaceutically acceptable salt thereof, wherein:

$R_5$, $R_6$, $R_7$, $Y_2$, $Y_3$, $Y_4$, $Y_5$, A, B, o1, and o2 are each as defined herein;

the Linker is a group that covalently binds to

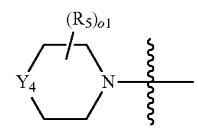

and the Degron;

the Degron is capable of binding to aubiquitin ligase, such as an E3 ubiquitin ligase (i.e., cereblon); and the Targeting Ligand is capable of binding to a targeted protein, such as BTK.

In one embodiment, the present application provides a compound of Formula III:

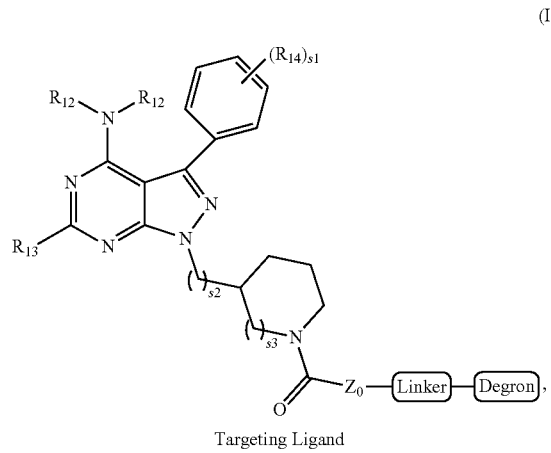

Targeting Ligand or an enantiomer, diastereomer, stereoisomer, or pharmaceutically acceptable salt thereof, wherein:

$R_{12}$, $R_{13}$, $R_{14}$, $Z_0$, s1, s2, and s3 are each as defined herein;

the Linker is a group that covalently binds to $Z_0$ and the Degron;

the Degron is capable of binding to a ubiquitin ligase, such as an E3 ubiquitin ligase (i.e., cereblon); and the Targeting Ligand is capable of binding to a targeted protein, such as BTK.

The present application further relates to a Degron of Formula D0:

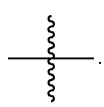

or an enantiomer, diastereomer, or stereoisomer thereof, wherein Y, $Z_4$, $R_{28}$, $R_{29}$, $R_{30}$, $R_{31}$, $R_{35}$, v, and q are each as defined herein, and the Degron covalently binds to a Linker via The present application further relates to a Degron of Formula D1 or Formula D4:

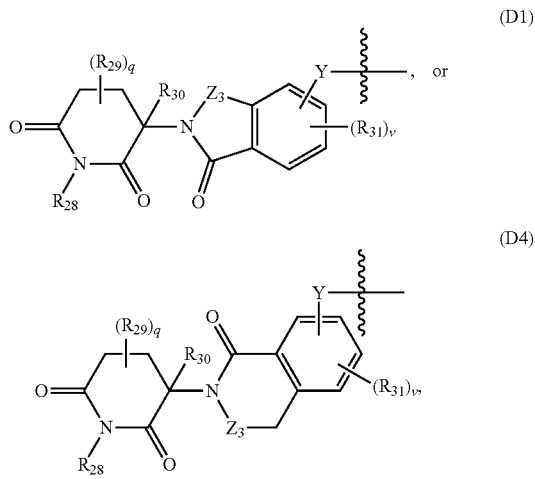

or an enantiomer, diastereomer, or stereoisomer thereof, wherein Y, $Z_3$, $R_{28}$, $R_{29}$, $R_{30}$, $R_{31}$, v, and q are each as defined herein, and the Degron covalently binds to a Linker via

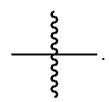

The present application further relates to a Degron of Formula D2:

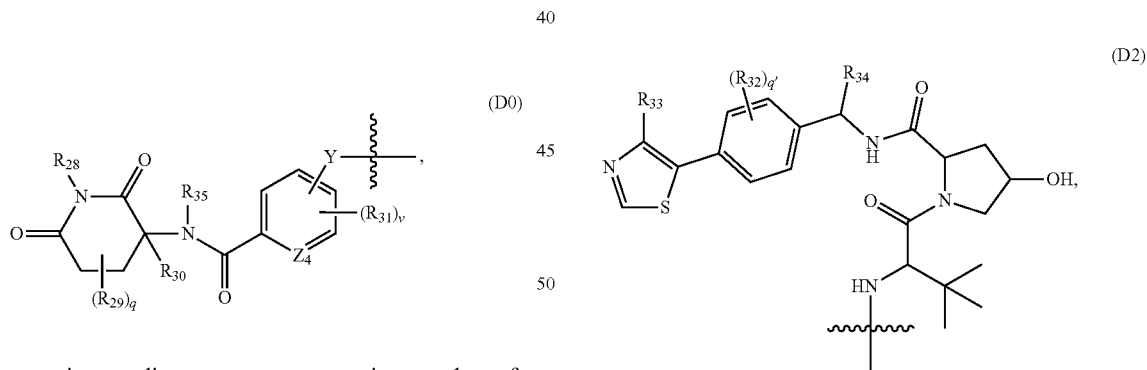

or an enantiomer, diastereomer, or stereoisomer thereof, wherein $R_{32}$, $R_{33}$, $R_{34}$, and q' are each as defined herein, and the Degron covalently binds to a Linker via The present application further relates to a Degron of Formula D3:

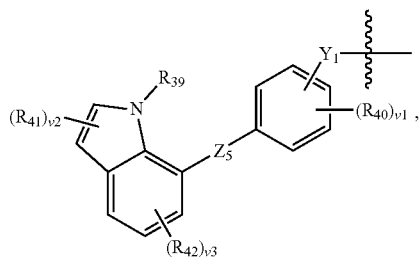
(D3)

or an enantiomer, diastereomer, or stereoisomer thereof, wherein $Y_1$, $Z_5$, $R_{39}$, $R_{40}$, $R_{41}$, $R_{42}$, v1, v2, and v3 are each as defined herein, and the Degron covalently binds to a Linker via

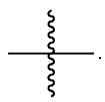

The present application further relates to a Linker of Formula L1:

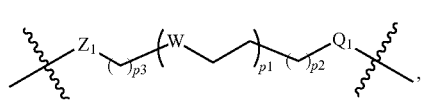
(L1)

or an enantiomer, diastereomer, or stereoisomer thereof, wherein p1, p2, p3, W, $Q_1$, and $Z_1$ are each as defined herein, the Linker is covalently bonded to a Degron via the

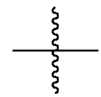

next to $Q_1$, and covalently bonded to a Targeting Ligand via the

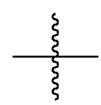

next to $Z_1$.

The present application further relates to a Linker of Formula L2:

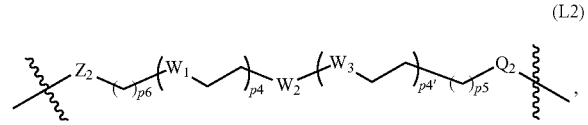
(L2)

or an enantiomer, diastereomer, or stereoisomer thereof, wherein p4, p4', p5, p6, $W_1$, $W_2$, $W_3$, $Q_2$, and $Z_2$ are each as defined herein, the Linker is covalently bonded to a Degron via the

next to $Q_2$, and covalently bonded to the Targeting Ligand via the

next to $Z_2$.

Targeting Ligand

Targeting Ligand (TL) (or target protein moiety or target protein ligand or ligand) is a small molecule which is capable of binding to a target protein of interest, such as BTK.

In one embodiment, a Targeting Ligand is a compound of Formula TL-I or TL-II:

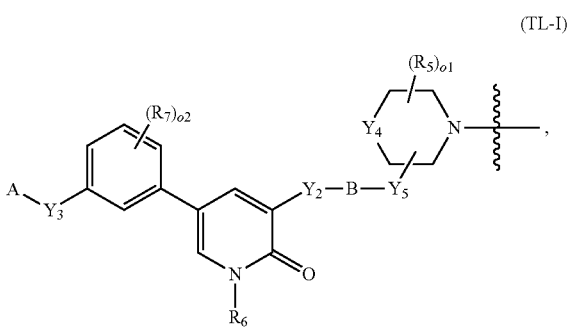
(TL-I)

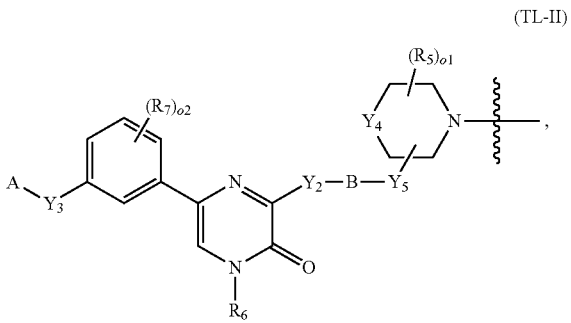
(TL-II)

or an enantiomer, diasteromer, stereoisomer, or pharmaceutically acceptable salt thereof, wherein:

A is phenyl or 5- or 6-membered heteroaryl containing 1 or 2 heteroatoms selected from N and S, wherein the phenyl or heteroaryl is optionally substituted with 1 to 3 $R_8$;

B is phenyl or 5- or 6-membered heteroaryl containing 1 or 2 heteroatoms selected from N and S, wherein the phenyl or heteroaryl is optionally substituted with 1 to 3 $R_9$;

$Y_2$ is $NR_{10a}$ or O;

$Y_3$ is $C(O)NR_{10b}$ or $NR_{10b}C(O)$;

$Y_4$ is $NR_5'$ or, when B is bonded to $Y_4$, N, or, when $Y_5$ is bonded to $Y_4$, N;

$Y_5$ is absent, C(O), or $CH_2$;

$R_5'$ is H, $(C_1$-$C_4)$ alkyl, $(C_1$-$C_4)$ haloalkyl, $(C_1$-$C_4)$ alkoxy, $(C_1$-$C_4)$ haloalkoxy, or halogen;

each $R_5$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, or oxo;

$R_6$ is H, $(C_1$-$C_4)$ alkyl, or $(C_1$-$C_4)$ haloalkyl;

each $R_7$ is independently $(C_1$-$C_4)$ alkyl, $(C_1$-$C_4)$ haloalkyl, $(C_1$-$C_4)$ alkoxy, $(C_1$-$C_4)$ haloalkoxy, $(C_1$-$C_4)$ hydroxyalkyl, halogen, OH, or $NH_2$;

each $R_8$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, OH, $NH_2$, or $(C_3$-$C_6)$ cycloalkyl; or two $R_8$ together with the atoms to which they are attached form a $(C_5$-$C_7)$ cycloalkyl ring; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;

each $R_9$ is independently $(C_1$-$C_4)$ alkyl, $(C_1$-$C_4)$ haloalkyl, $(C_1$-$C_4)$ alkoxy, $(C_1$-$C_4)$ haloalkoxy, or halogen;

$R_{10a}$ and $R_{10b}$ are each independently H, $(C_1$-$C_4)$ alkyl, or $(C_1$-$C_4)$ haloalkyl; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;

each $R_{11}$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, oxo, OH, or $NH_2$; and o1 and o2 are each independently 0, 1, 2, or 3, wherein the Targeting Ligand is bonded to the Linker via the

next to

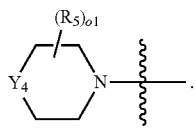

In some embodiments, A is phenyl optionally substituted with 1 to 3 $R_8$. In other embodiments, A is 5- or 6-membered heteroaryl containing 1 or 2 heteroatoms selected from N and S optionally substituted with 1 to 3 $R_8$. In other embodiments, A is phenyl or thiophenyl wherein each is optionally substituted with 1 to 3 $R_8$. In other embodiments, A is phenyl or thiophenyl wherein each is substituted with 1 to 3 $R_8$. In other embodiments, A is phenyl or thiophenyl wherein each is optionally substituted with 1 to 2 $R_8$. In other embodiments, A is phenyl or thiophenyl wherein each is substituted with 1 to 2 $R_8$. In other embodiments, A is phenyl substituted with 1 to 2 $R_8$. In other embodiments, A is phenyl substituted with 3 $R_8$. In other embodiments, A is thiophenyl substituted with 1 to 2 $R_8$.

In some embodiments, B is phenyl optionally substituted with 1 to 3 $R_9$. In other embodiments, B is 5- or 6-membered heteroaryl containing 1 or 2 heteroatoms selected from N and S, optionally substituted with 1 to 3 $R_9$. In other embodiments, B is 5-membered heteroaryl containing 1 or 2 heteroatoms selected from N and S, optionally substituted with 1 to 3 $R_9$. In other embodiments, B is 6-membered heteroaryl containing 1 or 2 heteroatoms selected from N and S, optionally substituted with 1 to 3 $R_9$. In other embodiments, B is 5- or 6-membered heteroaryl containing 1 or 2 heteroatoms selected from N and S. In other embodiments, B is 5-membered heteroaryl containing 1 or 2 heteroatoms selected from N and S. In other embodiments, B is 6-membered heteroaryl containing 1 or 2 heteroatoms selected from N and S. In other embodiments, B is pyridinyl optionally substituted with 1 to 3 $R_9$. In other embodiments, B is phenyl. In other embodiments, B is pyridinyl.

In some embodiments, $Y_2$ is $NR_{10a}$. In other embodiments, $Y_2$ is O.

In some embodiments, $Y_3$ is $C(O)NR_{10b}$. In other embodiments, $Y_3$ is $NR_{10b}C(O)$.

In some embodiments, $Y_4$ is $NR_5'$. In other embodiments, $Y_4$ is N.

In some embodiments, $Y_5$ is absent. In other embodiments, $Y_5$ is C(O). In other embodiments, $Y_5$ is $CH_2$.

In some embodiments, $R_5'$ is H, $(C_1$-$C_3)$ alkyl, $(C_1$-$C_3)$ haloalkyl, $(C_1$-$C_3)$ alkoxy, $(C_1$-$C_3)$ haloalkoxy, or halogen. In some embodiments, $R_5'$ is $(C_1$-$C_3)$ alkyl, $(C_1$-$C_3)$ haloalkyl, $(C_1$-$C_3)$ alkoxy, $(C_1$-$C_3)$ haloalkoxy, or halogen. In other embodiments, $R_5'$ is $(C_1$-$C_3)$ alkyl, $(C_1$-$C_3)$ haloalkyl, $(C_1$-$C_3)$ alkoxy, or $(C_1$-$C_3)$ haloalkoxy. In other embodiments, $R_5'$ is $(C_1$-$C_3)$ alkyl, $(C_1$-$C_3)$ haloalkyl, or halogen. In other embodiments, $R_5'$ is $(C_1$-$C_3)$ alkyl or halogen. In other embodiments, $R_5'$ is methyl, ethyl, n-propyl, or i-propyl. In other embodiments, $R_5'$ is methyl or ethyl. In other embodiments, $R_5'$ is methyl. In other embodiments, $R_5'$ is H.

In some embodiments, each $R_5$ is independently $(C_1$-$C_3)$ alkyl, $(C_1$-$C_3)$ haloalkyl, $(C_1$-$C_3)$ alkoxy, $(C_1$-$C_3)$ haloalkoxy, halogen, or oxo. In other embodiments, each $R_5$ is independently $(C_1$-$C_3)$ alkyl, $(C_1$-$C_3)$ haloalkyl, $(C_1$-$C_3)$ alkoxy, or $(C_1$-$C_3)$ haloalkoxy. In other embodiments, each $R_5$ is independently $(C_1$-$C_3)$ alkyl, $(C_1$-$C_3)$ haloalkyl, halogen, or oxo. In other embodiments, each $R_5$ is independently $(C_1$-$C_3)$ alkyl, halogen, or oxo. In other embodiments, each $R_5$ is independently $(C_1$-$C_3)$ alkyl or oxo. In other embodiments, each $R_5$ is independently methyl, ethyl, n-propyl, i-propyl, or oxo. In other embodiments, each $R_5$ is independently methyl, ethyl, or oxo. In other embodiments, each $R_5$ is independently methyl or oxo.

In some embodiments, $R_6$ is H, $(C_1$-$C_3)$ alkyl, or $(C_1$-$C_3)$ haloalkyl. In other embodiments, $R_6$ is H or $(C_1$-$C_4)$ alkyl. In other embodiments, $R_6$ is H or $(C_1$-$C_3)$ alkyl. In other embodiments, $R_6$ is H, methyl, ethyl, n-propyl, or i-propyl. In other embodiments, $R_6$ is H, methyl, or ethyl. In other embodiments, $R_6$ is $(C_1$-$C_4)$ alkyl. In other embodiments, $R_6$ is methyl, ethyl, n-propyl, or i-propyl. In other embodiments, $R_6$ is H. In other embodiments, $R_6$ is methyl or ethyl. In other embodiments, $R_6$ is methyl.

In some embodiments, each $R_7$ is independently $(C_1$-$C_3)$ alkyl, $(C_1$-$C_3)$ haloalkyl, $(C_1$-$C_3)$ alkoxy, $(C_1$-$C_3)$ haloalkoxy, $(C_1$-$C_3)$ hydroxyalkyl, halogen, OH, or $NH_2$. In other embodiments, each $R_7$ is independently $(C_1$-$C_4)$ alkyl, $(C_1$-$C_4)$ haloalkyl, $(C_1$-$C_4)$ alkoxy, $(C_1$-$C_4)$ haloalkoxy, $(C_1$-$C_4)$ hydroxyalkyl, halogen, or OH. In other embodiments, each $R_7$ is independently $(C_1$-$C_4)$ alkyl, $(C_1$-$C_4)$ haloalkyl, $(C_1$-$C_4)$ alkoxy, $(C_1$-$C_4)$ haloalkoxy, $(C_1$-$C_4)$ hydroxyalkyl, or OH. In other embodiments, each $R_7$ is independently $(C_1$-$C_4)$ alkyl, $(C_1$-$C_4)$ haloalkyl, $(C_1$-$C_4)$ hydroxyalkyl, halogen, or OH. In other embodiments, each $R_7$ is independently $(C_1$-$C_4)$ alkyl, $(C_1$-$C_4)$ alkoxy, $(C_1$-$C_4)$ hydroxyalkyl, or OH. In other embodiments, each $R_7$ is independently $(C_1$-$C_4)$ alkyl, $(C_1$-$C_4)$ hydroxyalkyl, or OH. In other embodiments, each $R_7$ is independently $(C_1$-$C_4)$ alkyl or $(C_1$-$C_4)$ hydroxyalkyl. In other embodiments, each $R_7$ is independently $(C_1-C_3)$ alkyl or $(C_1-C_3)$ hydroxyalkyl. In other embodiments, each $R_7$ is independently $(C_1-C_3)$ alkyl. In other embodiments, each $R_7$ is independently $(C_1-C_3)$ hydroxyalkyl. In other embodiments, each $R_7$ is independently methyl, ethyl, n-propyl, i-propyl, or $(C_1-C_3)$ hydroxyalkyl. In other embodiments, each $R_7$ is independently methyl, ethyl, n-propyl, i-propyl, $CH_2OH$, $CH_2CH_2OH$, $CH_2CH_2CH_2OH$, $CH(OH)CH_3$, $CH(OH)CH_2CH_3$, or $CH_2CH(OH)CH_3$. In other embodiments, each $R_7$ is independently methyl, ethyl, $CH_2OH$, $CH_2CH_2OH$, or $CH(OH)CH_3$. In other embodiments, each $R_7$ is independently methyl, ethyl, $CH_2OH$, or $CH_2CH_2OH$. In other embodiments, each $R_7$ is independently methyl or $CH_2OH$.

In some embodiments, each $R_8$ is independently $(C_1-C_3)$ alkyl, $(C_1-C_3)$ haloalkyl, $(C_1-C_3)$ alkoxy, $(C_1-C_3)$ haloalkoxy, halogen, OH, $NH_2$, or $(C_3-C_6)$ cycloalkyl. In other embodiments, each $R_8$ is independently $(C_1-C_4)$ alkyl, $(C_1-C_4)$ haloalkyl, $(C_1-C_4)$ alkoxy, $(C_1-C_4)$ haloalkoxy, or halogen. In other embodiments, each $R_8$ is independently $(C_1-C_4)$ alkyl, $(C_1-C_4)$ haloalkyl, $(C_1-C_4)$ alkoxy, $(C_1-C_4)$ haloalkoxy, halogen, or $(C_3-C_6)$ cycloalkyl. In other embodiments, each $R_8$ is independently $(C_1-C_4)$ alkyl, $(C_1-C_4)$ haloalkyl, halogen, or $(C_3-C_6)$ cycloalkyl. In other embodiments, each $R_8$ is independently $(C_1-C_4)$ alkyl, halogen, or $(C_3-C_6)$ cycloalkyl. In other embodiments, each $R_8$ is independently methyl, ethyl, n-propyl, i-propyl, n-butyl, i-butyl, t-butyl, F, Cl, cyclopropyl, cyclobutyl, cyclopentyl, or cyclohexyl. In other embodiments, each $R_8$ is independently n-propyl, i-propyl, n-butyl, i-butyl, t-butyl, F, Cl, cyclopropyl, cyclobutyl, or cyclopentyl. In other embodiments, each $R_8$ is independently i-propyl, i-butyl, t-butyl, F, or cyclopropyl. In other embodiments, each $R_8$ is independently i-propyl, t-butyl, F, or cyclopropyl. In other embodiments, each $R_8$ is independently t-butyl, F, or cyclopropyl. In other embodiments, at least one $R_8$ is t-butyl. In other embodiments, at least one $R_8$ is F. In other embodiments, at least one $R_8$ is cyclopropyl. In other embodiments, at least one $R_8$ is F, and at least one $R_8$ is cyclopropyl.

In some embodiments, two $R_8$ together with the atoms to which they are attached form a $(C_5-C_7)$ cycloalkyl ring. In some embodiments, two $R_8$ together with the atoms to which they are attached form a cyclopentyl ring. In some embodiments, two $R_8$ together with the atoms to which they are attached form a cyclohexyl ring.

In some embodiments, each $R_9$ is independently $(C_1-C_3)$ alkyl, $(C_1-C_3)$ haloalkyl, $(C_1-C_3)$ alkoxy, $(C_1-C_3)$ haloalkoxy, or halogen. In other embodiments, each $R_9$ is independently $(C_1-C_3)$ alkyl, $(C_1-C_3)$ haloalkyl, or halogen. In other embodiments, each $R_9$ is independently $(C_1-C_3)$ alkoxy, $(C_1-C_3)$ haloalkoxy, or halogen. In other embodiments, each $R_9$ is independently $(C_1-C_3)$ alkyl, $(C_1-C_3)$ alkoxy, or halogen. In other embodiments, each $R_9$ is independently $(C_1-C_3)$ alkyl, or halogen. In other embodiments, each $R_9$ is independently methyl, ethyl, n-propyl, i-propyl, F or Cl.

In some embodiments, at least one $R_8$ and $R_{10b}$ together with the atoms to which they are attached form a 5-membered heterocycloalkyl or heteroaryl containing 1 or 2 heteroatoms selected from N, O, and S and optionally substituted with 1 to 3 $R_{11}$. In other embodiments, at least one $R_8$ and $R_{10b}$ together with the atoms to which they are attached form a 6-membered heterocycloalkyl or heteroaryl containing 1 or 2 heteroatoms selected from N, O, and S and optionally substituted with 1 to 3 $R_{11}$. In other embodiments, at least one $R_8$ and $R_{10b}$ together with the atoms to which they are attached form a 5- or 6-membered heterocycloalkyl containing 1 or 2 heteroatoms selected from N, O, and S and optionally substituted with 1 to 3 $R_{11}$. In other embodiments, at least one $R_8$ and $R_{10b}$ together with the atoms to which they are attached form a 5- or 6-membered heteroaryl containing 1 or 2 heteroatoms selected from N, O, and S and optionally substituted with 1 to 3 $R_{11}$.

In other embodiments, at least one $R_8$ and $R_{10b}$ together with the atoms to which they are attached form a 5-membered heterocycloalkyl containing 1 or 2 heteroatoms selected from N, O, and S and optionally substituted with 1 to 3 $R_{11}$. In other embodiments, at least one $R_8$ and $R_{10b}$ together with the atoms to which they are attached form a 6-membered heterocycloalkyl containing 1 or 2 heteroatoms selected from N, O, and S and optionally substituted with 1 to 3 $R_{11}$. In other embodiments, at least one $R_8$ and $R_{10b}$ together with the atoms to which they are attached form a 5-membered heteroaryl containing 1 or 2 heteroatoms selected from N, O, and S and optionally substituted with 1 to 3 $R_{11}$. In other embodiments, at least one $R_8$ and $R_{10b}$ together with the atoms to which they are attached form a 6-membered heteroaryl containing 1 or 2 heteroatoms selected from N, O, and S and optionally substituted with 1 to 3 $R_{11}$.

In some embodiments, $R_{10a}$ is H, $(C_1-C_3)$ alkyl, or $(C_1-C_3)$ haloalkyl. In other embodiments, $R_{10a}$ is $(C_1-C_4)$ alkyl or $(C_1-C_4)$ haloalkyl. In other embodiments, $R_{10a}$ is H or $(C_1-C_4)$ alkyl. In other embodiments, $R_{10a}$ is H, methyl, ethyl, n-propyl, or i-propyl. In other embodiments, $R_{10a}$ is H, methyl or ethyl. In other embodiments, $R_{10a}$ is $(C_1-C_4)$ alkyl. In other embodiments, $R_{10a}$ is methyl, ethyl, n-propyl, or i-propyl. In other embodiments, $R_{10a}$ is methyl or ethyl. In other embodiments, $R_{10a}$ is H.

In some embodiments, $R_{10b}$ is H, $(C_1-C_3)$ alkyl, or $(C_1-C_3)$ haloalkyl. In other embodiments, $R_{10b}$ is $(C_1-C_4)$ alkyl or $(C_1-C_4)$ haloalkyl. In other embodiments, $R_{10b}$ is H or $(C_1-C_4)$ alkyl. In other embodiments, $R_{10b}$ is H, methyl, ethyl, n-propyl, or i-propyl. In other embodiments, $R_{10b}$ is H, methyl or ethyl. In other embodiments, $R_{10b}$ is $(C_1-C_4)$ alkyl. In other embodiments, $R_{10b}$ is methyl, ethyl, n-propyl, or i-propyl. In other embodiments, $R_{10b}$ is methyl or ethyl. In other embodiments, $R_{10b}$ is H.

In some embodiments, each $R_{11}$ is independently $(C_1-C_3)$ alkyl, $(C_1-C_3)$ haloalkyl, $(C_1-C_3)$ alkoxy, $(C_1-C_3)$ haloalkoxy, halogen, oxo. OH, or $NH_2$. In other embodiments, each $R_{11}$ is independently $(C_1-C_3)$ alkyl, $(C_1-C_3)$ haloalkyl, $(C_1-C_3)$ alkoxy, $(C_1-C_3)$ haloalkoxy, or halogen. In other embodiments, each $R_{11}$ is independently halogen, oxo, OH, or $NH_2$. In other embodiments, each $R_{11}$ is independently halogen, OH, or $NH_2$. In other embodiments, each $R_{11}$ is independently $(C_1-C_3)$ alkyl, $(C_1-C_3)$ haloalkyl, $(C_1-C_3)$ alkoxy, or $(C_1-C_3)$ haloalkoxy. In other embodiments, each $R_{11}$ is independently $(C_1-C_3)$ alkyl, $(C_1-C_3)$ haloalkyl, or halogen. In other embodiments, each $R_{11}$ is independently oxo. In other embodiments, each $R_{11}$ is independently methyl, ethyl, n-propyl, i-propyl, F, or Cl.

In some embodiments, o1 is 0. In other embodiments, o1 is 1. In other embodiments, o1 is 2. In other embodiments, o1 is 3. In other embodiments, o1 is 0 or 1. In other embodiments, o1 is 1 or 2. In other embodiments, o1 is 2 or 3. In other embodiments, o1 is 0, 1 or 2. In other embodiments, o1 is 1, 2, or 3.

In some embodiments, o2 is 0. In other embodiments, o2 is 1. In other embodiments, o2 is 2. In other embodiments, o2 is 3. In other embodiments, o2 is 0 or 1. In other embodiments, o2 is 1 or 2. In other embodiments, o2 is 2 or 3. In other embodiments, o2 is 0, 1 or 2. In other embodiments, o2 is 1, 2, or 3.

Any of the groups described herein for any of A, B, $Y_2$, $Y_3$, $Y_4$, $Y_5$, $R_5$, $R_5'$, $R_6$, $R_7$, $R_8$, $R_9$, $R_{10a}$, $R_{10b}$, $R_{11}$, o1, and o2 can be combined with any of the groups described herein for one or more of the remainder of A, B, $Y_2$, $Y_3$, $Y_4$, $Y_5$, $R_5$, $R_5'$, $R_6$, $R_7$, $R_8$, $R_9$, $R_{10a}$, $R_{10b}$, $R_{11}$, o1, and o2, and may further be combined with any of the groups described herein for the Linker.

For example, for a Targeting Ligand of Formula TL-I:

(1) In one embodiment, B is pyridinyl and $Y_2$ is $NR_{10a}$.

(2) In one embodiment, B is pyridinyl, $Y_2$ is $NR_{10a}$, and $R_6$ is $(C_1-C_4)$ alkyl.

(3) In one embodiment, B is pyridinyl, $Y_2$ is $NR_{10a}$, $R_6$ is $(C_1-C_4)$ alkyl, and each $R_7$ is independently $(C_1-C_4)$ alkyl or $(C_1-C_4)$ hydroxyalkyl.

(4) In one embodiment, B is pyridinyl, $Y_2$ is $NR_{10a}$, $R_6$ is $(C_1-C_4)$ alkyl, and each $R_7$ is independently $(C_1-C_4)$ alkyl.

(5) In one embodiment, B is pyridinyl, $Y_2$ is $NR_{10a}$, $R_6$ is $(C_1-C_4)$ alkyl, and each $R_7$ is independently $(C_1-C_4)$ hydroxyalkyl.

(6) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and $Y_3$ is $C(O)NR_{10b}$.

(7) In one embodiment, B is pyridinyl, $Y_2$ is $NR_{10a}$, $R_6$ is $(C_1-C_4)$ alkyl, each $R_7$ is independently $(C_1-C_4)$ alkyl, and $Y_3$ is $C(O)NR_{10b}$.

(8) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and $Y_3$ is $C(O)NR_{10b}$.

(9) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_1-C_7)$ cycloalkyl ring.

(10) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.

(11) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl.

(12) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently halogen or $(C_3-C_6)$ cycloalkyl.

(13) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and two $R_8$ together with the atoms to which they are attached form a $(C_5-C_7)$ cycloalkyl ring.

(14) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(15) In one embodiment, B is pyridinyl, $Y_2$ is $NR_{10a}$, $R_6$ is $(C_1-C_4)$ alkyl, each $R_2$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl.

(16) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl.

(17) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently halogen or $(C_3-C_6)$ cycloalkyl.

(18) In one embodiment, B is pyridinyl, $Y_2$ is $NR_{10a}$, $R_6$ is $(C_1-C_4)$ alkyl, each $R_2$ is independently $(C_1-C_4)$ alkyl, $Y_3$ is $C(O)NR_{10b}$, and two $R_8$ together with the atoms to which they are attached form a $(C_1-C_7)$ cycloalkyl ring.

(19) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_1-C_7)$ cycloalkyl ring.

(20) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.

(21) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl.

(22) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently halogen or $(C_3-C_6)$ cycloalkyl.

(23) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and two $R_8$ together with the atoms to which they are attached form a $(C_1-C_7)$ cycloalkyl ring.

(24) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(25) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl.

(26) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl.

(27) In one embodiment, B is pyridinyl, $Y_2$ is $NR_{10a}$, $R_6$ is $(C_1-C_4)$ alkyl, each $R_2$ is independently $(C_1-C_4)$ alkyl or $(C_1-C_4)$ hydroxyalkyl, and each $R_8$ is independently halogen or $(C_3-C_6)$ cycloalkyl.

(28) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and two $R_8$ together with the atoms to which they are attached form a $(C_5-C_7)$ cycloalkyl ring.

(29) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(30) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl.

(31) In one embodiment, B is pyridinyl, $Y_2$ is $NR_{10a}$, $R_6$ is ($C_1$-$C_4$) alkyl, each $R_7$ is independently ($C_1$-$C_4$) alkyl, and each $R_8$ is independently ($C_1$-$C_4$) alkyl.
(32) In one embodiment, B is pyridinyl, $Y_2$ is $NR_{10a}$, $R_6$ is ($C_1$-$C_4$) alkyl, each $R_7$ is independently ($C_1$-$C_4$) alkyl, and each $R_8$ is independently halogen or ($C_3$-$C_6$) cycloalkyl.
(33) In one embodiment, B is pyridinyl, $Y_2$ is $NR_{10a}$, $R_6$ is ($C_1$-$C_4$) alkyl, each $R_7$ is independently ($C_1$-$C_4$) alkyl, and two $R_8$ together with the atoms to which they are attached form a ($C_5$-$C_7$) cycloalkyl ring.
(34) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and each $R_8$ is independently ($C_1$-$C_4$) alkyl, halogen, or ($C_3$-$C_6$) cycloalkyl, or two $R_8$ together with the atoms to which they are attached form a ($C_5$-$C_7$) cycloalkyl ring.
(35) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and each $R_8$ is independently ($C_1$-$C_4$) alkyl, halogen, or ($C_3$-$C_6$) cycloalkyl.
(36) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and each $R_8$ is independently ($C_1$-$C_4$) alkyl.
(37) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and each $R_8$ is independently halogen or ($C_3$-$C_6$) cycloalkyl.
(38) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and two $R_8$ together with the atoms to which they are attached form a ($C_5$-$C_7$) cycloalkyl ring.
(39) In one embodiment, B, $Y_2$, $Y_3$, $R_6$, $R_7$, and $R_8$ are each as defined, where applicable, in any one of (1)-(38), and A is phenyl.
(40) In one embodiment, B, $Y_2$, $Y_3$, $R_6$, $R_7$, and $R_8$ are each as defined, where applicable, in any one of (1)-(38), and A is thiophenyl.
(41) In one embodiment, B, $Y_2$, $Y_3$, $R_6$, $R_7$, and $R_8$ are each as defined, where applicable, in any one of (1)-(38), and $R_{10a}$ is H.
(42) In one embodiment, B, $Y_2$, $Y_3$, $R_6$, $R_7$, and $R_8$ are each as defined, where applicable, in any one of (1)-(38), and $R_{10b}$ is H.
(43) In one embodiment, B, $Y_2$, $Y_3$, $R_6$, $R_7$, and $R_8$ are each as defined, where applicable, in any one of (1)-(38), $R_{10a}$ is H, and $R_{10b}$ is H.
(44) In one embodiment, B, $Y_2$, $Y_3$, $R_6$, $R_7$, and $R_8$ are each as defined, where applicable, in any one of (1)-(38), A is phenyl, and $R_{10a}$ is H.
(45) In one embodiment, B, $Y_2$, $Y_3$, $R_6$, $R_7$, and $R_8$ are each as defined, where applicable, in any one of (1)-(38), A is phenyl, and $R_{10b}$ is H.
(46) In one embodiment, B, $Y_2$, $Y_3$, $R_6$, $R_7$, and $R_8$ are each as defined, where applicable, in any one of (1)-(38), A is phenyl, $R_{10a}$ is H, and $R_{10b}$ is H.
(47) In one embodiment, B, $Y_2$, $Y_3$, $R_6$, $R_7$, and $R_8$ are each as defined, where applicable, in any one of (1)-(38), A is thiophenyl, and $R_{10a}$ is H.
(48) In one embodiment, B, $Y_2$, $Y_3$, $R_6$, $R_7$, and $R_8$ are each as defined, where applicable, in any one of (1)-(38), and $R_{10b}$ is H.
(49) In one embodiment, B, $Y_2$, $Y_3$, $R_6$, $R_7$, and $R_8$ are each as defined, where applicable, in any one of (1)-(38), A is thiophenyl, $R_{10a}$ is H, and $R_{10b}$ is H.
(50) In one embodiment, B is pyridinyl, $Y_2$ is $NR_{10a}$, $R_6$ is ($C_1$-$C_4$) alkyl, each $R_7$ is independently ($C_1$-$C_4$) alkyl or ($C_1$-$C_4$) hydroxyalkyl, $Y_3$ is $C(O)NR_{10b}$, and $R_8$ and $R_{10}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(51) In one embodiment, B is pyridinyl, $Y_2$ is $NR_{10a}$, $R_6$ is ($C_1$-$C_4$) alkyl, each $R_7$ is independently ($C_1$-$C_4$) alkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(52) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(53) In one embodiment, B is pyridinyl, $Y_2$ is $NR_{10a}$, $R_6$ is ($C_1$-$C_4$) alkyl, each $R_7$ is independently ($C_1$-$C_4$) alkyl or ($C_1$-$C_4$) hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(54) In one embodiment, B is pyridinyl, $Y_2$ is $NR_{10a}$, $R_6$ is ($C_1$-$C_4$) alkyl, each $R_7$ is independently ($C_1$-$C_4$) alkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(55) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(56) In one embodiment, B, $Y_2$, $Y_3$, $R_6$, $R_7$, $R_8$, and $R_{10b}$ are each as defined, where applicable, in any one of (50)-(55), and A is phenyl.
(57) In one embodiment, B, $Y_2$, $Y_3$, $R_6$, $R_7$, $R_8$, and $R_{10b}$ are each as defined, where applicable, in any one of (50)-(55), and A is thiophenyl.
(58) In one embodiment, B, $Y_2$, $Y_3$, $R_6$, $R_7$, $R_8$, and $R_{10b}$ are each as defined, where applicable, in any one of (50)-(55), and $R_{10a}$ is H.
(59) In one embodiment, B, $Y_2$, $Y_3$, $R_6$, $R_7$, $R_8$, and $R_{10b}$ are each as defined, where applicable, in any one of (50)-(55), A is phenyl, and $R_{10a}$ is H.
(60) In one embodiment, B, $Y_2$, $Y_3$, $R_6$, $R_7$, $R_8$, and $R_{10b}$ are each as defined, where applicable, in any one of (50)-(55), A is thiophenyl, and $R_{10a}$ is H.
(61) In one embodiment, B, $Y_2$, $Y_3$, $R_6$, $R_7$, $R_8$, and $R_{10b}$ are each as defined, where applicable, in any one of (50)-(55), and $R_{10a}$ is H.
(62) In one embodiment, B is pyridinyl and A is phenyl.
(63) In one embodiment, B is pyridinyl and A is thiophenyl.
(64) In one embodiment, B is phenyl and A is phenyl.
(65) In one embodiment, B is phenyl and A is thiophenyl.
(66) In one embodiment, B is pyridinyl, A is phenyl, and $R_6$ is methyl.

(67) In one embodiment, B is pyridinyl, A is thiophenyl, and $R_6$ is methyl.

(68) In one embodiment, B is phenyl, A is phenyl, and $R_6$ is methyl.

(69) In one embodiment, B is phenyl, A is thiophenyl, and $R_6$ is methyl.

(70) In one embodiment, B is pyridinyl, A is phenyl, and $Y_2$ is $NR_{10a}$.

(71) In one embodiment, B is pyridinyl, A is thiophenyl, and $Y_2$ is $NR_{10a}$.

(72) In one embodiment, B is phenyl, A is phenyl, and $Y_2$ is $NR_{10a}$.

(73) In one embodiment, B is phenyl, A is thiophenyl, and $Y_2$ is $NR_{10a}$.

(74) In one embodiment, B is pyridinyl, A is phenyl, and $Y_3$ is $C(O)NR_{10b}$.

(75) In one embodiment, B is pyridinyl, A is thiophenyl, and $Y_3$ is $C(O)NR_{10b}$.

(76) In one embodiment, B is phenyl, A is phenyl, and $Y_3$ is $C(O)NR_{10b}$.

(77) In one embodiment, B is phenyl, A is thiophenyl, and $Y_3$ is $C(O)NR_{10b}$.

(78) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 0.

(79) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 1.

(80) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 2.

(81) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 2, and $R_5$ is $(C_1-C_4)$ alkyl or oxo.

(82) In one embodiment, A, B, $Y_2$, $Y_3$, $R_6$, $R_7$, $R_8$, $R_{10a}$, and $R_{10b}$ are each as defined, where applicable, in any one of (1)-(77), o2 is 1.

(83) In one embodiment, A, B, $Y_2$, $Y_3$, $R_6$, $R_7$, $R_8$, $R_{10a}$, and $R_{10b}$ are each as defined, where applicable, in any one of (1)-(77), o2 is 2.

(84) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 0 and o2 is 1.

(85) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 1 and o2 is 1.

(86) In one embodiment, A, B, $Y_2$, $Y_3$, $R_6$, $R_7$, $R_8$, $R_{10a}$, and $R_{10b}$ are each as defined, where applicable, in any one of (1)-(77), o1 is 2 and o2 is 1.

(87) In one embodiment, A, B, $Y_2$, $Y_3$, $R_6$, $R_7$, $R_8$, $R_{10a}$, $R_{10b}$, o1, and o2 are each as defined, where applicable, in any one of (1)-(86), $Y_5$ is absent.

(88) In one embodiment, A, B, $Y_2$, $Y_3$, $R_6$, $R_7$, $R_8$, $R_{10a}$, $R_{10b}$, o1, and o2 are each as defined, where applicable, in any one of (1)-(86), $Y_5$ is $C(O)$.

(89) In one embodiment, A, B, $Y_2$, $Y_3$, $R_6$, $R_7$, $R_8$, $R_{10a}$, $R_{10b}$, o1, and o2 are each as defined, where applicable, in any one of (1)-(86), $Y_5$ is $CH_2$.

In one embodiment, the compound of Formula TL-I is of Formula TL-Ia or TL-Ib:

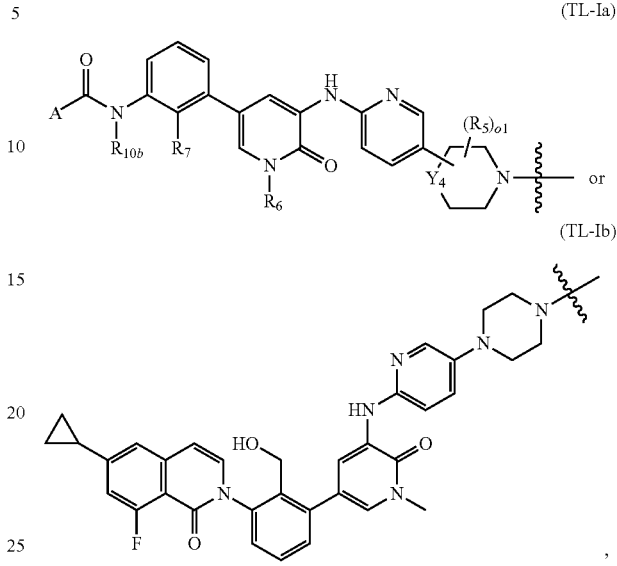

wherein A, $Y_4$, $R_5$, $R_6$, $R_7$, $R_{10b}$, and o1 are each as defined above in Formula TL-I, and can be combined as described above in Formula TL-I.

For example, for a Targeting Ligand of Formula TL-II:

(1) In one embodiment, B is phenyl and $Y_2$ is $NR_{10a}$.

(2) In one embodiment, B is phenyl, $Y_2$ is $NR_{10a}$, and $R_6$ is $(C_1-C_4)$ alkyl.

(3) In one embodiment, B is phenyl, $Y_2$ is $NR_{10a}$, $R_6$ is $(C_1-C_4)$ alkyl, and each $R_7$ is independently $(C_1-C_4)$ alkyl or $(C_1-C_4)$ hydroxyalkyl.

(4) In one embodiment, B is phenyl, $Y_2$ is $NR_{10a}$, $R_6$ is $(C_1-C_4)$ alkyl, and each $R_7$ is independently $(C_1-C_4)$ alkyl.

(5) In one embodiment, B is phenyl, $Y_2$ is $NR_{10a}$, $R_6$ is $(C_1-C_4)$ alkyl, and each $R_7$ is independently $(C_1-C_4)$ hydroxyalkyl.

(6) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and $Y_3$ is $C(O)NR_{10b}$.

(7) In one embodiment, B is phenyl, $Y_2$ is $NR_{10a}$, $R_6$ is $(C_1-C_4)$ alkyl, each $R_7$ is independently $(C_1-C_4)$ alkyl, and $Y_3$ is $C(O)NR_{10b}$.

(8) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and $Y_3$ is $C(O)NR_{10b}$.

(9) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(10) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.

(11) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl.

(12) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently halogen or $(C_3-C_6)$ cycloalkyl.

(13) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and two $R_8$ together with the atoms to which they are attached form a $(C_5-C_7)$ cycloalkyl ring.

(14) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(15) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl.

(16) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl.

(17) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently halogen or $(C_3-C_6)$ cycloalkyl.

(18) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and two $R_8$ together with the atoms to which they are attached form a $(C_5-C_7)$ cycloalkyl ring.

(19) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_1-C_7)$ cycloalkyl ring.

(20) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.

(21) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl.

(22) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently halogen or $(C_3-C_6)$ cycloalkyl.

(23) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and two $R_8$ together with the atoms to which they are attached form a $(C_1-C_7)$ cycloalkyl ring.

(24) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(25) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl.

(26) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl.

(27) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently halogen or $(C_3-C_6)$ cycloalkyl.

(28) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and two $R_8$ together with the atoms to which they are attached form a $(C_5-C_7)$ cycloalkyl ring.

(29) In one embodiment, B is phenyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(30) In one embodiment, B is phenyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl.

(31) In one embodiment, B is phenyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl.

(32) In one embodiment, B is phenyl, $Y_2$ is $NR_{10a}$, $R_6$ is $(C_1-C_4)$ alkyl, each $R_7$ is independently $(C_1-C_4)$ alkyl, and each $R_8$ is independently halogen or $(C_3-C_6)$ cycloalkyl.

(33) In one embodiment, B is phenyl, $Y_2$ is $NR_{10a}$, $R_6$ is $(C_1-C_4)$ alkyl, each $R_7$ is independently $(C_1-C_4)$ alkyl, and two $R_8$ together with the atoms to which they are attached form a $(C_5-C_7)$ cycloalkyl ring.

(34) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(35) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl.

(36) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl.

(37) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and each $R_8$ is independently halogen or $(C_3-C_6)$ cycloalkyl.

(38) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and two $R_8$ together with the atoms to which they are attached form a $(C_5-C_7)$ cycloalkyl ring.

(39) In one embodiment, B, $Y_2$, $Y_3$, $R_6$, $R_7$, and $R_8$ are each as defined, where applicable, in any one of (1)-(38), and A is phenyl.

(40) In one embodiment, B, $Y_2$, $Y_3$, $R_6$, $R_7$, and $R_8$ are each as defined, where applicable, in any one of (1)-(38), and A is thiophenyl.

(41) In one embodiment, B, $Y_2$, $Y_3$, $R_6$, $R_7$, and $R_8$ are each as defined, where applicable, in any one of (1)-(38), and $R_{10a}$ is H.

(42) In one embodiment, B, $Y_2$, $Y_3$, $R_6$, $R_7$, and $R_8$ are each as defined, where applicable, in any one of (1)-(38), and $R_{10b}$ is H.

(43) In one embodiment, B, $Y_2$, $Y_3$, $R_6$, $R_7$, and $R_8$ are each as defined, where applicable, in any one of (1)-(38), $R_{10a}$ is H, and $R_{10b}$ is H.

(44) In one embodiment, B, $Y_2$, $Y_3$, $R_6$, $R_7$, and $R_8$ are each as defined, where applicable, in any one of (1)-(38), A is phenyl, and $R_{10a}$ is H.

(45) In one embodiment, B, $Y_2$, $Y_3$, $R_6$, $R_7$, and $R_8$ are each as defined, where applicable, in any one of (1)-(38), A is phenyl, and $R_{10b}$ is H.

(46) In one embodiment, B, $Y_2$, $Y_3$, $R_6$, $R_7$, and $R_8$ are each as defined, where applicable, in any one of (1)-(38), A is phenyl, $R_{10a}$ is H, and $R_{10b}$ is H.

(47) In one embodiment, B, $Y_2$, $Y_3$, $R_6$, $R_7$, and $R_8$ are each as defined, where applicable, in any one of (1)-(38), A is thiophenyl, and $R_{10a}$ is H.

(48) In one embodiment, B, $Y_2$, $Y_3$, $R_6$, $R_7$, and $R_8$ are each as defined, where applicable, in any one of (1)-(38), A is thiophenyl, and $R_{10b}$ is H.

(49) In one embodiment, B, $Y_2$, $Y_3$, $R_6$, $R_7$, and $R_8$ are each as defined, where applicable, in any one of (1)-(38), A is thiophenyl, $R_{10a}$ is H, and $R_{10b}$ is H.

(50) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(51) In one embodiment, B is phenyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(52) In one embodiment, B is phenyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(53) In one embodiment, B is phenyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(54) In one embodiment, B is phenyl, $Y_2$ is $NR_{10a}$, $R_6$ is $(C_1-C_4)$ alkyl, each $R_7$ is independently $(C_1-C_4)$ alkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(55) In one embodiment, B is phenyl, $Y_2$ is $NR_{10a}$, $R_6$ is $(C_1-C_4)$ alkyl, each $R_7$ is independently $(C_1-C_4)$ hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(56) In one embodiment, B, $Y_2$, $Y_3$, $R_6$, $R_7$, $R_8$, and $R_{10b}$ are each as defined, where applicable, in any one of (50)-(55), and A is phenyl.

(57) In one embodiment, B, $Y_2$, $Y_3$, $R_6$, $R_7$, $R_8$, and $R_{10b}$ are each as defined, where applicable, in any one of (50)-(55), and A is thiophenyl.

(58) In one embodiment, B, $Y_2$, $Y_3$, $R_6$, $R_7$, $R_8$, and $R_{10b}$ are each as defined, where applicable, in any one of (50)-(55), and $R_{10a}$ is H.

(59) In one embodiment, B, $Y_2$, $Y_3$, $R_6$, $R_7$, $R_8$, and $R_{10b}$ are each as defined, where applicable, in any one of (50)-(55), A is phenyl, and $R_{10a}$ is H.

(60) In one embodiment, B, $Y_2$, $Y_3$, $R_6$, $R_7$, $R_8$, and $R_{10b}$ are each as defined, where applicable, in any one of (50)-(55), A is thiophenyl, and $R_{10a}$ is H.

(61) In one embodiment, B, $Y_2$, $Y_3$, $R_6$, $R_7$, $R_8$, and $R_{10b}$ are each as defined, where applicable, in any one of (50)-(55), and $R_{10a}$ is H.

(62) In one embodiment, B is pyridinyl and $Y_2$ is $NR_{10a}$.

(63) In one embodiment, B is pyridinyl, $Y_2$ is $NR_{10a}$, and $R_6$ is $(C_1-C_4)$ alkyl.

(64) In one embodiment, B is pyridinyl, $Y_2$ is $NR_{10a}$, $R_6$ is $(C_1-C_4)$ alkyl, and each $R_7$ is independently $(C_1-C_4)$ alkyl or $(C_1-C_4)$ hydroxyalkyl.

(65) In one embodiment, B is pyridinyl, $Y_2$ is $NR_{10a}$, $R_6$ is $(C_1-C_4)$ alkyl, and each $R_7$ is independently $(C_1-C_4)$ alkyl.

(66) In one embodiment, B is pyridinyl, $Y_2$ is $NR_{10a}$, $R_6$ is $(C_1-C_4)$ alkyl, and each $R_7$ is independently $(C_1-C_4)$ hydroxyalkyl.

(67) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and $Y_3$ is $C(O)NR_{10b}$.

(68) In one embodiment, B is pyridinyl, $Y_2$ is $NR_{10a}$, $R_6$ is $(C_1-C_4)$ alkyl, each $R_7$ is independently $(C_1-C_4)$ alkyl, and $Y_3$ is $C(O)NR_{10b}$.

(69) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and $Y_3$ is $C(O)NR_{10b}$.

(70) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.

(71) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.

(72) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently $(C_1-C_4)$ alkyl.

(73) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and each $R_8$ is independently halogen or $(C_3-C_6)$ cycloalkyl.

(74) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, $Y_3$ is $C(O)NR_{10b}$, and two $R_8$ together with the atoms to which they are attached form a $(C_5-C_7)$ cycloalkyl ring.

(75) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl, or two

(76) In one embodiment, B is pyridinyl, $Y_2$ is $NR_{10a}$, $R_6$ is $(C_1-C_4)$ alkyl, each $R_2$ is independently $(C_1-C_4)$ alkyl, $Y_3$ is $C(O)NR_{10b}$, and each $R_8$ is independently $(C_1-C_4)$ alkyl, halogen, or $(C_3-C_6)$ cycloalkyl.
(77) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently $(C_1-C_4)$ alkyl.
(78) In one embodiment, B is pyridinyl, $Y_2$ is $NR_{10a}$, $R_6$ is $(C_1-C_4)$ alkyl, each $R_7$ is independently $(C_1-C_4)$ alkyl, $Y_3$ is $C(O)NR_{10b}$, and each $R_8$ is independently halogen or $(C_3-C_6)$ cycloalkyl.
(79) In one embodiment, B is pyridinyl, $Y_2$ is $NR_{10a}$, $R_6$ is $(C_1-C_4)$ alkyl, each $R_2$ is independently $(C_1-C_4)$ alkyl, $Y_3$ is $C(O)NR_{10b}$, and two $R_8$ together with the atoms to which they are attached form a $(C_1-C_7)$ cycloalkyl ring.
(80) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl, or two $R_8$ together with the atoms to which they are attached form a $(C_1-C_7)$ cycloalkyl ring.
(81) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl, halogen, or $(C_3-C_6)$ cycloalkyl.
(82) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently $(C_1-C_4)$ alkyl.
(83) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and each $R_8$ is independently halogen or $(C_3-C_6)$ cycloalkyl.
(84) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, $Y_3$ is $C(O)NR_{10b}$, and two $R_8$ together with the atoms to which they are attached form a $(C_1-C_7)$ cycloalkyl ring.
(85) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.
(86) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl.
(87) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl.
(88) In one embodiment, B is pyridinyl, $Y_2$ is $NR_{10a}$, $R_6$ is $(C_1-C_4)$ alkyl, each $R_2$ is independently $(C_1-C_4)$ alkyl or $(C_1-C_4)$ hydroxyalkyl, and each $R_8$ is independently halogen or $(C_3-C_6)$ cycloalkyl.
(89) In one embodiment, B is pyridinyl, $Y_2$ is $NR_{10a}$, $R_6$ is $(C_1-C_4)$ alkyl, each $R_7$ is independently $(C_1-C_4)$ alkyl or $(C_1-C_4)$ hydroxyalkyl, and two $R_8$ together with the atoms to which they are attached form a $(C_5-C_7)$ cycloalkyl ring.
(90) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.
(91) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl.
(92) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently $(C_1-C_4)$ alkyl.
(93) In one embodiment, B is pyridinyl, $Y_2$ is $NR_{10a}$, $R_6$ is $(C_1-C_4)$ alkyl, each $R_7$ is independently $(C_1-C_4)$ alkyl, and each $R_8$ is independently halogen or $(C_3-C_6)$ cycloalkyl.
(94) In one embodiment, B is pyridinyl, $Y_2$ is $NR_{10a}$, $R_6$ is $(C_1-C_4)$ alkyl, each $R_7$ is independently $(C_1-C_4)$ alkyl, and two $R_8$ together with the atoms to which they are attached form a $(C_5-C_7)$ cycloalkyl ring.
(95) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.
(96) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl.
(97) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and each $R_8$ is independently $(C_1-C_4)$ alkyl.
(98) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and each $R_8$ is independently halogen or $(C_3-C_6)$ cycloalkyl.
(99) In one embodiment, B is pyridinyl, $Y_2$ is $NR_{10a}$, $R_6$ is $(C_1-C_4)$ alkyl, each $R_7$ is independently $(C_1-C_4)$ hydroxyalkyl, and two $R_8$ together with the atoms to which they are attached form a $(C_5-C_7)$ cycloalkyl ring.
(100) In one embodiment, B, $Y_2$, $Y_3$, $R_6$, $R_7$, and $R_8$ are each as defined, where applicable, in any one of (62)-(99), and A is phenyl.
(101) In one embodiment, B, $Y_2$, $Y_3$, $R_6$, $R_7$, and $R_8$ are each as defined, where applicable, in any one of (62)-(99), and A is thiophenyl.
(102) In one embodiment, B, $Y_2$, $Y_3$, $R_6$, $R_7$, and $R_8$ are each as defined, where applicable, in any one of (62)-(99), and $R_{10a}$ is H.
(103) In one embodiment, B, $Y_2$, $Y_3$, $R_6$, $R_7$, and $R_8$ are each as defined, where applicable, in any one of (62)-(99), and $R_{10b}$ is H.
(104) In one embodiment, B, $Y_2$, $Y_3$, $R_6$, $R_7$, and $R_8$ are each as defined, where applicable, in any one of (62)-(99), $R_{10a}$ is H, and $R_{10b}$ is H.
(105) In one embodiment, B, $Y_2$, $Y_3$, $R_6$, $R_7$, and $R_8$ are each as defined, where applicable, in any one of v, A is phenyl, and $R_{10a}$ is H.
(106) In one embodiment, B, $Y_2$, $Y_3$, $R_6$, $R_7$, and $R_8$ are each as defined, where applicable, in any one of (62)-(99), A is phenyl, and $R_{10b}$ is H.
(107) In one embodiment, B, $Y_2$, $Y_3$, $R_6$, $R_7$, and $R_8$ are each as defined, where applicable, in any one of (62)-(99), A is phenyl, $R_{10a}$ is H, and $R_{10b}$ is H.

(108) In one embodiment, B, $Y_2$, $Y_3$, $R_6$, $R_7$, and $R_8$ are each as defined, where applicable, in any one of (62)-(99), A is thiophenyl, and $R_{10a}$ is H.
(109) In one embodiment, B, $Y_2$, $Y_3$, $R_6$, $R_7$, and $R_8$ are each as defined, where applicable, in any one of (62)-(99), A is thiophenyl, and $R_{10b}$ is H.
(110) In one embodiment, B, $Y_2$, $Y_3$, $R_6$, $R_7$, and $R_8$ are each as defined, where applicable, in any one of (62)-(99), A is thiophenyl, $R_{10a}$ is H, and $R_{10b}$ is H.
(111) In one embodiment, B is pyridinyl, $Y_2$ is $NR_{10a}$, $R_6$ is ($C_1$-$C_4$) alkyl, each $R_7$ is independently ($C_1$-$C_4$) alkyl or ($C_1$-$C_4$) hydroxyalkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(112) In one embodiment, B is pyridinyl, $Y_2$ is $NR_{10a}$, $R_6$ is ($C_1$-$C_4$) alkyl, each $R_7$ is independently ($C_1$-$C_4$) alkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(113) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, $Y_3$ is $C(O)NR_{10b}$, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(114) In one embodiment, B is pyridinyl, $Y_2$ is $NR_{10a}$, $R_6$ is ($C_1$-$C_4$) alkyl, each $R_7$ is independently ($C_1$-$C_4$) alkyl or ($C_1$-$C_4$) hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(115) In one embodiment, B is pyridinyl, $Y_2$ is $NR_{10a}$, $R_6$ is ($C_1$-$C_4$) alkyl, each $R_7$ is independently ($C_1$-$C_4$) alkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(116) In one embodiment, B is pyridinyl, $Y_2$ is $NR_{10a}$, $R_6$ is ($C_1$-$C_4$) alkyl, each $R_7$ is independently ($C_1$-$C_4$) hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(117) In one embodiment, B, $Y_2$, $Y_3$, $R_6$, $R_7$, $R_8$, and $R_{10b}$ are each as defined, where applicable, in any one of (1)-(116), and A is phenyl.
(118) In one embodiment, B, $Y_2$, $Y_3$, $R_6$, $R_7$, $R_8$, and $R_{10b}$ are each as defined, where applicable, in any one of (111)-(116), and A is thiophenyl.
(119) In one embodiment, B, $Y_2$, $Y_3$, $R_6$, $R_7$, $R_8$, and $R_{10b}$ are each as defined, where applicable, in any one of (111)-(116), and $R_{10a}$ is H.
(120) In one embodiment, B, $Y_2$, $Y_3$, $R_6$, $R_7$, $R_8$, and $R_{10b}$ are each as defined, where applicable, in any one of (111)-(116), A is phenyl, and $R_{10a}$ is H.
(121) In one embodiment, B, $Y_2$, $Y_3$, $R_6$, $R_7$, $R_8$, and $R_{10b}$ are each as defined, where applicable, in any one of (111)-(116), A is thiophenyl, and $R_{10a}$ is H.
(122) In one embodiment, B, $Y_2$, $Y_3$, $R_6$, $R_7$, $R_8$, and $R_{10b}$ are each as defined, where applicable, in any one of (111)-(116), and $R_{10a}$ is H.
(123) In one embodiment, B is pyridinyl and A is phenyl.
(124) In one embodiment, B is pyridinyl and A is thiophenyl.
(125) In one embodiment, B is phenyl and A is phenyl.
(126) In one embodiment, B is phenyl and A is thiophenyl.
(127) In one embodiment, B is pyridinyl, A is phenyl, and $R_6$ is methyl.
(128) In one embodiment, B is pyridinyl, A is thiophenyl, and $R_6$ is methyl.
(129) In one embodiment, B is phenyl, A is phenyl, and $R_6$ is methyl.
(130) In one embodiment, B is phenyl, A is thiophenyl, and $R_6$ is methyl.
(131) In one embodiment, B is pyridinyl, A is phenyl, and $Y_2$ is $NR_{10a}$.
(132) In one embodiment, B is pyridinyl, A is thiophenyl, and $Y_2$ is $NR_{10a}$.
(133) In one embodiment, B is phenyl, A is phenyl, and $Y_2$ is $NR_{10a}$.
(134) In one embodiment, B is phenyl, A is thiophenyl, and $Y_2$ is $NR_{10a}$.
(135) In one embodiment, B is pyridinyl, A is phenyl, and $Y_3$ is $C(O)NR_{10b}$.
(136) In one embodiment, B is pyridinyl, A is thiophenyl, and $Y_3$ is $C(O)NR_{10b}$.
(137) In one embodiment, B is phenyl, A is phenyl, and $Y_3$ is $C(O)NR_{10b}$.
(138) In one embodiment, B is phenyl, A is thiophenyl, and $Y_3$ is $C(O)NR_{10b}$.
(139) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 0.
(140) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 1.
(141) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 2.
(142) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 2, and $R_5$ is ($C_1$-$C_4$) alkyl or oxo.
(143) In one embodiment, A, B, $Y_2$, $Y_3$, $R_6$, $R_7$, $R_8$, $R_{10a}$, and $R_{10b}$ are each as defined, where applicable, in any one of (1)-(138), o2 is 1.
(144) In one embodiment, A, B, $Y_2$, $Y_3$, $R_6$, $R_7$, $R_8$, $R_{10a}$, and $R_{10b}$ are each as defined, where applicable, in any one of (1)-(138), o2 is 2.
(145) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 0 and o2 is 1.
(146) In one embodiment, A, B, $Y_2$, $Y_3$, $R_6$, $R_7$, $R_8$, $R_{10a}$, and $R_{10b}$ are each as defined, where applicable, in any one of (1)-(138), o1 is 1 and o2 is 1.
(147) In one embodiment, A, B, $Y_2$, $Y_3$, $R_6$, $R_7$, $R_8$, $R_{10a}$, and $R_{10b}$ are each as defined, where applicable, in any one of (1)-(38), o1 is 2 and o2 is 1.
(148) In one embodiment, A, B, $Y_2$, $Y_3$, $R_6$, $R_7$, $R_8$, $R_{10a}$, $R_{10b}$, o1, and o2 are each as defined, where applicable, in any one of (1)-(147), $Y_5$ is absent.
(149) In one embodiment, A, B, $Y_2$, $Y_3$, $R_6$, $R_7$, $R_8$, $R_{10a}$, $R_{10b}$, o1, and o2 are each as defined, where applicable, in any one of (1)-(147), $Y_5$ is $C(O)$.

(150) In one embodiment, A, B, $Y_2$, $Y_3$, $R_6$, $R_7$, $R_8$, $R_{10a}$, $R_{10b}$, o1, and o2 are each as defined, where applicable, in any one of (1)-(147), $Y_5$ is $CH_2$.

In one embodiment, the compound of Formula TL-II is of Formula TL-IIa, TL-IIb, TL-IIc, TL-IId, or TL-IIe:

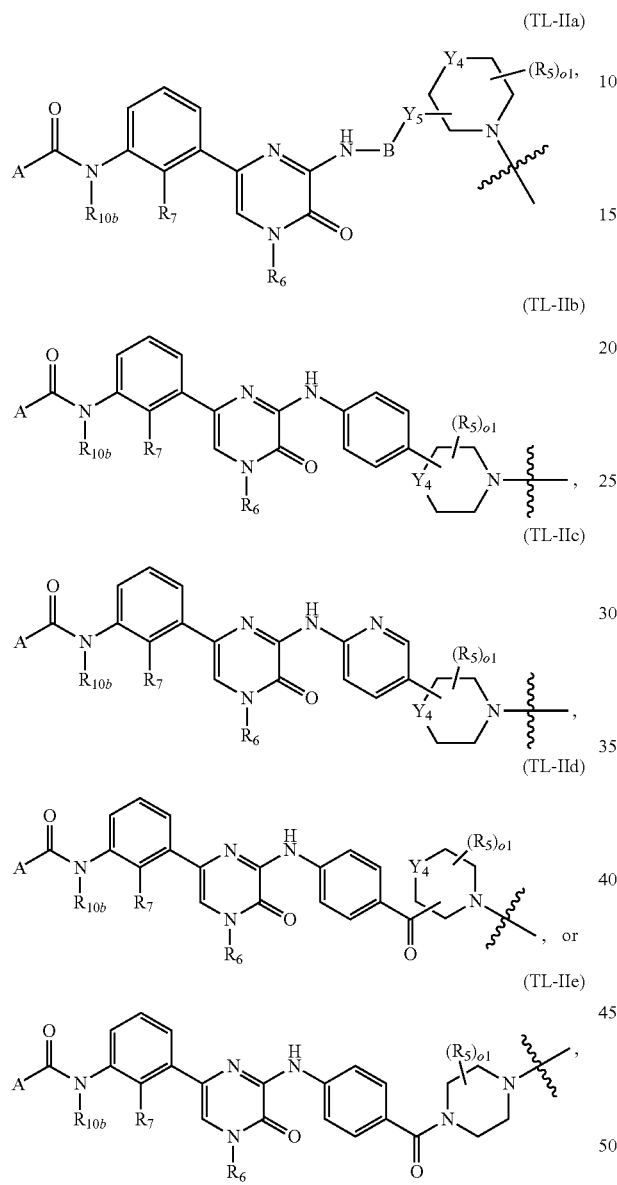

wherein A, B, $Y_4$, $R_5$, $R_6$, $R_7$, $R_{10b}$, and o1 are each as defined above in Formula TL-II, and can be combined as described above in Formula TL-II.

For example, for a Targeting Ligand of Formula TL-IIa, TL-IIb, TL-IIc, TL-IId, or TL-IIe, where applicable:

(1) In one embodiment, B is phenyl.
(2) In one embodiment, B is phenyl and $R_6$ is ($C_1$-$C_4$) alkyl.
(3) In one embodiment, B is phenyl, $R_6$ is ($C_1$-$C_4$) alkyl, and each $R_7$ is independently ($C_1$-$C_4$) alkyl or ($C_1$-$C_4$) hydroxyalkyl.
(4) In one embodiment, B is phenyl, $R_6$ is ($C_1$-$C_4$) alkyl, and each $R_7$ is independently ($C_1$-$C_4$) alkyl.
(5) In one embodiment, B is phenyl, $R_6$ is ($C_1$-$C_4$) alkyl, and each $R_7$ is independently ($C_1$-$C_4$) hydroxyalkyl.
(6) In one embodiment, B is phenyl, $R_6$ is ($C_1$-$C_4$) alkyl, each $R_7$ is independently ($C_1$-$C_4$) alkyl or ($C_1$-$C_4$) hydroxyalkyl, and each $R_8$ is independently ($C_1$-$C_4$) alkyl, halogen, or ($C_3$-$C_6$) cycloalkyl, or two $R_8$ together with the atoms to which they are attached form a ($C_1$-$C_7$) cycloalkyl ring.
(7) In one embodiment, B is phenyl, $R_6$ is ($C_1$-$C_4$) alkyl, each $R_7$ is independently ($C_1$-$C_4$) alkyl or ($C_1$-$C_4$) hydroxyalkyl, and each $R_8$ is independently ($C_1$-$C_4$) alkyl, halogen, or ($C_3$-$C_6$) cycloalkyl.
(8) In one embodiment, B is phenyl, $R_6$ is ($C_1$-$C_4$) alkyl, each $R_7$ is independently ($C_1$-$C_4$) alkyl or ($C_1$-$C_4$) hydroxyalkyl, and each $R_8$ is independently ($C_1$-$C_4$) alkyl.
(9) In one embodiment, B is phenyl, $R_6$ is ($C_1$-$C_4$) alkyl, each $R_7$ is independently ($C_1$-$C_4$) alkyl or ($C_1$-$C_4$) hydroxyalkyl, and each $R_8$ is independently halogen or ($C_3$-$C_6$) cycloalkyl.
(10) In one embodiment, B is phenyl, $R_6$ is ($C_1$-$C_4$) alkyl, each $R_7$ is independently ($C_1$-$C_4$) alkyl or ($C_1$-$C_4$) hydroxyalkyl, and two $R_8$ together with the atoms to which they are attached form a ($C_5$-$C_7$) cycloalkyl ring.
(11) In one embodiment, B is phenyl, $R_6$ is ($C_1$-$C_4$) alkyl, each $R_7$ is independently ($C_1$-$C_4$) alkyl, and each $R_8$ is independently ($C_1$-$C_4$) alkyl, halogen, or ($C_3$-$C_6$) cycloalkyl, or two $R_8$ together with the atoms to which they are attached form a ($C_5$-$C_7$) cycloalkyl ring.
(12) In one embodiment, B is phenyl, $R_6$ is ($C_1$-$C_4$) alkyl, each $R_7$ is independently ($C_1$-$C_4$) alkyl, and each $R_8$ is independently ($C_1$-$C_4$) alkyl, halogen, or ($C_3$-$C_6$) cycloalkyl.
(13) In one embodiment, B is phenyl, $R_6$ is ($C_1$-$C_4$) alkyl, each $R_7$ is independently ($C_1$-$C_4$) alkyl, and each $R_8$ is independently ($C_1$-$C_4$) alkyl.
(14) In one embodiment, B is phenyl, $R_6$ is ($C_1$-$C_4$) alkyl, each $R_7$ is independently ($C_1$-$C_4$) alkyl, and each $R_8$ is independently halogen or ($C_3$-$C_6$) cycloalkyl.
(15) In one embodiment, B is phenyl, $R_6$ is ($C_1$-$C_4$) alkyl, each $R_7$ is independently ($C_1$-$C_4$) alkyl, and two $R_8$ together with the atoms to which they are attached form a ($C_5$-$C_7$) cycloalkyl ring.
(16) In one embodiment, B is phenyl, $R_6$ is ($C_1$-$C_4$) alkyl, each $R_7$ is independently ($C_1$-$C_4$) hydroxyalkyl, and each $R_8$ is independently ($C_1$-$C_4$) alkyl, halogen, or ($C_3$-$C_6$) cycloalkyl, or two $R_8$ together with the atoms to which they are attached form a ($C_5$-$C_7$) cycloalkyl ring.
(17) In one embodiment, B is phenyl, $R_6$ is ($C_1$-$C_4$) alkyl, each $R_7$ is independently ($C_1$-$C_4$) hydroxyalkyl, and each $R_8$ is independently ($C_1$-$C_4$) alkyl, halogen, or ($C_3$-$C_6$) cycloalkyl.
(18) In one embodiment, B is phenyl, $R_6$ is ($C_1$-$C_4$) alkyl, each $R_7$ is independently ($C_1$-$C_4$) hydroxyalkyl, and each $R_8$ is independently ($C_1$-$C_4$) alkyl.
(19) In one embodiment, B is phenyl, $R_6$ is ($C_1$-$C_4$) alkyl, each $R_7$ is independently ($C_1$-$C_4$) hydroxyalkyl, and each $R_8$ is independently halogen or ($C_3$-$C_6$) cycloalkyl.
(20) In one embodiment, B is phenyl, $R_6$ is ($C_1$-$C_4$) alkyl, each $R_7$ is independently ($C_1$-$C_4$) hydroxyalkyl, and two $R_8$ together with the atoms to which they are attached form a ($C_5$-$C_7$) cycloalkyl ring.
(21) In one embodiment, B, $R_6$, $R_7$, and $R_8$ are each as defined, where applicable, in any one of (1)-(20), and A is phenyl.

(22) In one embodiment, B, $R_6$, $R_7$, and $R_8$ are each as defined, where applicable, in any one of (1)-(20), and A is thiophenyl.
(23) In one embodiment, B, $R_6$, $R_7$, and $R_8$ are each as defined, where applicable, in any one of (1)-(20), and $R_{10b}$ is H.
(24) In one embodiment, B, $R_6$, $R_7$, and $R_8$ are each as defined, where applicable, in any one of (1)-(20), A is phenyl, and $R_{10b}$ is H.
(25) In one embodiment, B, $R_6$, $R_7$, and $R_8$ are each as defined, where applicable, in any one of (1)-(20), A is thiophenyl, and $R_{10b}$ is H.
(26) In one embodiment, B is phenyl, $R_6$ is $(C_1-C_4)$ alkyl, each $R_7$ is independently $(C_1-C_4)$ alkyl or $(C_1-C_4)$ hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(27) In one embodiment, B is phenyl, $R_6$ is $(C_1-C_4)$ alkyl, each $R_7$ is independently $(C_1-C_4)$ alkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(28) In one embodiment, B is phenyl, $R_6$ is $(C_1-C_4)$ alkyl, each $R_7$ is independently $(C_1-C_4)$ hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.
(29) In one embodiment, B, $R_6$, $R_7$, $R_8$, and $R_{10b}$ are each as defined, where applicable, in any one of (26)-(28), and A is phenyl.
(30) In one embodiment, B, $R_6$, $R_7$, $R_8$, and $R_{10b}$ are each as defined, where applicable, in any one of (26)-(28), and A is thiophenyl.
(31) In one embodiment, B is pyridinyl.
(32) In one embodiment, B is pyridinyl and $R_6$ is $(C_1-C_4)$ alkyl.
(33) In one embodiment, B is pyridinyl, $R_6$ is $(C_1-C_4)$ alkyl, and each $R_7$ is independently $(C_1-C_4)$ alkyl or $(C_1-C_4)$ hydroxyalkyl.
(34) In one embodiment, B is pyridinyl, $R_6$ is $(C_1-C_4)$ alkyl, and each $R_7$ is independently $(C_1-C_4)$ alkyl.
(35) In one embodiment, B is pyridinyl, $R_6$ is $(C_1-C_4)$ alkyl, and each $R_7$ is independently $(C_1-C_4)$ hydroxyalkyl.
(36) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.
(37) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl, halogen, or $(C_3-C_6)$ cycloalkyl.
(38) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and each $R_8$ is independently $(C_1-C_4)$ alkyl.
(39) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and each $R_8$ is independently halogen or $(C_3-C_6)$ cycloalkyl.
(40) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and two $R_8$ together with the atoms to which they are attached form a $(C_5-C_7)$ cycloalkyl ring.
(41) In one embodiment, B is pyridinyl, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl, or two $R_8$ together with the atoms to which they are attached form a $(C_5-C_7)$ cycloalkyl ring.
(42) In one embodiment, B is pyridinyl, $R_6$ is $(C_1-C_4)$ alkyl, each $R_7$ is independently $(C_1-C_4)$ alkyl, and each $R_8$ is independently $(C_1-C_4)$ alkyl, halogen, or $(C_3-C_6)$ cycloalkyl.
(43) In one embodiment, B is pyridinyl, $R_6$ is $(C_1-C_4)$ alkyl, each $R_7$ is independently $(C_1-C_4)$ alkyl, and each $R_8$ is independently $(C_1-C_4)$ alkyl.
(44) In one embodiment, B is pyridinyl, $R_6$ is $(C_1-C_4)$ alkyl, each $R_7$ is independently $(C_1-C_4)$ alkyl, and each $R_8$ is independently halogen or $(C_3-C_6)$ cycloalkyl.
(45) In one embodiment, B is pyridinyl, $R_6$ is $(C_1-C_4)$ alkyl, each $R_7$ is independently $(C_1-C_4)$ alkyl, and two $R_8$ together with the atoms to which they are attached form a $(C_1-C_7)$ cycloalkyl ring.
(46) In one embodiment, B is pyridinyl, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl, or two $R_8$ together with the atoms to which they are attached form a $(C_1-C_7)$ cycloalkyl ring.
(47) In one embodiment, B is pyridinyl, $R_6$ is $(C_1-C_4)$ alkyl, each $R_7$ is independently $(C_1-C_4)$ hydroxyalkyl, and each $R_8$ is independently $(C_1-C_4)$ alkyl, halogen, or $(C_3-C_6)$ cycloalkyl.
(48) In one embodiment, B is pyridinyl, $R_6$ is $(C_1-C_4)$ alkyl, each $R_7$ is independently $(C_1-C_4)$ hydroxyalkyl, and each $R_8$ is independently $(C_1-C_4)$ alkyl.
(49) In one embodiment, B is pyridinyl, $R_6$ is $(C_1-C_4)$ alkyl, each $R_7$ is independently $(C_1-C_4)$ hydroxyalkyl, and each $R_8$ is independently halogen or $(C_3-C_6)$ cycloalkyl.
(50) In one embodiment, B is pyridinyl, $R_6$ is $(C_1-C_4)$ alkyl, each $R_7$ is independently $(C_1-C_4)$ hydroxyalkyl, and two $R_8$ together with the atoms to which they are attached form a $(C_5-C_7)$ cycloalkyl ring.
(51) In one embodiment, B, $R_6$, $R_7$, and $R_8$ are each as defined, where applicable, in any one of (31)-(50), and A is phenyl.
(52) In one embodiment, B, $R_6$, $R_7$, and $R_8$ are each as defined, where applicable, in any one of (31)-(50), and A is thiophenyl.
(53) In one embodiment, B, $R_6$, $R_7$, and $R_8$ are each as defined, where applicable, in any one of (31)-(50), and $R_{10b}$ is H.
(54) In one embodiment, B, $R_6$, $R_7$, and $R_8$ are each as defined, where applicable, in any one of (31)-(50), A is phenyl, and $R_{10b}$ is H.
(55) In one embodiment, B, $R_6$, $R_7$, and $R_8$ are each as defined, where applicable, in any one of (31)-(50), A is thiophenyl, and $R_{10b}$ is H.
(56) In one embodiment, B is pyridinyl, $R_6$ is $(C_1-C_4)$ alkyl, each $R_7$ is independently $(C_1-C_4)$ alkyl or $(C_1-C_4)$ hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(57) In one embodiment, B is pyridinyl, $R_6$ is ($C_1$-$C_4$) alkyl, each $R_7$ is independently ($C_1$-$C_4$) alkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(58) In one embodiment, B is pyridinyl, $R_6$ is ($C_1$-$C_4$) alkyl, each $R_7$ is independently ($C_1$-$C_4$) hydroxyalkyl, and $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$.

(59) In one embodiment, B, $R_6$, $R_7$, $R_8$, and $R_{10b}$ are each as defined, where applicable, in any one of (56)-(58), and A is phenyl.

(60) In one embodiment, B, $R_6$, $R_7$, $R_8$, and $R_{10b}$ are each as defined, where applicable, in any one of (56)-(58), and A is thiophenyl.

(61) In one embodiment, B is pyridinyl and A is phenyl.

(62) In one embodiment, B is pyridinyl and A is thiophenyl.

(63) In one embodiment, B is phenyl and A is phenyl.

(64) In one embodiment, B is phenyl and A is thiophenyl.

(65) In one embodiment, B is pyridinyl, A is phenyl, and $R_6$ is methyl.

(66) In one embodiment, B is pyridinyl, A is thiophenyl, and $R_6$ is methyl.

(67) In one embodiment, B is phenyl, A is phenyl, and $R_6$ is methyl.

(68) In one embodiment, B is phenyl, A is thiophenyl, and $R_6$ is methyl.

(69) In one embodiment, B is pyridinyl, and A is phenyl.

(70) In one embodiment, B is pyridinyl, and A is thiophenyl.

(71) In one embodiment, B is phenyl, and A is phenyl.

(72) In one embodiment, B is phenyl, and A is thiophenyl.

(73) In one embodiment, A, B, $R_6$, $R_7$, $R_8$, and $R_{10b}$ are each as defined, where applicable, in any one of (1)-(72), o1 is 0.

(74) In one embodiment, A, B, $R_6$, $R_7$, $R_8$, and $R_{10b}$ are each as defined, where applicable, in any one of (1)-(72), o1 is 1.

(75) In one embodiment, A, B, $R_6$, $R_7$, $R_8$, and $R_{10b}$ are each as defined, where applicable, in any one of (1)-(72), o1 is 2.

(76) In one embodiment, A, B, $R_6$, $R_7$, $R_8$, and $R_{10b}$ are each as defined, where applicable, in any one of (1)-(72), o1 is 2, and $R_8$ is ($C_1$-$C_4$) alkyl or oxo.

(77) In one embodiment, A, B, $R_5$, $R_6$, $R_7$, $R_8$, and $R_{10b}$ are each as defined, where applicable, in any one of (1)-(76), $Y_5$ is absent.

(78) In one embodiment, A, B, $R_5$, $R_6$, $R_7$, $R_8$, and $R_{10b}$ are each as defined, where applicable, in any one of (1)-(76), $Y_5$ is C(O).

(79) In one embodiment, A, B, $R_5$, $R_6$, $R_7$, $R_8$, and $R_{10b}$ are each as defined, where applicable, in any one of (1)-(76), $Y_5$ is $CH_2$.

In one embodiment, the compound of Formula TL-II is of Formula TL-IIf or TL-IIg:

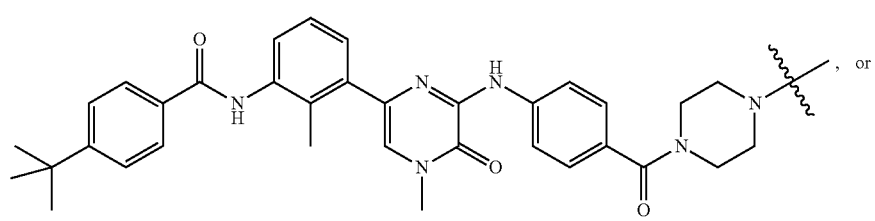

(TL-IIf), or

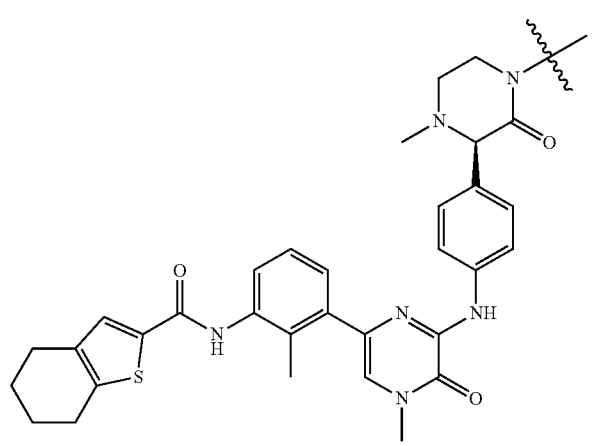

(TL-IIg)

In one embodiment, a Targeting Ligand is a compound of Formula TL-III:

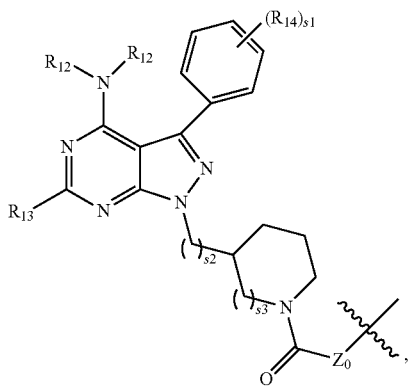
(TL-III)

or an enantiomer, diastereomer, stereoisomer, or pharmaceutically acceptable salt thereof, wherein:

$Z_0$ is $(C_1-C_4)$ alkylenyl, $(C_2-C_6)$ alkenylenyl, or

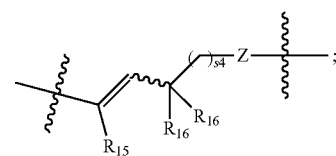

Z is $NR_{17}$,

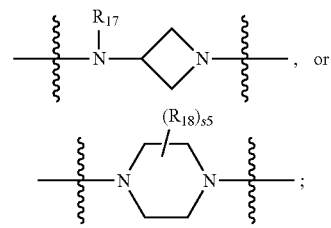

each $R_{12}$ is independently H, $(C_1-C_4)$ alkyl, or $(C_1-C_4)$ haloalkyl;

$R_{13}$ is H, $(C_1-C_4)$ alkyl, $(C_1-C_4)$ haloalkyl, or CN;

each $R_{14}$ is independently $(C_1-C_4)$ alkyl, $(C_1-C_4)$ haloalkyl, $(C_1-C_4)$ alkoxy, $(C_1-C_4)$ haloalkoxy, halogen, O-phenyl, OH, or $NH_2$;

$R_{15}$ is H, $(C_1-C_4)$ alkyl, halogen, or CN;

each $R_{16}$ is independently H, $(C_1-C_4)$ alkyl, or $(C_1-C_4)$ haloalkyl;

$R_{17}$ is H, $(C_1-C_4)$ alkyl, or $(C_1-C_4)$ haloalkyl;

each $R_{18}$ is independently $(C_1-C_4)$ alkyl, $(C_1-C_4)$ haloalkyl, $(C_1-C_4)$ alkoxy, $(C_1-C_4)$ haloalkoxy, halogen, or oxo;

s1 and s5 are each independently 0, 1, 2, or 3; and s2, s3, and s4 are each independently 0 or 1, wherein the Targeting Ligand is bonded to the Linker via the

next to $Z_0$.

In some embodiments, $Z_0$ is —$CH_2$—, —C(=$CH_2$)—, —CH($CH_3$)—, or —CHCH—. In some embodiments, $Z_0$ is —$CH_2$—. In other embodiments, $Z_0$ is —C(=$CH_2$)—. In other embodiments, $Z_0$ is —CH($CH_3$)—. In other embodiments, $Z_0$ is —CHCH—.

In other embodiments, $Z_0$ is

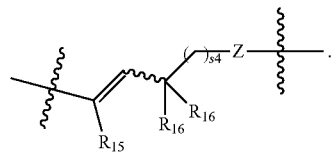

In some embodiments, Z is $NR_{17}$. In other embodiments, Z is

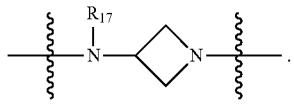

In other embodiments, Z is

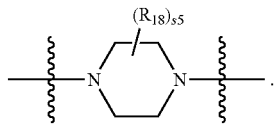

In other embodiments, Z is $NR_{17}$ or

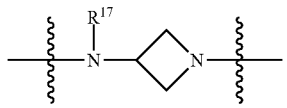

In other embodiments, Z is $NR_{17}$ or

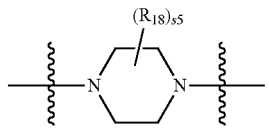

In other embodiments, Z is

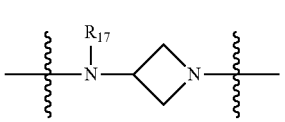
or
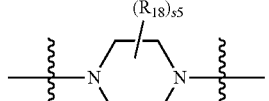

In some embodiments, $R_{17}$ is H, $(C_1-C_3)$ alkyl, or $(C_1-C_3)$ haloalkyl. In other embodiments, $R_{17}$ is $(C_1-C_3)$ alkyl or ($C_1$-$C_3$) haloalkyl. In other embodiments, $R_{17}$ is H or ($C_1$-$C_3$) alkyl. In other embodiments, $R_{17}$ is H, methyl, ethyl, n-propyl, or i-propyl. In other embodiments, $R_{17}$ is H, methyl, or ethyl. In other embodiments, $R_{17}$ is methyl.

In some embodiments, each $R_{18}$ is independently ($C_1$-$C_3$) alkyl, ($C_1$-$C_3$) haloalkyl, ($C_1$-$C_3$) alkoxy, ($C_1$-$C_3$) haloalkoxy, halogen, or oxo. In other embodiments, each $R_{18}$ is independently ($C_1$-$C_3$) alkyl, ($C_1$-$C_3$) haloalkyl, ($C_1$-$C_3$) alkoxy, ($C_1$-$C_3$) haloalkoxy, or halogen. In other embodiments, each $R_{18}$ is independently ($C_1$-$C_3$) alkyl, ($C_1$-$C_3$) haloalkyl, halogen, or oxo. In other embodiments, each $R_{18}$ is independently ($C_1$-$C_3$) alkoxy, ($C_1$-$C_3$) haloalkoxy, halogen, or oxo. In other embodiments, each $R_{18}$ is independently halogen or oxo. In other embodiments, each $R_{18}$ is independently ($C_1$-$C_3$) alkyl, halogen, or oxo. In other embodiments, each $R_{18}$ is independently methyl, ethyl, n-propyl, i-propyl, F, Cl, Br, I, or oxo. In other embodiments, each $R_{18}$ is independently methyl, ethyl, n-propyl, i-propyl, F, Cl, or oxo.

In some embodiments, each $R_{12}$ is independently H, ($C_1$-$C_3$) alkyl, or ($C_1$-$C_3$) haloalkyl. In other embodiments, each $R_{12}$ is independently ($C_1$-$C_3$) alkyl or ($C_1$-$C_3$) haloalkyl. In other embodiments, each $R_{12}$ is independently H or ($C_1$-$C_3$) alkyl. In other embodiments, each $R_{12}$ is independently H, methyl, ethyl, n-propyl, or i-propyl. In other embodiments, each $R_{12}$ is independently H, methyl, or ethyl. In other embodiments, each $R_{12}$ is independently H or methyl. In other embodiments, each $R_{12}$ is H.

In some embodiments, $R_{13}$ is H, ($C_1$-$C_3$) alkyl, ($C_1$-$C_3$) haloalkyl or CN. In other embodiments, $R_{13}$ is ($C_1$-$C_3$) alkyl, ($C_1$-$C_3$) haloalkyl or CN. In other embodiments, $R_{13}$H, ($C_1$-$C_3$) alkyl, or ($C_1$-$C_3$) haloalkyl. In other embodiments, $R_{13}$ ($C_1$-$C_3$) alkyl or ($C_1$-$C_3$) haloalkyl. In other embodiments, $R_{13}$ is H or CN. In other embodiments, $R_{13}$ is H.

In some embodiments, each $R_{14}$ is independently ($C_1$-$C_3$) alkyl, ($C_1$-$C_3$) haloalkyl, ($C_1$-$C_3$) alkoxy, ($C_1$-$C_3$) haloalkoxy, halogen, O-phenyl, OH, or $NH_2$. In other embodiments, each $R_{14}$ is independently ($C_1$-$C_3$) alkyl, ($C_1$-$C_3$) haloalkyl, ($C_1$-$C_3$) alkoxy, ($C_1$-$C_3$) haloalkoxy, or halogen. In other embodiments, each $R_{14}$ is independently ($C_1$-$C_3$) alkyl, ($C_1$-$C_3$) haloalkyl, ($C_1$-$C_3$) alkoxy, ($C_1$-$C_3$) haloalkoxy, or O-phenyl. In other embodiments, each $R_{14}$ is independently ($C_1$-$C_3$) alkoxy, ($C_1$-$C_3$) haloalkoxy, O-phenyl, or OH. In other embodiments, each $R_{14}$ is independently ($C_1$-$C_3$) alkyl, ($C_1$-$C_3$) haloalkyl, ($C_1$-$C_3$) alkoxy, or ($C_1$-$C_3$) haloalkoxy. In other embodiments, each $R_{14}$ is independently O-phenyl, OH, or $NH_2$. In other embodiments, each $R_{14}$ is independently ($C_1$-$C_3$) alkyl, ($C_1$-$C_3$) haloalkyl, ($C_1$-$C_3$) alkoxy, halogen, or O-phenyl. In other embodiments, each $R_{14}$ is independently ($C_1$-$C_4$) alkyl, halogen, or O-phenyl. In other embodiments, each $R_{14}$ is independently methyl, ethyl, n-propyl, i-propyl, F, Cl, Br, I, or O-phenyl. In other embodiments, each $R_{14}$ is independently methyl, F, Cl, or O-phenyl. In other embodiments, each $R_{14}$ is independently F, Cl, Br, I, or O-phenyl. In other embodiments, each $R_{14}$ is independently F, Cl, or O-phenyl. In other embodiments, each $R_{14}$ is independently F or O-phenyl.

In some embodiments, $R_{15}$ is H, ($C_1$-$C_3$) alkyl, halogen, or CN. In other embodiments, $R_{15}$ is ($C_1$-$C_3$) alkyl, halogen, or CN. In other embodiments, $R_{15}$ is H, ($C_1$-$C_3$) alkyl, or CN. In other embodiments, $R_{15}$ is H, methyl, ethyl, n-propyl, i-propyl, or CN. In other embodiments, $R_{15}$ is H, methyl, ethyl, or CN. In other embodiments, $R_{15}$ is H, methyl, or CN. In other embodiments, $R_{15}$ is H or CN.

In some embodiments, each $R_{16}$ is independently H, ($C_1$-$C_3$) alkyl, or ($C_1$-$C_3$) haloalkyl. In other embodiments, each $R_{16}$ is independently ($C_1$-$C_3$) alkyl or ($C_1$-$C_3$) haloalkyl. In other embodiments, each $R_{16}$ is independently H or ($C_1$-$C_3$) alkyl. In other embodiments, each $R_{16}$ is independently H, methyl, ethyl, n-propyl, or i-propyl. In other embodiments, each $R_{16}$ is independently H, methyl, or ethyl. In other embodiments, each $R_{16}$ is independently H or methyl. In other embodiments, each $R_{16}$ is H. In other embodiments, each $R_{16}$ is methyl. In other embodiments, one $R_{16}$ is H and the other $R_{16}$ is methyl.

In some embodiments, s1 is 0. In other embodiments, s1 is 1. In other embodiments, s1 is 2. In other embodiments, s1 is 3. In other embodiments, s1 is 0 or 1. In other embodiments, s1 is 1 or 2. In other embodiments, s1 is 2 or 3. In other embodiments, s1 is 0, 1, or 2. In other embodiments, s1 is 1, 2, or 3.

In some embodiments, s2 is 0. In other embodiments, s2 is 1.

In some embodiments, s3 is 0. In other embodiments, s3 is 1.

In some embodiments, s4 is 0. In other embodiments, s4 is 1.

In some embodiments, s5 is 0. In other embodiments, s5 is 1. In other embodiments, s5 is 2. In other embodiments, s5 is 3. In other embodiments, s5 is 0 or 1. In other embodiments, s5 is 1 or 2. In other embodiments, s5 is 2 or 3. In other embodiments, s5 is 0, 1, or 2. In other embodiments, s5 is 1, 2, or 3.

Any of the groups described herein for any of $Z_0$, Z, $R_{12}$, $R_{13}$, $R_{14}$, $R_{15}$, $R_{16}$, $R_{17}$, $R_{18}$, s1, s2, s3, s4, and s5 can be combined with any of the groups described herein for one or more of the remainder of $Z_0$, Z, $R_{12}$, $R_{13}$, $R_{14}$, $R_{15}$, $R_{16}$, $R_{17}$, $R_{18}$, s1, s2, s3, s4, and s5, and may further be combined with any of the groups described herein for the Linker.

For example, for a Targeting Ligand of Formula TL-III:
(1) In one embodiment, each $R_{12}$ is H and $R_{13}$ is H.
(2) In one embodiment, each $R_{12}$ is H, $R_{13}$ is H, and s2 is 0.
(3) In one embodiment, each $R_{12}$ is H, $R_{13}$ is H, and s2 is 1.
(4) In one embodiment, each $R_{12}$ is H, $R_{13}$ is H, s2 is 0, and s3 is 0.
(5) In one embodiment, each $R_{12}$ is H, $R_{13}$ is H, s2 is 1, and s3 is 0.
(6) In one embodiment, each $R_{12}$ is H, $R_{13}$ is H, s2 is 0, and s3 is 1.
(7) In one embodiment, each $R_{12}$ is H, $R_{13}$ is H, s2 is 1, and s3 is 1.
(8) In one embodiment, each $R_{12}$ is H, $R_{13}$ is H, s2 is 0, s3 is 0, and each $R_{14}$ is independently halogen or O-phenyl.
(9) In one embodiment, each $R_{12}$ is H, $R_{13}$ is H, s2 is 1, s3 is 0, and each $R_{14}$ is independently halogen or O-phenyl.
(10) In one embodiment, each $R_{12}$ is H, $R_{13}$ is H, s2 is 0, s3 is 1, and each $R_{14}$ is independently halogen or O-phenyl.
(11) In one embodiment, each $R_{12}$ is H, $R_{13}$ is H, s2 is 1, s3 is 1, and each $R_{14}$ is independently halogen or O-phenyl.
(12) In one embodiment, each $R_{12}$ is H, $R_{13}$ is H, s2 is 0, s3 is 0, each $R_{14}$ is independently halogen or O-phenyl, and $R_{15}$ is H or CN.
(13) In one embodiment, each $R_{12}$ is H, $R_{13}$ is H, s2 is 1, s3 is 0, each $R_{14}$ is independently halogen or O-phenyl, and $R_5$ is H or CN.
(14) In one embodiment, each $R_{12}$ is H, $R_{13}$ is H, s2 is 0, s3 is 1, each $R_{14}$ is independently halogen or O-phenyl, and $R_{15}$ is H or CN.

(15) In one embodiment, each $R_{12}$ is H, $R_{13}$ is H, s2 is 1, s3 is 1, each $R_{14}$ is independently halogen or O-phenyl, and $R_{15}$ is H or CN.

(16) In one embodiment, each $R_{12}$ is H, $R_{13}$ is H, s2 is 0, s3 is 0, each $R_{14}$ is independently halogen or O-phenyl, $R_{15}$ is H or CN, and each $R_{16}$ is independently H or $(C_1-C_4)$ alkyl.

(17) In one embodiment, each $R_{12}$ is H, $R_{13}$ is H, s2 is 1, s3 is 0, each $R_{14}$ is independently halogen or O-phenyl, $R_{15}$ is H or CN, and each $R_{16}$ is independently H or $(C_1-C_4)$ alkyl.

(18) In one embodiment, each $R_{12}$ is H, $R_{13}$ is H, s2 is 0, s3 is 1, each $R_{14}$ is independently halogen or O-phenyl, $R_{15}$ is H or CN, and each $R_{16}$ is independently H or $(C_1-C_4)$ alkyl.

(19) In one embodiment, each $R_{12}$ is H, $R_{13}$ is H, s2 is 1, s3 is 1, each $R_{14}$ is independently halogen or O-phenyl, $R_{15}$ is H or CN, and each $R_{16}$ is independently H or $(C_1-C_4)$ alkyl.

(20) In one embodiment, Z is $NR_{17}$ and $R_{17}$ is H or $(C_1-C_3)$ alkyl.

(21) In one embodiment, Z is $NR_{17}$ and $R_{17}$ is H, methyl or ethyl.

(22) In one embodiment, Z is $NR_{17}$ and $R_{17}$ is H.

(23) In one embodiment, Z is $NR_{17}$ and $R_{17}$ is methyl or ethyl.

(24) In one embodiment, Z is

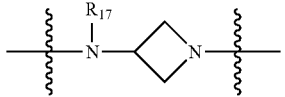

and $R_{17}$ is H or $(C_1-C_3)$ alkyl.

(25) In one embodiment, Z is

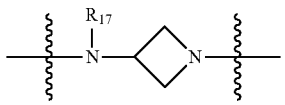

and $R_{17}$ is H, methyl or ethyl.

(26) In one embodiment, Z is

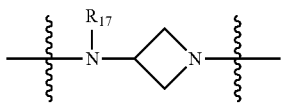

and $R_{17}$ is H.

(27) In one embodiment, Z is

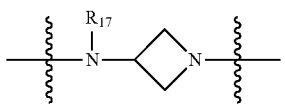

and $R_{17}$ is methyl or ethyl.

(28) In one embodiment, Z is

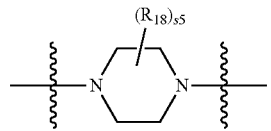

and s5 is 0.

(29) In one embodiment, Z is $NR_{17}$, $R_{17}$ is H or $(C_1-C_3)$ alkyl, and $R_{15}$ is H or CN.

(30) In one embodiment, Z is $NR_{17}$, $R_{17}$ is H, methyl or ethyl, and $R_{15}$ is H or CN.

(31) In one embodiment, Z is $NR_{17}$, $R_{17}$ is H, and $R_{15}$ is H or CN.

(32) In one embodiment, Z is $NR_{17}$, $R_{17}$ is methyl or ethyl, and $R_{15}$ is H or CN.

(33) In one embodiment, Z is

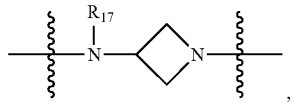

$R_{17}$ is H or $(C_1-C_3)$ alkyl, and $R_{15}$ is H or CN.

(34) In one embodiment, Z is

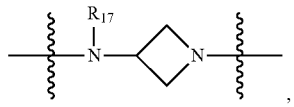

$R_{17}$ is H, methyl or ethyl, and $R_{15}$ is H or CN.

(35) In one embodiment, Z is

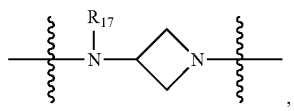

$R_{17}$ is H, and $R_{15}$ is H or CN.

(36) In one embodiment, Z is

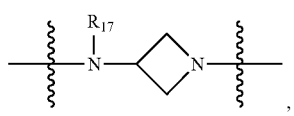

$R_{17}$ is methyl or ethyl, and $R_{15}$ is H or CN.

(37) In one embodiment, Z is

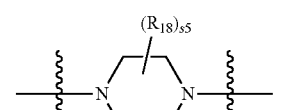

s5 is 0, and $R_{15}$ is H or CN.

(38) In one embodiment, each $R_{16}$ is methyl. In other embodiments, each $R_{16}$ is H. In yet other embodiments one $R_{16}$ is H and the other $R_{16}$ is methyl.

(39) In one embodiment, Z is $NR_{17}$ and s2 is 0.
(40) In one embodiment, Z is $NR_{17}$ and s2 is 1.
(41) In one embodiment, Z is $NR_{17}$ and s3 is 0.
(42) In one embodiment, Z is $NR_{17}$ and s3 is 1.
(43) In one embodiment, Z is $NR_{17}$, s2 is 0, and s3 is 0.
(44) In one embodiment, Z is $NR_{17}$, s2 is 1, and s3 is 0.
(45) In one embodiment, Z is $NR_{17}$, s2 is 0, and s3 is 1.
(46) In one embodiment, Z is $NR_{7}$, s2 is 1, and s3 is 1.
(47) In one embodiment, Z is

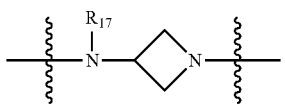

and s2 is 0.

(48) In one embodiment, Z is

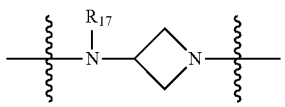

and s2 is 1.

(49) In one embodiment, Z is

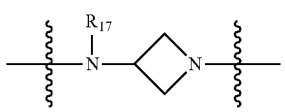

and s3 is 0.

(50) In one embodiment, Z is

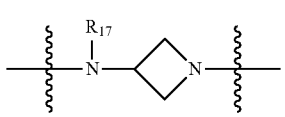

and s3 is 1.

(51) In one embodiment, Z is

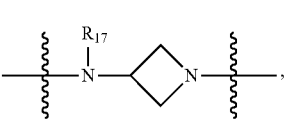

s2 is 0, and s3 is 0.

(52) In one embodiment, Z is

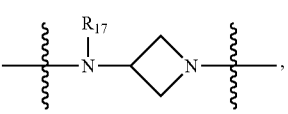

s2 is 1, and s3 is 0.

(53) In one embodiment, Z is

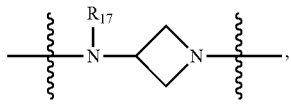

s2 is 0, and s3 is 1.

(54) In one embodiment, Z is

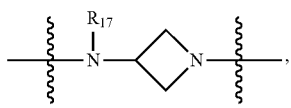

s2 is 1, and s3 is 1.

(55) In one embodiment, Z is

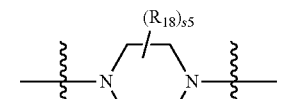

and s2 is 0.

(56) In one embodiment, Z is

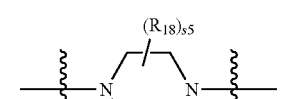

and s2 is 1.

(57) In one embodiment, Z is

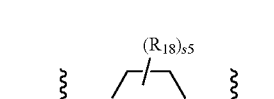

and s3 is 0.

(58) In one embodiment, Z is

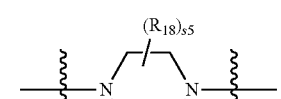

and s3 is 1.

(59) In one embodiment, Z is

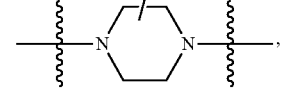

s2 is 0, and s3 is 0.

(60) In one embodiment, Z is

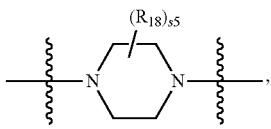

s2 is 1, and s3 is 0.

(61) In one embodiment, Z is

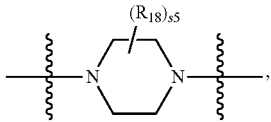

s2 is 0, and s3 is 1.

(62) In one embodiment, Z is

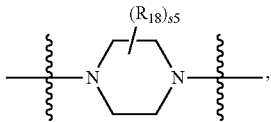

s2 is 1, and s3 is 1.

(63) In one embodiment, Z, $R_{12}$, $R_3$, $R_{14}$, $R_{15}$, $R_{16}$, $R_{17}$, s2, s3 and s5 are each as defined, where applicable, in any one of (1)-(62), s1 is 1.

(64) In one embodiment, Z, $R_{12}$, $R_{13}$, $R_{14}$, $R_{15}$, $R_{16}$, $R_{17}$, s2, s3 and s5 are each as defined, where applicable, in any one of (1)-(62), s1 is 2.

(65) In one embodiment, Z, $R_{12}$, $R_{13}$, $R_{14}$, $R_{15}$, $R_{16}$, $R_{17}$, s2, s3 and s5 are each as defined, where applicable, in any one of (1)-(62), s4 is 0.

(66) In one embodiment, Z, $R_{12}$, $R_{13}$, $R_{14}$, $R_{15}$, $R_{16}$, $R_{17}$, s2, s3 and s5 are each as defined, where applicable, in any one of (1)-(62), s4 is 1.

(67) In one embodiments, Z, $R_{12}$, $R_{13}$, $R_{14}$, $R_{15}$, $R_{16}$, $R_{17}$, s2, s3, s4, and s5 are each as defined, where applicable, in any one of (1)-(67), $Z_0$ is —$CH_2$—.

(68) In one embodiments, Z, $R_{12}$, $R_{13}$, $R_{14}$, $R_{15}$, $R_{16}$, $R_{17}$, s2, s3, s4, and s5 are each as defined, where applicable, in any one of (1)-(67), $Z_0$ is —C(=$CH_2$)—.

(69) In one embodiments, Z, $R_{12}$, $R_{13}$, $R_{14}$, $R_{15}$, $R_{16}$, $R_{17}$, s2, s3, s4, and s5 are each as defined, where applicable, in any one of (1)-(67), $Z_0$ is —CH($CH_3$)—.

(70) In one embodiments, Z, $R_{12}$, $R_{13}$, $R_{14}$, $R_{15}$, $R_{16}$, $R_{17}$, s2, s3, s4, and s5 are each as defined, where applicable, in any one of (1)-(67), $Z_0$ is —CHCH—.

(71) In one embodiments, Z, $R_{12}$, $R_{13}$, $R_{14}$, $R_{15}$, $R_{16}$, $R_{17}$, s2, s3, s4, and s5 are each as defined, where applicable, in any one of (1)-(67), $Z_0$ is

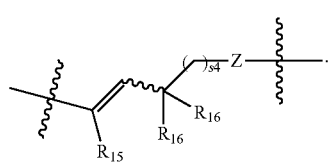

In one embodiment, the compound of Formula TL-III is of Formula TL-IIIa:

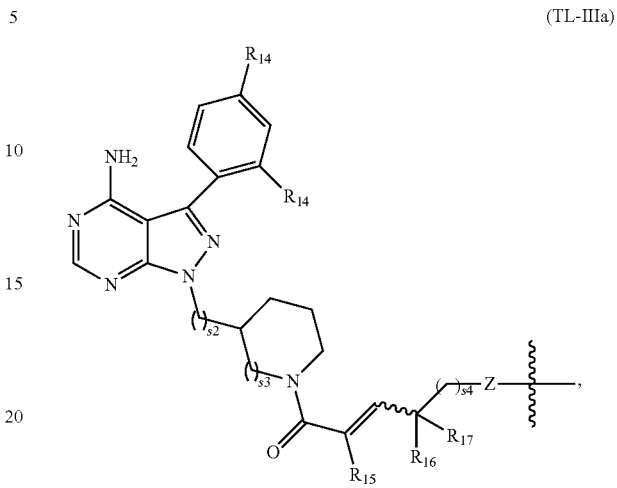

(TL-IIIa)

wherein Z, $R_{14}$, $R_{15}$, $R_{16}$, $R_{17}$, $R_{15}$, s2, s3, s4, and s5 are each as defined above in Formula TL-III, and can be combined as described above in Formula TL-III.

For example, for a Targeting Ligand of Formula TL-IIIa:

(1) In one embodiment, s2 is 0, and s3 is 0.

(2) In one embodiment, s2 is 1, and s3 is 0.

(3) In one embodiment, s2 is 0, and s3 is 1.

(4) In one embodiment, s2 is 1, and s3 is 1.

(5) In one embodiment, s2 is 0, s3 is 0, and each $R_{14}$ is independently halogen or O-phenyl.

(6) In one embodiment, s2 is 1, s3 is 0, and each $R_{14}$ is independently halogen or O-phenyl.

(7) In one embodiment, s2 is 0, s3 is 1, and each $R_{14}$ is independently halogen or O-phenyl.

(8) In one embodiment, s2 is 1, s3 is 1, and each $R_{14}$ is independently halogen or O-phenyl.

(9) In one embodiment, s2 is 0, s3 is 0, each $R_{14}$ is independently halogen or O-phenyl, and $R_{15}$ is H or CN.

(10) In one embodiment, s2 is 1, s3 is 0, each $R_{14}$ is independently halogen or O-phenyl, and $R_1$ is H or CN.

(11) In one embodiment, s2 is 0, s3 is 1, each $R_{14}$ is independently halogen or O-phenyl, and $R_5$ is H or CN.

(12) In one embodiment, s2 is 1, s3 is 1, each $R_{14}$ is independently halogen or O-phenyl, and $R_{15}$ is H or CN.

(13) In one embodiment, s2 is 0, s3 is 0, each $R_{14}$ is independently halogen or O-phenyl, $R_{15}$ is H or CN, and each $R_{16}$ is independently H or ($C_1$-$C_4$) alkyl.

(14) In one embodiment, s2 is 1, s3 is 0, each $R_{14}$ is independently halogen or O-phenyl, $R_{15}$ is H or CN, and each $R_{16}$ is independently H or ($C_1$-$C_4$) alkyl.

(15) In one embodiment, s2 is 0, s3 is 1, each $R_{14}$ is independently halogen or O-phenyl, $R_{15}$ is H or CN, and each $R_{16}$ is independently H or ($C_1$-$C_4$) alkyl.

(16) In one embodiment, s2 is 1, s3 is 1, each $R_{14}$ is independently halogen or O-phenyl, $R_5$ is H or CN, and each $R_{16}$ is independently H or ($C_1$-$C_4$) alkyl.

(17) In one embodiment, Z is $NR_{17}$ and $R_{17}$ is H or ($C_1$-$C_3$) alkyl.

(18) In one embodiment, Z is $NR_{17}$ and $R_{17}$ is H, methyl or ethyl.

(19) In one embodiment, Z is $NR_{17}$ and $R_{17}$ is H.

(20) In one embodiment, Z is $NR_{17}$ and $R_{17}$ is methyl or ethyl.

(21) In one embodiment, Z is

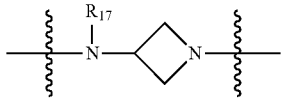

and $R_{17}$ is H or $(C_1\text{-}C_3)$ alkyl.

(22) In one embodiment, Z is

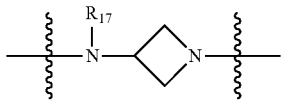

and $R_{17}$ is H, methyl or ethyl.

(23) In one embodiment, Z is

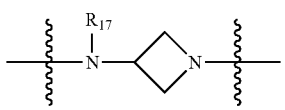

and $R_{17}$ is H.

(24) In one embodiment, Z is

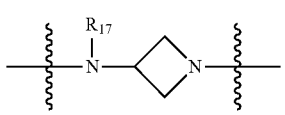

and $R_{17}$ is methyl or ethyl.

(25) In one embodiment, Z is

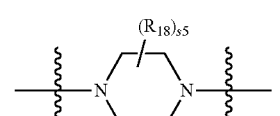

and s5 is 0.

(26) In one embodiment, Z is $NR_{17}$, $R_{17}$ is H or $(C_1\text{-}C_3)$ alkyl, and $R_{15}$ is H or CN.

(27) In one embodiment, Z is $NR_{17}$, $R_{17}$ is H, methyl or ethyl, and $R_{15}$ is H or CN.

(28) In one embodiment, Z is $NR_{17}$, $R_{17}$ is H, and $R_{15}$ is H or CN.

(29) In one embodiment, Z is $NR_{17}$, $R_{17}$ is methyl or ethyl, and $R_{15}$ is H or CN.

(30) In one embodiment, Z is

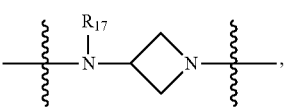

$R_{17}$ is H or $(C_1\text{-}C_3)$ alkyl, and $R_{15}$ is H or CN.

(31) In one embodiment, Z is

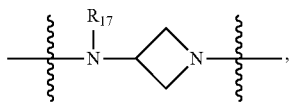

$R_{17}$ is H, methyl or ethyl, and $R_{15}$ is H or CN.

(32) In one embodiment, Z is

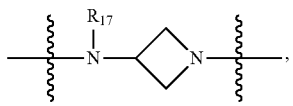

$R_{17}$ is H, and $R_{15}$ is H or CN.

(33) In one embodiment, Z is

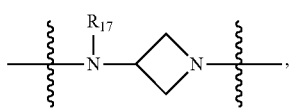

$R_{17}$ is methyl or ethyl, and $R_{15}$ is H or CN.

(34) In one embodiment, Z is

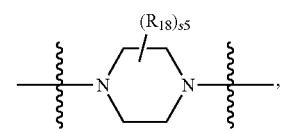

s5 is 0, and $R_{15}$ is H or CN.

(35) In one embodiment, each $R_{16}$ is methyl. In other embodiments, each $R_{16}$ is H. In yet other embodiments one $R_{16}$ is H and the other $R_{16}$ is methyl.

(36) In one embodiment, Z is $NR_{17}$ and s2 is 0.
(37) In one embodiment, Z is $NR_{17}$ and s2 is 1.
(38) In one embodiment, Z is $NR_{17}$ and s3 is 0.
(39) In one embodiment, Z is $NR_{17}$ and s3 is 1.
(40) In one embodiment, Z is $NR_{17}$, s2 is 0, and s3 is 0.
(41) In one embodiment, Z is $NR_{17}$, s2 is 1, and s3 is 0.
(42) In one embodiment, Z is $NR_{17}$, s2 is 0, and s3 is 1.
(43) In one embodiment, Z is $NR_{17}$, s2 is 1, and s3 is 1.
(44) In one embodiment, Z is

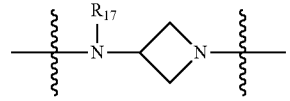

and s2 is 0.

(45) In one embodiment, Z is

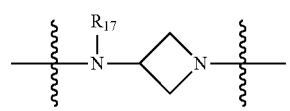

and s2 is 1.

(46) In one embodiment, Z is

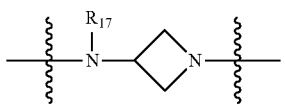

and s3 is 0.

(47) In one embodiment, Z is

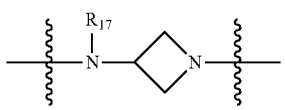

and s3 is 1.

(48) In one embodiment, Z is

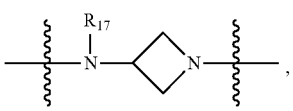

s2 is 0, and s3 is 0.

(49) In one embodiment, Z is

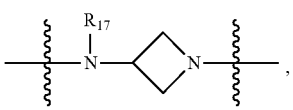

s2 is 1, and s3 is 0.

(50) In one embodiment, Z is

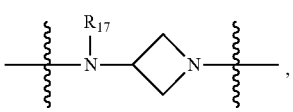

s2 is 0, and s3 is 1.

(51) In one embodiment, Z is

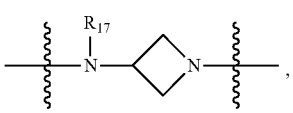

s2 is 1, and s3 is 1.

(52) In one embodiment, Z is

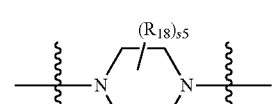

and s2 is 0.

(53) In one embodiment, Z is

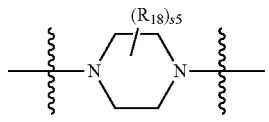

and s2 is 1.

(54) In one embodiment, Z is

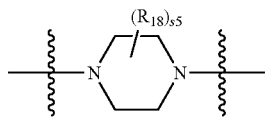

and s3 is 0.

(55) In one embodiment, Z is

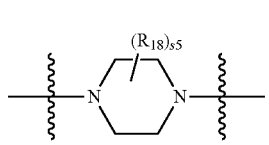

and s3 is 1.

(56) In one embodiment, Z is

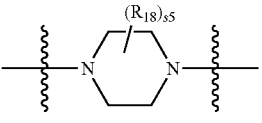

s2 is 0, and s3 is 0.

(57) In one embodiment, Z is

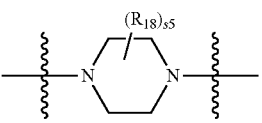

s2 is 1, and s3 is 0.

(58) In one embodiment, Z is

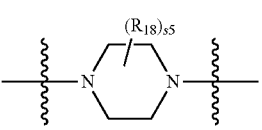

s2 is 0, and s3 is 1.

(59) In one embodiment, Z is

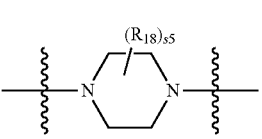

s2 is 1, and s3 is 1.

(60) In one embodiment, Z, $R_{14}$, $R_{15}$, $R_{16}$, $R_{17}$, $R_{18}$, s2, s3, and s5 are each as defined, where applicable, in any one of (1)-(59), s4 is 0.
(61) In one embodiment, Z, $R_{14}$, $R_{15}$, $R_{16}$, $R_{17}$, s2, s3 and s5 are each as defined, where applicable, in any one of (1)-(59), s4 is 1.

In one embodiment, the compound of Formula TL-III is of Formula TL-IIIb:

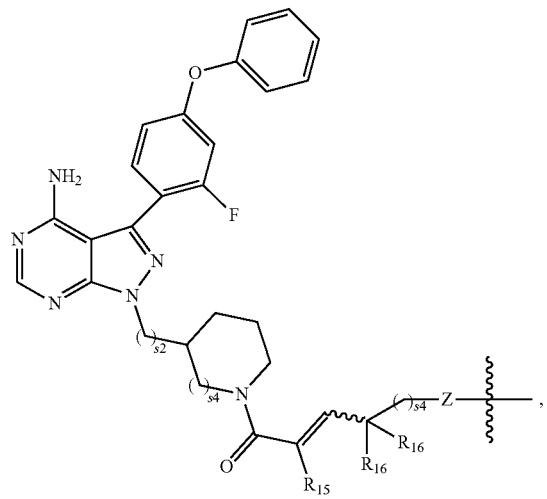

(TL-IIIb)

wherein Z, $R_{15}$, $R_{16}$, $R_{17}$, $R_{18}$, s2, s3, s4, and s5 are each as defined above in Formula TL-III, and can be combined as described above in Formula TL-III.

For example, for a Targeting Ligand of Formula TL-IIIb:
(1) In one embodiment, s2 is 0, and s3 is 0.
(2) In one embodiment, s2 is 1, and s3 is 0.
(3) In one embodiment, s2 is 0, and s3 is 1.
(4) In one embodiment, s2 is 1, and s3 is 1.
(5) In one embodiment, s2 is 0, s3 is 0, and $R_{15}$ is H or CN.
(6) In one embodiment, s2 is 1, s3 is 0, and $R_{15}$ is H or CN.
(7) In one embodiment, s2 is 0, s3 is 1, and $R_{15}$ is H or CN.
(8) In one embodiment, s2 is 1, s3 is 1, and $R_{15}$ is H or CN.
(9) In one embodiment, s2 is 0, s3 is 0, $R_{15}$ is H or CN, and each $R_{16}$ is independently H or ($C_1$-$C_4$) alkyl.
(10) In one embodiment, s2 is 1, s3 is 0, $R_{15}$ is H or CN, and each $R_{16}$ is independently H or ($C_1$-$C_4$) alkyl.
(11) In one embodiment, s2 is 0, s3 is 1, $R_1$ is H or CN, and each $R_{16}$ is independently H or ($C_1$-$C_4$) alkyl.
(12) In one embodiment, s2 is 1, s3 is 1, $R_{15}$ is H or CN, and each $R_{16}$ is independently H or ($C_1$-$C_4$) alkyl.
(13) In one embodiment, Z is $NR_{17}$ and $R_{17}$ is H or ($C_1$-$C_3$) alkyl.
(14) In one embodiment, Z is $NR_{17}$ and $R_{17}$ is H, methyl or ethyl.
(15) In one embodiment, Z is $NR_{17}$ and $R_{17}$ is H.
(16) In one embodiment, Z is $NR_{17}$ and $R_{17}$ is methyl or ethyl.
(17) In one embodiment, Z is

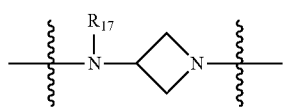

and $R_{17}$ is H or ($C_1$-$C_3$) alkyl.

(18) In one embodiment, Z is

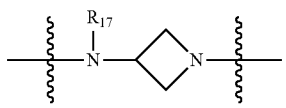

and $R_{17}$ is H, methyl or ethyl.

(19) In one embodiment, Z is

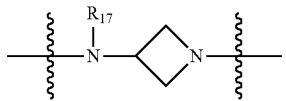

and $R_{17}$ is H.

(20) In one embodiment, Z is

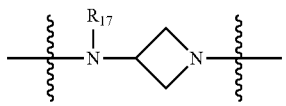

and $R_{17}$ is methyl or ethyl.

(21) In one embodiment, Z is

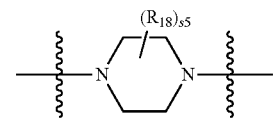

and s5 is 0.

(22) In one embodiment, Z is $NR_{17}$, $R_{17}$ is H or ($C_1$-$C_3$) alkyl, and $R_{15}$ is H or CN.
(23) In one embodiment, Z is $NR_{17}$, $R_{17}$ is H, methyl or ethyl, and $R_{15}$ is H or CN.
(24) In one embodiment, Z is $NR_{17}$, $R_{17}$ is H, and $R_{15}$ is H or CN.
(25) In one embodiment, Z is $NR_{17}$, $R_{17}$ is methyl or ethyl, and $R_{15}$ is H or CN.
(26) In one embodiment, Z is

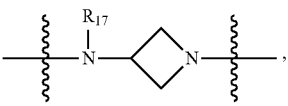

$R_{17}$ is H or ($C_1$-$C_3$) alkyl, and $R_{15}$ is H or CN.

(27) In one embodiment, Z is

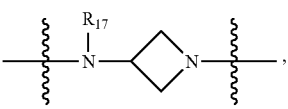

$R_{17}$ is H, methyl or ethyl, and $R_{15}$ is H or CN.

(28) In one embodiment, Z is

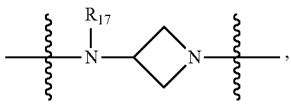

$R_{17}$ is H, and $R_{15}$ is H or CN.

(29) In one embodiment, Z is

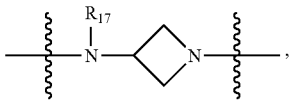

$R_{17}$ is methyl or ethyl, and $R_{15}$H or CN.

(30) In one embodiment, Z is

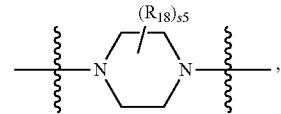

s5 is 0, and $R_5$ is H or CN.

(31) In one embodiment, each $R_{16}$ is methyl. In other embodiments, each $R_{16}$ is H. In yet other embodiments one $R_{16}$ is H and the other $R_{16}$ is methyl.
(32) In one embodiment, Z is $NR_{17}$ and s2 is 0.
(33) In one embodiment, Z is $NR_{17}$ and s2 is 1.
(34) In one embodiment, Z is $NR_{17}$ and s3 is 0.
(35) In one embodiment, Z is $NR_{17}$ and s3 is 1.
(36) In one embodiment, Z is $NR_{17}$, s2 is 0, and s3 is 0.
(37) In one embodiment, Z is $NR_{17}$, s2 is 1, and s3 is 0.
(38) In one embodiment, Z is $NR_{17}$, s2 is 0, and s3 is 1.
(39) In one embodiment, Z is $NR_{17}$, s2 is 1, and s3 is 1.
(40) In one embodiment, Z is

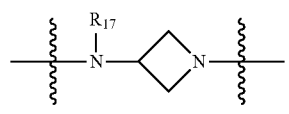

and s2 is 0.

(41) In one embodiment, Z is

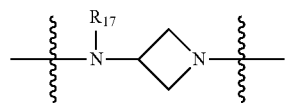

and s2 is 1.

(42) In one embodiment, Z is

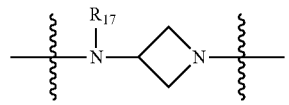

and s3 is 0.

(43) In one embodiment, Z is

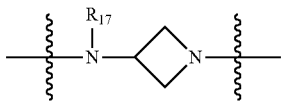

and s3 is 1.

(44) In one embodiment, Z is

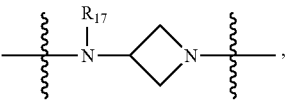

s2 is 0, and s3 is 0.

(45) In one embodiment, Z is

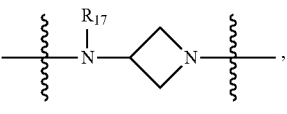

s2 is 1, and s3 is 0.

(46) In one embodiment, Z is

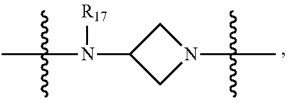

s2 is 0, and s3 is 1.

(47) In one embodiment, Z is

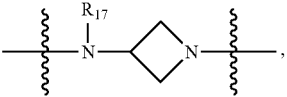

s2 is 1, and s3 is 1.

(48) In one embodiment, Z is

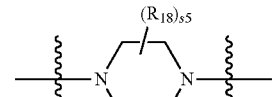

and s2 is 0.

(49) In one embodiment, Z is

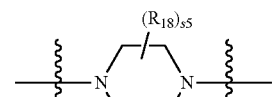

and s2 is 1.

(50) In one embodiment, Z is

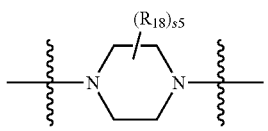

and s3 is 0.

(51) In one embodiment, Z is

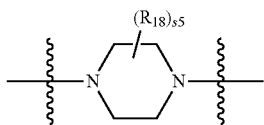

and s3 is 1.

(52) In one embodiment, Z is

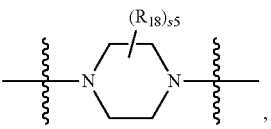

s2 is 0, and s3 is 0.

(53) In one embodiment, Z is

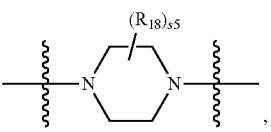

s2 is 1, and s3 is 0.

(54) In one embodiment, Z is

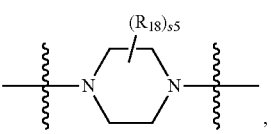

s2 is 0, and s3 is 1.

(55) In one embodiment, Z is

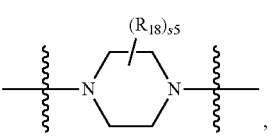

s2 is 1, and s3 is 1.

(56) In one embodiment, Z, $R_{15}$, $R_{16}$, $R_{17}$, $R_{18}$, s2, s3, and s5 are each as defined, where applicable, in any one of (1)-(55), s4 is 0.

(57) In one embodiment, Z, $R_{15}$, $R_{16}$, $R_{17}$, $R_{18}$, s2, s3, and s5 are each as defined, where applicable, in any one of (1)-(55), s4 is 1.

In one embodiment, the compound of Formula TL-III is of Formula TL-IIIc, TL-IIId, TL-IIIe, or TL-IIIf:

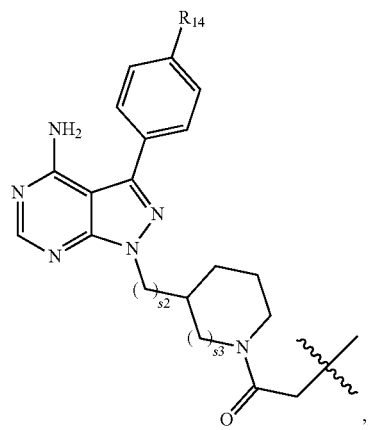
(TL-IIIc)

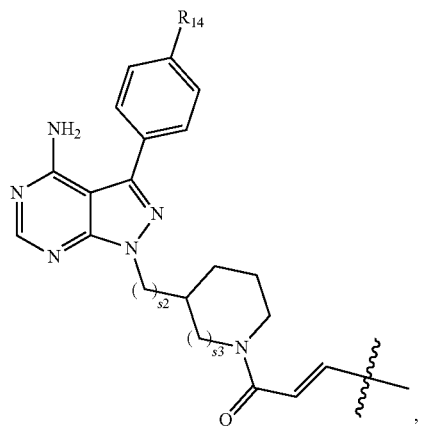
(TL-IIId)

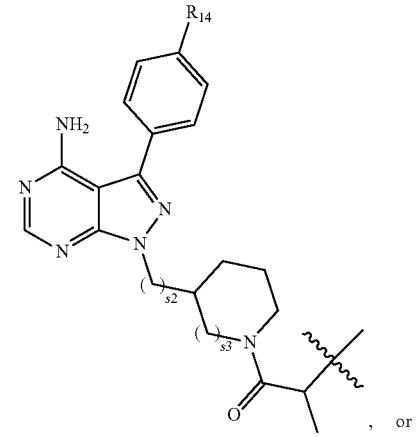
(TL-IIIe)

, or

-continued (TL-IIIf)

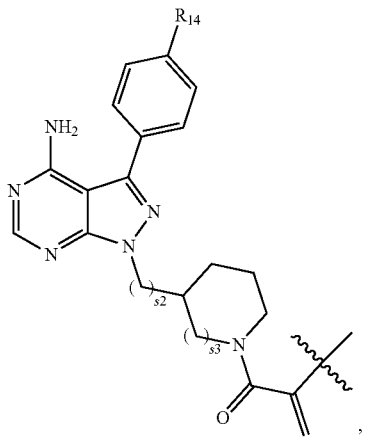

, wherein Z, $R_{15}$, $R_{16}$, $R_{17}$, $R_{18}$, s2, s3, s4, and s5 are each as defined above in Formula TL-III, and can be combined as described above in Formula TL-III.

For example, for a Targeting Ligand of Formula TL-IIIc, TL-IIId, TL-IIIe, or TL-IIIf:

(58) In one embodiment, s2 is 0, and s3 is 0.
(59) In one embodiment, s2 is 1, and s3 is 0.
(60) In one embodiment, s2 is 0, and s3 is 1.
(61) In one embodiment, s2 is 1, and s3 is 1.
(62) In one embodiment, s2 is 0, s3 is 0, and each $R_{14}$ is independently halogen or O-phenyl.
(63) In one embodiment, s2 is 1, s3 is 0, and each $R_{14}$ is independently halogen or O-phenyl.
(64) In one embodiment, s2 is 0, s3 is 1, and each $R_{14}$ is independently halogen or O-phenyl.
(65) In one embodiment, s2 is 1, s3 is 1, and each $R_{14}$ is independently halogen or O-phenyl.

In one embodiment, the compound of Formula TL-III is of Formula TL-IIIg, TL-IIIh, TL-IIIi, TL-IIIj, TL-IIIk, or TL-IIIl:

(TL-IIIg)

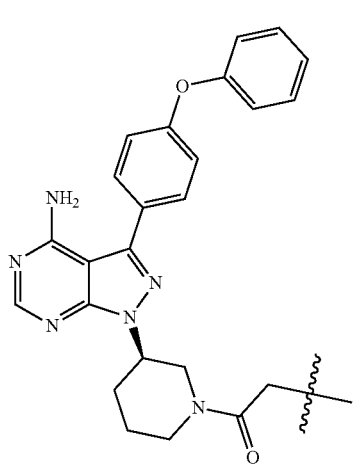

,

-continued (TL-IIIh)

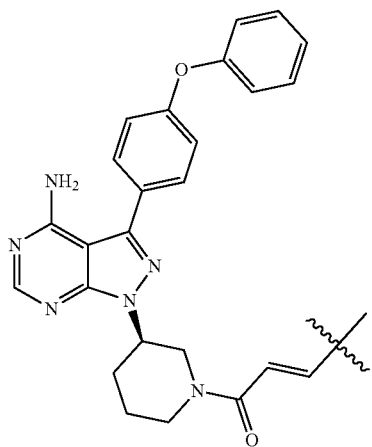

, (TL-IIIi)

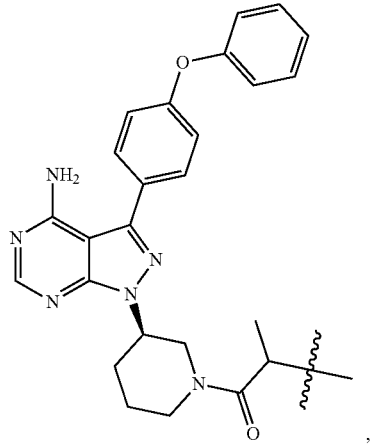

, (TL-IIIj)

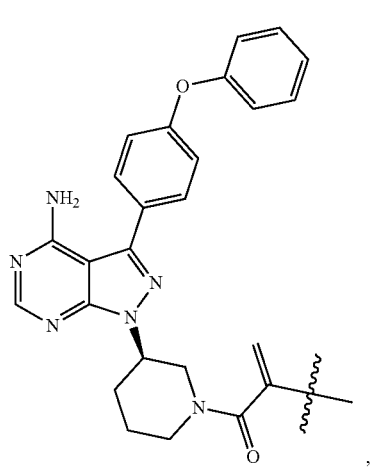

,

-continued (TL-IIIk)

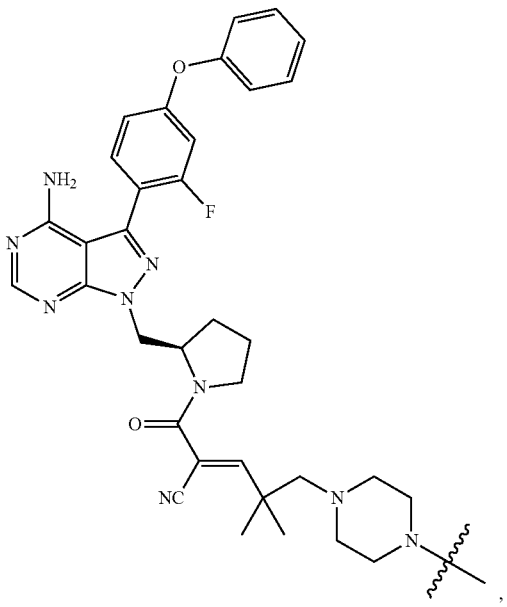

(TL-IIIl)

or an enantiomer, diastereomer, stereoisomer, or pharmaceutically acceptable salt thereof Degron The Degron serves to link a targeted protein, through a Linker and a Targeting Ligand, to a ubiquitin ligase for proteasomal degradation. In one embodiment, the Degron is capable of binding to a ubiquitin ligase, such as an E3 ubiquitin ligase. In one embodiment, the Degron is capable of binding to cereblon.

In one embodiment, the Degron is of Formula D0:

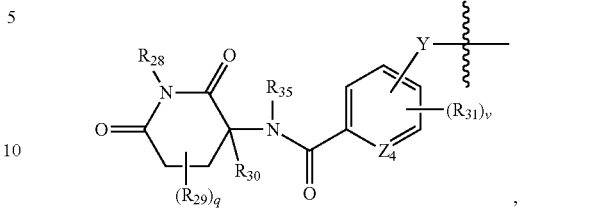

(D0)

or an enantiomer, diastereomer, or stereoisomer thereof, wherein:

Y is a bond, $(CH_2)_{1-6}$, $(CH_2)_{0-6}$, $(CH_2)_{0-6}$—C(O)NR$_{26}$, $(CH_2)_{0-6}$—NR$_{26}$C(O), $(CH_2)_{0-6}$—NH, or $(CH_2)_{0-6}$—NR$_{27}$;

$Z_4$ is N or CR$_{36}$;

$R_{26}$ is H or $C_1$-$C_6$ alkyl;

$R_{27}$ is $C_1$-$C_6$ alkyl or C(O)—$C_1$-$C_6$ alkyl;

$R_{28}$ is H or $C_1$-$C_3$ alkyl;

each $R_{29}$ is independently $C_1$-$C_3$ alkyl;

$R_{30}$ is H, deuterium, $C_1$-$C_3$ alkyl, F, or Cl;

each $R_{31}$ is independently halogen, OH, $C_1$-$C_6$ alkyl, or $C_1$-$C_6$ alkoxy; or at least one $R_{31}$ and at least one $R_{37}$ together with the atoms to which they are attached form a 5- or 6-membered cycloalkyl, aryl, heterocycloalky containing 1 or 2 heteroatoms selected from N, O, and S, or heteroaryl containing 1 or 2 heteroatoms selected from N, O, and S, each optionally substituted with 1 to 3 $R_{37}$';

$R_{35}$ is H, $(C_1$-$C_4)$ alkyl, $(C_1$-$C_4)$ haloalkyl; or $R_{35}$ and $R_{36}$ together with the atoms to which they are attached form a 5- or 6-membered heterocycloalkyl or heteroaryl containing 1 or 2 heteroatoms selected from N, O, and S and optionally substituted with 1 to 3 $R_{37}$;

$R_{36}$ is H or $C_1$-$C_3$ alkyl, or $R_{36}$ and $R_{35}$ together with the atoms to which they are attached form a 5- or 6-membered heterocycloalkyl or heteroaryl containing 1 or 2 heteroatoms selected from N, O, and S and optionally substituted with 1 to 3 $R_{37}$;

each $R_{37}$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, oxo, OH, or NH$_2$; or at least one $R_{37}$ and at least one $R_{31}$ together with the atoms to which they are attached form a 5- or 6-membered cycloalkyl, aryl, heterocycloalkyl containing 1 or 2 heteroatoms selected from N, O, and S, or heteroaryl containing 1 or 2 heteroatoms selected from N, O, and S, each optionally substituted with 1 to 3 $R_{37}$';

each $R_{37}$' is independently $(C_1$-$C_4)$ alkyl, $(C_1$-$C_4)$ haloalkyl, $(C_1$-$C_4)$ alkoxy, $(C_1$-$C_4)$ haloalkoxy, halogen, oxo, OH, or NH$_2$;

q is 0, 1, or 2; and v is 0, 1, 2, or 3, wherein the Degron is covalently bonded to the Linker via

In one embodiment, $Z_4$ is N.

In one embodiment, $Z_4$ is N or CH.

In one embodiment, $Z_4$ is CR$_{36}$; and R$_{36}$ is H. In one embodiment, $Z_4$ is CR$_{36}$; and R$_{36}$ is $C_1$-$C_3$ alkyl selected from methyl, ethyl, and propyl.

In one embodiment, Y is a bond.

In one embodiment, Y is a bond, O, or NH.

In one embodiment, Y is $(CH_2)_1$, $(CH_2)_2$, $(CH_2)_3$, $(CH_2)_4$, $(CH_2)_5$, or $(CH_2)_6$. In one embodiment, Y is $(CH_2)_1$, $(CH_2)_2$, or $(CH_2)_3$. In one embodiment, Y is $CH_2$ or $(CH_2)_2$.

In one embodiment, Y is O, $CH_2$—O, $(CH_2)_2$—O, $(CH_2)_3$—O, $(CH_2)_4$—O, $(CH_2)_5$—O, or $(CH_2)_6$—O. In one embodiment, Y is O, $CH_2$—O, $(CH_2)_2$—O, or $(CH_2)_3$—O. In one embodiment, Y is O or $CH_2$—O. In one embodiment, Y is O.

In one embodiment, Y is $C(O)NR_{26}$, $CH_2$—$C(O)NR_{26}$, $(CH_2)_2$—$C(O)NR_{26}$, $(CH_2)_3$—$C(O)NR_{26}$, $(CH_2)_4$—$C(O)NR_{26}$, $(CH_2)_5$—$C(O)NR_{26}$, or $(CH_2)$—$C(O)NR_{26}$. In one embodiment, Y is $C(O)R_{26}$, $CH_2$—$C(O)NR_{26}$, $(CH_2)_2$—$C(O)NR_{26}$, or $(CH_2)_3$—$C(O)NR_{26}$. In one embodiment, Y is $C(O)NR_{26}$ or $CH_2$—$C(O)NR_{26}$. In one embodiment, Y is $C(O)NR_{26}$.

In one embodiment, Y is $NR_{26}C(O)$, $CH_2$—$NR_{26}C(O)$, $(CH_2)_2$—$NR_{26}C(O)$, $(CH_2)_3$—$NR_{26}C(O)$, $(CH_2)_4$—$NR_{26}C(O)$, $(CH_2)_5$—$NR_{26}C(O)$, or $(CH_2)$—$NR_{26}C(O)$. In one embodiment, Y is $NR_{26}C(O)$, $CH_2$—$NR_{26}C(O)$, $(CH_2)_2$—$NR_{26}C(O)$, or $(CH_2)_3$—$NR_{26}C(O)$. In one embodiment, Y is $NR_{26}C(O)$ or $CH_2$—$NR_{26}C(O)$. In one embodiment, Y is $NR_{26}C(O)$.

In one embodiment, $R_{26}$ is H. In one embodiment, $R_{26}$ is selected from methyl, ethyl, propyl, butyl, i-butyl, t-butyl, pentyl, i-pentyl, and hexyl. In one embodiment, $R_{26}$ is $C_1$-$C_3$ alkyl selected from methyl, ethyl, and propyl.

In one embodiment, Y is NH, $CH_2$—NH, $(CH_2)_2$—NH, $(CH_2)_3$—NH, $(CH_2)_4$—NH, $(CH_2)$—NH, or $(CH_2)$—NH. In one embodiment, Y is NH, $CH_2$—NH, $(CH_2)_2$—NH, or $(CH_2)_3$—NH. In one embodiment, Y is NH or $CH_2$—NH. In one embodiment, Y is NH.

In one embodiment, Y is $NR_{27}$, $CH_2$—$NR_{27}$, $(CH_2)_2$—$NR_{27}$, $(CH_2)_3$—$NR_{27}$, $(CH_2)_4$—$NR_{27}$, $(CH_2)$—$NR_2$—, or $(CH_2)$—$NR_2$—. In one embodiment, Y is $NR_{27}$, $CH_2$—$NR_{27}$, $(CH_2)_2$—$NR_{27}$, or $(CH_2)_3$—$NR_{27}$. In one embodiment, Y is $NR_{27}$ or $CH_2$—$NR_{27}$. In one embodiment, Y is $NR_{27}$.

In one embodiment, $R_{27}$ is selected from methyl, ethyl, propyl, butyl, i-butyl, t-butyl, pentyl, i-pentyl, and hexyl. In one embodiment, $R_{27}$ is $C_1$-$C_3$ alkyl selected from methyl, ethyl, and propyl.

In one embodiment, $R_{27}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, $R_{27}$ is C(O)—$C_1$-$C_3$ alkyl selected from C(O)-methyl, C(O)-ethyl, and C(O)-propyl.

In one embodiment, $R_{28}$ is H.

In one embodiment, $R_{28}$ is $C_1$-$C_3$ alkyl selected from methyl, ethyl, and propyl. In one embodiment, $R_{28}$ is methyl.

In one embodiment, q is 0.
In one embodiment, q is 1.
In one embodiment, q is 2.

In one embodiment, each $R_{29}$ is independently $C_1$-$C_3$ alkyl selected from methyl, ethyl, and propyl.

In one embodiment, v is 0.
In one embodiment, v is 1.
In one embodiment, v is 2.
In one embodiment, v is 3.

In one embodiment, $R_{30}$ is H, deuterium, or $C_1$-$C_3$ alkyl. In another embodiment, $R_{30}$ is H or $C_1$-$C_3$ alkyl. In a further embodiment, $R_{30}$ is in the (S) or (R) configuration. In a further embodiment, $R_{30}$ is in the (S) configuration. In one embodiment, the compound comprises a racemic mixture of (S)—$R_{30}$ and (R)—$R_{30}$.

In one embodiment, $R_{30}$ is H.

In one embodiment, $R_{30}$ is deuterium.

In one embodiment, $R_{30}$ is $C_1$-$C_3$ alkyl selected from methyl, ethyl, and propyl. In one embodiment, $R_{30}$ is methyl.

In one embodiment, $R_{30}$ is F or Cl. In a further embodiment, $R_{30}$ is in the (S) or (R) configuration. In a further embodiment, $R_{30}$ is in the (R) configuration. In one embodiment, the compound comprises a racemic mixture of (S)—$R_{30}$ and (R)—$R_{30}$. In one embodiment, $R_{30}$ is F.

In one embodiment, each $R_{31}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each $R_{31}$ is independently selected from F, Cl, OH, methyl, ethyl, propyl, butyl, i-butyl, t-butyl, methoxy, and ethoxy.

In one embodiment, at least one $R_{31}$ and at least one $R_{37}$ together with the atoms to which they are attached form a 5- or 6-membered cycloalkyl, aryl, heterocycloalky containing 1 or 2 heteroatoms selected from N, O, and S, or heteroaryl containing 1 or 2 heteroatoms selected from N, O, and S, each optionally substituted with 1 to 3 $R_{37}'$.

In one embodiment, at least one $R_{31}$ and at least one $R_{37}$ together with the atoms to which they are attached form 5- or 6-membered cycloalkyl optionally substituted with 1 to 3 $R_{37}'$.

In one embodiment, at least one $R_3$ and at least one $R_{37}$ together with the atoms to which they are attached form phenyl optionally substituted with 1 to 3 $R_{37}'$.

In one embodiment, at least one $R_{31}$ and at least one $R_{37}$ together with the atoms to which they are attached form 5- or 6-membered heterocycloalky containing 1 or 2 heteroatoms selected from N, O, and S, optionally substituted with 1 to 3 $R_{37}'$.

In one embodiment, at least one $R_{31}$ and at least one $R_{37}$ together with the atoms to which they are attached form 5- or 6-membered heteroaryl containing 1 or 2 heteroatoms selected from N, O, and S, optionally substituted with 1 to 3 $R_{37}'$.

In one embodiment, $R_{35}$ is H, or $(C_1$-$C_4)$ alkyl, $(C_1$-$C_4)$ haloalkyl. In one embodiment, $R_{35}$ is H.

In one embodiment, $R_{35}$ and $R_{36}$ together with the atoms to which they are attached form a 5- or 6-membered heterocycloalkyl or heteroaryl containing 1 or 2 heteroatoms selected from N, O, and S and optionally substituted with 1 to 3 $R_{37}$.

In one embodiment, $R_{35}$ and $R_{36}$ together with the atoms to which they are attached form a 5- or 6-membered heterocycloalkyl containing 1 or 2 heteroatoms selected from N, O, and S and optionally substituted with 1 to 3 $R_{37}$.

In one embodiment, $R_{35}$ and $R_{36}$ together with the atoms to which they are attached form a 5-membered heterocycloalkyl containing 1 nitrogen atom and optionally substituted with 1 to 3 $R_{37}$. In one embodiment, $R_{35}$ and $R_{36}$ together with the atoms to which they are attached form a 5-membered heterocycloalkyl containing 1 nitrogen atom and optionally substituted with 1 oxo.

In one embodiment, $R_{35}$ and $R_{36}$ together with the atoms to which they are attached form a 6-membered heterocycloalkyl containing 1 nitrogen atom and optionally substituted with 1 to 3 $R_{37}$. In one embodiment, $R_{35}$ and $R_{36}$ together with the atoms to which they are attached form a 6-membered heterocycloalkyl containing 1 nitrogen atom and optionally substituted with 1 oxo.

In one embodiment, $R_{36}$ is H or $C_1$-$C_3$ alkyl. In one embodiment, $R_{36}$ is H. In one embodiment, $R_{36}$ is $C_1$-$C_3$ alkyl selected from methyl, ethyl, and propyl.

In one embodiment, $R_{36}$ and $R_{35}$ together with the atoms to which they are attached form a 5- or 6-membered heterocycloalkyl or heteroaryl containing 1 or 2 heteroatoms selected from N, O, and S and optionally substituted with 1 to 3 $R_{37}$, as described herein.

In one embodiment, each $R_{37}$ is independently $(C_1-C_4)$ alkyl, $(C_1-C_4)$ haloalkyl, $(C_1-C_4)$ alkoxy, $(C_1-C_4)$ haloalkoxy, halogen, oxo, OH, or $NH_2$. In one embodiment, each $R_3$ is independently $(C_1-C_4)$ alkyl, halogen, oxo, OH, or $NH_2$. In one embodiment, each $R_1$ is independently $(C_1-C_4)$ alkyl, halogen, or oxo.

In one embodiment, at least one $R_{37}$ and at least one $R_{31}$ together with the atoms to which they are attached form a 5- or 6-membered cycloalkyl, aryl, heterocycloalkyl containing 1 or 2 heteroatoms selected from N, O, and S, or heteroaryl containing 1 or 2 heteroatoms selected from N, O, and S, each optionally substituted with 1 to 3 $R_{37}'$, as described herein.

In one embodiment, each $R_{37}'$ is independently $(C_1-C_4)$ alkyl, $(C_1-C_4)$ haloalkyl, $(C_1-C_4)$ alkoxy, $(C_1-C_4)$ haloalkoxy, halogen, oxo, OH or $NH_2$. In one embodiment, each $R_{37}'$ is independently $(C_1-C_4)$ alkyl, halogen, oxo, OH, or $NH_2$. In one embodiment, each $R_{37}'$ is independently $(C_1-C_4)$ alkyl or halogen.

Any of the groups described herein for any of Y, $Z_4$, $R_{26}$, $R_{27}$, $R_2$, $R_{29}$, $R_{30}$, $R_{31}$, $R_{35}$, $R_{36}$, $R_{37}$, $R_{37}'$, q and v can be combined with any of the groups described herein for one or more of the remainder of Y, $Z_4$, $R_{26}$, $R_{27}$, $R_{28}$, $R_{29}$, $R_{30}$, $R_{31}$, $R_{35}$, $R_{36}$, $R_{37}$, $R_{37}'$, q and v, and may further be combined with any of the groups described herein for the Linker.

For a Degron of Formula D0:
(1) In one embodiment, $Z_4$ is N and Y is a bond.
(2) In one embodiment, $Z_4$ is N and Y is $(CH_2)_{0-6}$—NH. In a further embodiment, Y is NH.
(3) In one embodiment, $Z_4$ is N and Y is $(CH_2)_{0-6}$—O. In a further embodiment, Y is O.
(4) In one embodiment, $Z_4$ is CH and Y is a bond.
(5) In one embodiment, $Z_4$ is CH and Y is $(CH_2)_{0-6}$—NH. In a further embodiment, Y is NH.
(6) In one embodiment, $Z_4$ is CH and Y is $(CH_2)_{0-6}$—O. In a further embodiment, Y is O.
(7) In one embodiment, $Z_4$ and Y are as described in any of (1)-(6); and $R_{35}$ is H.
(8) In one embodiment, $Z_4$ and Y are as described in any of (1)-(6); and $R_{35}$ is $(C_1-C_4)$ alkyl or $(C_1-C_4)$ haloalkyl.
(9) In one embodiment, $Z_4$ is $CR_{36}$ and Y is a bond.
(10) In one embodiment, $Z_4$ is $CR_{36}$ and Y is $(CH_2)_{0-6}$—NH. In a further embodiment, Y is NH.
(11) In one embodiment, $Z_4$ is $CR_{36}$ and Y is $(CH_2)_{0-6}$—O. In a further embodiment, Y is O.
(12) In one embodiment, $Z_4$ and Y are as described in any of (9)-(11); and $R_{35}$ is H.
(13) In one embodiment, $Z_4$ and Y are as described in any of (9)-(11); and $R_{35}$ is $(C_1-C_4)$ alkyl or $(C_1-C_4)$ haloalkyl.
(14) In one embodiment, $Z_4$ and Y are as described in any of (9)-(11); and $R_{35}$ and $R_{36}$ together with the atoms to which they are attached form a 5- or 6-membered heterocycloalkyl or heteroaryl containing 1 or 2 heteroatoms selected from N, O, and S and optionally substituted with 1 to 3 $R_{37}$.
(15) In one embodiment, $Z_4$ and Y are as described in any of (9)-(11); and $R_{35}$ and $R_{36}$ together with the atoms to which they are attached form a 5-membered heterocycloalkyl containing 1 or 2 heteroatoms selected from N, O, and S and optionally substituted with 1 to 3 $R_{37}$. In a further embodiment, the 5-membered heterocycloalkyl contains 1 nitrogen atom optionally substituted with 1 to 3 $R_{37}$.
(16) In one embodiment, $Z_4$ and Y are as described in any of (9)-(11); and $R_{35}$ and $R_{36}$ together with the atoms to which they are attached form a 6-membered heterocycloalkyl containing 1 or 2 heteroatoms selected from N, O, and S and optionally substituted with 1 to 3 $R_{37}$. In a further embodiment, the 6-membered heterocycloalkyl contains 1 nitrogen atom optionally substituted with 1 to 3 $R_{37}$.
(17) In one embodiment, $Z_4$, Y, $R_3$, and $R_{36}$ are as described in any of (14)-(16); and each $R_{37}$ is independently $(C_1-C_4)$ alkyl, $(C_1-C_4)$ haloalkyl, $(C_1-C_4)$ alkoxy, $(C_1-C_4)$ haloalkoxy, halogen, oxo, OH, or $NH_2$. In a further embodiment, at least one $R_{37}$ is oxo.
(18) In one embodiment, $Z_4$, Y, $R_{35}$, and $R_{36}$ are as described in any of (14)-(16); and at least one $R_{31}$ and at least one $R_{37}$ together with the atoms to which they are attached form a 5- or 6-membered cycloalkyl, aryl, heterocycloalky containing 1 or 2 heteroatoms selected from N, O, and S, or heteroaryl containing 1 or 2 heteroatoms selected from N, O, and S, each optionally substituted with 1 to 3 $R_{37}'$.
(19) In one embodiment, $Z_4$, Y, $R_{35}$, and $R_{36}$ are as described in any of (14)-(16); and at least one $R_{31}$ and at least one $R_{37}$ together with the atoms to which they are attached form 5- or 6-membered cycloalkyl optionally substituted with 1 to 3 $R_{37}'$.
(20) In one embodiment, $Z_4$, Y, $R_{35}$, and $R_{36}$ are as described in any of (14)-(16); and at least one $R_{31}$ and at least one $R_{37}$ together with the atoms to which they are attached form phenyl optionally substituted with 1 to 3 $R_{37}'$.
(21) In one embodiment, $Z_4$, Y, $R_{35}$, and $R_{36}$ are as described in any of (14)-(16); and at least one $R_{31}$ and at least one $R_{37}$ together with the atoms to which they are attached form 5- or 6-membered heterocycloalky containing 1 or 2 heteroatoms selected from N, O, and S, optionally substituted with 1 to 3 $R_{37}'$.
(22) In one embodiment, $Z_4$, Y, $R_{35}$, and $R_{36}$ are as described in any of (14)-(16); and at least one $R_{31}$ and at least one $R_{37}$ together with the atoms to which they are attached form 5- or 6-membered heteroaryl containing 1 or 2 heteroatoms selected from N, O, and S, optionally substituted with 1 to 3 $R_{37}'$.
(23) In one embodiment, $Z_4$, Y, $R_{31}$, $R_{35}$, $R_{36}$, and $R_{37}$ are as described, where applicable, in any of (1)-(17); and v is 0.
(24) In one embodiment, $Z_4$, Y, $R_{31}$, $R_{35}$, $R_{36}$, and $R_{37}$ are as described, where applicable, in any of (1)-(22); and v is 1, 2, or 3.
(25) In one embodiment, $Z_4$, Y, $R_{31}$, $R_{35}$, $R_{36}$, $R_{37}$, and v are as described, where applicable, in any of (1)-(24); and q is 0.
(26) In one embodiment, $Z_4$, Y, $R_{31}$, $R_3$, $R_{36}$, $R_{37}$, and v are as described, where applicable, in any of (1)-(24); and q is 1 or 2.
(27) In one embodiment, $Z_4$, Y, $R_{31}$, $R_{35}$, $R_{36}$, $R_{37}$, v, and q are as described, where applicable, in any of (1)-(26); and $R_{28}$ is H.
(28) In one embodiment, $Z_4$, Y, $R_{28}$, $R_{31}$, $R_{35}$, $R_{36}$, $R_{37}$, v, and q are as described, where applicable, in any of (1)-(27); and $R_{30}$ is H.

In one embodiment, the Degron of Formula D0 is of Formula D0a, D0b, D0c, or D0d:

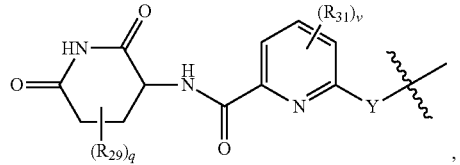
(D0a)

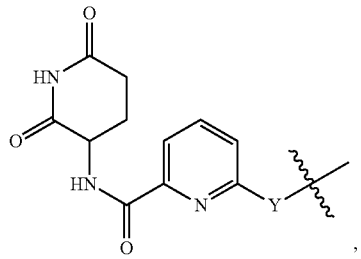
(D0b)

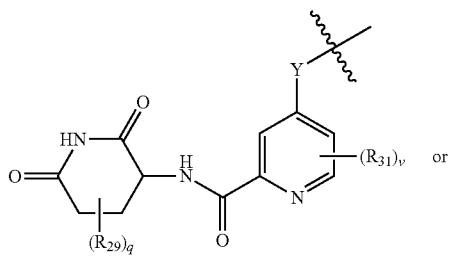
(D0c)

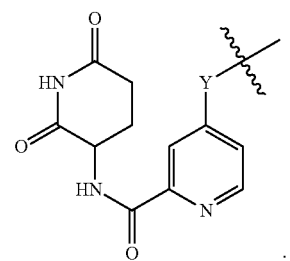
(D0d)

or an enantiomer, diastereomer, or stereoisomer thereof, wherein Y, $R_{26}$, $R_{27}$, $R_{29}$, $R_{31}$, q, and v are each as defined, where applicable, in Formula D0, and can be selected, where applicable, from any moieties or combinations thereof described above.

In one embodiment, Y is a bond, O, or NH. In one embodiment, Y is a bond. In one embodiment, Y is O. In one embodiment, Y is NH.

In one embodiment, the Degron of Formula D0 is of Formula D1 or D4:

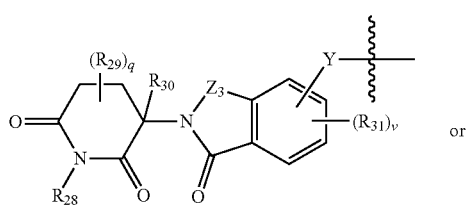
(D1)

or

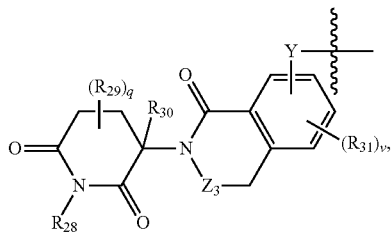
(D4)

or an enantiomer, diastereomer, or stereoisomer thereof, wherein:
Y, $R_{26}$, $R_{27}$, $R_{28}$, $R_{29}$, $R_{30}$, $R_{31}$, q, and v are each as defined, where applicable, in Formula D0;
$Z_3$ is C(O) or $C(R_{15})_2$; and
each $R_{38}$ is independently H or $C_1$-$C_3$ alkyl.

In one embodiment, $Z_3$ is C(O).
In one embodiment, $Z_3$ is C(O) or $CH_2$.
In one embodiment, $Z_3$ is $C(R_{38})_2$; and each $R_{28}$ is H. In one embodiment, $Z_3$ is $C(R_{38})_2$; and one of $R_{35}$ is H, and the other is $C_1$-$C_3$ alkyl selected from methyl, ethyl, and propyl.
In one embodiment, $Z_3$ is $C(R_{38})_2$; and each $R_{38}$ is independently selected from methyl, ethyl, and propyl.

Y, $R_2$, $R_{27}$, $R_{28}$, $R_{29}$, $R_{30}$, $R_{31}$, q, and v can be selected, where applicable, from any moieties or combinations thereof described above.

Any of the groups described herein for any of Y, $Z_3$, $R_{26}$, $R_{27}$, $R_{28}$, $R_{29}$, $R_{30}$, $R_{31}$, q and v can be combined, where applicable, with any of the groups described herein for one or more of the remainder of Y, $Z_3$, $R_{26}$, $R_{27}$, $R_{28}$, $R_{29}$, $R_{30}$, $R_{31}$, q and v, and may further be combined with any of the groups described herein for the Linker.

For example, for a Degron of Formula D1 or Formula D4:
(1) In one embodiment, $Z_3$ is C(O) and Y is a bond.
(2) In one embodiment, $Z_3$ is C(O) and Y is $(CH_2)_{0-6}$—NH. In a further embodiment, Y is NH.
(3) In one embodiment, $Z_3$ is C(O) and Y is $(CH_2)_{0-6}$—O. In a further embodiment, Y is O.
(4) In one embodiment, $Z_3$ is C(O); Y is a bond; and q and v are each 0.
(5) In one embodiment, $Z_3$ is C(O); Y is $(CH_2)_{0-6}$—NH; and q and v are each 0. In a further embodiment, Y is NH.
(6) In one embodiment, $Z_3$ is C(O); Y is $(CH_2)_{0-6}$—O; and q and v are each 0. In a further embodiment, Y is O.
(7) In one embodiment, $Z_3$ is C(O); Y is a bond; and $R_{28}$ is H.
(8) In one embodiment, $Z_3$ is C(O); Y is NH; and $R_{28}$ is H.
(9) In one embodiment, $Z_3$ is C(O); Y is O; and $R_{28}$ is H.
(10) In one embodiment, $Z_3$ is C(O); Y is NH; and $R_{30}$ is H.
(11) In one embodiment, $Z_3$ is C(O); Y is a bond; $R_{28}$ is H; and $R_{30}$ is H.
(12) In one embodiment, $Z_3$ is C(O); Y is NH; $R_{28}$ is H; and $R_{30}$ is H.
(13) In one embodiment, $Z_3$ is C(O); Y is $(CH_2)_{0-6}$—O; and $R_{28}$ is H. In a further embodiment, Y is O.
(14) In one embodiment, $Z_3$ is C(O); Y is $(CH_2)_{0-6}$—O; and $R_{30}$ is H. In a further embodiment, Y is O.
(15) In one embodiment, $Z_3$ is C(O); Y is $(CH_2)_{0-6}$—O; $R_{28}$ is H; and $R_{30}$ is H. In a further embodiment, Y is O.

(16) In one embodiment, q and v are each 0; and Y, $Z_3$, $R_{28}$, $R_{30}$, and $R_{31}$ are each as defined in any of (1)-(3) and (7)-(15).
(17) In one embodiment, $Z_3$ is $CH_2$ and Y is a bond.
(18) In one embodiment, $Z_3$ is $CH_2$ and Y is $(CH_2)_{0-6}$—NH. In a further embodiment, Y is NH.
(19) In one embodiment, $Z_3$ is $CH_2$ and Y is $(CH_2)_{0-6}$—O. In a further embodiment, Y is O.
(20) In one embodiment, $Z_3$ is $CH_2$; Y is a bond; and q and v are each 0.
(21) In one embodiment, $Z_3$ is $CH_2$; Y is NH; and q and v are each 0.
(22) In one embodiment, $Z_3$ is $CH_2$; Y is $(CH_2)_{0-6}$—O; and q and v are each 0. In a further embodiment, Y is O.
(23) In one embodiment, $Z_3$ is $CH_2$; Y is a bond; and $R_{28}$ is H.
(24) In one embodiment, $Z_3$ is $CH_2$; Y is a bond; and $R_{30}$ is H.
(25) In one embodiment, $Z_3$ is $CH_2$; Y is NH; and $R_{28}$ is H.
(26) In one embodiment, $Z_3$ is $CH_2$; Y is NH; and $R_{30}$ is H.
(27) In one embodiment, $Z_3$ is $CH_2$; Y is a bond; $R_{28}$ is H; and $R_{30}$ is H.
(28) In one embodiment, $Z_3$ is $CH_2$; Y is NH; $R_{28}$ is H; and $R_{30}$ is H.
(29) In one embodiment, $Z_3$ is $CH_2$; Y is $(CH_2)_{0-6}$—O; and $R_2$ is H. In a further embodiment, Y is O.
(30) In one embodiment, $Z_3$ is $CH_2$; Y is $(CH_2)_{0-6}$—O; and $R_{30}$ is H. In a further embodiment, Y is O.
(31) In one embodiment, $Z_3$ is $CH_2$; Y is $(CH_2)_{0-6}$—O; $R_2$ is H; and $R_{30}$ is H. In a further embodiment, Y is O.
(32) In one embodiment, q and v are each 0; and Y, $Z_3$, $R_{28}$, $R_{30}$, and $R_{31}$ are each as defined in any of (17)-(19) and (23)-(31).

In one embodiment, the Degron of Formula D1 is of Formula D1a, D1b, D1c, D1d, D1e, D1f, D1g, D1h, D1i, D1j, D1k, or D1l:

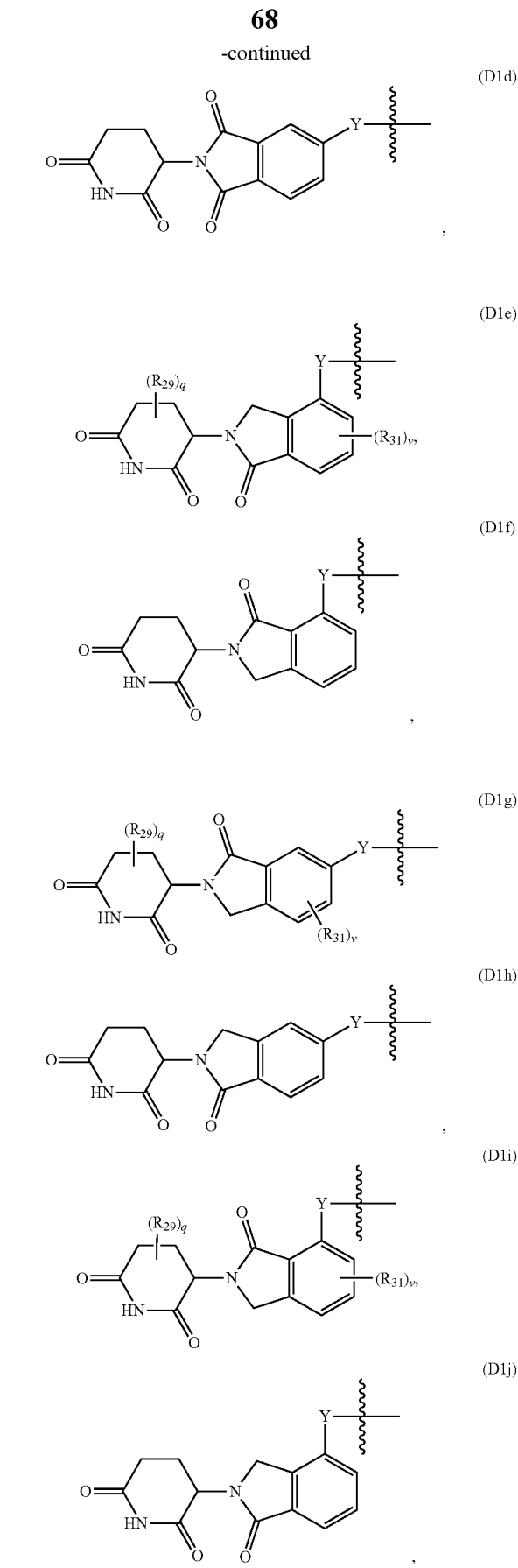

-continued

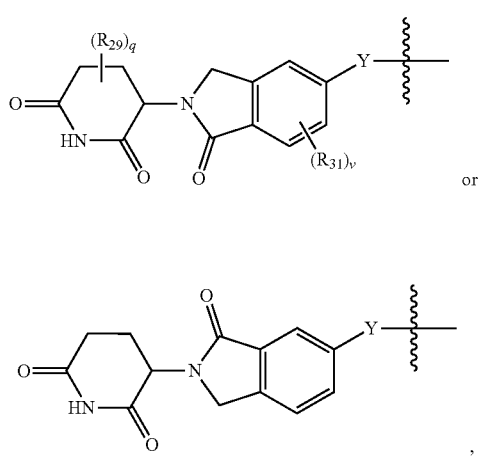
(D1k)

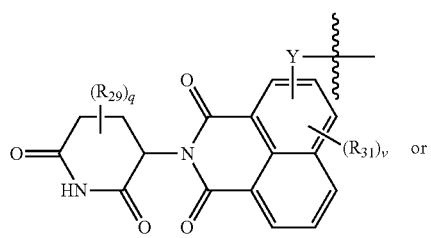
(D1l)

or an enantiomer, diastereomer, or stereoisomer thereof, wherein Y, $R_{26}$, $R_{27}$, $R_{29}$, $R_{31}$, q, and v are each as defined, where applicable, in Formula D0 or D1, and can be selected, where applicable, from any moieties or combinations thereof described above.

In one embodiment, Y is a bond, O, or NH. In one embodiment, Y is a bond. In one embodiment, Y is O. In one embodiment, Y is NH.

In one embodiment, wherein the Degron of Formula D4 is of Formula D4a or D4b:

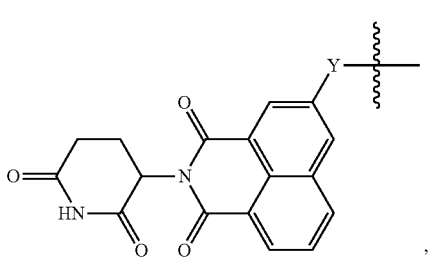
(D4a)

(D4b)

or an enantiomer, diastereomer, or stereoisomer thereof, wherein Y, $R_{26}$, $R_{27}$, $R_{29}$, $R_{31}$, q, and v are each as defined, where applicable, in Formula D0 or D4, and can be selected, where applicable, from any moieties or combinations thereof described above.

In one embodiment, Y is a bond, O, or NH. In one embodiment, Y is a bond. In one embodiment, Y is O. In one embodiment, Y is NH.

In one embodiment, the Degron is of Formula D2:

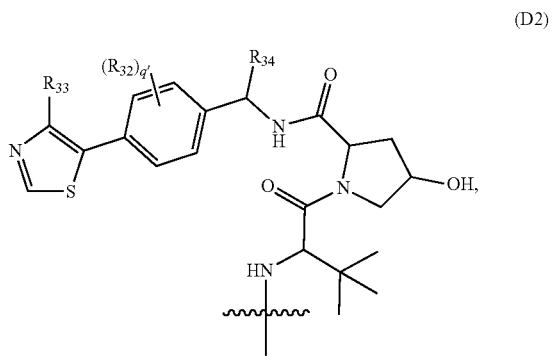
(D2)

or an enantiomer, diastereomer, or stereoisomer thereof, wherein:
each $R_{32}$ is independently $C_1$-$C_3$ alkyl;
q' is 0, 1, 2, 3 or 4;
$R_{33}$ is H or $C_1$-$C_3$ alkyl; and
$R_{34}$ is H or $C_1$-$C_3$ alkyl,
wherein the Degron is covalently bonded to another moiety (e.g., a compound, or a Linker) via

In one embodiment, q' is 0.
In one embodiment, q' is 1.
In one embodiment, q' is 2.
In one embodiment, q' is 3.
In one embodiment, each $R_{32}$ is independently $C_1$-$C_3$ alkyl selected from methyl, ethyl, and propyl.
In one embodiment, $R_{33}$ is methyl, ethyl, or propyl. In one embodiment, $R_{33}$ is methyl.
In one embodiment, $R_{34}$ is hydrogen, methyl, ethyl, or propyl. In one embodiment, $R_{34}$ is methyl, ethyl, or propyl In one embodiment, $R_{34}$ is methyl. In one embodiment, $R_{34}$ is hydrogen.

In one embodiment, the Degron is of Formula D2a or D2a':

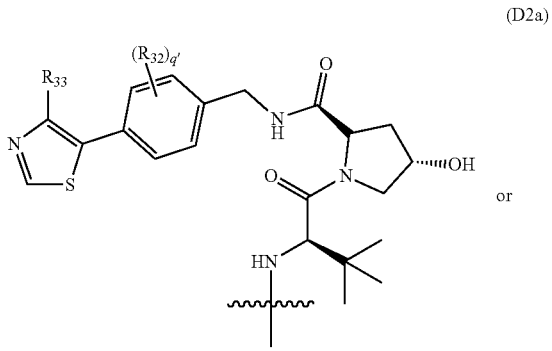
(D2a)

or

-continued

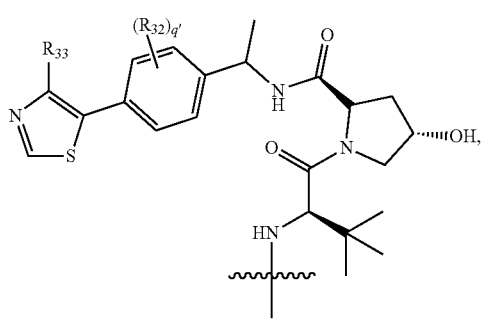
(D2a')

or an enantiomer, diastereomer, or stereoisomer thereof, wherein:

each $R_{32}$ is independently $C_1$-$C_3$ alkyl;

q' is 0, 1, 2, 3 or 4; and $R_{33}$ is H or $C_1$-$C_3$ alkyl, wherein the Degron is covalently bonded to another moiety (e.g., a compound, or a Linker) via

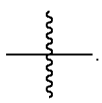

In one embodiment, q' is 0.
In one embodiment, q' is 1.
In one embodiment, q' is 2.
In one embodiment, q' is 3.
In one embodiment, each $R_{32}$ is independently $C_1$-$C_3$ alkyl selected from methyl, ethyl, and propyl.
In one embodiment, $R_{33}$ is methyl, ethyl, or propyl. In one embodiment, $R_{33}$ is methyl.
In one embodiment, the Degron is of Formula D2b or D2b':

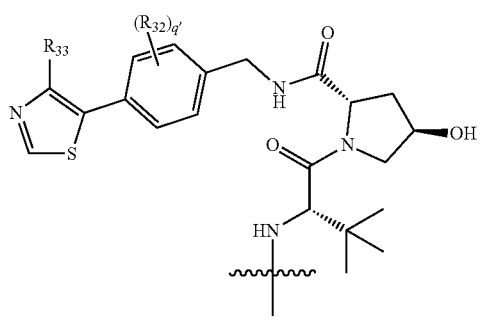
(D2b)

or

-continued

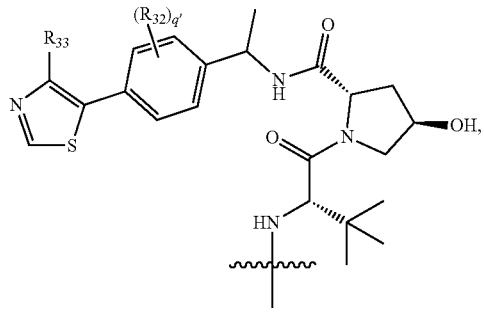
(D2b')

or an enantiomer, diastereomer, or stereoisomer thereof, wherein:

each $R_{32}$ is independently $C_1$-$C_3$ alkyl;

q' is 0, 1, 2, 3 or 4; and $R_3$ is H or $C_1$-$C_3$ alkyl, wherein the Degron is covalently bonded to another moiety (e.g., a compound, or a Linker) via

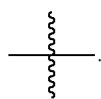

In one embodiment, q' is 0.
In one embodiment, q' is 1.
In one embodiment, q' is 2.
In one embodiment, q' is 3.
In one embodiment, each $R_{32}$ is independently $C_1$-$C_3$ alkyl selected from methyl, ethyl, and propyl.
In one embodiment, $R_{33}$ is methyl, ethyl, or propyl. In one embodiment, $R_{33}$ is methyl.
In one embodiment, the Degron is of Formula D2c or D2c':

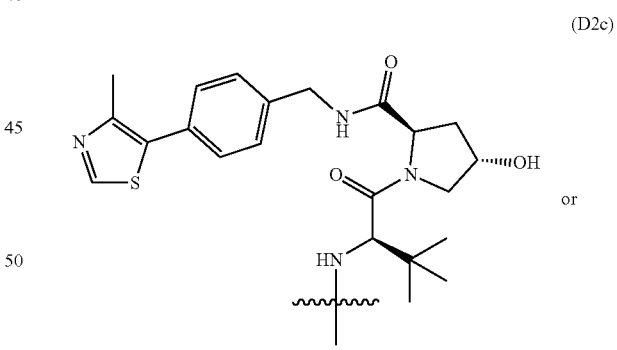
(D2c)

or

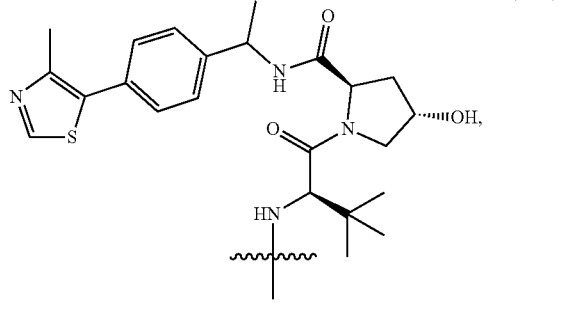
(D2c')

or an enantiomer, diastereomer, or stereoisomer thereof, wherein the Degron is covalently bonded to another moiety (e.g., a compound, or a Linker) via

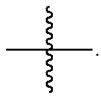

In one embodiment, the Degron is of Formula D2d or D2d':

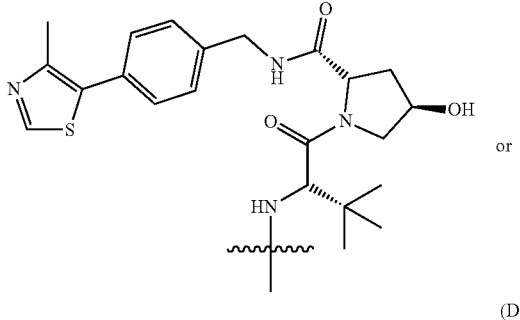

(D2d)

or

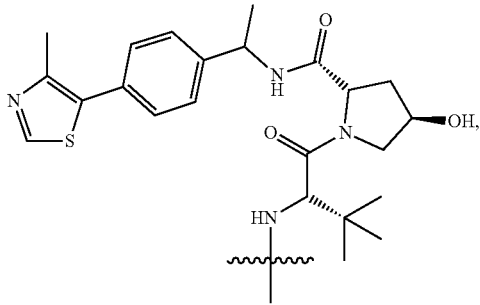

(D2d')

or an enantiomer, diastereomer, or stereoisomer thereof, wherein the Degron is covalently bonded to another moiety (e.g., a compound, or a Linker) via

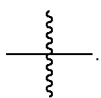

In one embodiment, the Degron is of Formula D3:

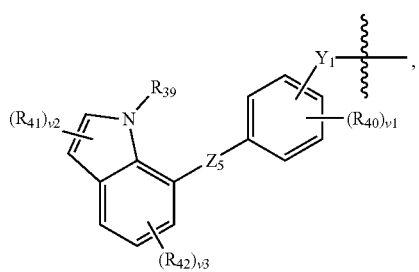

(D3)

or an enantiomer, diastereomer, or stereoisomer thereof, wherein:
$Y_1$ is a bond, $(CH_2)_{1-6}$, $(CH_2)_{0-6}$—O, $(CH_2)_{0-6}$—C(O)NR$_{43}$, $(CH_2)_{0-6}$—NR$_{43}$C(O), $(CH_2)_{0-6}$—NH, or $(CH_2)_{0-6}$—NR$_{44}$;
$Z_5$ is a bond, $(CH_2)_{0-6}$—C(O)NR$_{43}$, NR$_{43}$C(O)—$(CH_2)_{0-6}$, $(CH_2)_{0-6}$—S(O)$_{0-2}$NR$_{43}$, NR$_{43}$S(O)$_{0-2}$—$(CH_2)_{0-6}$, $(CH_2)_{0-6}$—NR$_{43}$C(O), C(O)NR$_{43}$—$(CH_2)_{0-6}$, $(CH_2)_{0-6}$—NR$_{43}$S(O)$_{0-2}$, or S(O)$_{0-2}$NR$_{43}$—$(CH_2)_{0-6}$;
$R_{43}$ is H or $C_1$-$C_6$ alkyl;
$R_{44}$ is $C_1$-$C_6$ alkyl, S(O)$_{0-2}$—$C_1$-$C_6$ alkyl, or C(O)—$C_1$-$C_6$ alkyl;
$R_{39}$ is H or $C_1$-$C_3$ alkyl;
each $R_{40}$ is independently halogen, CN, OH, $C_1$-$C_6$ alkyl, or $C_1$-$C_6$ alkoxy;
each $R_{41}$ is independently halogen, CN, or $C_1$-$C_6$ alkyl;
each $R_{42}$ is independently halogen, CN, OH, $C_1$-$C_6$ alkyl, or $C_1$-$C_6$ alkoxy;
v1 is 0, 1, 2, 3 or 4;
v2 is 0, 1, or 2; and
v3 is 0, 1, 2 or 3,
wherein the Degron is covalently bonded to the Linker via

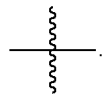

In one embodiment, v1 is 0.
In one embodiment, v1 is 1.
In one embodiment, v1 is 2.
In one embodiment, v1 is 3.
In one embodiment, v1 is 4.
In one embodiment, v2 is 0.
In one embodiment, v2 is 1.
In one embodiment, v2 is 2.
In one embodiment, v3 is 0.
In one embodiment, v3 is 1.
In one embodiment, v3 is 2.
In one embodiment, v3 is 3.
In one embodiment, $Z_5$ is $(CH_2)_{0-6}$—C(O)NR$_{43}$, NR$_{43}$C(O)—$(CH_2)_{0-6}$, $(CH_2)_{0-6}$—S(O)$_{0-2}$NR$_{43}$, NR$_{43}$S(O)$_{0-2}$—$(CH_2)_{0-6}$, $(CH_2)_{0-6}$—NR$_{43}$C(O), C(O)NR$_{43}$—$(CH_2)_{0-6}$, $(CH_2)_{0-6}$—NR$_{43}$S(O)$_{0-2}$, or S(O)$_{0-2}$NR$_{43}$—$(CH_2)_6$.
In one embodiment, $Z_5$ is $(CH_2)_{0-6}$—C(O)NR$_{43}$, NR$_{43}$C(O)—$(CH_2)_{0-6}$, $(CH_2)_0$—C(O)NR$_{43}$, NR$_{43}$C(O)—$(CH_2)_0$, $(CH_2)_1$—C(O)NR$_{43}$, NR$_{43}$C(O)—$(CH_2)_1$, $(CH_2)_2$—C(O)NR$_{43}$, NR$_{43}$C(O)—$(CH_2)_2$, $(CH_2)_3$—C(O)NR$_{43}$, NR$_{43}$C(O)—$(CH_2)_3$, $(CH_2)_4$—C(O)NR$_{43}$, NR$_{43}$C(O)—$(CH_2)_4$, $(CH_2)$—C(O)NR$_{43}$, NR$_{43}$C(O)—$(CH_2)_5$, $(CH_2)_6$—C(O)NR$_{43}$, or NR$_{43}$C(O)—$(CH_2)_6$.
In one embodiment, $Z_5$ is $(CH_2)_{0-6}$—S(O)$_{0-2}$NR$_{43}$, NR$_{43}$S(O)$_2$—$(CH_2)_{0-6}$, $(CH_2)$—S(O)$_{0-2}$NR$_{43}$, NR$_{43}$S(O)$_{0-2}$—$(CH_2)_0$, $(CH_2)_1$—S(O)$_{0-2}$NR$_{43}$, NR$_{43}$S(O)$_{0-2}$—$(CH_2)_1$, $(CH_2)_2$—S(O)$_{0-2}$NR$_{43}$, NR$_{43}$S(O)$_{0-2}$—$(CH_2)_2$, $(CH_2)_3$—S(O)$_{0-2}$NR$_{43}$, NR$_{43}$S(O)$_{0-2}$—$(CH_2)_3$, $(CH_2)_4$—S(O)$_{0-2}$NR$_{43}$, NR$_{43}$S(O)$_{0-2}$—$(CH_2)_4$, $(CH_2)_5$—S(O)$_{0-2}$NR$_{43}$, NR$_{43}$S(O)$_{0-2}$—$(CH_2)_5$, $(CH_2)_6$—S(O)$_{0-2}$NR$_{43}$, or NR$_{43}$S(O)$_{0-2}$—$(CH_2)_6$.
In one embodiment, $Z_5$ is $(CH_2)_{0-6}$—S(O)$_2$NR$_{43}$, NR$_{43}$S(O)$_2$—$(CH_2)_{0-6}$, $(CH_2)$—S(O)$_2$NR$_{43}$, NR$_{43}$S(O)$_2$—$(CH_2)_0$, $(CH_2)_1$—S(O)$_2$NR$_{43}$, NR$_{43}$S(O)$_2$—$(CH_2)_1$, $(CH_2)_2$—S(O)$_2$NR$_{43}$, NR$_{43}$S(O)$_2$—$(CH_2)_2$, $(CH_2)_3$—S(O)$_2$NR$_{43}$, NR$_{43}$S(O)$_2$—$(CH_2)_3$, $(CH_2)_4$—S(O)$_2$NR$_{43}$, NR$_{43}$S(O)$_2$—$(CH_2)_4$, $(CH_2)_5$—S(O)$_2$NR$_{43}$, NR$_{43}$S(O)$_2$—$(CH_2)_5$, $(CH_2)_6$—S(O)$_2$NR$_{43}$, or NR$_{43}$S(O)$_2$—$(CH_2)_6$.
In one embodiment, $Z_5$ is $(CH_2)_{0-6}$—NR$_{43}$C(O), C(O)NR$_{43}$—$(CH_2)_{0-6}$, $(CH_2)_1$—NR$_{43}$C(O), C(O)NR$_{43}$—$(CH_2)_1$, (CH$_2$)$_2$—NR$_{43}$C(O), C(O)NR$_{43}$—(CH$_2$)$_2$, (CH$_2$)$_3$—NR$_{43}$C(O), C(O)NR$_{43}$—(CH$_2$)$_3$, (CH$_2$)$_4$—NR$_{43}$C(O), C(O)NR$_{43}$—(CH$_2$)$_4$, (CH$_2$)$_5$—NR$_{43}$C(O), C(O)NR$_{43}$—(CH$_2$)$_5$, or (CH$_2$)$_6$—NR$_{43}$C(O), C(O)NR$_{43}$—(CH$_2$)$_6$.

In one embodiment, Z$_5$ is (CH$_2$)$_{0-6}$—NR$_{43}$S(O)$_{0-2}$, S(O)$_{0-2}$NR$_{43}$—(CH$_2$)$_{0-6}$, (CH$_2$)$_1$—NR$_{43}$S(O)$_{0-2}$, S(O)$_{0-2}$NR$_{43}$—(CH$_2$)$_1$, (CH$_2$)$_2$—NR$_{43}$S(O)$_{0-2}$, S(O)$_{0-2}$NR$_{43}$—(CH$_2$)$_2$, (CH$_2$)$_3$—NR$_{43}$S(O)$_{0-2}$, S(O)$_{0-2}$NR$_{43}$—(CH$_2$)$_3$, (CH$_2$)$_4$—NR$_{43}$S(O)$_{0-2}$, S(O)$_{0-2}$NR$_{43}$—(CH$_2$)$_4$, (CH$_2$)$_5$—NR$_{43}$S(O)$_{0-2}$, S(O)$_{0-2}$NR$_{43}$—(CH$_2$)$_5$, (CH$_2$)$_6$—NR$_{43}$S(O)$_{0-2}$, or S(O)$_{0-2}$NR$_{43}$—(CH$_2$)$_6$.

In one embodiment, Z$_5$ is (CH$_2$)$_{0-6}$—NR$_{43}$S(O)$_2$, S(O)$_2$NR$_{43}$—(CH$_2$)$_{0-6}$, (CH$_2$)$_1$—NR$_{43}$S(O)$_2$, S(O)$_2$NR$_{43}$—(CH$_2$)$_1$, (CH$_2$)$_2$—NR$_{43}$S(O)$_2$, S(O)$_2$NR$_{43}$—(CH$_2$)$_2$, (CH$_2$)$_3$—NR$_{43}$S(O)$_2$, S(O)$_2$NR$_{43}$—(CH$_2$)$_3$, (CH$_2$)$_4$—NR$_{43}$S(O)$_2$, S(O)$_2$NR$_{43}$—(CH$_2$)$_4$, (CH$_2$)$_5$—NR$_{43}$S(O)$_2$, S(O)$_2$NR$_{43}$—(CH$_2$)$_5$, (CH$_2$)$_6$—NR$_{43}$S(O)$_2$, or S(O)$_2$NR$_{43}$—(CH$_2$)$_6$.

In one embodiment, Y$_1$ is a bond.
In one embodiment, Y$_1$ is a bond, O, or NH.
In one embodiment, Y$_1$ is (CH$_2$)$_1$, (CH$_2$)$_2$, (CH$_2$)$_3$, (CH$_2$)$_4$, (CH$_2$), or (CH$_2$)$_6$. In one embodiment, Y$_1$ is (CH$_2$)$_1$, (CH$_2$)$_2$, or (CH$_2$)$_3$. In one embodiment, Y$_1$ is (CH$_2$)$_1$ or (CH$_2$)$_2$.

In one embodiment, Y$_1$ is O, CH$_2$—O, (CH$_2$)$_2$—O, (CH$_2$)$_3$—O, (CH$_2$)$_4$—O, (CH$_2$)$_5$—O, or (CH$_2$)$_6$—O. In one embodiment, Y$_1$ is O, CH$_2$—O, (CH$_2$)$_2$—O, or (CH$_2$)$_3$—O. In one embodiment, Y$_1$ is O or CH$_2$—O. In one embodiment, Y$_1$ is O.

In one embodiment, Y$_1$ is C(O)NR$_{43}$, CH$_2$—C(O)NR$_{43}$, (CH$_2$)$_2$—C(O)NR$_{43}$, (CH$_2$)$_3$—C(O)NR$_{43}$, (CH$_2$)$_4$—C(O)NR$_{43}$, (CH$_2$)—C(O)NR$_{43}$, or (CH$_2$)—C(O)NR$_{43}$. In one embodiment, Y$_1$ is C(O) R$_{43}$, CH$_2$—C(O)NR$_{43}$, (CH$_2$)$_2$—C(O)NR$_{43}$, or (CH$_2$)$_3$—C(O)NR$_{43}$. In one embodiment, Y$_1$ is C(O)NR$_{43}$ or CH$_2$—C(O)NR$_{43}$. In one embodiment, Y$_1$ is C(O)NR$_{43}$.

In one embodiment, Y$_1$ is NR$_{43}$C(O), CH$_2$—NR$_{43}$C(O), (CH$_2$)$_2$—NR$_{43}$C(O), (CH$_2$)$_3$—NR$_{43}$C(O), (CH$_2$)$_4$—NR$_{43}$C(O), (CH$_2$)—NR$_{43}$C(O), or (CH$_2$)$_6$—NR$_{43}$C(O). In one embodiment, Y$_1$ is NR$_{43}$C(O), CH$_2$—NR$_{43}$C(O), (CH$_2$)$_2$—NR$_{43}$C(O), or (CH$_2$)$_3$—NR$_{43}$C(O). In one embodiment, Y$_1$ is NR$_{43}$C(O) or CH$_2$—NR$_{43}$C(O). In one embodiment, Y$_1$ is NR$_{43}$C(O).

In one embodiment, R$_{43}$ is H. In one embodiment, R$_{43}$ is selected from methyl, ethyl, propyl, butyl, i-butyl, t-butyl, pentyl, i-pentyl, and hexyl. In one embodiment, R$_{43}$ is C$_1$-C$_3$ alkyl selected from methyl, ethyl, and propyl.

In one embodiment, Y$_1$ is NH, CH$_2$—NH, (CH$_2$)$_2$—NH, (CH$_2$)$_3$—NH, (CH$_2$)$_4$—NH, (CH$_2$)$_5$—NH, or (CH$_2$)—NH. In one embodiment, Y$_1$ is NH, CH$_2$—NH, (CH$_2$)$_2$—NH, or (CH$_2$)$_3$—NH. In one embodiment, Y$_1$ is NH or CH$_2$—NH. In one embodiment, Y$_1$ is NH.

In one embodiment, Y$_1$ is NR$_{44}$, CH$_2$—NR$_{44}$, (CH$_2$)$_2$—NR$_{44}$, (CH$_2$)$_3$—NR$_{44}$, (CH$_2$)$_4$—NR$_{44}$, (CH$_2$)—NR$_{44}$, or (CH$_2$)$_6$—NR$_{44}$. In one embodiment, Y$_1$ is NR$_{44}$, CH$_2$—NR$_{44}$, (CH$_2$)$_2$—NR$_{44}$, or (CH$_2$)$_3$—NR$_{44}$. In one embodiment, Y$_1$ is NR$_{44}$ or CH$_2$—NR$_{44}$. In one embodiment, Y$_1$ is NR$_{44}$.

In one embodiment, R$_{44}$ is selected from methyl, ethyl, propyl, butyl, i-butyl, t-butyl, pentyl, i-pentyl, and hexyl. In one embodiment, R$_{44}$ is C$_1$-C$_3$ alkyl selected from methyl, ethyl, and propyl.

In one embodiment, R$_{44}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, R$_{44}$ is C(O)—C$_1$-C$_3$ alkyl selected from C(O)-methyl, C(O)-ethyl, and C(O)-propyl.

In one embodiment, R$_{39}$ is H.

In one embodiment, R$_{39}$ C$_1$-C$_3$ alkyl selected from methyl, ethyl, and propyl.

In one embodiment, R$_{43}$ is H.
In one embodiment, R$_{43}$ C$_1$-C$_3$ alkyl selected from methyl, ethyl, and propyl.

In one embodiment, one or more R$_{40}$ is C$_1$-C$_6$ alkyl or C$_1$-C$_6$ alkoxy.
In one embodiment, one or more R$_{40}$ is halogen, CN, or OH.
In one embodiment, one or more R$_{40}$ is halogen, CN, or C$_1$-C$_6$ alkyl.
In one embodiment, one or more R$_{40}$ is halogen or CN.
In one embodiment, one or more R$_{40}$ is CN.
In one embodiment, one or more R$_{41}$ is C$_1$-C$_6$ alkyl.
In one embodiment, one or more R$_{41}$ is halogen or CN.
In one embodiment, one or more R$_{41}$ is halogen or C$_1$-C$_6$ alkyl.
In one embodiment, one or more R$_{41}$ is CN.
In one embodiment, one or more R$_{42}$ is C$_1$-C$_6$ alkyl or C$_1$-C$_6$ alkoxy.
In one embodiment, one or more R$_{42}$ is halogen, CN, or OH.
In one embodiment, one or more R$_{42}$ is halogen, CN, or C$_1$-C$_6$ alkyl.
In one embodiment, one or more R$_{42}$ is halogen or C$_1$-C$_6$ alkyl.
In one embodiment, one or more R$_{42}$ is C$_1$-C$_6$ alkyl.

Any of the groups described herein for any of Y$_1$, Z$_5$, R$_{39}$, R$_{40}$, R$_{41}$, R$_{42}$, R$_{43}$, R$_{44}$, v1, v2, and v3 can be combined with any of the groups described herein for one or more of the remainder of Y$_1$, Z$_5$, R$_{39}$, R$_{40}$, R$_{41}$, R$_{42}$, R$_{43}$, R$_{44}$, v, v2, and v3, and may further be combined with any of the groups described herein for the Linker.

In one embodiment, the Degron of Formula D3 is of Formula D3a of D3b:

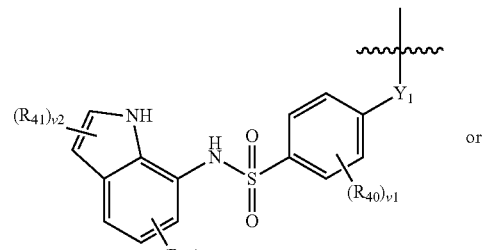

(D3a)

or

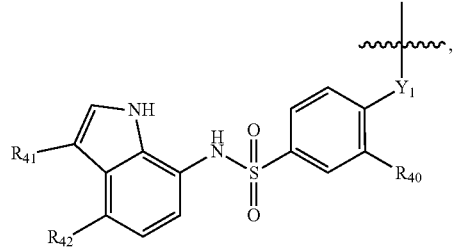

(D3b)

or an enantiomer, diastereomer, or stereoisomer thereof, wherein Y$_1$, R$_{40}$, R$_{41}$, R$_{42}$, R$_{43}$, R$_{44}$, v1, v2, and v3 are each as defined, where applicable, in Formula D3, and can be selected, where applicable, from any moieties or combinations thereof described above, wherein the Degron is covalently bonded to the Linker via

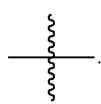

In one embodiment, the Degron of Formula D3 is of Formula D3c:

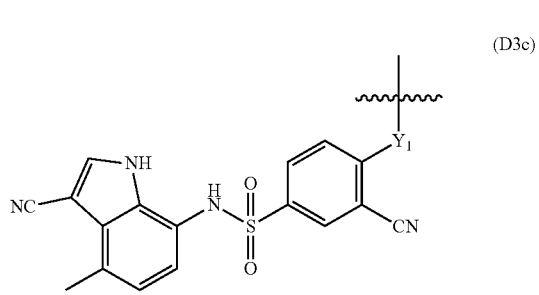

(D3c)

or an enantiomer, diastereomer, or stereoisomer thereof, wherein $Y_1$, $R_{43}$, and $R_{44}$ are each as defined, where applicable, in Formula D3, and can be selected, where applicable, from any moieties or combinations thereof described above, wherein the Degron is covalently bonded to the Linker via

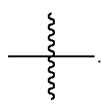

In one embodiment, $Y_1$ is NH.

Linker

The Linker is a bond, a carbon chain, carbocyclic ring, or heterocyclic ring that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl$)_2$, CN, $C_3$-$C_8$ cycloalkyl, heterocyclyl, phenyl, and heteroaryl).

In one embodiment, the Linker comprises at least 5 chain atoms (e.g., C, O, N, and S). In one embodiment, the Linker comprises less than 25 chain atoms (e.g., C, O, N, and S). In one embodiment, the Linker comprises less than 20 chain atoms (e.g., C, O, N, and S). In one embodiment, the Linker comprises 4, 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 7, 9, 11, 13, 15, 17, or 19 chain atoms (e.g., C, O, N, and S). In one embodiment, the Linker comprises 5, 7, 9, or 11 chain atoms (e.g., C, O, N, and S). In one embodiment, the Linker comprises 11, 13, 15, 17, or 19 chain atoms (e.g., C, O, N, and S). In one embodiment, the Linker comprises 11, 13, 15, 17, 19, 21, or 23 chain atoms (e.g., C, O, N, and S). In one embodiment, the Linker comprises 6, 8, 10, 12, 14, 16, 18, 20, 22, or 24 chain atoms (e.g., C, O, N, and S). In one embodiment, the Linker comprises 6, 8, 10, 12, 14, 16, 18, or 20 chain atoms (e.g., C, O, N, and S). In one embodiment, the Linker comprises 6, 8, 10, or 12 chain atoms (e.g., C, O, N, and S). In one embodiment, the Linker comprises 12, 14, 16, 18, or 20 chain atoms (e.g., C, O, N, and S).

In one embodiment, the Linker comprises from 11 to 19 chain atoms (e.g., C, O, N, and S).

In one embodiment, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl$)_2$, and CN). In one embodiment, the non-bulky substitution is located on the chain carbon atom proximal to the Degron (i.e., the carbon atom is separated from the carbon atom to which the Degron is bonded by at least 3, 4, or 5 chain atoms in the Linker). In one embodiment, the non-bulky substitution is located on the chain carbon atom proximal to the Targeting Ligand (i.e., the carbon atom is separated from the carbon atom to which the Degron is bonded by at least 3, 4, or 5 chain atoms in the Linker).

In one embodiment, the Linker is of Formula L1:

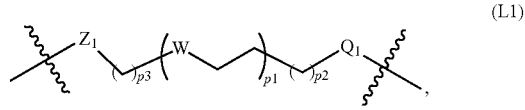

(L1)

or an enantiomer, diastereomer, or stereoisomer thereof, wherein p1 is an integer selected from 0 to 12;

p2 is an integer selected from 0 to 12;

p3 is an integer selected from 1 to 6;

each W is independently absent, $CH_2$, O, S, or $NR_{24}$;

$Z_1$ is absent, C(O), $CH_2$, O, $(CH_2)_jNR_{24}$, $O(CH_2)_jC(O)NR_{24}$, $C(O)NR_{24}$, $(CH_2)C(O)NR_{24}$, $NR_{24}C(O)$, $(CH_2)_j NR_{24}C(O)$, $(CH_2)_k NR_{24}(CH_2)_j C(O)NR_{24}$, or $NR_{24}(CH_2)_j C(O)NR_{24}$;

each $R_{24}$ is independently H or $C_1$-$C_3$ alkyl;

j is 1, 2, or 3;

k is 1, 2, or 3; and $Q_1$ is absent, C(O), $NHC(O)CH_2$, $OCH_2C(O)$, or $O(CH_2)_{1-2}$;

wherein the Linker is covalently bonded to a Degron via the

next to $Q_1$, and covalently bonded to a Targeting Ligand via the

next to $Z_1$, or the Linker is covalently bonded to a Degron via the

next to $Z_1$, and covalently bonded to a Targeting Ligand via the

next to $Q_1$.

In one embodiment, the total number of chain atoms in the Linker is less than 30. In a further embodiment, the total number of chain atoms in the Linker is less than 20.

For a Linker of Formula L1:
(1) In one embodiment, p1 is an integer selected from 0 to 10.
(2) In one embodiment, p1 is an integer selected from 1 to 10.
(3) In one embodiment, p1 is selected from 1, 2, 3, 4, 5, and 6.
(4) In one embodiment, p1 is 0, 1, 3, or 5.
(5) In one embodiment, p1 is 0, 1, 2, or 3.
(6) In one embodiment, p1 is 0.
(7) In one embodiment, p1 is 1.
(8) In one embodiment, p1 is 2.
(9) In one embodiment, p1 is 3.
(10) In one embodiment, p1 is 4.
(11) In one embodiment, p1 is 5.
(12) In one embodiment, p2 is an integer selected from 0 to 10.
(13) In one embodiment, p2 is selected from 0, 1, 2, 3, 4, 5, and 6.
(14) In one embodiment, p2 is 0, 1, 2, or 3.
(15) In one embodiment, p2 is 0.
(16) In one embodiment, p2 is 1.
(17) In one embodiment, p2 is 2.
(18) In one embodiment, p2 is 3.
(19) In one embodiment, p3 is an integer selected from 1 to 5.
(20) In one embodiment, p3 is 2, 3, 4, or 5.
(21) In one embodiment, p3 is 0, 1, 2, or 3.
(22) In one embodiment, p3 is 0.
(23) In one embodiment, p3 is 1.
(24) In one embodiment, p3 is 2.
(25) In one embodiment, p3 is 3.
(26) In one embodiment, p3 is 4.
(27) In one embodiment, at least one W is $CH_2$.
(28) In one embodiment, at least one W is O.
(29) In one embodiment, at least one W is S.
(30) In one embodiment, at least one W is NH.
(31) In one embodiment, at least one W is $NR_{24}$; and each $R_{24}$ is independently $C_1$-$C_3$ alkyl selected from methyl, ethyl, and propyl.
(32) In one embodiment, each W is O.
(33) In one embodiment, each W is $CH_2$.
(34) In one embodiment, j is 1, 2, or 3.
(35) In one embodiment, j is 1.
(36) In one embodiment, j is 2.
(37) In one embodiment, j is 3.
(38) In one embodiment, j is 2 or 3.
(39) In one embodiment, j is 1 or 2.
(40) In one embodiment, k is 1, 2, or 3.
(41) In one embodiment, k is 1.
(42) In one embodiment, k is 2.
(43) In one embodiment, k is 3.
(44) In one embodiment, k is 2 or 3.
(45) In one embodiment, k is 1 or 2.
(46) In one embodiment, $Q_1$ is absent.
(47) In one embodiment, $Q_1$ is $NHC(O)CH_2$.
(48) In one embodiment, $Q_1$ is $O(CH_2)_{1-2}$.
(49) In one embodiment, $Q_1$ is $OCH_2$.
(50) In one embodiment, $Q_1$ is $OCH_2CH_2$.
(51) In one embodiment, $Q_1$ is $OCH_2C(O)$.
(52) In one embodiment, $Q_1$ is $C(O)$.
(53) In one embodiment, $Z_1$ is absent.
(54) In one embodiment, $Z_1$ is $O(CH_2)_jC(O)NR_{24}$; and $R_{24}$ is $C_1$-$C_3$ alkyl selected from methyl, ethyl, and propyl.
(55) In one embodiment, $Z_1$ is $O(CH_2)_jC(O)NR_{24}$; and $R_{24}$ is H.
(56) In one embodiment, $Z_1$ is $O(CH_2)_jC(O)NR_{24}$; $R_{24}$ is $C_1$-$C_3$ alkyl selected from methyl, ethyl, and propyl; and j is 1.
(57) In one embodiment, $Z_1$ is $O(CH_2)_jC(O)NR_{24}$; $R_{24}$ is H; and j is 1.
(58) In one embodiment, $Z_1$ is $O(CH_2)_jC(O)NR_{24}$; $R_{24}$ is $C_1$-$C_3$ alkyl selected from methyl, ethyl, and propyl; and j is 2.
(59) In one embodiment, $Z_1$ is $O(CH_2)_jC(O)NR_{24}$; $R_{24}$ is H; and j is 2.
(60) In one embodiment, $Z_1$ is $O(CH_2)_jC(O)NR_{24}$; $R_{24}$ is $C_1$-$C_3$ alkyl selected from methyl, ethyl, and propyl; and j is 3.
(61) In one embodiment, $Z_1$ is $O(CH_2)_jC(O)NR_{24}$; and $R_{24}$ is H; and j is 3.
(62) In one embodiment, $Z_1$ is $C(O)NR_{24}$; and $R_{24}$ is H.
(63) In one embodiment, $Z_1$ is $C(O)NR_{24}$; and $R_{24}$ is $C_1$-$C_3$ alkyl selected from methyl, ethyl, and propyl.
(64) In one embodiment, $Z_1$ is $(CH_2)_jC(O)NR_{24}$; and $R_{24}$ is H.
(65) In one embodiment, $Z_1$ is $(CH_2)_jC(O)NR_{24}$; and $R_{24}$ is $C_1$-$C_3$ alkyl selected from methyl, ethyl, and propyl.
(66) In one embodiment, $Z_1$ is $(CH_2)_jC(O)NR_{24}$; $R_{24}$ is H; and j is 1.
(67) In one embodiment, $Z_1$ is $(CH_2)_jC(O)NR_{24}$; $R_{24}$ is $C_1$-$C_3$ alkyl selected from methyl, ethyl, and propyl; and j is 1.
(68) In one embodiment, $Z_1$ is $(CH_2)_jC(O)NR_{24}$; $R_{24}$ is H; and j is 2.
(69) In one embodiment, $Z_1$ is $(CH_2)_jC(O)NR_{24}$; $R_{24}$ is $C_1$-$C_3$ alkyl selected from methyl, ethyl, and propyl; and j is 2.
(70) In one embodiment, $Z_1$ is $(CH_2)_jC(O)NR_{24}$; $R_{24}$ is H; and j is 3.
(71) In one embodiment, $Z_1$ is $(CH_2)_jC(O)NR_{24}$; $R_{24}$ is $C_1$-$C_3$ alkyl selected from methyl, ethyl, and propyl; and j is 3.
(72) In one embodiment, $Z_1$ is $NR_{24}C(O)$; and $R_{24}$ is H.
(73) In one embodiment, $Z_1$ is $NR_{24}C(O)$; and $R_{24}$ is $C_1$-$C_3$ alkyl selected from methyl, ethyl, and propyl.
(74) In one embodiment, $Z_1$ is $(CH_2)_jNR_{24}C(O)$; and $R_{24}$ is H.
(75) In one embodiment, $Z_1$ is $(CH_2)_jNR_{24}C(O)$; and $R_{24}$ is $C_1$-$C_3$ alkyl selected from methyl, ethyl, and propyl.
(76) In one embodiment, $Z_1$ is $(CH_2)_jNR_{24}C(O)$; $R_{24}$ is H; and j is 1.

(77) In one embodiment, $Z_1$ is $(CH_2)_j NR_{24}C(O)$; $R_{24}$ is $C_1$-$C_3$ alkyl selected from methyl, ethyl, and propyl; and j is 1

(78) In one embodiment, $Z_1$ is $(CH_2)_j NR_{24}C(O)$; $R_{24}$ is H; and j is 2.

(79) In one embodiment, $Z_1$ is $(CH_2)_j NR_{24}C(O)$; $R_{24}$ is $C_1$-$C_3$ alkyl selected from methyl, ethyl, and propyl; and j is 2.

(80) In one embodiment, $Z_1$ is $(CH_2)_j NR_{24}C(O)$; $R_{24}$ is H; and j is 3.

(81) In one embodiment, $Z_1$ is $(CH_2)_j NR_{24}C(O)$; $R_{24}$ is $C_1$-$C_3$ alkyl selected from methyl, ethyl, and propyl; and j is 3.

(82) In one embodiment, $Z_1$ is $(CH_2)NR_{24}(CH_2)_j C(O)NR_{24}$; and each $R_{24}$ is independently H or $C_1$-$C_3$ alkyl selected from methyl, ethyl, and propyl.

(83) In one embodiment, $Z_1$ is $(CH_2)_k NR_{24}(CH_2)_j C(O)NR_{24}$; and one of $R_{24}$ is H and one of $R_{24}$ is $C_1$-$C_3$ alkyl selected from methyl, ethyl, and propyl. In one embodiment, $Z_1$ is $(CH_2)_k NR_{24}(CH_2)_j C(O)NH$.

(84) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and j is 1.

(85) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and k is 1.

(86) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; j is 1; and k is 1.

(87) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and j is 1. In one embodiment, $Z_1$ is $(CH_2)_k NR_{24}(CH_2)C(O)NH$.

(88) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and k is 1. In one embodiment, $Z_1$ is $(CH_2)NR_{24}(CH_2)_j C(O)NH$.

(89) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; j is 1; and k is 1. In one embodiment, $Z_1$ is $(CH_2)NR_{24}(CH_2)C(O)NH$. In one embodiment, $Z_1$ is $(CH_2)N(CH_3)(CH_2)C(O)NH$.

(90) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and j is 2.

(91) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and k is 2.

(92) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and j is 2. In one embodiment, $Z_1$ is $(CH_2)_k NR_{24}(CH_2)C(O)NH$.

(93) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and k is 2. In one embodiment, $Z_1$ is $(CH_2)_2 NR_{24}(CH_2)_j C(O)NH$.

(94) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and j is 3.

(95) In one embodiment, $Z_1$ is $(CH_2)_k NR_{24}(CH_2)_j C(O)NR_{24}$; each $R_{24}$ is independently H or $C_1$-$C_3$ alkyl selected from methyl, ethyl, and propyl; and k is 3.

(96) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and j is 3. In one embodiment, $Z_1$ is $(CH_2)_k NR_{24}(CH_2)_3 C(O)NH$.

(97) In one embodiment, $Z_1$ is $(CH_2)_k NR_{24}(CH_2)_j C(O)NR_{24}$; one of $R_{24}$ is H and one of $R_{24}$ is $C_1$-$C_3$ alkyl selected from methyl, ethyl, and propyl; and k is 3. In one embodiment, $Z_1$ is $(CH_2)_3 NR_{24}(CH_2)_j C(O)NH$.

(98) In one embodiment, $Z_1$ is $NR_{24}(CH_2)_j C(O)NR_{24}$; and each $R_{24}$ is independently H or $C_1$-$C_3$ alkyl selected from methyl, ethyl, and propyl.

(99) In one embodiment, $Z_1$ is $NR_{24}(CH_2)_j C(O)NR_{24}$; and each $R_{24}$ is H.

(100) In one embodiment, $Z_1$ is $NR_{24}(CH_2)_j C(O)NR_{24}$; one of $R_{24}$ is H and one of $R_{24}$ is $C_1$-$C_3$ alkyl selected from methyl, ethyl, and propyl; and j is 1.

(101) In one embodiment, $Z_1$ is $NR_{24}(CH_2)_j C(O)NR_{24}$; $R_{24}$ is H; and j is 1.

(102) In one embodiment, $Z_1$ is $NR_{24}(CH_2)_j C(O)NR_{24}$; one of $R_{24}$ is H and one of $R_{24}$ is $C_1$-$C_3$ alkyl selected from methyl, ethyl, and propyl; and j is 2.

(103) In one embodiment, $Z_1$ is $NR_{24}(CH_2)_j C(O)NR_{24}$; $R_{24}$ is H; and j is 2.

(104) In one embodiment, $Z_1$ is $NR_{24}(CH_2)_j C(O)NR_{24}$; one of $R_{24}$ is H and one of $R_{24}$ is $C_1$-$C_3$ alkyl selected from methyl, ethyl, and propyl; and j is 3.

(105) In one embodiment, $Z_1$ is absent and p3 is 1.
(106) In one embodiment, $Z_1$ is absent and p3 is 2.
(107) In one embodiment, $Z_1$ is absent and p3 is 3.
(108) In one embodiment, $Z_1$ is absent, p3 is 1, and p1 is 1-8.
(109) In one embodiment, $Z_1$ is absent, p3 is 1, and p1 is 1.
(110) In one embodiment, $Z_1$ is absent, p3 is 1, and p1 is 2.
(111) In one embodiment, $Z_1$ is absent, p3 is 1, and p1 is 3.
(112) In one embodiment, $Z_1$ is absent, p3 is 1, and p1 is 4.
(113) In one embodiment, $Z_1$ is absent, p3 is 1, and p1 is 5.
(114) In one embodiment, $Z_1$ is absent, p3 is 1, and p1 is 6.
(115) In one embodiment, $Z_1$ is absent, p3 is 1, and p1 is 7.
(116) In one embodiment, $Z_1$ is absent, p3 is 1, and p1 is 8.
(117) In one embodiment, $Z_1$ is absent, p3 is 1, and W is O.
(118) In one embodiment, $Z_1$ is absent, p3 is 1, p1 is 1, and W is O.
(119) In one embodiment, $Z_1$ is absent, p3 is 1, p1 is 2, and W is O.
(120) In one embodiment, $Z_1$ is absent, p3 is 1, p1 is 3, and W is O.
(121) In one embodiment, $Z_1$ is absent, p3 is 1, p1 is 4, and W is O.
(122) In one embodiment, $Z_1$ is absent, p3 is 1, p1 is 5, and W is O.
(123) In one embodiment, $Z_1$ is absent, p3 is 1, p1 is 6, and W is O.
(124) In one embodiment, $Z_1$ is absent, p3 is 1, p1 is 7, and W is O.
(125) In one embodiment, $Z_1$ is absent, p3 is 1, p1 is 8, and W is O.
(126) In one embodiment, $Z_1$ is absent, p3 is 1, p1 is 1, and W is $CH_2$.
(127) In one embodiment, $Z_1$ is absent, p3 is 1, p1 is 2, and W is $CH_2$.
(128) In one embodiment, $Z_1$ is absent, p3 is 1, p1 is 3, and W is $CH_2$.
(129) In one embodiment, $Z_1$ is absent, p3 is 1, p1 is 4, and W is $CH_2$.
(130) In one embodiment, $Z_1$ is absent, p3 is 1, p1 is 5, and W is $CH_2$.
(131) In one embodiment, $Z_1$ is absent, p3 is 1, p1 is 6, and W is $CH_2$.
(132) In one embodiment, $Z_1$ is absent, p3 is 1, p1 is 7, and W is $CH_2$.
(133) In one embodiment, $Z_1$ is absent, p3 is 1, p1 is 8, and W is $CH_2$.

(134) In one embodiment, $Z_1$ is absent, p3 is 2, p1 is 1, and W is O.
(135) In one embodiment, $Z_1$ is absent, p3 is 2, p1 is 2, and W is O.
(136) In one embodiment, $Z_1$ is absent, p3 is 2, p1 is 3, and W is O.
(137) In one embodiment, $Z_1$ is absent, p3 is 2, p1 is 4, and W is O.
(138) In one embodiment, $Z_1$ is absent, p3 is 2, p1 is 5, and W is O.
(139) In one embodiment, $Z_1$ is absent, p3 is 2, p1 is 6, and W is O.
(140) In one embodiment, $Z_1$ is absent, p3 is 2, p1 is 7, and W is O.
(141) In one embodiment, $Z_1$ is absent, p3 is 2, p1 is 8, and W is O.
(142) In one embodiment, $Z_1$ is absent, p3 is 2, p1 is 1, and W is $CH_2$.
(143) In one embodiment, $Z_1$ is absent, p3 is 2, p1 is 2, and W is $CH_2$.
(144) In one embodiment, $Z_1$ is absent, p3 is 2, p1 is 3, and W is $CH_2$.
(145) In one embodiment, $Z_1$ is absent, p3 is 2, p1 is 4, and W is $CH_2$.
(146) In one embodiment, $Z_1$ is absent, p3 is 2, p1 is 5, and W is $CH_2$.
(147) In one embodiment, $Z_1$ is absent, p3 is 2, p1 is 6, and W is $CH_2$.
(148) In one embodiment, $Z_1$ is absent, p3 is 2, p1 is 7, and W is $CH_2$.
(149) In one embodiment, $Z_1$ is absent, p3 is 2, p1 is 8, and W is $CH_2$.
(150) In one embodiment, $Z_1$ is absent, p3 is 3, p1 is 1, and W is O.
(151) In one embodiment, $Z_1$ is absent, p3 is 3, p1 is 2, and W is O.
(152) In one embodiment, $Z_1$ is absent, p3 is 3, p1 is 3, and W is O.
(153) In one embodiment, $Z_1$ is absent, p3 is 3, p1 is 4, and W is O.
(154) In one embodiment, $Z_1$ is absent, p3 is 3, p1 is 5, and W is O.
(155) In one embodiment, $Z_1$ is absent, p3 is 3, p1 is 6, and W is O.
(156) In one embodiment, $Z_1$ is absent, p3 is 3, p1 is 7, and W is O.
(157) In one embodiment, $Z_1$ is absent, p3 is 3, p1 is 8, and W is O.
(158) In one embodiment, $Z_1$ is absent, p3 is 3, p1 is 1, and W is $CH_2$.
(159) In one embodiment, $Z_1$ is absent, p3 is 3, p1 is 2, and W is $CH_2$.
(160) In one embodiment, $Z_1$ is absent, p3 is 3, p1 is 3, and W is $CH_2$.
(161) In one embodiment, $Z_1$ is absent, p3 is 3, p1 is 4, and W is $CH_2$.
(162) In one embodiment, $Z_1$ is absent, p3 is 3, p1 is 5, and W is $CH_2$.
(163) In one embodiment, $Z_1$ is absent, p3 is 3, p1 is 6, and W is $CH_2$.
(164) In one embodiment, $Z_1$ is absent, p3 is 3, p1 is 7, and W is $CH_2$.
(165) In one embodiment, $Z_1$ is absent, p3 is 3, p1 is 8, and W is $CH_2$.
(166) In one embodiment, p1, $Z_1$, p3, and W are each as defined, where applicable, in any one of (1)-(165), and p2 is 0.
(167) In one embodiment, p1, $Z_1$, p3, and W are each as defined, where applicable, in anyone of (1)-(165), and p2 is 1.
(168) In one embodiment, p1, $Z_1$, p3, and W are each as defined, where applicable, in any one of (1)-(165), and p2 is 2.
(169) In one embodiment, p1, $Z_1$, p3, p2, and W are each as defined, where applicable, in any one of (1)-(168), and $Q_1$ is absent.
(170) In one embodiment, p1, $Z_1$, p3, p2, and W are each as defined, where applicable, in any one of (1)-(168), and $Q_1$ is $NHC(O)CH_2$.
(171) In one embodiment, p1, $Z_1$, p3, p2, and W are each as defined, where applicable, in any one of (1)-(168), and $Q_1$ is $O(CH_2)_{1-2}$.
(172) In one embodiment, p1, $Z_1$, p3, p2, and W are each as defined, where applicable, in any one of (1)-(168), and $Q_1$ is $O(CH_2)$.
(173) In one embodiment, p1, $Z_1$, p3, p2, and W are each as defined, where applicable, in any one of (1)-(168), and $Q_1$ is $O(CH_2CH_2)$.
(174) In one embodiment, p1, $Z_1$, p3, p2, and W are each as defined, where applicable, in any one of (1)-(168), and $Q_1$ is C(O).
(175) (175) In one embodiment, p1, $Z_1$, p3, p2, and W are each as defined, where applicable, in any one of (1)-(168), and $Q_1$ is $OCH_2C(O)$.
(176) In one embodiment, $Q_1$ is absent, C(O), $NHC(O)CH_2$, $OCH_2C(O)$, or $O(CH_2)_{1-2}$, p1 is an integer selected from 0 to 12, p2 is an integer selected from 0 to 12, p3 is an integer selected from 1 and 3 to 6, and $Z_1$ is absent, C(O), O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$.
(177) In one embodiment, $Q_1$ is $NHC(O)CH_2$, p1 is 2, p2 is 0, p3 is 1, and $Z_1$ is absent, C(O), O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$.
(178) In one embodiment, $Q_1$ is absent, C(O), $NHC(O)CH_2$, $OCH_2C(O)$, or $O(CH_2)_{1-2}$, p1 is an integer selected from 0 to 12, p2 is an integer selected from 0 to 12, p3 is an integer selected from 2 to 6, and $Z_1$ is C(O), $CH_2$, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$.
(179) In one embodiment, $Q_1$ is $NHC(O)CH_2$, p1 is 2, p2 is 0, p3 is 2, and $Z_1$ is C(O), $CH_2$, O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$.
(180) In one embodiment, p1 is an integer selected from 0 to 12, p2 is an integer selected from 0 to 12, p3 is an integer selected from 1 to 6, $Z_1$ is absent, C(O), $CH_2$, O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$, and $Q_1$ is absent, C(O), $OCH_2C(O)$, or $O(CH_2)_{1-2}$.
(181) In one embodiment, p1 is 2, p2 is 0, p3 is 1, $Z_1$ is $CH_2$, and $Q_1$ is absent, C(O), $OCH_2C(O)$, or $O(CH_2)_{1-2}$.
(182) In one embodiment, p1 is 2, p2 is 0, p3 is 2, $Z_1$ is absent, and $Q_1$ is absent, C(O), $OCH_2C(O)$, or $O(CH_2)_{1-2}$.
(183) In one embodiment, p2 is an integer selected from 0 to 12, p3 is an integer selected from 1 to 6, $Z_1$ is absent, C(O), $CH_2$, O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$, $Q_1$ is absent, C(O), NHC(O)CH$_2$, OCH$_2$C(O), or O(CH$_2$)$_{1-2}$, and p1 is 0, 1, 3, 4, 5, 6, 7, 8, 9, 10, 11, or 12.

(184) In one embodiment, p2 is 0, p3 is 1, $Z_1$ is CH$_2$, $Q_1$ is NHC(O)CH$_2$, and p1 is 0, 1, 3, 4, 5, 6, 7, 8, 9, 10, 11, or 12.

(185) In one embodiment, p2 is 0, p3 is 2, $Z_1$ is absent, $Q_1$ is NHC(O)CH$_2$, and p1 is 0, 1, 3, 4, 5, 6, 7, 8, 9, 10, 11, or 12.

(186) In one embodiment, p1 is an integer selected from 0 to 12, p3 is an integer selected from 1 to 6, $Z_1$ is absent, C(O), CH$_2$, O, (CH$_2$)$_j$NR$_{24}$, O(CH$_2$)$_j$C(O)NR$_{24}$, C(O)NR$_{24}$, (CH$_2$)$_j$C(O)NR$_{24}$, NR$_{24}$C(O), (CH$_2$)$_j$NR$_{24}$C(O), (CH$_2$)$_k$NR$_{24}$(CH$_2$)$_j$C(O)NR$_{24}$, or NR$_{24}$(CH$_2$)$_j$C(O)NR$_{24}$, $Q_1$ is absent, C(O), NHC(O)CH$_2$, OCH$_2$C(O), or O(CH$_2$)$_{1-2}$, and p2 is an integer selected from 1 to 12.

(187) In one embodiment, p1 is 2, p3 is 1, $Z_1$ is CH$_2$, $Q_1$ is NHC(O)CH$_2$, and p2 is an integer selected from 1 to 12.

(188) In one embodiment, p1 is 2, p3 is 2, $Z_1$ is absent, $Q_1$ is NHC(O)CH$_2$, and p2 is an integer selected from 1 to 12.

(189) In one embodiment, p1 is an integer selected from 0 to 12, p2 is an integer selected from 0 to 12, $Z_1$ is C(O), CH$_2$, O, (CH$_2$)$_j$NR$_{24}$, O(CH$_2$)$_j$C(O)NR$_{24}$, C(O)NR$_{24}$, (CH$_2$)$_j$C(O)NR$_{24}$, NR$_{24}$C(O), (CH$_2$)$_j$NR$_{24}$C(O), (CH$_2$)$_k$NR$_{24}$(CH$_2$)$_j$C(O)NR$_{24}$, or NR$_{24}$(CH$_2$)$_j$C(O)NR$_{24}$, $Q_1$ is absent, C(O), NHC(O)CH$_2$, OCH$_2$C(O), or O(CH$_2$)$_{1-2}$, and p3 is an integer selected from 2 to 6.

(190) In one embodiment, p1 is 2, p2 is 0, $Z_1$ is CH$_2$, $Q_1$ is NHC(O)CH$_2$, and p3 is an integer selected from 2 to 6.

(191) In one embodiment, p1 is an integer selected from 0 to 12, p2 is an integer selected from 0 to 12, $Z_1$ is absent, C(O), O, (CH$_2$)NR$_{24}$, O(CH$_2$)$_j$C(O)NR$_{24}$, C(O)NR$_{24}$, (CH$_2$)—C(O)NR$_{24}$, NR$_{24}$C(O), (CH$_2$)$_j$NR$_{24}$C(O), (CH$_2$)$_k$NR$_{24}$(CH$_2$)$_j$C(O)NR$_{24}$, or NR$_{24}$(CH$_2$)$_j$C(O)NR$_{24}$, $Q_1$ is absent, C(O), NHC(O)CH$_2$, OCH$_2$C(O), or O(CH$_2$)$_{1-2}$, and p3 is an integer selected from 1 and 3 to 6.

(192) In one embodiment, p1 is 2, p2 is 0, $Z_1$ is absent, $Q_1$ is NHC(O)CH$_2$, and p3 is an integer selected from 1 and 3 to 6.

In one embodiment, the Linker-Targeting Ligand (TL) has the structure selected from Table L:

TABLE L

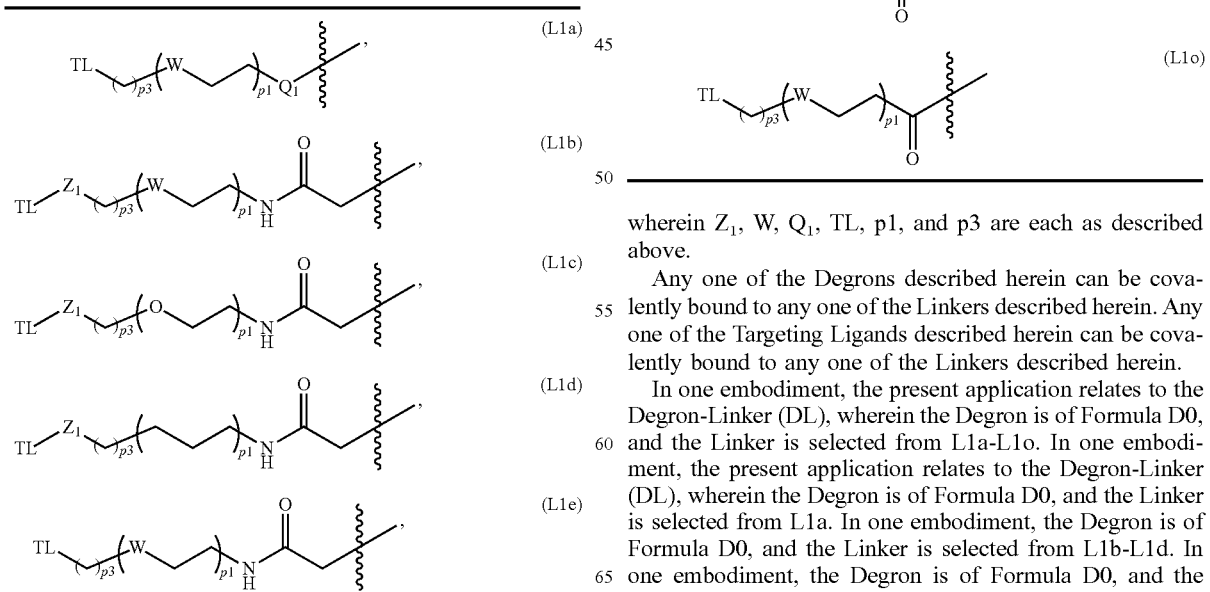

wherein $Z_1$, W, $Q_1$, TL, p1, and p3 are each as described above.

Any one of the Degrons described herein can be covalently bound to any one of the Linkers described herein. Any one of the Targeting Ligands described herein can be covalently bound to any one of the Linkers described herein.

In one embodiment, the present application relates to the Degron-Linker (DL), wherein the Degron is of Formula D0, and the Linker is selected from L1a-L1o. In one embodiment, the present application relates to the Degron-Linker (DL), wherein the Degron is of Formula D0, and the Linker is selected from L1a. In one embodiment, the Degron is of Formula D0, and the Linker is selected from L1b-L1d. In one embodiment, the Degron is of Formula D0, and the Linker is selected from L1e-L1g. In one embodiment, the Degron is of Formula D0, and the Linker is L1h-L1j. In one embodiment, the Degron is of Formula D0, and the Linker is L1p or L1q. In one embodiment, the Degron is of Formula D0, and the Linker is L1a, L1b, L1e, L1h, L1k, L1l or L1o. In one embodiment, the Degron is of Formula D0, and the Linker is L1c, L1d, L1f, L1g, L1i, L1j, L1m, or L1n. In one embodiment, the Degron is of Formula D0, and the Linker is L1k. In one embodiment, the Degron is of Formula D0, and the Linker is L1l or L1o. In one embodiment, the Degron is of Formula D0, and the Linker is L1c or L1d. In one embodiment, the Degron is of Formula D0, and the Linker is L1f or L1g. In one embodiment, the Degron is of Formula D0, and the Linker is L1i or L1j. In one embodiment, the Degron is of Formula D0, and the Linker is L1m or L1n.

In one embodiment, the present application relates to the Degron-Linker (DL), wherein the Degron is of Formula D0a, D0b, D0c, or D0d, and the Linker is selected from L1a-L1o. In one embodiment, the present application relates to the Degron-Linker (DL), wherein the Degron is of Formula D0a, D0b, D0c, or D0d, and the Linker is selected from L1a. In one embodiment, the Degron is of Formula D0a, D0b, D0c, or D0d, and the Linker is selected from L1b-L1d. In one embodiment, the Degron is of Formula D0a, D0b, D0c, or D0d, and the Linker is selected from L1e-L1g. In one embodiment, the Degron is of Formula D0a, D0b, D0c, or D0d, and the Linker is L1h-L1j. In one embodiment, the Degron is of Formula D0a, D0b, D0c, or D0d, and the Linker is L1p or L1q. In one embodiment, the Degron is of Formula D0a, D0b, D0c, or D0d, and the Linker is L1a, L1b, L1e, L1h, L1k, L1 or L1o. In one embodiment, the Degron is of Formula D0a, D0b, D0c, or D0d, and the Linker is L1c, L1d, L1f, L1g, L1i, L1j, L1m, or L1n.

In one embodiment, the Degron is of Formula D0a, D0b, D0c, or D0d, and the Linker is L1k. In one embodiment, the Degron is of Formula D0a, D0b, D0c, or D0d, and the Linker is L1l or L1o. In one embodiment, the Degron is of Formula D0a, D0b, D0c, or D0d, and the Linker is L1c or L1d. In one embodiment, the Degron is of Formula D0a, D0b, D0c, or D0d, and the Linker is L1f or L1g. In one embodiment, the Degron is of Formula D0a, D0b, D0c, or D0d, and the Linker is L1i or L1j. In one embodiment, the Degron is of Formula D0a, D0b, D0c, or D0d, and the Linker is L1m or L1n.

In one embodiment, the present application relates to the Degron-Linker (DL), wherein the Degron is of Formula D1, and the Linker is selected from L1a-L1o. In one embodiment, the present application relates to the Degron-Linker (DL), wherein the Degron is of Formula D1, and the Linker is selected from L1a. In one embodiment, the Degron is of Formula D1, and the Linker is selected from L1b-L1d. In one embodiment, the Degron is of Formula D1, and the Linker is selected from L1e-L1g. In one embodiment, the Degron is of Formula D1, and the Linker is L1h-L1j. In one embodiment, the Degron is of Formula D1, and the Linker is L1p or L1q. In one embodiment, the Degron is of Formula D, and the Linker is L1a, L1b, L1e, L1h, L1k, L1l or L1o. In one embodiment, the Degron is of Formula D1, and the Linker is L1c, L1d, L1f, L1g, L1i, L1j, L1m, or L1n. In one embodiment, the Degron is of Formula D1, and the Linker is L1k. In one embodiment, the Degron is of Formula D1, and the Linker is L1l or L1o. In one embodiment, the Degron is of Formula D1, and the Linker is L1c or L1d. In one embodiment, the Degron is of Formula D1, and the Linker is L1f or L1g. In one embodiment, the Degron is of Formula D1, and the Linker is L1i or L1j. In one embodiment, the Degron is of Formula D1, and the Linker is L1m or L1n.

In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L1a-L1o. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L1a. In one embodiment, the Degron is of Formula D1a, D1b, D1c, D1d, D1e, D1f, D1g, D1h, D1i, D1j, D1k, or D1l, and the Linker is selected from L1b-L1d. In one embodiment, the Degron is of Formula D1a, D1b, D1c, D1d, D1e, D1f, D1g, D1h, D1i, D1j, D1k, or D1l, and the Linker is selected from L1e-L1g. In one embodiment, the Degron is of Formula D1a, D1b, D1c, D1d, D1e, D1f, D1g, D1h, D1i, D1j, D1k, or D1l, and the Linker is L1h-L1j. In one embodiment, the Degron is of Formula D1a, D1b, D1c, D1d, D1e, D1f, D1g, D1h, D1i, D1j, D1k, or D1l, and the Linker is L1p or L1q. In one embodiment, the Degron is of Formula D1a, D1b, D1c, D1d, D1e, D1f, D1g, D1h, D1i, D1j, D1k, or D1l, and the Linker is L1a, L1b, L1e, L1h, L1k, L1l or L1o. In one embodiment, the Degron is of Formula D1a, D1b, D1c, D1d, D1e, D1f, D1g, D1h, D1i, D1j, D1k, or D1l, and the Linker is L1c, L1d, L1f, L1g, L1i, L1j, L1m, or L1n. In one embodiment, the Degron is of Formula D1a, D1b, D1c, D1d, D1e, D1f, D1g, D1h, D1i, D1j, D1k, or D1l, and the Linker is L1k. In one embodiment, the Degron is of Formula D1a, D1b, D1c, D1d, D1e, D1f, D1g, D1h, D1i, D1j, D1k, or D1l, and the Linker is L1l or L1o. In one embodiment, the Degron is of Formula D1a, D1b, D1c, D1d, D1e, D1f, D1g, D1h, D1i, D1j, D1k, or D1l, and the Linker is L1c or L1d. In one embodiment, the Degron is of Formula D1a, D1b, D1c, D1d, D1e, D1f, D1g, D1h, D1i, D1j, D1k, or D1l, and the Linker is L1f or L1g. In one embodiment, the Degron is of Formula D1a, D1b, D1c, D1d, D1e, D1f, D1g, D1h, D1i, D1j, D1k, or D1l, and the Linker is L1i or L1j. In one embodiment, the Degron is of Formula D1a, D1b, D1c, D1d, D1e, D1f, D1g, D1h, D1i, D1j, D1k, or D1l, and the Linker is L1m or L1n.

In one embodiment, the present application relates to the Degron-Linker (DL), wherein the Degron is of Formula D4, and the Linker is selected from L1a-L1o. In one embodiment, the present application relates to the Degron-Linker (DL), wherein the Degron is of Formula D4, and the Linker is selected from L1a. In one embodiment, the Degron is of Formula D4, and the Linker is selected from L1b-L1d. In one embodiment, the Degron is of Formula D4, and the Linker is selected from L1e-L1g. In one embodiment, the Degron is of Formula D41, and the Linker is L1h-L1j. In one embodiment, the Degron is of Formula D4, and the Linker is L1p or L1q. In one embodiment, the Degron is of Formula D4, and the Linker is L1a, L1b, L1e, L1h, L1k, L1l or L1o. In one embodiment, the Degron is of Formula D4, and the Linker is L1c, L1d, L1f, L1g, L1i, L1j, L1m, or L1n. In one embodiment, the Degron is of Formula D4, and the Linker is L1k. In one embodiment, the Degron is of Formula D4, and the Linker is L1l or L1o.

In one embodiment, the Degron is of Formula D4, and the Linker is L1c or L1d. In one embodiment, the Degron is of Formula D4, and the Linker is L1f or L1g. In one embodiment, the Degron is of Formula D4, and the Linker is L1i or L1j. In one embodiment, the Degron is of Formula D4, and the Linker is L1m or L1n.

In one embodiment, the present application relates to the Degron-Linker (DL), wherein the Degron is of Formula D4a or D4b, and the Linker is selected from L1a-L1o. In one embodiment, the present application relates to the Degron-Linker (DL), wherein the Degron is of Formula D4a or D4b, and the Linker is selected from L1a. In one embodiment, the Degron is of Formula D4a or D4b, and the Linker is selected from L1b-L1d. In one embodiment, the Degron is of Formula D4a or D4b, and the Linker is selected from L1e-L1g. In one embodiment, the Degron is of Formula D4a or D4b, and the Linker is L1h-L1j. In one embodiment, the Degron is of Formula D4a or D4b, and the Linker is L1p or L1q. In one embodiment, the Degron is of Formula D4a or D4b, and the Linker is L1a, L1b, L1e, L1h, L1k, L1l or L1o. In one embodiment, the Degron is of Formula D4a or D4b and the Linker is L1c, L1d, L1f, L1g, L1i, L1j, L1m, or L1n. In one embodiment, the Degron is of Formula D4a or D4b, and the Linker is L1k. In one embodiment, the Degron is of Formula D4a or D4b, and the Linker is L1l or L1o. In one embodiment, the Degron is of Formula D4a or D4b, and the Linker is L1c or L1d. In one embodiment, the Degron is of Formula D4a or D4b, and the Linker is L1f or L1g. In one embodiment, the Degron is of Formula D4a or D4b, and the Linker is L1i or L1j. In one embodiment, the Degron is of Formula D4a or D4b, and the Linker is L1m or L1n.

In one embodiment, the present application relates to the Degron-Linker (DL), wherein the Degron is of Formula D2, and the Linker is selected from L1a-L1o. In one embodiment, the present application relates to the Degron-Linker (DL), wherein the Degron is of Formula D2, and the Linker is selected from L1a. In one embodiment, the Degron is of Formula D2, and the Linker is selected from L1b-L1d. In one embodiment, the Degron is of Formula D2, and the Linker is selected from L1e-L1g. In one embodiment, the Degron is of Formula D2, and the Linker is L1h-L1j. In one embodiment, the Degron is of Formula D2, and the Linker is L1p or L1q. In one embodiment, the Degron is of Formula D2, and the Linker is L1a, L1b, L1e, L1h, L1k, L1l or L1o. In one embodiment, the Degron is of Formula D2, and the Linker is L1c, L1d, L1f, L1g, L1i, L1j, L1m, or L1n. In one embodiment, the Degron is of Formula D2, and the Linker is L1k. In one embodiment, the Degron is of Formula D2, and the Linker is L1l or L1o.

In one embodiment, the Degron is of Formula D2, and the Linker is L1c or L1d. In one embodiment, the Degron is of Formula D2, and the Linker is L1f or L1g. In one embodiment, the Degron is of Formula D2, and the Linker is L1i or L1j. In one embodiment, the Degron is of Formula D2, and the Linker is L1m or L1n.

In one embodiment, the present application relates to the Degron-Linker (DL), wherein the Degron is of Formula D2a, D2a', D2b, or D2b', and the Linker is selected from L1a-L1o. In one embodiment, the present application relates to the Degron-Linker (DL), wherein the Degron is of Formula D2a, D2a', D2b, or D2b', and the Linker is selected from L1a. In one embodiment, the Degron is of Formula D2a, D2a', D2b, or D2b', and the Linker is selected from L1b-L1d. In one embodiment, the Degron is of Formula D2a, D2a', D2b, or D2b', and the Linker is selected from L1e-L1g. In one embodiment, the Degron is of Formula D2a, D2a', D2b, or D2b', and the Linker is L1h-L1j. In one embodiment, the Degron is of Formula D2a, D2a', D2b, or D2b', and the Linker is L1p or L1q. In one embodiment, the Degron is of Formula D2a, D2a', D2b, or D2b', and the Linker is L1a, L1b, L1e, L1h, L1k, L1l or L1o. In one embodiment, the Degron is of Formula D2a, D2a', D2b, or D2b', and the Linker is L1c, L1d, L1f, L1g, L1i, L1j, L1m, or L1n. In one embodiment, the Degron is of Formula D2a, D2a', D2b, or D2b', and the Linker is L1k. In one embodiment, the Degron is of Formula D2a, D2a', D2b, or D2b', and the Linker is L1l or L1o. In one embodiment, the Degron is of Formula D2a, D2a', D2b, or D2b', and the Linker is L1c or L1d. In one embodiment, the Degron is of Formula D2a, D2a', D2b, or D2b', and the Linker is L1f or L1g. In one embodiment, the Degron is of Formula D2a, D2a', D2b, or D2b', and the Linker is L1i or L1j. In one embodiment, the Degron is of Formula D2a, D2a', D2b, or D2b', and the Linker is L1m or L1n.

In one embodiment, the present application relates to the Degron-Linker (DL), wherein the Degron is of Formula D2c, D2c', D2d, or D2d', and the Linker is selected from L1a-L1o. In one embodiment, the present application relates to the Degron-Linker (DL), wherein the Degron is of Formula D2c, D2c', D2d, or D2d', and the Linker is selected from L1a. In one embodiment, the Degron is of Formula D2c, D2c', D2d, or D2d', and the Linker is selected from L1b-L1d. In one embodiment, the Degron is of Formula D2c, D2c', D2d, or D2d', and the Linker is selected from L1e-L1g. In one embodiment, the Degron is of Formula D2c, D2c', D2d, or D2d', and the Linker is L1h-L1j. In one embodiment, the Degron is of Formula D2c, D2c', D2d, or D2d', and the Linker is L1p or L1q. In one embodiment, the Degron is of Formula D2c, D2c', D2d, or D2d', and the Linker is L1a, L1b, L1e, L1h, L1k, L1l or L1o. In one embodiment, the Degron is of Formula D2c, D2c', D2d, or D2d', and the Linker is L1c, L1d, L1f, L1g, L1i, L1j, L1m, or L1n. In one embodiment, the Degron is of Formula D2c, D2c', D2d, or D2d', and the Linker is L1k. In one embodiment, the Degron is of Formula D2c, D2c', D2d, or D2d', and the Linker is L1l or L1o. In one embodiment, the Degron is of Formula D2c, D2c', D2d, or D2d', and the Linker is L1c or L1d. In one embodiment, the Degron is of Formula D2c, D2c', D2d, or D2d', and the Linker is L1f or L1g. In one embodiment, the Degron is of Formula D2c, D2c', D2d, or D2d', and the Linker is L1i or L1j. In one embodiment, the Degron is of Formula D2c, D2c', D2d, or D2d', and the Linker is L1m or L1n.

In one embodiment, the present application relates to the Degron-Linker (DL), wherein the Degron is of Formula D3, and the Linker is selected from L1a-L1o. In one embodiment, the present application relates to the Degron-Linker (DL), wherein the Degron is of Formula D3, and the Linker is selected from L1a. In one embodiment, the Degron is of Formula D3, and the Linker is selected from L1b-L1d. In one embodiment, the Degron is of Formula D3, and the Linker is selected from L1e-L1g. In one embodiment, the Degron is of Formula D3, and the Linker is L1h-L1j. In one embodiment, the Degron is of Formula D3, and the Linker is L1p or L1q. In one embodiment, the Degron is of Formula D3, and the Linker is L1a, L1b, L1e, L1h, L1k, L1l or L1o. In one embodiment, the Degron is of Formula D3, and the Linker is L1c, L1d, L1f, L1g, L1i, L1j, L1m, or L1n. In one embodiment, the Degron is of Formula D3, and the Linker is L1k. In one embodiment, the Degron is of Formula D3, and the Linker is L1l or L1o. In one embodiment, the Degron is of Formula D3, and the Linker is L1c or L1d. In one embodiment, the Degron is of Formula D3, and the Linker is L1f or L1g. In one embodiment, the Degron is of Formula D3, and the Linker is L1i or L1j. In one embodiment, the Degron is of Formula D3, and the Linker is L1m or L1n.

In one embodiment, the present application relates to the Degron-Linker (DL), wherein the Degron is of Formula D3a, D3b, or D3c, and the Linker is selected from L1a-L1o. In one embodiment, the present application relates to the Degron-Linker (DL), wherein the Degron is of Formula D3a, D3b, or D3c, and the Linker is selected from L1a. In one embodiment, the Degron is of Formula D3a, D3b, or D3c, and the Linker is selected from L1b-L1d. In one embodiment, the Degron is of Formula D3a, D3b, or D3c, and the Linker is selected from L1e-L1g. In one embodiment, the Degron is of Formula D3a, D3b, or D3c, and the Linker is L1h-L1j. In one embodiment, the Degron is of Formula D3a, D3b, or D3c, and the Linker is L1p or L1q. In one embodiment, the Degron is of Formula D3a, D3b, or D3c, and the Linker is L1a, L1b, L1e, L1h, L1k, L1l or L1o. In one embodiment, the Degron is of Formula D3a, D3b, or D3c, and the Linker is L1c, L1d, L f, L1g, L1i, L1j, L1m, or L1n. In one embodiment, the Degron is of Formula D3a, D3b, or D3c, and the Linker is L1k. In one embodiment, the Degron is of Formula D3a, D3b, or D3c, and the Linker is L1l or L1o. In one embodiment, the Degron is of Formula D3a, D3b, or D3c, and the Linker is L1c or L1d. In one embodiment, the Degron is of Formula D3a, D3b, or D3c, and the Linker is L1f or L1g. In one embodiment, the Degron is of Formula D3a, D3b, or D3c, and the Linker is L1i or L1j. In one embodiment, the Degron is of Formula D3a, D3b, or D3c, and the Linker is L1m or L1n.

In one embodiment, the Linker is of Formula L2:

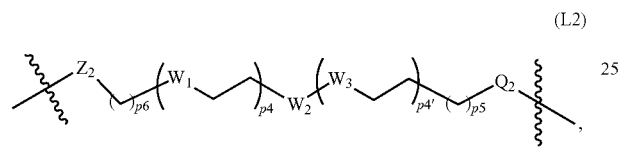

(L2)

or an enantiomer, diastereomer, or stereoisomer thereof, wherein p4 and p4' are each independently an integer selected from 0 to 12;

p5 is an integer selected from 0 to 12;

p6 is an integer selected from 1 to 6;

each $W_1$ is independently absent, $CH_2$, O, S, or $NR_{25}$;

$W_2$ is $NR_{25}C(O)(CH_2)_{0-2}$ or

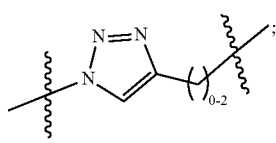

each $W_3$ is independently absent, $CH_2$, O, S, or $NR_{25}$;

$Z_2$ is absent, C(O), $CH_2$, O, $(CH_2)_{j1}NR_{25}$, $O(CH_2)_{j1}C(O)NR_{25}$, $C(O)NR_{25}$, $(CH_2)_{j1}C(O)NR_{25}$, $NR_{25}C(O)$, $(CH_2)_{j1}NR_{25}C(O)$, $(CH_2)_{k1}NR_{25}(CH_2)_{j1}C(O)NR_{25}$, or $NR_{25}(CH_2)_{j1}C(O)NR_{25}$;

each $R_2$ is independently H or $C_1$-$C_3$ alkyl;

j1 is 1, 2, or 3;

k1 is 1, 2, or 3; and $Q_2$ is absent, C(O), $NHC(O)CH_2$, or $O(CH_2)_{1-2}$;

wherein the Linker is covalently bonded to a Degron via

the next to $Q_2$, and covalently bonded to a Targeting Ligand via the

next to $Z_2$, or the Linker is covalently bonded to a Degron via the

next to $Z_2$, and covalently bonded to a Targeting Ligand via the

next to $Q_2$.

For a Linker of Formula L2:

(1) In one embodiment, p4 is an integer selected from 0 to 10
(2) In one embodiment, p4 is an integer selected from 1 to 10.
(3) In one embodiment, p4 is selected from 1, 2, 3, 4, 5, and 6.
(4) In one embodiment, p4 is 0, 1, 3, or 5.
(5) In one embodiment, p4 is 0, 1, 2, or 3.
(6) In one embodiment, p4 is 0.
(7) In one embodiment, p4 is 1.
(8) In one embodiment, p4 is 2.
(9) In one embodiment, p4 is 3.
(10) In one embodiment, p4 is 4.
(11) In one embodiment, p4 is 5.
(12) In one embodiment, p4' is an integer selected from 0 to 10.
(13) In one embodiment, p4' is an integer selected from 1 to 10.
(14) In one embodiment, p4' is selected from 1, 2, 3, 4, 5, and 6.
(15) In one embodiment, p4' is 0, 1, 3, or 5.
(16) In one embodiment, p4' is 0, 1, 2, or 3.
(17) In one embodiment, p4' is 0.
(18) In one embodiment, p4' is 1.
(19) In one embodiment, p4' is 2.
(20) In one embodiment, p4' is 3.
(21) In one embodiment, p4' is 4.
(22) In one embodiment, p4' is 5.
(23) In one embodiment, p5 is an integer selected from 0 to 10.
(24) In one embodiment, p5 is selected from 0, 1, 2, 3, 4, 5, and 6.
(25) In one embodiment, p5 is 0, 1, 2, or 3.
(26) In one embodiment, p5 is 0.
(27) In one embodiment, p5 is 1.
(28) In one embodiment, p5 is 2.
(29) In one embodiment, p5 is 3.

(30) In one embodiment, p6 is an integer selected from 1 to 5.
(31) In one embodiment, p6 is 2, 3, 4, or 5.
(32) In one embodiment, p6 is 0, 1, 2, or 3.
(33) In one embodiment, p6 is 0.
(34) In one embodiment, p6 is 1.
(35) In one embodiment, p6 is 2.
(36) In one embodiment, p6 is 3.
(37) In one embodiment, p6 is 4.
(38) In one embodiment, at least one $W_1$ is $CH_2$.
(39) In one embodiment, at least one $W_1$ is O.
(40) In one embodiment, at least one $W_1$ is S.
(41) In one embodiment, at least one $W_1$ is NH.
(42) In one embodiment, at least one $W_1$ is $NR_{25}$; and each $R_{25}$ is independently $C_1$-$C_3$ alkyl selected from methyl, ethyl, and propyl.
(43) In one embodiment, each $W_1$ is O.
(44) In one embodiment, each $W_1$ is $CH_2$.
(45) In one embodiment, $W_2$ is $NR_{25}(O)CH_2$—; and $R_{25}$ is $C_1$-$C_3$ alkyl selected from methyl, ethyl, and propyl.
(46) In one embodiment, $W_2$ is $NR_{25}C(O)CH_2$—; and $R_{25}$ is H.
(47) In one embodiment, $W_2$ is

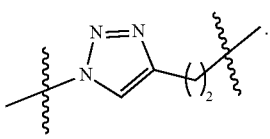

(48) In one embodiment, $W_2$ is

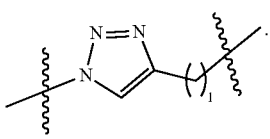

(49) In one embodiment, $W_2$ is

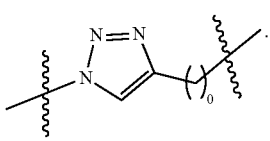

(50) In one embodiment, at least one $W_3$ is $CH_2$.
(51) In one embodiment, at least one $W_3$ is O.
(52) In one embodiment, at least one $W_3$ is S.
(53) In one embodiment, at least one $W_3$ is NH.
(54) In one embodiment, at least one $W_3$ is $NR_{25}$; and each $R_{25}$ is independently $C_1$-$C_3$ alkyl selected from methyl, ethyl, and propyl.
(55) In one embodiment, each $W_3$ is O.
(56) In one embodiment, each $W_3$ is $CH_2$.
(57) In one embodiment, j1 is 1, 2, or 3.
(58) In one embodiment, j1 is 1.
(59) In one embodiment, j1 is 2.
(60) In one embodiment, j1 is 3.
(61) In one embodiment, j1 is 2 or 3.
(62) In one embodiment, j1 is 1 or 2.
(63) In one embodiment, k1 is 1, 2, or 3.
(64) In one embodiment, k1 is 1.
(65) In one embodiment, k1 is 2.
(66) In one embodiment, k1 is 3.
(67) In one embodiment, k1 is 2 or 3.
(68) In one embodiment, k1 is 1 or 2.
(69) In one embodiment, $Q_2$ is absent.
(70) In one embodiment, $Q_2$ is $NHC(O)CH_2$.
(71) In one embodiment, $Q_2$ is $O(CH_2)_{1-2}$.
(72) In one embodiment, $Q_2$ is $OCH_2$.
(73) In one embodiment, $Q_2$ is $OCH_2CH_2$.
(74) In one embodiment, $Q_2$ is $OCH_2C(O)$.
(75) In one embodiment, $Q_2$ is $C(O)$.
(76) In one embodiment, $Z_2$ is absent.
(77) In one embodiment, $Z_2$ is $O(CH_2)_{j1}C(O)NR_{25}$; and $R_{25}$ is $C_1$-$C_3$ alkyl selected from methyl, ethyl, and propyl.
(78) In one embodiment, $Z_2$ is $O(CH_2)_{j1}C(O)NR_{25}$; and $R_{25}$ is H.
(79) In one embodiment, $Z_2$ is $O(CH_2)_{j1}C(O)NR_{25}$; $R_{25}$ is $C_1$-$C_3$ alkyl selected from methyl, ethyl, and propyl; and j1 is 1.
(80) In one embodiment, $Z_2$ is $O(CH_2)_{j1}C(O)NR_{25}$; $R_{25}$ is H; and j1 is 1.
(81) In one embodiment, $Z_2$ is $O(CH_2)_{j1}C(O)NR_{25}$; $R_{25}$ is $C_1$-$C_3$ alkyl selected from methyl, ethyl, and propyl; and j1 is 2.
(82) In one embodiment, $Z_2$ is $O(CH_2)_{j1}C(O)NR_{25}$; $R_{25}$ is H; and j1 is 2.
(83) In one embodiment, $Z_2$ is $O(CH_2)_{j1}C(O)NR_{25}$; $R_{25}$ is $C_1$-$C_3$ alkyl selected from methyl, ethyl, and propyl; and j1 is 3.
(84) In one embodiment, $Z_2$ is $O(CH_2)_{j1}C(O)NR_{25}$; and $R_{25}$ is H; and j1 is 3.
(85) In one embodiment, $Z_2$ is $C(O)NR_{25}$; and $R_{25}$ is H.
(86) In one embodiment, $Z_2$ is $C(O)NR_{25}$; and $R_{25}$ is $C_1$-$C_3$ alkyl selected from methyl, ethyl, and propyl.
(87) In one embodiment, $Z_2$ is $(CH_2)_{j1}C(O)NR_{25}$; and $R_{25}$ is H.
(88) In one embodiment, $Z_2$ is $(CH_2)_{j1}C(O)NR_{25}$; and $R_{25}$ is $C_1$-$C_3$ alkyl selected from methyl, ethyl, and propyl.
(89) In one embodiment, $Z_2$ is $(CH_2)_{j1}C(O)NR_{25}$; $R_2$ is H; and j1 is 1.
(90) In one embodiment, $Z_2$ is $(CH_2)_{j1}C(O)NR_{25}$; $R_{25}$ is $C_1$-$C_3$ alkyl selected from methyl, ethyl, and propyl; and j1 is 1
(91) In one embodiment, $Z_2$ is $(CH_2)_{j1}C(O)NR_2$; $R_{25}$ is H; and j1 is 2.
(92) In one embodiment, $Z_2$ is $(CH_2)_{j1}C(O)NR_{25}$; $R_{25}$ is $C_1$-$C_3$ alkyl selected from methyl, ethyl, and propyl; and j1 is 2.
(93) In one embodiment, $Z_2$ is $(CH_2)_{j1}C(O)NR_2$; $R_{25}$ is H; and j1 is 3.
(94) In one embodiment, $Z_2$ is $(CH_2)_{j1}C(O)NR_{25}$; $R_{25}$ is $C_1$-$C_3$ alkyl selected from methyl, ethyl, and propyl; and j1 is 3.
(95) In one embodiment, $Z_2$ is $NR_{25}C(O)$; and $R_{25}$ is H.
(96) In one embodiment, $Z_2$ is $NR_{25}C(O)$; and $R_{25}$ is $C_1$-$C_3$ alkyl selected from methyl, ethyl, and propyl.
(97) In one embodiment, $Z_2$ is $(CH_2)_{j1}NR_{25}C(O)$; and $R_{25}$ is H.
(98) In one embodiment, $Z_2$ is $(CH_2)_{j1}NR_{25}C(O)$; and $R_{25}$ is $C_1$-$C_3$ alkyl selected from methyl, ethyl, and propyl.
(99) In one embodiment, $Z_2$ is $(CH_2)_{j1}NR_{25}C(O)$; $R_2$ is H; and j1 is 1.
(100) In one embodiment, $Z_2$ is $(CH_2)_{j1}NR_{25}C(O)$; $R_{25}$ is $C_1$-$C_3$ alkyl selected from methyl, ethyl, and propyl; and j1 is 1
(101) In one embodiment, $Z_2$ is $(CH_2)_{j1}NR_{25}C(O)$; $R_{25}$ is H; and j1 is 2.

(102) In one embodiment, $Z_2$ is $(CH_2)_{j1}NR_{25}C(O)$; $R_{25}$ is $C_1$-$C_3$ alkyl selected from methyl, ethyl, and propyl; and j1 is 2.

(103) In one embodiment, $Z_2$ is $(CH_2)_{j1}NR_{25}C(O)$; $R_{25}$ is H; and j1 is 3.

(104) In one embodiment, $Z_2$ is $(CH_2)_{j1}NR_{25}C(O)$; $R_2$ is $C_1$-$C_3$ alkyl selected from methyl, ethyl, and propyl; and j1 is 3.

(105) In one embodiment, $Z_2$ is $(CH_2)_{k1}NR_{25}(CH_2)_{j1}C(O)NR_{25}$; and each $R_{25}$ is independently H or $C_1$-$C_3$ alkyl selected from methyl, ethyl, and propyl.

(106) In one embodiment, $Z_2$ is $(CH_2)_{k1}NR_{25}(CH_2)_{j1}C(O)NR_{25}$; and one of $R_{25}$ is H and one of $R_{25}$ is $C_1$-$C_3$ alkyl selected from methyl, ethyl, and propyl. In one embodiment, $Z_2$ is $(CH_2)_{k1}NR_{25}(CH_2)_{j1}C(O)NH$.

(107) In one embodiment, $Z_2$ is $(CH_2)_{k1}NR_{25}(CH_2)_{j1}C(O)NR_{25}$; each $R_2$ is independently H or $C_1$-$C_3$ alkyl selected from methyl, ethyl, and propyl; and j1 is 1.

(108) In one embodiment, $Z_2$ is $(CH_2)_{k1}NR_{25}(CH_2)_{j1}C(O)NR_{25}$; each $R_2$ is independently H or $C_1$-$C_3$ alkyl selected from methyl, ethyl, and propyl; and k1 is 1.

(109) In one embodiment, $Z_2$ is $(CH_2)_{k1}NR_{25}(CH_2)_{j1}C(O)NR_{25}$; each $R_{25}$ is independently H or $C_1$-$C_3$ alkyl selected from methyl, ethyl, and propyl; j is 1; and k1 is 1.

(110) In one embodiment, $Z_2$ is $(CH_2)_{k1}NR_{25}(CH_2)_{j1}C(O)NR_{25}$; one of $R_{25}$ is H and one of $R_{25}$ is $C_1$-$C_3$ alkyl selected from methyl, ethyl, and propyl; and j1 is 1. In one embodiment, $Z_2$ is $(CH_2)_{k1}NR_{25}(CH_2)C(O)NH$.

(111) In one embodiment, $Z_2$ is $(CH_2)_{k1}NR_{25}(CH_2)_{j1}C(O)NR_{25}$; one of $R_{25}$ is H and one of $R_{25}$ is $C_1$-$C_3$ alkyl selected from methyl, ethyl, and propyl; and k1 is 1. In one embodiment, $Z_2$ is $(CH_2)NR_{25}(CH_2)_{j1}C(O)NH$.

(112) In one embodiment, $Z_2$ is $(CH_2)_{k1}NR_{25}(CH_2)_{j1}C(O)NR_{25}$; one of $R_{25}$ is H and one of $R_2$ is $C_1$-$C_3$ alkyl selected from methyl, ethyl, and propyl; j1 is 1; and k1 is 1. In one embodiment, $Z_2$ is $(CH_2)NR_{25}(CH_2)C(O)NH$. In one embodiment, $Z_2$ is $(CH_2)N(CH_3)(CH_2)C(O)NH$.

(113) In one embodiment, $Z_2$ is $(CH_2)_{k1}NR_{25}(CH_2)_{j1}C(O)NR_2$; each $R_{25}$ is independently H or $C_1$-$C_3$ alkyl selected from methyl, ethyl, and propyl; and j1 is 2.

(114) In one embodiment, $Z_2$ is $(CH_2)_{k1}NR_{25}(CH_2)_{j1}C(O)NR_{25}$; each $R_{25}$ is independently H or $C_1$-$C_3$ alkyl selected from methyl, ethyl, and propyl; and k1 is 2.

(115) In one embodiment, $Z_2$ is $(CH_2)_{k1}NR_{25}(CH_2)_{j1}C(O)NR_{25}$; one of $R_{25}$ is H and one of $R_{25}$ is $C_1$-$C_3$ alkyl selected from methyl, ethyl, and propyl; and j1 is 2. In one embodiment, $Z_2$ is $(CH_2)_{k1}NR_{25}(CH_2)_2C(O)NH$.

(116) In one embodiment, $Z_2$ is $(CH_2)_{k1}NR_{25}(CH_2)_{j1}C(O)NR_{25}$; one of $R_{25}$ is H and one of $R_{25}$ is $C_1$-$C_3$ alkyl selected from methyl, ethyl, and propyl; and k1 is 2. In one embodiment, $Z_2$ is $(CH_2)_2NR_{25}(CH_2)_{j1}C(O)NH$.

(117) In one embodiment, $Z_2$ is $(CH_2)_{k1}NR_{25}(CH_2)_{j1}C(O)NR_{25}$; each $R_{25}$ is independently H or $C_1$-$C_3$ alkyl selected from methyl, ethyl, and propyl; and j1 is 3.

(118) In one embodiment, $Z_2$ is $(CH_2)_{k1}NR_{25}(CH_2)_{j1}C(O)NR_{25}$; each $R_{25}$ is independently H or $C_1$-$C_3$ alkyl selected from methyl, ethyl, and propyl; and k1 is 3.

(119) In one embodiment, $Z_2$ is $(CH_2)_{k1}NR_{25}(CH_2)_{j1}C(O)NR_{25}$; one of $R_{25}$ is H and one of $R_{25}$ is $C_1$-$C_3$ alkyl selected from methyl, ethyl, and propyl; and j1 is 3. In one embodiment, $Z_2$ is $(CH_2)_{k1}NR_{25}(CH_2)_3C(O)NH$.

(120) In one embodiment, $Z_2$ is $(CH_2)_{j1}NR_{25}(CH_2)_{j1}C(O)NR_{25}$; one of $R_{25}$ is H and one of $R_{25}$ is $C_1$-$C_3$ alkyl selected from methyl, ethyl, and propyl; and k1 is 3. In one embodiment, $Z_2$ is $(CH_2)_3NR_{25}(CH_2)_{j1}C(O)NH$.

(121) In one embodiment, $Z_2$ is $NR_{21}(CH_2)_{j1}C(O)NR_{25}$; and each $R_{25}$ is independently H or $C_1$-$C_3$ alkyl selected from methyl, ethyl, and propyl.

(122) In one embodiment, $Z_2$ is $NR_{25}(CH_2)_{j1}C(O)NR_{25}$; and each $R_{25}$ is H.

(123) In one embodiment, $Z_2$ is $NR_{25}(CH_2)_{j1}C(O)NR_{25}$; one of $R_2$ is H and one of $R_{25}$ is $C_1$-$C_3$ alkyl selected from methyl, ethyl, and propyl; and j1 is 1.

(124) In one embodiment, $Z_2$ is $NR_{21}(CH_2)_{j1}C(O)NR_{25}$; $R_{25}$ is H; and j1 is 1.

(125) In one embodiment, $Z_2$ is $NR_{25}(CH_2)_{j1}C(O)NR_{25}$; one of $R_{25}$ is H and one of $R_{25}$ is $C_1$-$C_3$ alkyl selected from methyl, ethyl, and propyl; and j1 is 2.

(126) In one embodiment, $Z_2$ is $NR_{25}(CH_2)_{j1}C(O)NR_2$; $R_{25}$ is H; and j1 is 2.

(127) In one embodiment, $Z_2$ is $NR_5(CH_2)_{j1}C(O)NR_{25}$; one of $R_{25}$ is H and one of $R_{25}$ is $C_1$-$C_3$ alkyl selected from methyl, ethyl, and propyl; and j1 is 3.

(128) In one embodiment, $Z_2$ is absent and p6 is 1.
(129) In one embodiment, $Z_2$ is absent and p6 is 2.
(130) In one embodiment, $Z_2$ is absent and p6 is 3.
(131) In one embodiment, $Z_2$ is absent, p6 is 1, and p4 is 1-5.
(132) In one embodiment, $Z_2$ is absent, p6 is 1, and p4 is 1.
(133) In one embodiment, $Z_2$ is absent, p6 is 1, and p4 is 2.
(134) In one embodiment, $Z_2$ is absent, p6 is 1, and p4 is 3.
(135) In one embodiment, $Z_2$ is absent, p6 is 1, and p4 is 4.
(136) In one embodiment, $Z_2$ is absent, p6 is 1, and p4 is 5.
(137) In one embodiment, $Z_2$ is absent, p6 is 2, and p4 is 1-5.
(138) In one embodiment, $Z_2$ is absent, p6 is 2, and p4 is 1.
(139) In one embodiment, $Z_2$ is absent, p6 is 2, and p4 is 2.
(140) In one embodiment, $Z_2$ is absent, p6 is 2, and p4 is 3.
(141) In one embodiment, $Z_2$ is absent, p6 is 2, and p4 is 4.
(142) In one embodiment, $Z_2$ is absent, p6 is 2, and p4 is 5.
(143) In one embodiment, $Z_2$ is absent, p6 is 2, and p4 is 1-5.
(144) In one embodiment, $Z_2$ is absent, p6 is 2, and p4 is 1.
(145) In one embodiment, $Z_2$ is absent, p6 is 2, and p4 is 2.
(146) In one embodiment, $Z_2$ is absent, p6 is 2, and p4 is 3.
(147) In one embodiment, $Z_2$ is absent, p6 is 2, and p4 is 4.
(148) In one embodiment, $Z_2$ is absent, p6 is 2, and p4 is 5.
(149) In one embodiment, $Z_2$ is absent, p6 is 1, p4 is 1, and p4' is 1.
(150) In one embodiment, $Z_2$ is absent, p6 is 1, p4 is 1, and p4' is 2.
(151) In one embodiment, $Z_2$ is absent, p6 is 1, p4 is 1, and p4' is 3.
(152) In one embodiment, $Z_2$ is absent, p6 is 1, p4 is 1, and p4' is 4.
(153) In one embodiment, $Z_2$ is absent, p6 is 1, p4 is 1, and p4' is 5.
(154) In one embodiment, $Z_2$ is absent, p6 is 1, p4 is 2, and p4' is 1.
(155) In one embodiment, $Z_2$ is absent, p6 is 1, p4 is 2, and p4' is 2.
(156) In one embodiment, $Z_2$ is absent, p6 is 1, p4 is 2, and p4' is 3.
(157) In one embodiment, $Z_2$ is absent, p6 is 1, p4 is 2, and p4' is 4.
(158) In one embodiment, $Z_2$ is absent, p6 is 1, p4 is 2, and p4' is 5.
(159) In one embodiment, $Z_2$ is absent, p6 is 1, p4 is 3, and p4' is 1.
(160) In one embodiment, $Z_2$ is absent, p6 is 1, p4 is 3, and p4' is 2.
(161) In one embodiment, $Z_2$ is absent, p6 is 1, p4 is 3, and p4' is 3.
(162) In one embodiment, $Z_2$ is absent, p6 is 1, p4 is 3, and p4' is 4.

(163) In one embodiment, $Z_2$ is absent, p6 is 1, p4 is 3, and p4' is 5.
(164) In one embodiment, $Z_2$ is absent, p6 is 1, p4 is 4, and p4' is 1.
(165) In one embodiment, $Z_2$ is absent, p6 is 1, p4 is 4, and p4' is 2.
(166) In one embodiment, $Z_2$ is absent, p6 is 1, p4 is 4, and p4' is 3.
(167) In one embodiment, $Z_2$ is absent, p6 is 1, p4 is 4, and p4' is 4.
(168) In one embodiment, $Z_2$ is absent, p6 is 1, p4 is 4, and p4' is 5.
(169) In one embodiment, $Z_2$ is absent, p6 is 1, p4 is 5, and p4' is 1.
(170) In one embodiment, $Z_2$ is absent, p6 is 1, p4 is 5, and p4' is 2.
(171) In one embodiment, $Z_2$ is absent, p6 is 1, p4 is 5, and p4' is 3.
(172) In one embodiment, $Z_2$ is absent, p6 is 1, p4 is 5, and p4' is 4.
(173) In one embodiment, $Z_2$ is absent, p6 is 1, p4 is 5, and p4' is 5.
(174) In one embodiment, $Z_2$ is absent, p6 is 2, p4 is 1, and p4' is 1.
(175) In one embodiment, $Z_2$ is absent, p6 is 2, p4 is 1, and p4' is 2.
(176) In one embodiment, $Z_2$ is absent, p6 is 2, p4 is 1, and p4' is 3.
(177) In one embodiment, $Z_2$ is absent, p6 is 2, p4 is 1, and p4' is 4.
(178) In one embodiment, $Z_2$ is absent, p6 is 2, p4 is 1, and p4' is 5.
(179) In one embodiment, $Z_2$ is absent, p6 is 2, p4 is 2, and p4' is 1.
(180) In one embodiment, $Z_2$ is absent, p6 is 2, p4 is 2, and p4' is 2.
(181) In one embodiment, $Z_2$ is absent, p6 is 2, p4 is 2, and p4' is 3.
(182) In one embodiment, $Z_2$ is absent, p6 is 2, p4 is 2, and p4' is 4.
(183) In one embodiment, $Z_2$ is absent, p6 is 2, p4 is 2, and p4' is 5.
(184) In one embodiment, $Z_2$ is absent, p6 is 2, p4 is 3, and p4' is 1.
(185) In one embodiment, $Z_2$ is absent, p6 is 2, p4 is 3, and p4' is 2.
(186) In one embodiment, $Z_2$ is absent, p6 is 2, p4 is 3, and p4' is 3.
(187) In one embodiment, $Z_2$ is absent, p6 is 2, p4 is 3, and p4' is 4.
(188) In one embodiment, $Z_2$ is absent, p6 is 2, p4 is 3, and p4' is 5.
(189) In one embodiment, $Z_2$ is absent, p6 is 2, p4 is 4, and p4' is 1.
(190) In one embodiment, $Z_2$ is absent, p6 is 2, p4 is 4, and p4' is 2.
(191) In one embodiment, $Z_2$ is absent, p6 is 2, p4 is 4, and p4' is 3.
(192) In one embodiment, $Z_2$ is absent, p6 is 2, p4 is 4, and p4' is 4.
(193) In one embodiment, $Z_2$ is absent, p6 is 2, p4 is 4, and p4' is 5.
(194) In one embodiment, $Z_2$ is absent, p6 is 2, p4 is 5, and p4' is 1.
(195) In one embodiment, $Z_2$ is absent, p6 is 2, p4 is 5, and p4' is 2.
(196) In one embodiment, $Z_2$ is absent, p6 is 2, p4 is 5, and p4' is 3.
(197) In one embodiment, $Z_2$ is absent, p6 is 2, p4 is 5, and p4' is 4.
(198) In one embodiment, $Z_2$ is absent, p6 is 2, p4 is 5, and p4' is 5.
(199) In one embodiment, $Z_2$ is absent, p6 is 1, and $W_1$ is O.
(200) In one embodiment, $Z_2$ is absent, p6 is 2, and $W_1$ is O.
(201) In one embodiment, $Z_2$ is absent, p6 is 3, and $W_1$ is O.
(202) In one embodiment, $Z_2$ is absent, p6 is 1, p4 is 1, p4' is 1, and $W_1$ is O.
(203) In one embodiment, $Z_2$ is absent, p6 is 1, p4 is 1, p4' is 2, and $W_1$ is O.
(204) In one embodiment, $Z_2$ is absent, p6 is 1, p4 is 1, p4' is 3, and $W_1$ is O.
(205) In one embodiment, $Z_2$ is absent, p6 is 1, p4 is 1, p4' is 4, and $W_1$ is O.
(206) In one embodiment, $Z_2$ is absent, p6 is 1, p4 is 1, p4' is 5, and $W_1$ is O.
(207) In one embodiment, $Z_2$ is absent, p6 is 1, p4 is 2, p4' is 1, and $W_1$ is O.
(208) In one embodiment, $Z_2$ is absent, p6 is 1, p4 is 2, p4' is 2, and $W_1$ is O.
(209) In one embodiment, $Z_2$ is absent, p6 is 1, p4 is 2, p4' is 3, and $W_1$ is O.
(210) In one embodiment, $Z_2$ is absent, p6 is 1, p4 is 2, p4' is 4, and $W_1$ is O.
(211) In one embodiment, $Z_2$ is absent, p6 is 1, p4 is 2, p4' is 5, and $W_1$ is O.
(212) In one embodiment, $Z_2$ is absent, p6 is 1, p4 is 3, p4' is 1, and $W_1$ is O.
(213) In one embodiment, $Z_2$ is absent, p6 is 1, p4 is 3, p4' is 2, and $W_1$ is O.
(214) In one embodiment, $Z_2$ is absent, p6 is 1, p4 is 3, p4' is 3, and $W_1$ is O.
(215) In one embodiment, $Z_2$ is absent, p6 is 1, p4 is 3, p4' is 4, and $W_1$ is O.
(216) In one embodiment, $Z_2$ is absent, p6 is 1, p4 is 3, p4' is 5, and $W_1$ is O.
(217) In one embodiment, $Z_2$ is absent, p6 is 1, p4 is 4, p4' is 1, and $W_1$ is O.
(218) In one embodiment, $Z_2$ is absent, p6 is 1, p4 is 4, p4' is 2, and $W_1$ is O.
(219) In one embodiment, $Z_2$ is absent, p6 is 1, p4 is 4, p4' is 3, and $W_1$ is O.
(220) In one embodiment, $Z_2$ is absent, p6 is 1, p4 is 4, p4' is 4, and $W_1$ is O.
(221) In one embodiment, $Z_2$ is absent, p6 is 1, p4 is 4, p4' is 5, and $W_1$ is O.
(222) In one embodiment, $Z_2$ is absent, p6 is 1, p4 is 5, p4' is 1, and W is O.
(223) In one embodiment, $Z_2$ is absent, p6 is 1, p4 is 5, p4' is 2, and W is O.
(224) In one embodiment, $Z_2$ is absent, p6 is 1, p4 is 5, p4' is 3, and W is O.
(225) In one embodiment, $Z_2$ is absent, p6 is 1, p4 is 5, p4' is 4, and W is O.
(226) In one embodiment, $Z_2$ is absent, p6 is 1, p4 is 5, p4' is 5, and W is O.
(227) In one embodiment, $Z_2$ is absent, p6 is 1, p4 is 1, p4' is 1, and $W_1$ is $CH_2$.
(228) In one embodiment, $Z_2$ is absent, p6 is 1, p4 is 1, p4' is 2, and $W_1$ is $CH_2$.
(229) In one embodiment, $Z_2$ is absent, p6 is 1, p4 is 1, p4' is 3, and $W_1$ is $CH_2$.
(230) In one embodiment, $Z_2$ is absent, p6 is 1, p4 is 1, p4' is 4, and $W_1$ is $CH_2$.

(231) In one embodiment, $Z_2$ is absent, p6 is 1, p4 is 1, p4' is 5, and $W_1$ is $CH_2$.
(232) In one embodiment, $Z_2$ is absent, p6 is 1, p4 is 2, p4' is 1, and $W_1$ is $CH_2$.
(233) In one embodiment, $Z_2$ is absent, p6 is 1, p4 is 2, p4' is 2, and $W_1$ is $CH_2$.
(234) In one embodiment, $Z_2$ is absent, p6 is 1, p4 is 2, p4' is 3, and $W_1$ is $CH_2$.
(235) In one embodiment, $Z_2$ is absent, p6 is 1, p4 is 2, p4' is 4, and $W_1$ is $CH_2$.
(236) In one embodiment, $Z_2$ is absent, p6 is 1, p4 is 2, p4' is 5, and $W_1$ is $CH_2$.
(237) In one embodiment, $Z_2$ is absent, p6 is 1, p4 is 3, p4' is 1, and $W_1$ is $CH_2$.
(238) In one embodiment, $Z_2$ is absent, p6 is 1, p4 is 3, p4' is 2, and $W_1$ is $CH_2$.
(239) In one embodiment, $Z_2$ is absent, p6 is 1, p4 is 3, p4' is 3, and $W_1$ is $CH_2$.
(240) In one embodiment, $Z_2$ is absent, p6 is 1, p4 is 3, p4' is 4, and $W_1$ is $CH_2$.
(241) In one embodiment, $Z_2$ is absent, p6 is 1, p4 is 3, p4' is 5, and $W_1$ is $CH_2$.
(242) In one embodiment, $Z_2$ is absent, p6 is 1, p4 is 4, p4' is 1, and $W_1$ is $CH_2$.
(243) In one embodiment, $Z_2$ is absent, p6 is 1, p4 is 4, p4' is 2, and $W_1$ is $CH_2$.
(244) In one embodiment, $Z_2$ is absent, p6 is 1, p4 is 4, p4' is 3, and $W_1$ is $CH_2$.
(245) In one embodiment, $Z_2$ is absent, p6 is 1, p4 is 4, p4' is 4, and $W_1$ is $CH_2$.
(246) In one embodiment, $Z_2$ is absent, p6 is 1, p4 is 4, p4' is 5, and $W_1$ is $CH_2$.
(247) In one embodiment, $Z_2$ is absent, p6 is 1, p4 is 5, p4' is 1, and W is $CH_2$.
(248) In one embodiment, $Z_2$ is absent, p6 is 1, p4 is 5, p4' is 2, and W is $CH_2$.
(249) In one embodiment, $Z_2$ is absent, p6 is 1, p4 is 5, p4' is 3, and W is $CH_2$.
(250) In one embodiment, $Z_2$ is absent, p6 is 1, p4 is 5, p4' is 4, and W is $CH_2$.
(251) In one embodiment, $Z_2$ is absent, p6 is 1, p4 is 5, p4' is 5, and W is $CH_2$.
(252) In one embodiment, $Z_2$ is absent, p6 is 2, p4 is 1, p4' is 1, and $W_1$ is O.
(253) In one embodiment, $Z_2$ is absent, p6 is 2, p4 is 1, p4' is 2, and $W_1$ is O.
(254) In one embodiment, $Z_2$ is absent, p6 is 2, p4 is 1, p4' is 3, and $W_1$ is O.
(255) In one embodiment, $Z_2$ is absent, p6 is 2, p4 is 1, p4' is 4, and $W_1$ is O.
(256) In one embodiment, $Z_2$ is absent, p6 is 2, p4 is 1, p4' is 5, and $W_1$ is O.
(257) In one embodiment, $Z_2$ is absent, p6 is 2, p4 is 2, p4' is 1, and $W_1$ is O.
(258) In one embodiment, $Z_2$ is absent, p6 is 2, p4 is 2, p4' is 2, and $W_1$ is O.
(259) In one embodiment, $Z_2$ is absent, p6 is 2, p4 is 2, p4' is 3, and $W_1$ is O.
(260) In one embodiment, $Z_2$ is absent, p6 is 2, p4 is 2, p4' is 4, and $W_1$ is O.
(261) In one embodiment, $Z_2$ is absent, p6 is 2, p4 is 2, p4' is 5, and $W_1$ is O.
(262) In one embodiment, $Z_2$ is absent, p6 is 2, p4 is 3, p4' is 1, and $W_1$ is O.
(263) In one embodiment, $Z_2$ is absent, p6 is 2, p4 is 3, p4' is 2, and $W_1$ is O.
(264) In one embodiment, $Z_2$ is absent, p6 is 2, p4 is 3, p4' is 3, and $W_1$ is O.
(265) In one embodiment, $Z_2$ is absent, p6 is 2, p4 is 3, p4' is 4, and $W_1$ is O.
(266) In one embodiment, $Z_2$ is absent, p6 is 2, p4 is 3, p4' is 5, and $W_1$ is O.
(267) In one embodiment, $Z_2$ is absent, p6 is 2, p4 is 4, p4' is 1, and $W_1$ is O.
(268) In one embodiment, $Z_2$ is absent, p6 is 2, p4 is 4, p4' is 2, and $W_1$ is O.
(269) In one embodiment, $Z_2$ is absent, p6 is 2, p4 is 4, p4' is 3, and $W_1$ is O.
(270) In one embodiment, $Z_2$ is absent, p6 is 2, p4 is 4, p4' is 4, and $W_1$ is O.
(271) In one embodiment, $Z_2$ is absent, p6 is 2, p4 is 4, p4' is 5, and $W_1$ is O.
(272) In one embodiment, $Z_2$ is absent, p6 is 2, p4 is 5, p4' is 1, and W is O.
(273) In one embodiment, $Z_2$ is absent, p6 is 2, p4 is 5, p4' is 2, and W is O.
(274) In one embodiment, $Z_2$ is absent, p6 is 2, p4 is 5, p4' is 3, and W is O.
(275) In one embodiment, $Z_2$ is absent, p6 is 2, p4 is 5, p4' is 4, and W is O.
(276) In one embodiment, $Z_2$ is absent, p6 is 2, p4 is 5, p4' is 5, and W is O.
(277) In one embodiment, $Z_2$ is absent, p6 is 2, p4 is 1, p4' is 1, and $W_1$ is $CH_2$.
(278) In one embodiment, $Z_2$ is absent, p6 is 2, p4 is 1, p4' is 2, and $W_1$ is $CH_2$.
(279) In one embodiment, $Z_2$ is absent, p6 is 2, p4 is 1, p4' is 3, and $W_1$ is $CH_2$.
(280) In one embodiment, $Z_2$ is absent, p6 is 2, p4 is 1, p4' is 4, and $W_1$ is $CH_2$.
(281) In one embodiment, $Z_2$ is absent, p6 is 2, p4 is 1, p4' is 5, and $W_1$ is $CH_2$.
(282) In one embodiment, $Z_2$ is absent, p6 is 2, p4 is 2, p4' is 1, and $W_1$ is $CH_2$.
(283) In one embodiment, $Z_2$ is absent, p6 is 2, p4 is 2, p4' is 2, and $W_1$ is $CH_2$.
(284) In one embodiment, $Z_2$ is absent, p6 is 2, p4 is 2, p4' is 3, and $W_1$ is $CH_2$.
(285) In one embodiment, $Z_2$ is absent, p6 is 2, p4 is 2, p4' is 4, and $W_1$ is $CH_2$.
(286) In one embodiment, $Z_2$ is absent, p6 is 2, p4 is 2, p4' is 5, and $W_1$ is $CH_2$.
(287) In one embodiment, $Z_2$ is absent, p6 is 2, p4 is 3, p4' is 1, and $W_1$ is $CH_2$.
(288) In one embodiment, $Z_2$ is absent, p6 is 2, p4 is 3, p4' is 2, and $W_1$ is $CH_2$.
(289) In one embodiment, $Z_2$ is absent, p6 is 2, p4 is 3, p4' is 3, and $W_1$ is $CH_2$.
(290) In one embodiment, $Z_2$ is absent, p6 is 2, p4 is 3, p4' is 4, and $W_1$ is $CH_2$.
(291) In one embodiment, $Z_2$ is absent, p6 is 2, p4 is 3, p4' is 5, and $W_1$ is $CH_2$.
(292) In one embodiment, $Z_2$ is absent, p6 is 2, p4 is 4, p4' is 1, and $W_1$ is $CH_2$.
(293) In one embodiment, $Z_2$ is absent, p6 is 2, p4 is 4, p4' is 2, and $W_1$ is $CH_2$.
(294) In one embodiment, $Z_2$ is absent, p6 is 2, p4 is 4, p4' is 3, and $W_1$ is $CH_2$.
(295) In one embodiment, $Z_2$ is absent, p6 is 2, p4 is 4, p4' is 4, and $W_1$ is $CH_2$.
(296) In one embodiment, $Z_2$ is absent, p6 is 2, p4 is 4, p4' is 5, and $W_1$ is $CH_2$.

(297) In one embodiment, $Z_2$ is absent, p6 is 2, p4 is 5, p4' is 1, and W is $CH_2$.
(298) In one embodiment, $Z_2$ is absent, p6 is 2, p4 is 5, p4' is 2, and $W_1$ is $CH_2$.
(299) In one embodiment, $Z_2$ is absent, p6 is 2, p4 is 5, p4' is 3, and $W_1$ is $CH_2$.
(300) In one embodiment, $Z_2$ is absent, p6 is 2, p4 is 5, p4' is 4, and $W_1$ is $CH_2$.
(301) In one embodiment, $Z_2$ is absent, p6 is 2, p4 is 5, p4' is 5, and $W_1$ is $CH_2$.
(302) In one embodiment, p4, p4', $Z_2$, p6, $W_1$, $W_2$, and $W_3$ are each as defined, where applicable, in any one of (1)-(301), and p5 is 0.
(303) In one embodiment, p4, p4', $Z_2$, p6, $W_1$, $W_2$, and $W_3$ are each as defined, where applicable, in any one of (1)-(301), and p5 is 1.
(304) In one embodiment, p4, p4', $Z_2$, p6, $W_1$, $W_2$, and $W_3$ are each as defined, where applicable, in any one of (1)-(301), and p5 is 2.
(305) In one embodiment, p4, p4', $Z_2$, p6, p5, $W_1$, and $W_3$ are each as defined, where applicable, in any one of (1)-(44) and (50)-(304), and $W_2$ is O.
(306) In one embodiment, p4, p4', $Z_2$, p6, p5, $W_1$, and $W_3$ are each as defined, where applicable, in any one of (1)-(44) and (50)-(304), and $W_2$ is $CH_2$.
(307) In one embodiment, p4, p4', $Z_2$, p6, p5, $W_1$, and $W_2$ are each as defined, where applicable, in any one of (1)-(49) and (57)-(306), and $W_3$ is $NR_2C(O)CH_2$.
(308) In one embodiment, p4, p4', $Z_2$, p6, p5, $W_1$ and $W_2$ are each as defined, where applicable, in any one of (1)-(49) and (57)-(306), and $W_3$ is $NHC(O)CH_2$.
(309) In one embodiment, p4, p4', $Z_2$, p6, p5, $W_1$, and $W_2$ are each as defined, where applicable, in any one of (1)-(49) and (57)-(306), and $W_3$ is

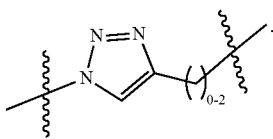

(310) In one embodiment, p4, p4', $Z_2$, p6, p5, $W_1$ and $W_2$ are each as defined, where applicable, in any one of (1)-(49) and (57)-(306), and $W_3$ is

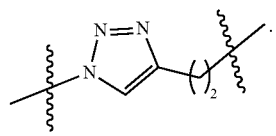

(311) In one embodiment, p4, p4', $Z_2$, p6, p5, and $W_1$ are each as defined, where applicable, in any one of (1)-(310), and $Q_2$ is absent.
(312) In one embodiment, p4, p4', $Z_2$, p6, p5, $W_1$, $W_2$, and $W_3$ are each as defined, where applicable, in any one of (1)-(310), and $Q_2$ is $NHC(O)CH_2$.
(313) In one embodiment, p4, p4', $Z_2$, p6, p5, $W_1$, $W_2$, and $W_3$ are each as defined, where applicable, in any one of (1)-(310), and $Q_2$ is $O(CH_2)_{1-2}$.
(314) In one embodiment, p4, p4', $Z_2$, p6, p5, $W_1$, $W_2$, and $W_3$ are each as defined, where applicable, in any one of (1)-(310), and $Q_2$ is $O(CH_2)$.
(315) In one embodiment, p4, p4', $Z_2$, p6, p5, $W_1$, $W_2$, and $W_3$ are each as defined, where applicable, in any one of (1)-(310), and $Q_2$ is $O(CH_2CH_2)$.
(316) In one embodiment, p4, p4', $Z_2$, p6, p5, $W_1$, $W_2$, and $W_3$ are each as defined, where applicable, in any one of (1)-(310), and $Q_2$ is $C(O)$.
(317) In one embodiment, p4, p4', $Z_2$, p6, p5, $W_1$. $W_2$, and $W_3$ are each as defined, where applicable, in any one of (1)-(310), and $Q_2$ is $OCH_2C(O)$.

In one embodiment, the Linker-Targeting Ligand (TL) has the structure selected from Tale M:

TABLE M

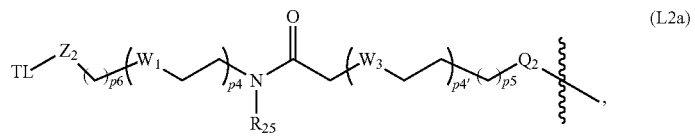

(L2a)

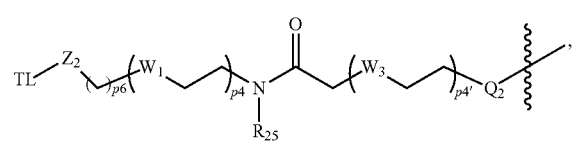

(L2b)

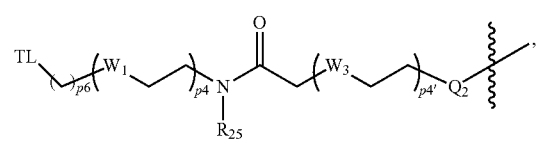

(L2c)

TABLE M-continued
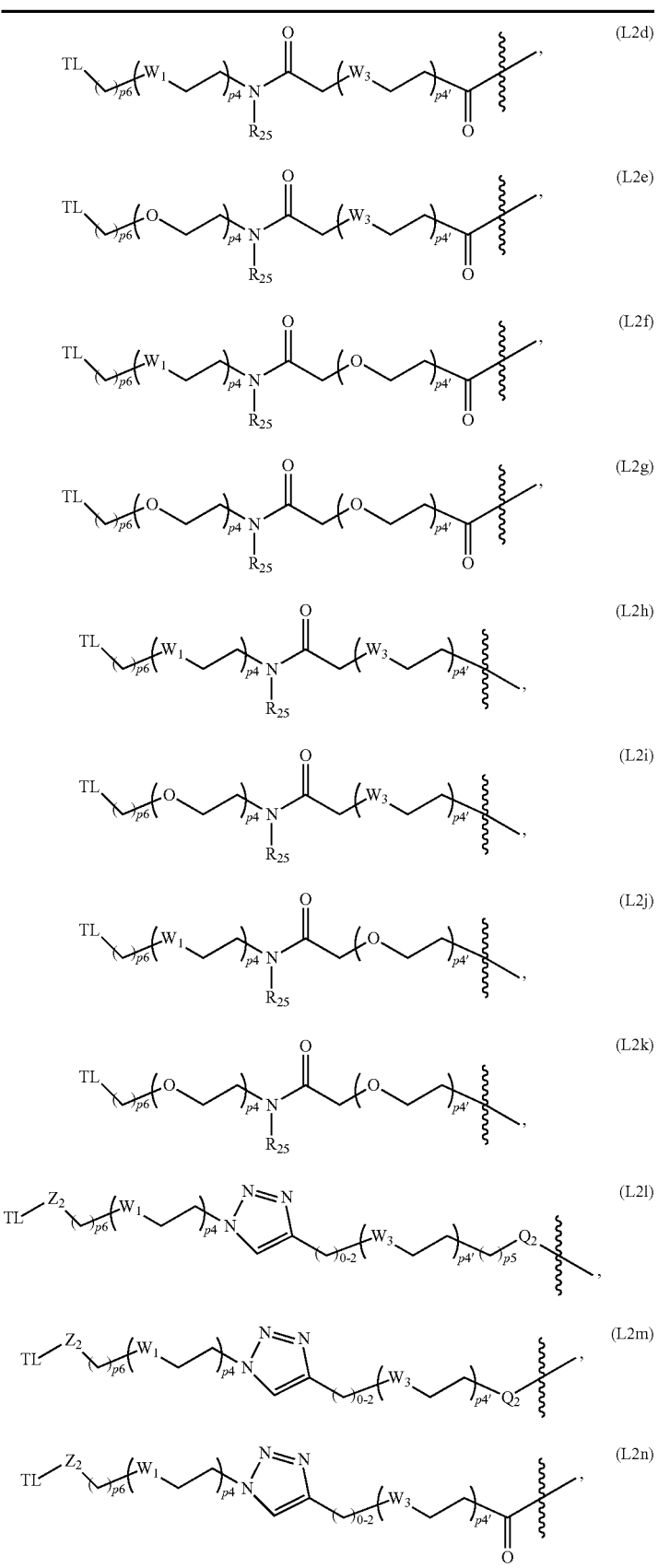

TABLE M-continued
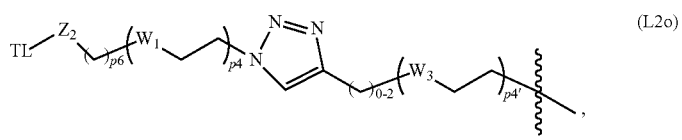 (L2o)
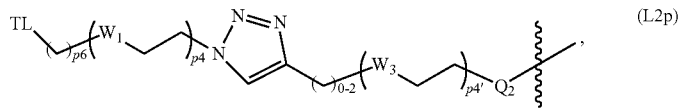 (L2p)
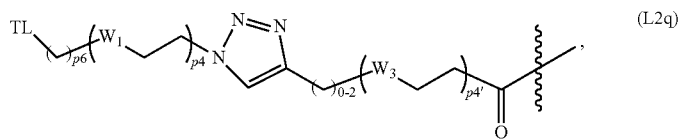 (L2q)
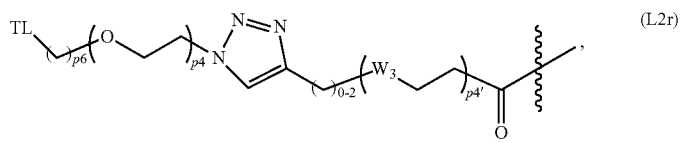 (L2r)
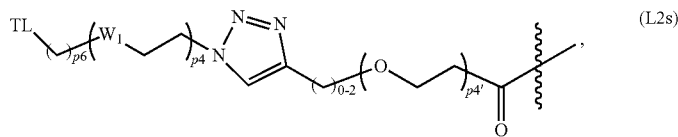 (L2s)
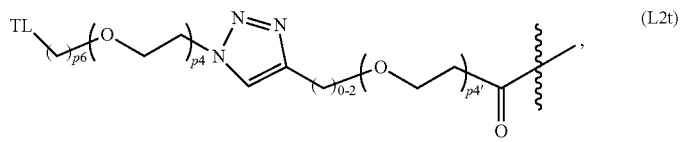 (L2t)
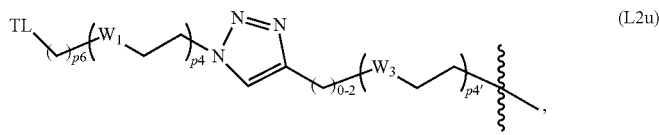 (L2u)
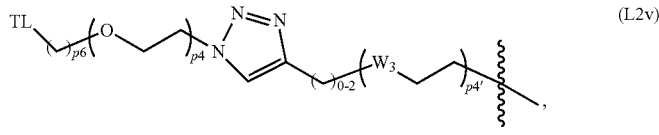 (L2v)
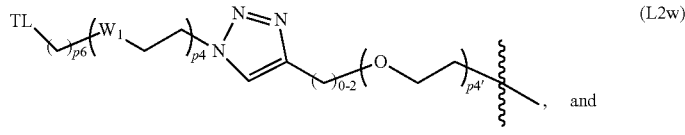 (L2w) , and
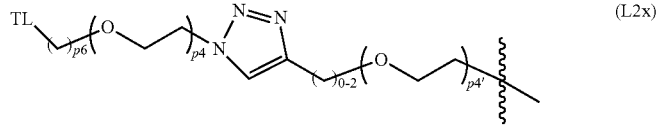 (L2x)

wherein $Z_2$, $W_1$, $W_3$, $Q_2$, TL, $R_{25}$, p4, p4', and p6 are each as described above.

Any one of the Degrons described herein can be covalently bound to any one of the Linkers described herein. Any one of the Targeting Ligands described herein can be covalently bound to any one of the Linkers described herein.

In one embodiment, the present application relates to the Degron-Linker (DL), wherein the Degron is of Formula D0, and the Linker is selected from L2a-L2x. In one embodiment, the present application relates to the Degron-Linker (DL), wherein the Degron is of Formula D0, and the Linker is selected from L2a-L2c. In one embodiment, the present application relates to the Degron-Linker (DL), wherein the Degron is of Formula D0, and the Linker is selected from L2d-L2g. In one embodiment, the present application relates to the Degron-Linker (DL), wherein the Degron is of Formula D0, and the Linker is selected from L2h-L2k. In one embodiment, the present application relates to the Degron-Linker (DL), wherein the Degron is of Formula D0, and the Linker is selected from L2l-L2m. In one embodiment, the present application relates to the Degron-Linker (DL), wherein the Degron is of Formula D0, and the Linker is selected from L2n-L2p. In one embodiment, the present application relates to the Degron-Linker (DL), wherein the Degron is of Formula D0, and the Linker is selected from L2q-L2t. In one embodiment, the present application relates to the Degron-Linker (DL), wherein the Degron is of Formula D0, and the Linker is selected from L2u-L2x.

In one embodiment, the present application relates to the Degron-Linker (DL), wherein the Degron is of Formula D0a, D0b, D0c, or D0d, and the Linker is selected from L2a-L2x. In one embodiment, the present application relates to the Degron-Linker (DL), wherein the Degron is of Formula D0a, D0b, D0c, or D0d, and the Linker is selected from L2a-L2c. In one embodiment, the present application relates to the Degron-Linker (DL), wherein the Degron is of Formula D0a, D0b, D0c, or D0d, and the Linker is selected from L2d-L2g. In one embodiment, the present application relates to the Degron-Linker (DL), wherein the Degron is of Formula D0a, D0b, D0c, or D0d, and the Linker is selected from L2h-L2k. In one embodiment, the present application relates to the Degron-Linker (DL), wherein the Degron is of Formula D0a, D0b, D0c, or D0d, and the Linker is selected from L2l-L2m. In one embodiment, the present application relates to the Degron-Linker (DL), wherein the Degron is of Formula D0a, D0b, D0c, or D0d, and the Linker is selected from L2n-L2p. In one embodiment, the present application relates to the Degron-Linker (DL), wherein the Degron is of Formula D0a, D0b, D0c, or D0d, and the Linker is selected from L2q-L2t. In one embodiment, the present application relates to the Degron-Linker (DL), wherein the Degron is of Formula D0a, D0b, D0c, or D0d, and the Linker is selected from L2u-L2x.

In one embodiment, the present application relates to the Degron-Linker (DL), wherein the Degron is of Formula D1, and the Linker is selected from L2a-L2x. In one embodiment, the present application relates to the Degron-Linker (DL), wherein the Degron is of Formula D1, and the Linker is selected from L2a-L2c. In one embodiment, the present application relates to the Degron-Linker (DL), wherein the Degron is of Formula D1, and the Linker is selected from L2d-L2g. In one embodiment, the present application relates to the Degron-Linker (DL), wherein the Degron is of Formula D1, and the Linker is selected from L2h-L2k. In one embodiment, the present application relates to the Degron-Linker (DL), wherein the Degron is of Formula D1, and the Linker is selected from L2l-L2m. In one embodiment, the present application relates to the Degron-Linker (DL), wherein the Degron is of Formula D1, and the Linker is selected from L2n-L2p. In one embodiment, the present application relates to the Degron-Linker (DL), wherein the Degron is of Formula D1, and the Linker is selected from L2q-L2t. In one embodiment, the present application relates to the Degron-Linker (DL), wherein the Degron is of Formula D1, and the Linker is selected from L2u-L2x.

In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2a-L2x. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2a-L2c. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2d-L2g. In one embodiment, the present application relates to the Degron-Linker (DL), wherein the Degron is of Formula D1a, D1b, D1c, D1d, D1e, D1f, D1g, D1h, D1i, D1j, D1k, or D1i, and the Linker is selected from L2h-L2k. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2l-L2m. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2n-L2p. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2q-L2t. In one embodiment, the present application relates to the Degron-Linker (DL), wherein the Degron is of Formula D1a, D1b, D1c, D1d, D1e, D1f, D1g, D1h, D1i, D1j, D1k, or D1l, and the Linker is selected from L2u-L2x.

In one embodiment, the present application relates to the Degron-Linker (DL), wherein the Degron is of Formula D4, and the Linker is selected from L2a-L2x. In one embodiment, the present application relates to the Degron-Linker (DL), wherein the Degron is of Formula D4, and the Linker is selected from L2a-L2c. In one embodiment, the present application relates to the Degron-Linker (DL), wherein the Degron is of Formula D4, and the Linker is selected from L2d-L2g. In one embodiment, the present application relates to the Degron-Linker (DL), wherein the Degron is of Formula D4, and the Linker is selected from L2h-L2k. In one embodiment, the present application relates to the Degron-Linker (DL), wherein the Degron is of Formula D4, and the Linker is selected from L2l-L2m. In one embodiment, the present application relates to the Degron-Linker (DL), wherein the Degron is of Formula D4, and the Linker is selected from L2n-L2p. In one embodiment, the present application relates to the Degron-Linker (DL), wherein the Degron is of Formula D4, and the Linker is selected from L2q-L2t. In one embodiment, the present application relates to the Degron-Linker (DL), wherein the Degron is of Formula D4, and the Linker is selected from L2u-L2x.

In one embodiment, the present application relates to the Degron-Linker (DL), wherein the Degron is of Formula 4a or D4b, and the Linker is selected from L2a-L2x. In one embodiment, the present application relates to the Degron-Linker (DL), wherein the Degron is of Formula D4a or D4b, and the Linker is selected from L2a-L2c. In one embodiment, the present application relates to the Degron-Linker (DL), wherein the Degron is of D4a or D4b, and the Linker is selected from L2d-L2g. In one embodiment, the present application relates to the Degron-Linker (DL), wherein the Degron is of Formula D4a or D4b, and the Linker is selected from L2h-L2k. In one embodiment, the present application relates to the Degron-Linker (DL), wherein the Degron is of Formula D4a or D4b, and the Linker is selected from L2l-L2m. In one embodiment, the present application relates to the Degron-Linker (DL), wherein the Degron is of Formula D4a or D4b, and the Linker is selected from L2n-L2p. In one embodiment, the present application relates to the Degron-Linker (DL), wherein the Degron is of Formula D4a or D4b, and the Linker is selected from L2q-L2t. In one embodiment, the present application relates to the Degron-Linker (DL), wherein the Degron is of Formula D4a or D4b, and the Linker is selected from L2u-L2x.

In one embodiment, the present application relates to the Degron-Linker (DL), wherein the Degron is of Formula D2, and the Linker is selected from L2a-L2x. In one embodiment, the present application relates to the Degron-Linker (DL), wherein the Degron is of Formula D2, and the Linker is selected from L2a-L2c. In one embodiment, the present application relates to the Degron-Linker (DL), wherein the Degron is of Formula D2, and the Linker is selected from L2d-L2g. In one embodiment, the present application relates to the Degron-Linker (DL), wherein the Degron is of Formula D2, and the Linker is selected from L2h-L2k. In one embodiment, the present application relates to the Degron-Linker (DL), wherein the Degron is of Formula D2, and the Linker is selected from L2l-L2m. In one embodiment, the present application relates to the Degron-Linker (DL), wherein the Degron is of Formula D2, and the Linker is selected from L2n-L2p. In one embodiment, the present application relates to the Degron-Linker (DL), wherein the Degron is of Formula D2, and the Linker is selected from L2q-L2t. In one embodiment, the present application relates to the Degron-Linker (DL), wherein the Degron is of Formula D2, and the Linker is selected from L2u-L2x.

In one embodiment, the present application relates to the Degron-Linker (DL), wherein the Degron is of Formula D2a, D2a', D2b, or D2b', and the Linker is selected from L2a-L2x. In one embodiment, the present application relates to the Degron-Linker (DL), wherein the Degron is of Formula D2a, D2a', D2b, or D2b', and the Linker is selected from L2a-L2c. In one embodiment, the present application relates to the Degron-Linker (DL), wherein the Degron is of Formula D2a, D2a', D2b, or D2b', and the Linker is selected from L2d-L2g. In one embodiment, the present application relates to the Degron-Linker (DL), wherein the Degron is of Formula D2a, D2a', D2b, or D2b', and the Linker is selected from L2h-L2k. In one embodiment, the present application relates to the Degron-Linker (DL), wherein the Degron is of Formula D2a, D2a', D2b, or D2b', and the Linker is selected from L2l-L2m. In one embodiment, the present application relates to the Degron-Linker (DL), wherein the Degron is of Formula D2a, D2a', D2b, or D2b', and the Linker is selected from L2n-L2p. In one embodiment, the present application relates to the Degron-Linker (DL), wherein the Degron is of Formula D2a, D2a', D2b, or D2b', and the Linker is selected from L2q-L2t. In one embodiment, the present application relates to the Degron-Linker (DL), wherein the Degron is of Formula D2a, D2a', D2b, or D2b', and the Linker is selected from L2u-L2x.

In one embodiment, the present application relates to the Degron-Linker (DL), wherein the Degron is of Formula D2c, D2c', D2d, or D2d', and the Linker is selected from L2a-L2x. In one embodiment, the present application relates to the Degron-Linker (DL), wherein the Degron is of Formula D2c, D2c', D2d, or D2d', and the Linker is selected from L2a-L2c. In one embodiment, the present application relates to the Degron-Linker (DL), wherein the Degron is of Formula D2c, D2c', D2d, or D2d', and the Linker is selected from L2d-L2g. In one embodiment, the present application relates to the Degron-Linker (DL), wherein the Degron is of Formula D2c, D2c', D2d, or D2d', and the Linker is selected from L2h-L2k. In one embodiment, the present application relates to the Degron-Linker (DL), wherein the Degron is of Formula D2c, D2c', D2d, or D2d', and the Linker is selected from L2l-L2m. In one embodiment, the present application relates to the Degron-Linker (DL), wherein the Degron is of Formula D2c, D2c', D2d, or D2d', and the Linker is selected from L2n-L2p. In one embodiment, the present application relates to the Degron-Linker (DL), wherein the Degron is of Formula D2c, D2c', D2d, or D2d', and the Linker is selected from L2q-L2t. In one embodiment, the present application relates to the Degron-Linker (DL), wherein the Degron is of Formula D2c, D2c', D2d, or D2d', and the Linker is selected from L2u-L2x.

In one embodiment, the present application relates to the Degron-Linker (DL), wherein the Degron is of Formula D3, and the Linker is selected from L2a-L2x. In one embodiment, the present application relates to the Degron-Linker (DL), wherein the Degron is of Formula D3, and the Linker is selected from L2a-L2c. In one embodiment, the present application relates to the Degron-Linker (DL), wherein the Degron is of Formula D3, and the Linker is selected from L2d-L2g. In one embodiment, the present application relates to the Degron-Linker (DL), wherein the Degron is of Formula D3, and the Linker is selected from L2h-L2k. In one embodiment, the present application relates to the Degron-Linker (DL), wherein the Degron is of Formula D3, and the Linker is selected from L2l-L2m. In one embodiment, the present application relates to the Degron-Linker (DL), wherein the Degron is of Formula D3, and the Linker is selected from L2n-L2p. In one embodiment, the present application relates to the Degron-Linker (DL), wherein the Degron is of Formula D3, and the Linker is selected from L2q-L2t. In one embodiment, the present application relates to the Degron-Linker (DL), wherein the Degron is of Formula D3, and the Linker is selected from L2u-L2x.

In one embodiment, the present application relates to the Degron-Linker (DL), wherein the Degron is of Formula D3a, D3b, or D3c, and the Linker is selected from L2a-L2x. In one embodiment, the present application relates to the Degron-Linker (DL), wherein the Degron is of Formula D3a, D3b, or D3c, and the Linker is selected from L2a-L2c. In one embodiment, the present application relates to the Degron-Linker (DL), wherein the Degron is of Formula D3a, D3b, or D3c, and the Linker is selected from L2d-L2g. In one embodiment, the present application relates to the Degron-Linker (DL), wherein the Degron is of Formula D3a, D3b, or D3c, and the Linker is selected from L2h-L2k. In one embodiment, the present application relates to the Degron-Linker (DL), wherein the Degron is of Formula D3a, D3b, or D3c, and the Linker is selected from L2l-L2m. In one embodiment, the present application relates to the Degron-Linker (DL), wherein the Degron is of Formula D3a, D3b, or D3c, and the Linker is selected from L2n-L2p. In one embodiment, the present application relates to the Degron-Linker (DL), wherein the Degron is of Formula D3a, D3b, or D3c, and the Linker is selected from L2q-L2t. In one embodiment, the present application relates to the Degron-Linker (DL), wherein the Degron is of Formula D3a, D3b, or D3c, and the Linker is selected from L2u-L2x.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can also be modified to modulate metabolic stability and pharmacokinetic (PK) and pharmacodynamics (PD) parameters.

Some embodiments of the present application relate to the bifunctional compounds having one of the following structures in Table A, Table A1, Table B, Table B1, or Table C:

TABLE A

Structure

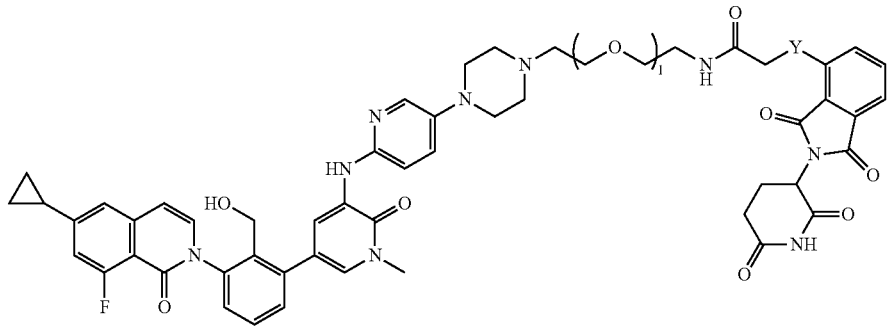

Y = O, NH

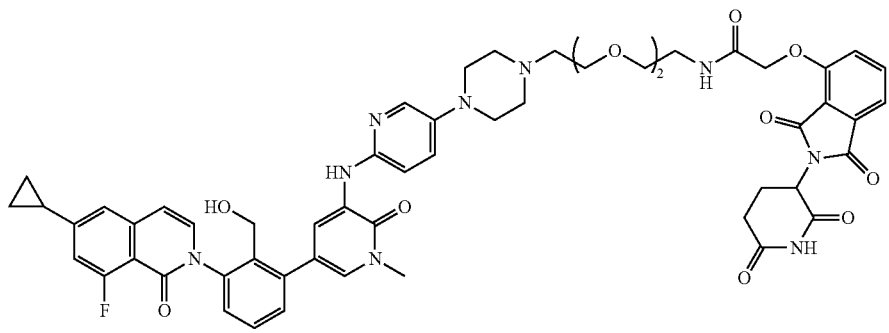

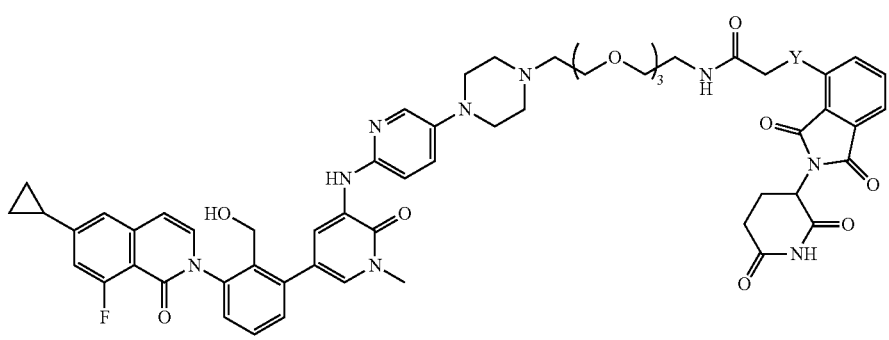

Y = O, NH

TABLE A-continued

Structure

Y = O, NH

Y = O, NH

Y = O, NH

TABLE A-continued
Structure
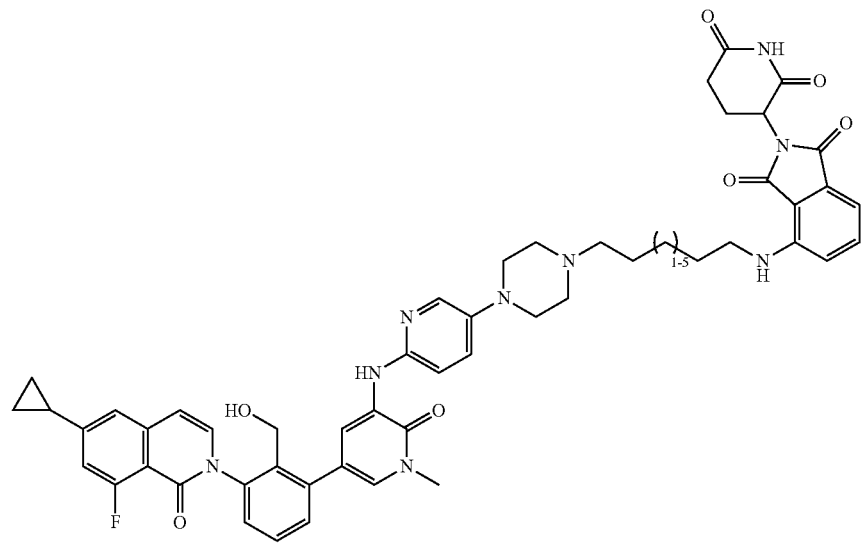
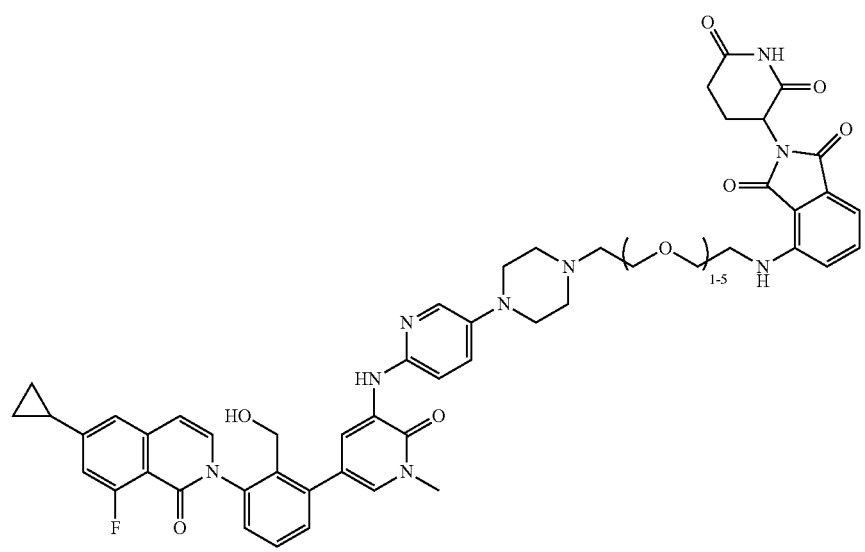
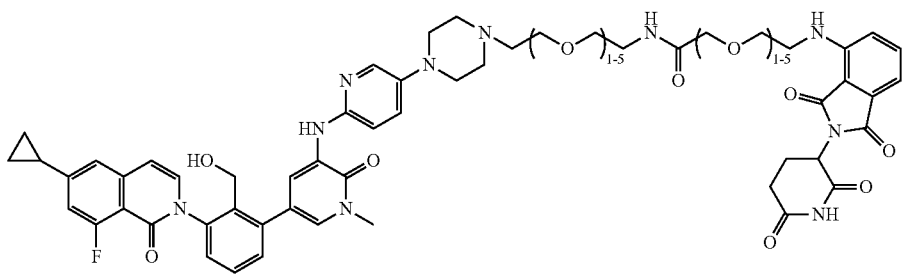

TABLE A-continued
Structure
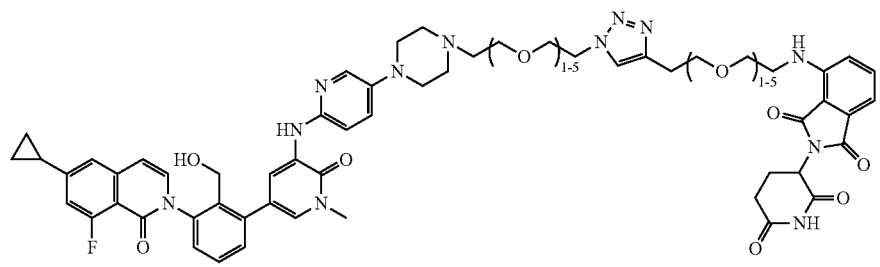
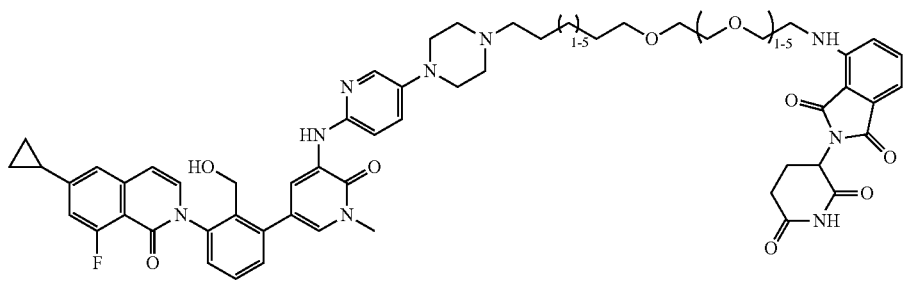
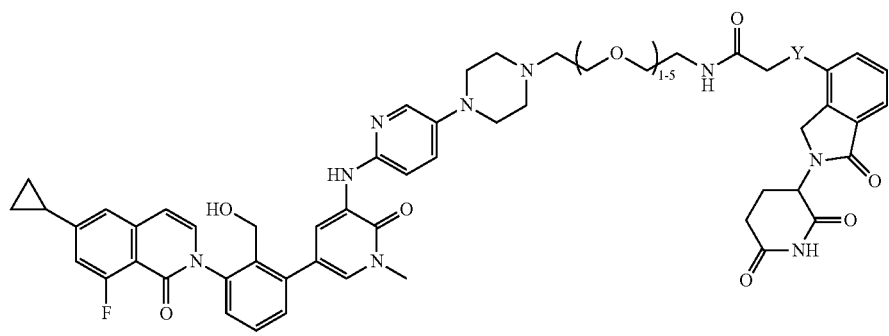
Y = O, NH
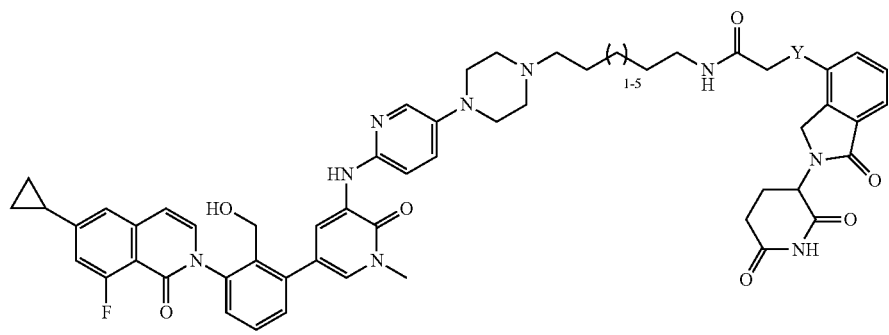
Y = O, NH TABLE A-continued
Structure
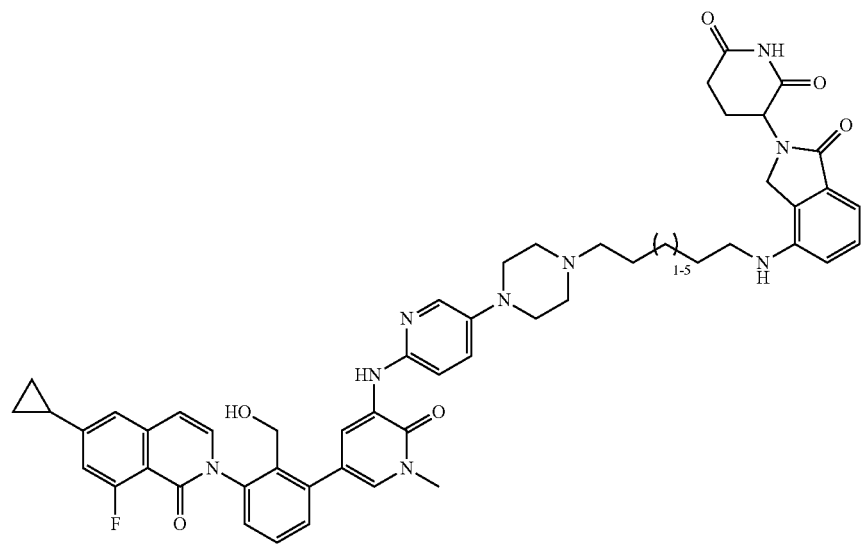
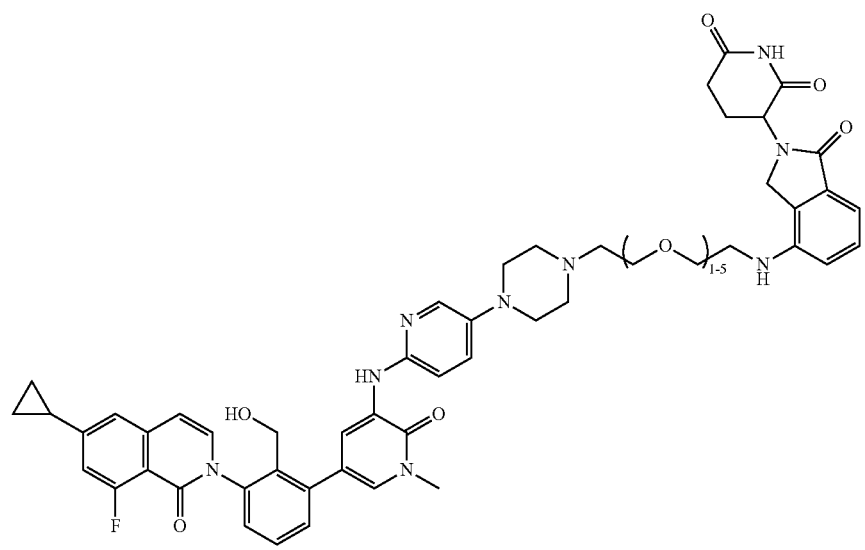
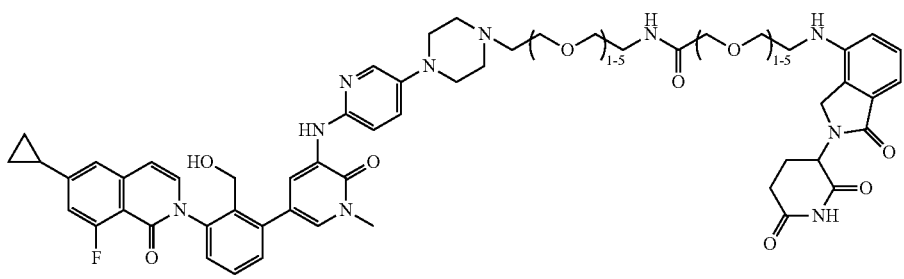

TABLE A-continued

Structure

TABLE A-continued
Structure
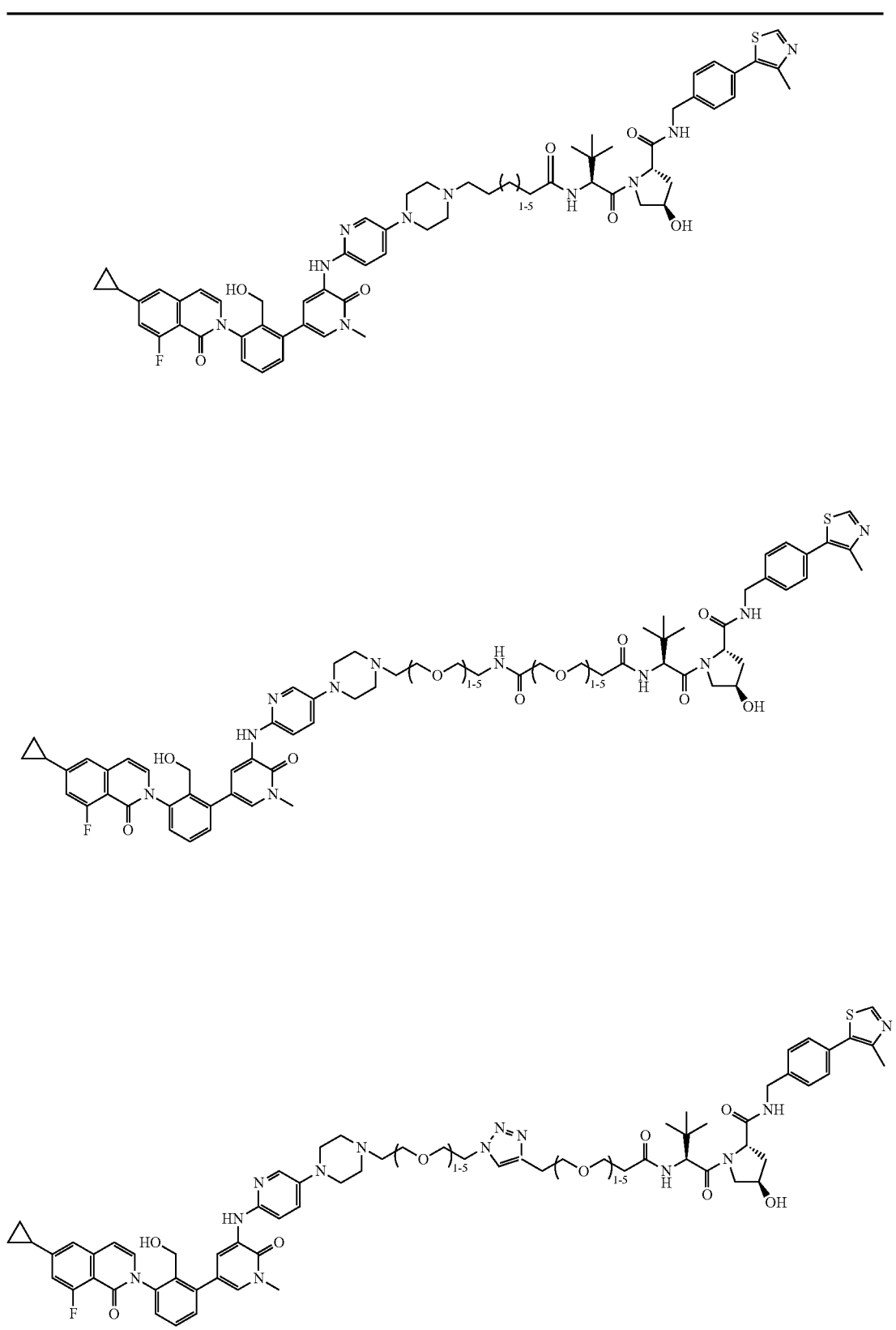

TABLE A-continued
| Structure |
| --- |
| 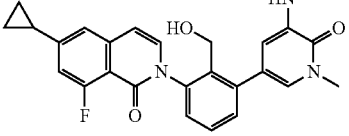 |
TABLE A1
| Structure |
| --- |
| 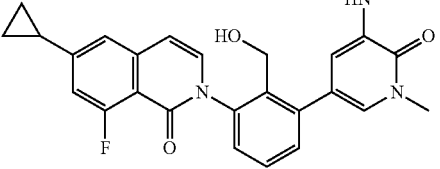
(I-0) |
TABLE B
| Structure |
| --- |
| 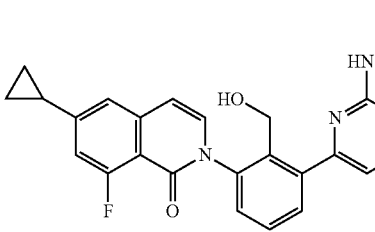
Y = O, NH |

TABLE B-continued
Structure
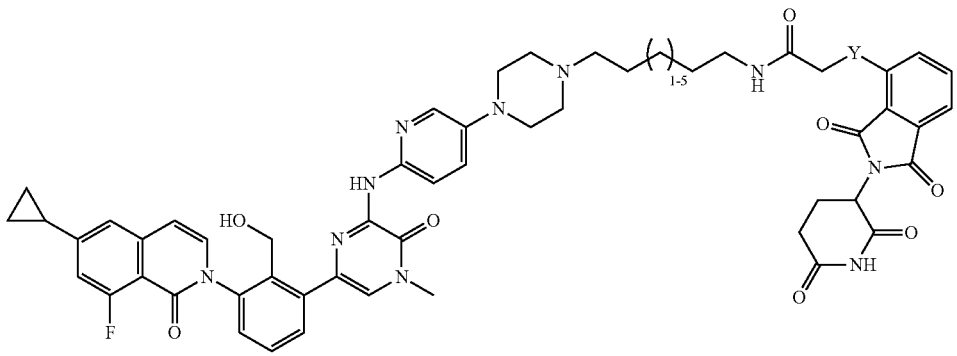
Y = O, NH
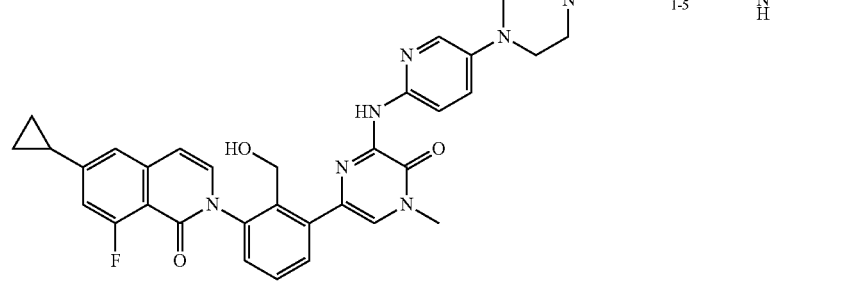
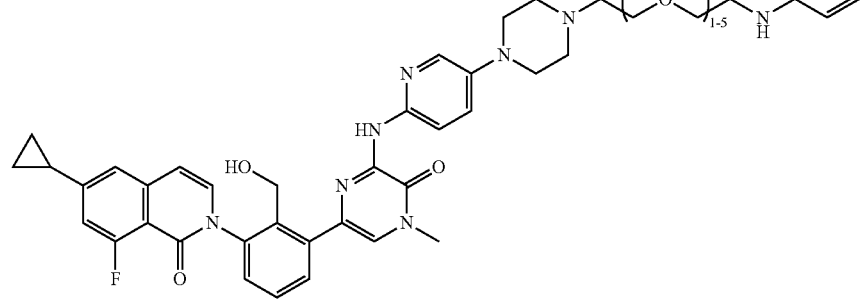

TABLE B-continued
Structure
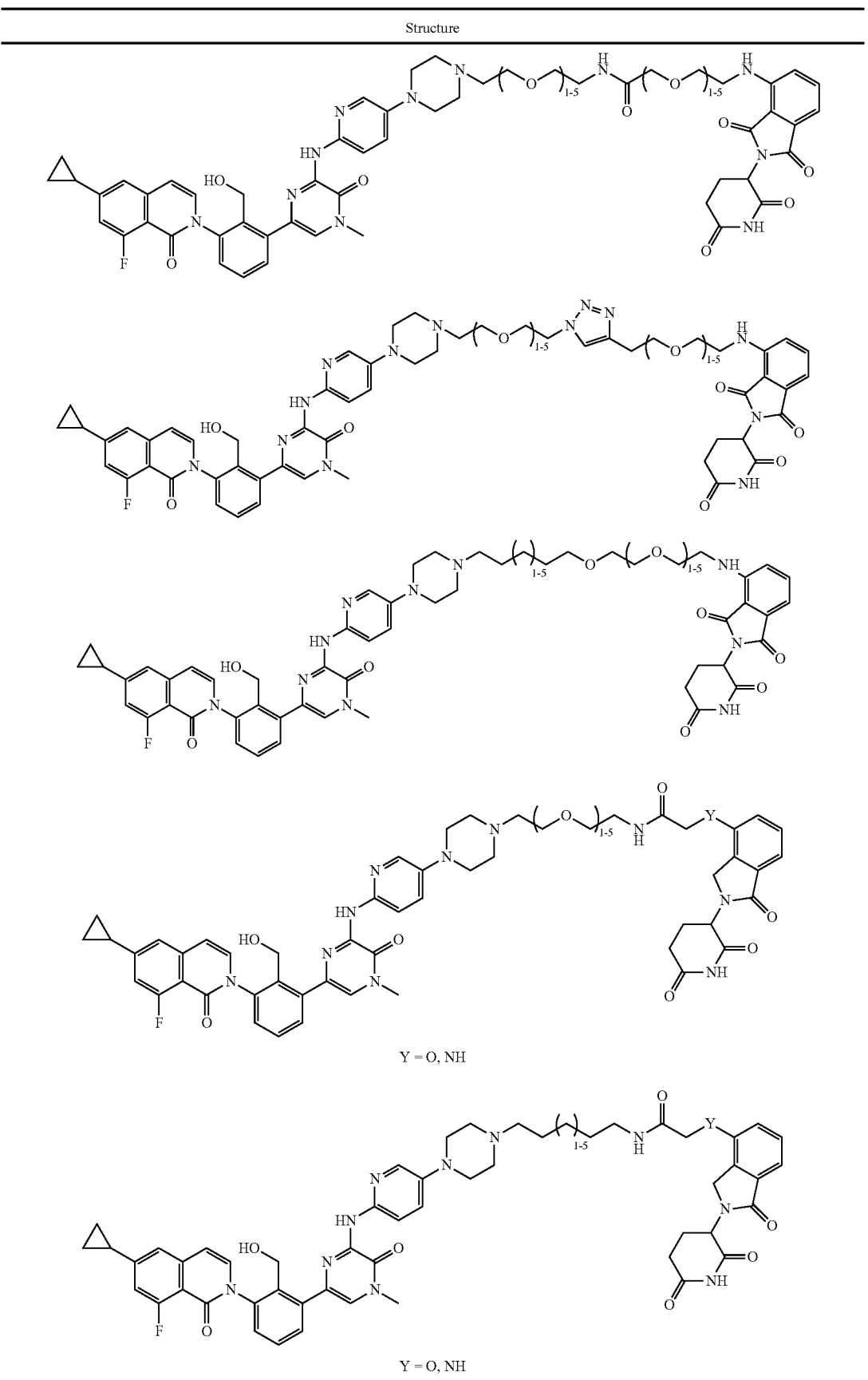
Y = O, NH
Y = O, NH

TABLE B-continued
Structure
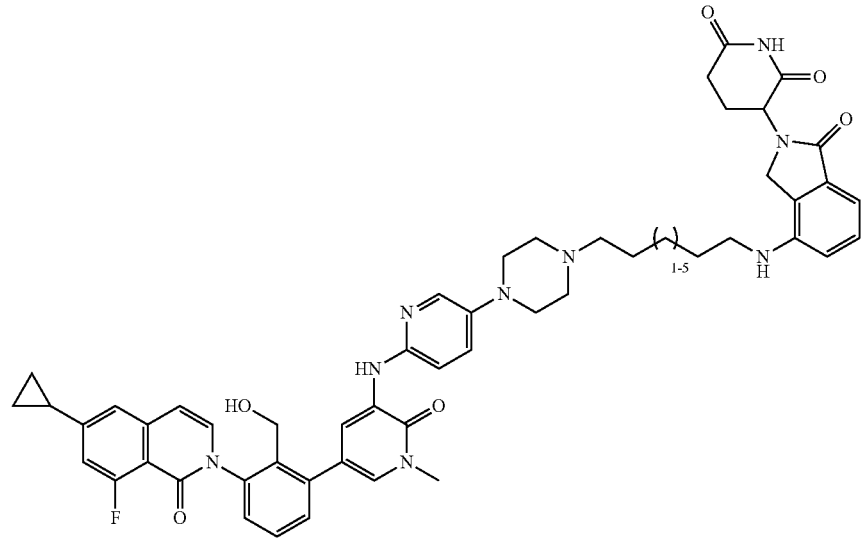
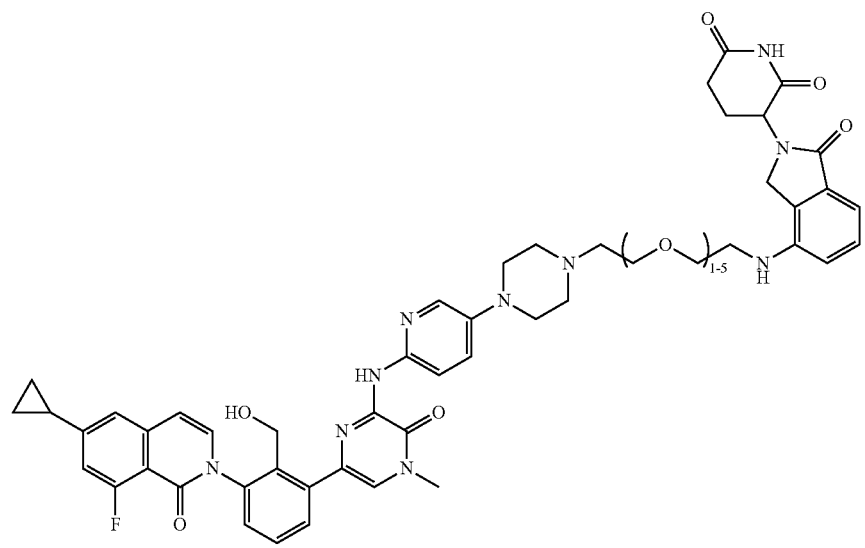
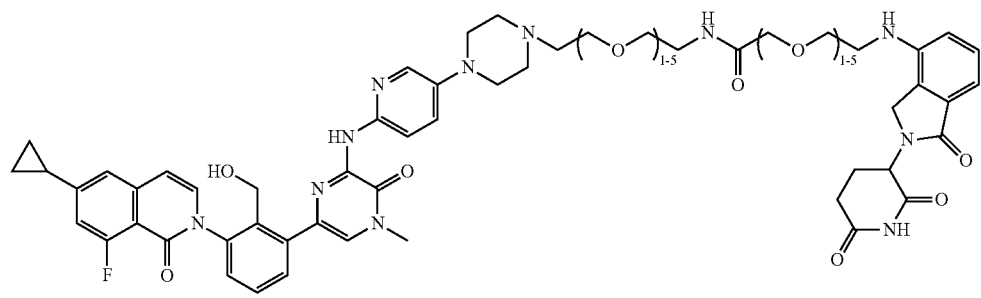

TABLE B-continued
Structure
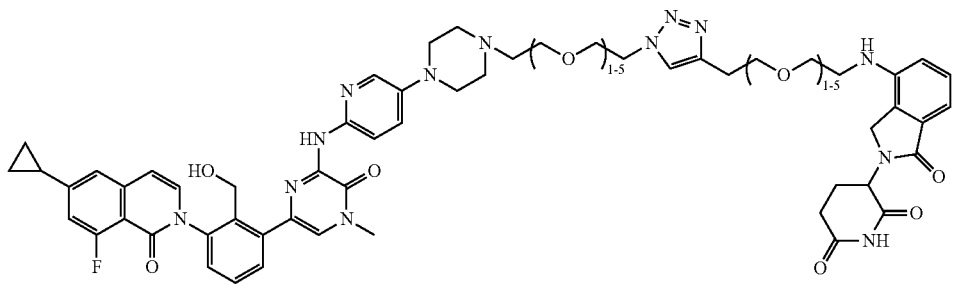
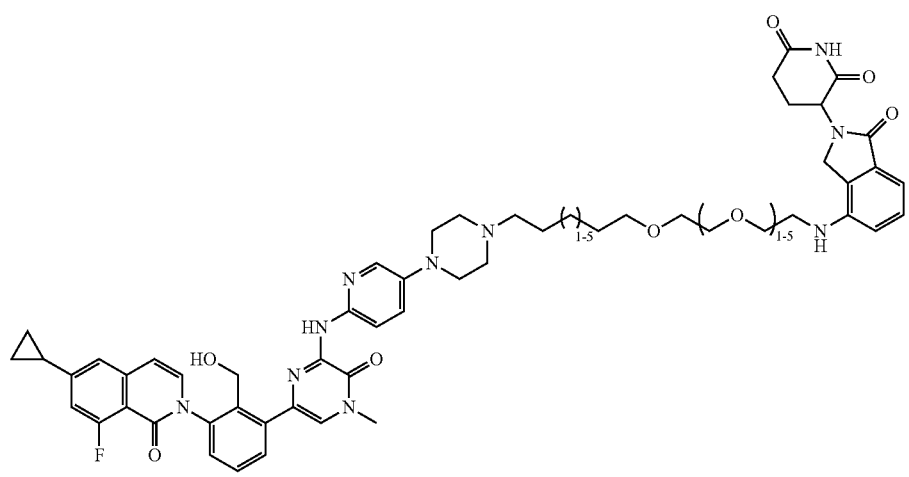
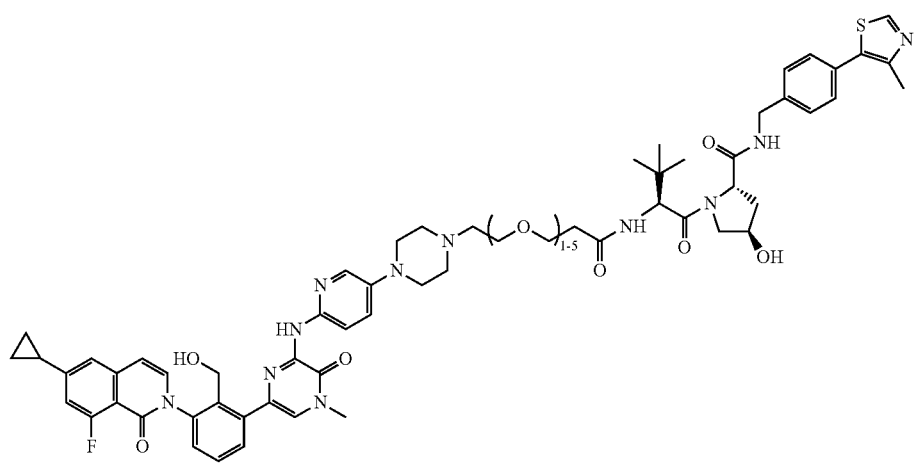

TABLE B-continued
Structure
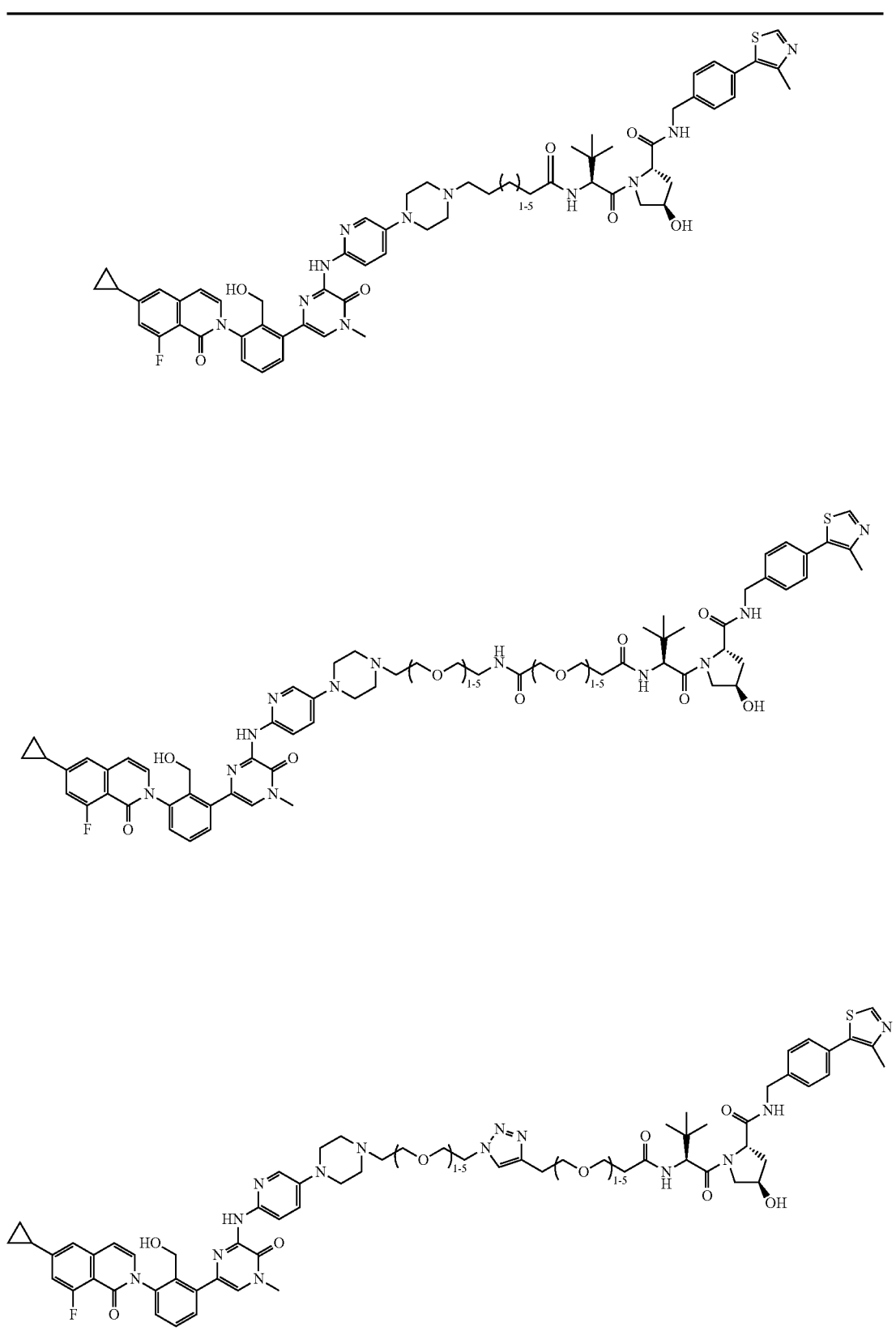

TABLE B-continued
Structure
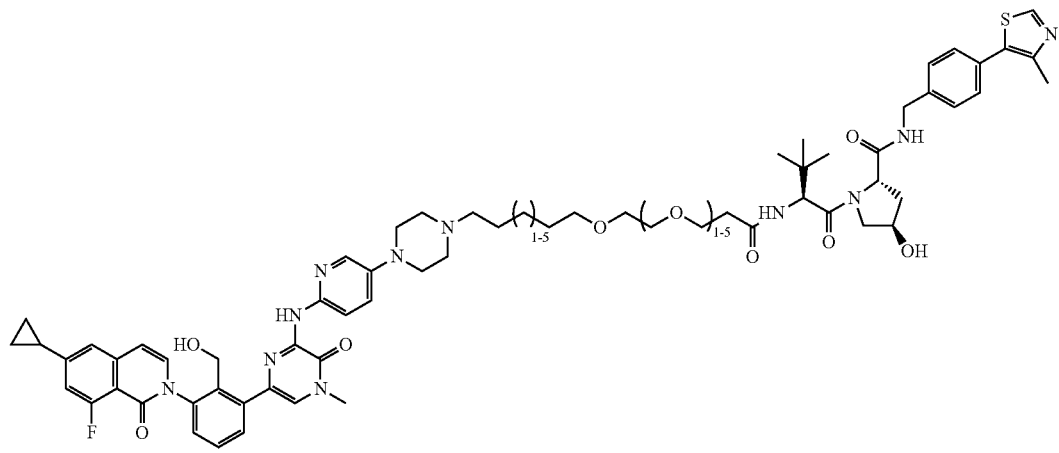
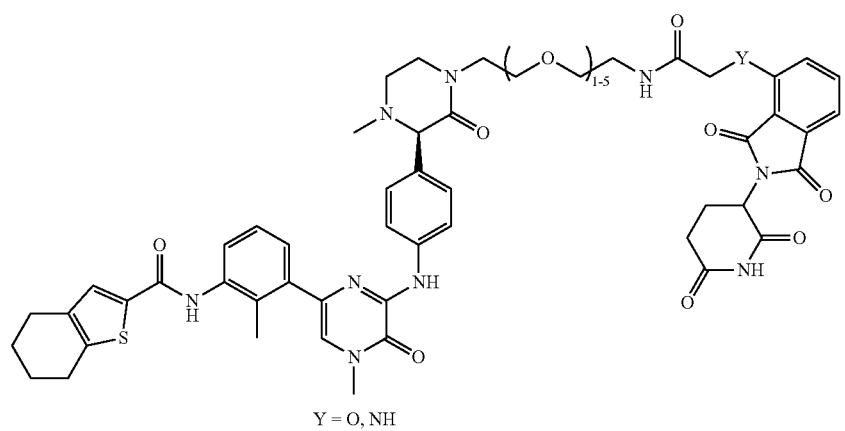
Y = O, NH
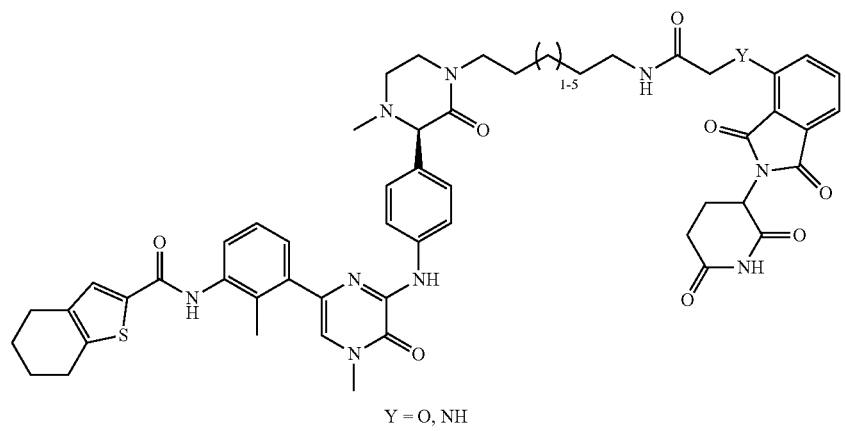
Y = O, NH TABLE B-continued Structure TABLE B-continued Structure TABLE B-continued Structure

Y = O, NH

TABLE B-continued
Structure
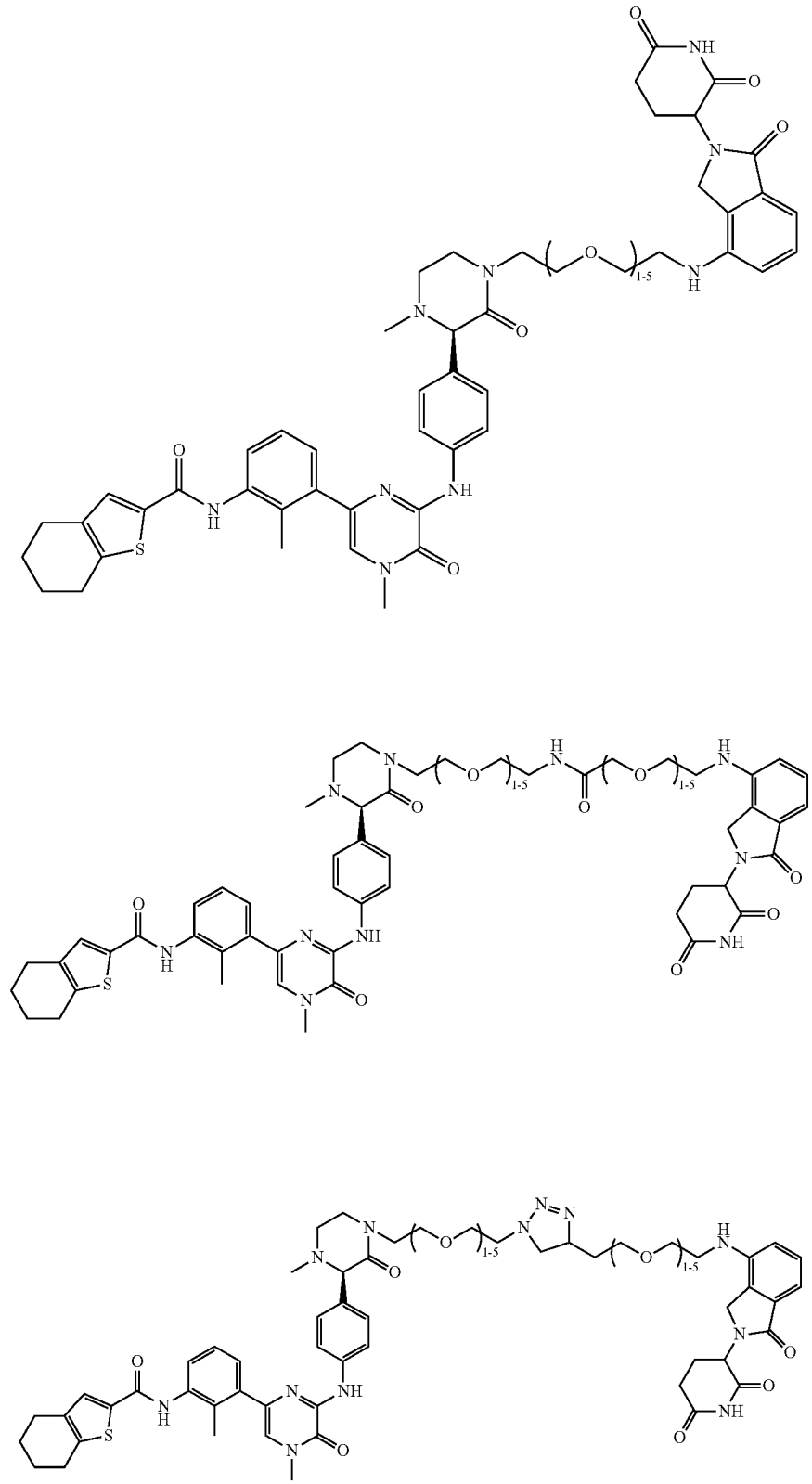

147                                                                                               148
TABLE B-continued
Structure
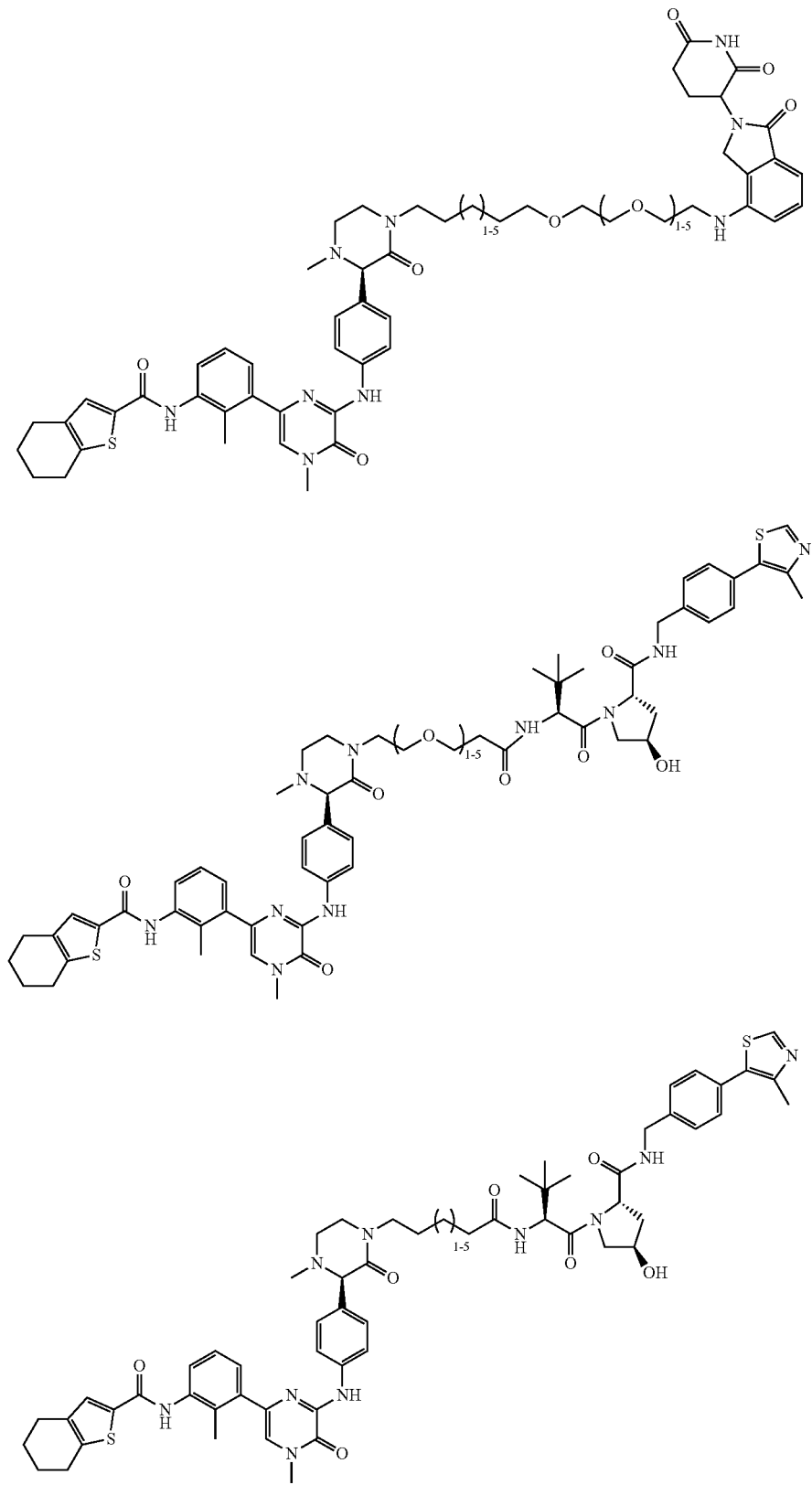

149 150
TABLE B-continued
Structure
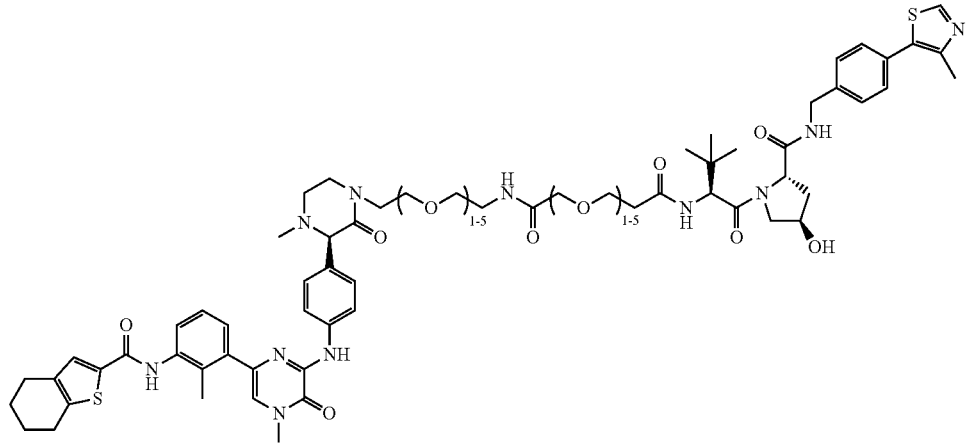
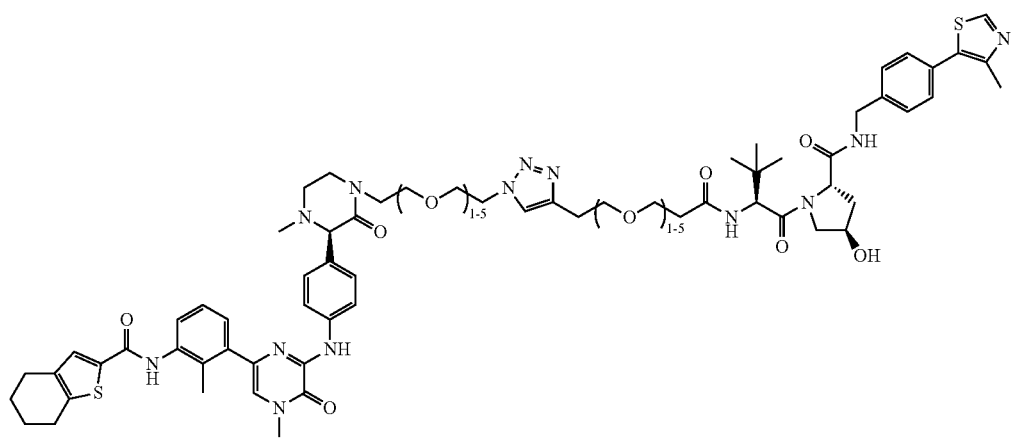
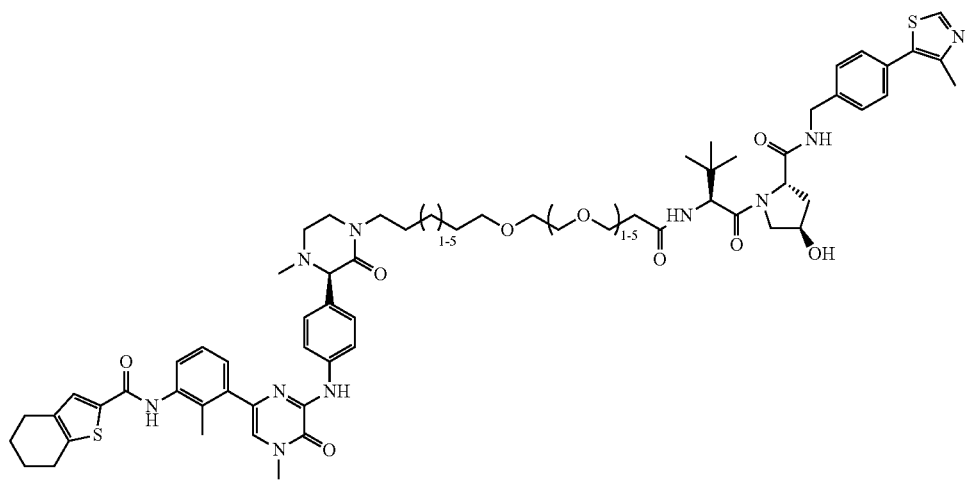

TABLE B-continued
Structure
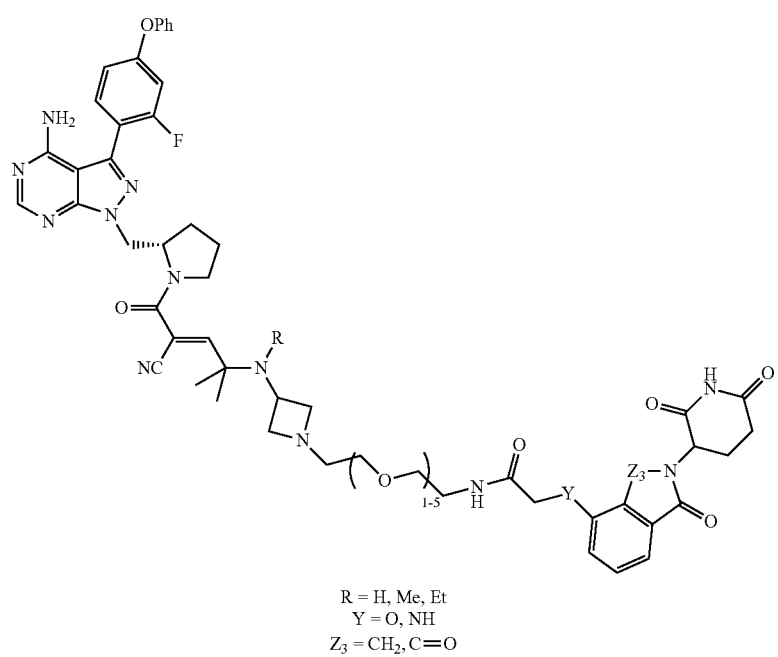
$Z_3$ = CH$_2$, C=O
Y = O, NH
R = H, Me, Et
R = H, Me, Et
Y = O, NH
$Z_3$ = CH$_2$, C=O 153 154
TABLE B-continued
Structure
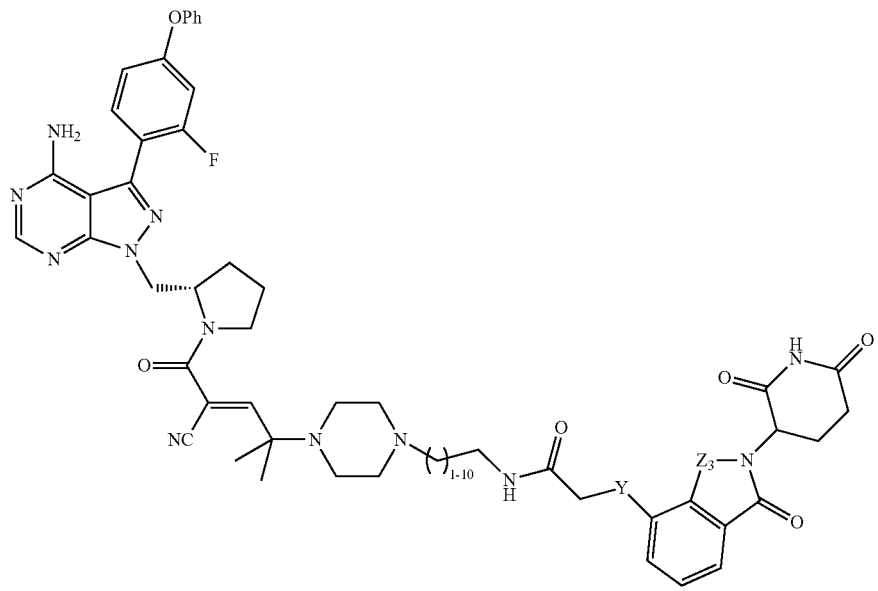
Z₃ = CH₂, C=O
Y = O, NH
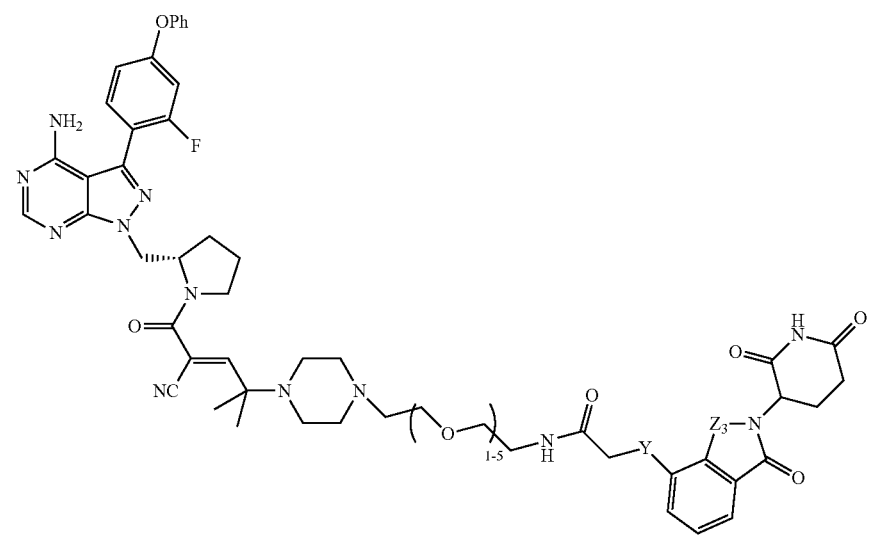
Y = O, NH
Z₃ = CH₂, C=O TABLE B-continued
Structure
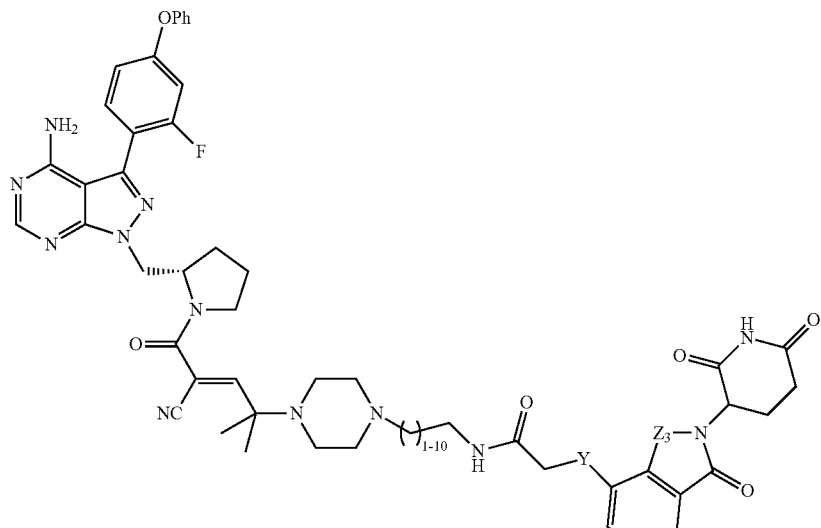
Z₃ = CH₂, C═O
Y = O, NH
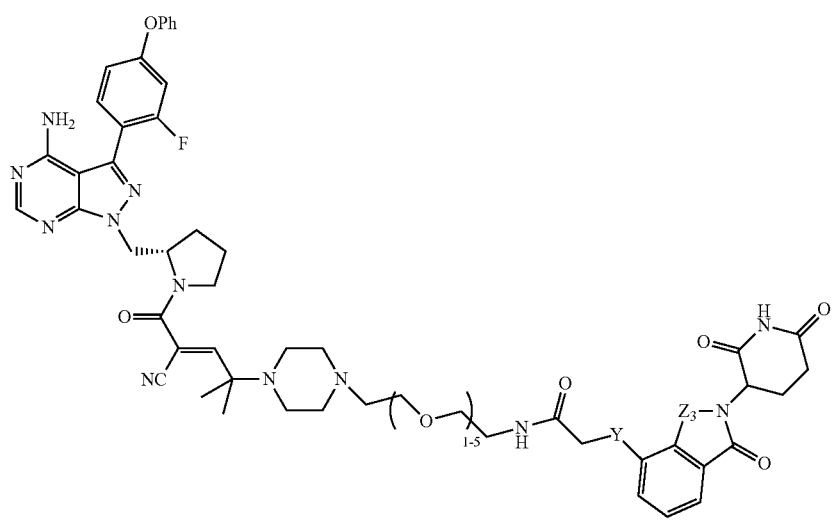
Z₃ = CH₂, C═O
Y = O, NH TABLE B-continued
Structure
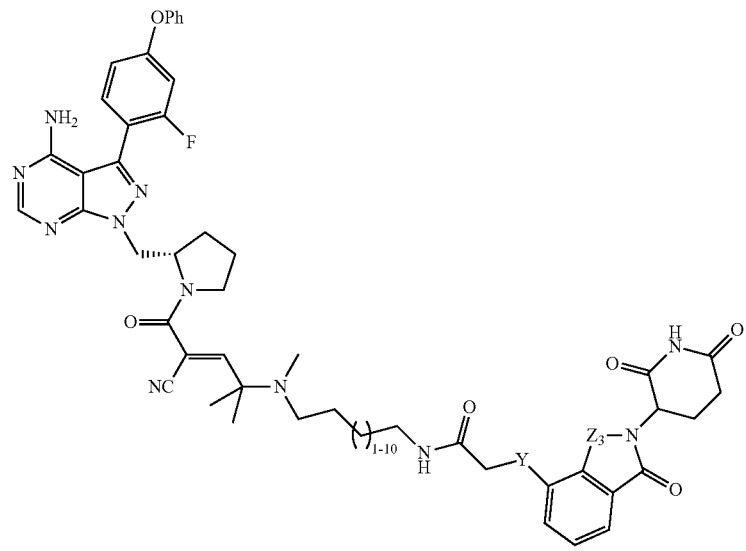
Y = O, NH
Z₃ = CH₂, C=O
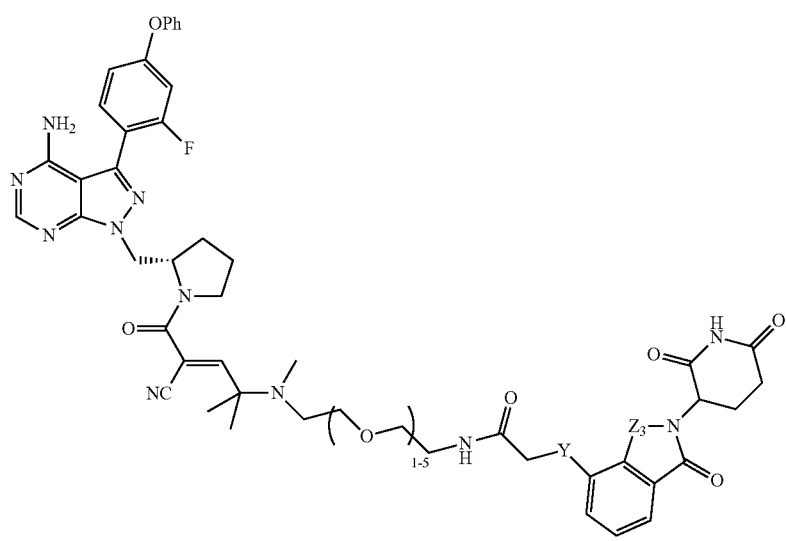
Z₃ = CH₂, C=O
Y = O, NH TABLE B-continued
Structure
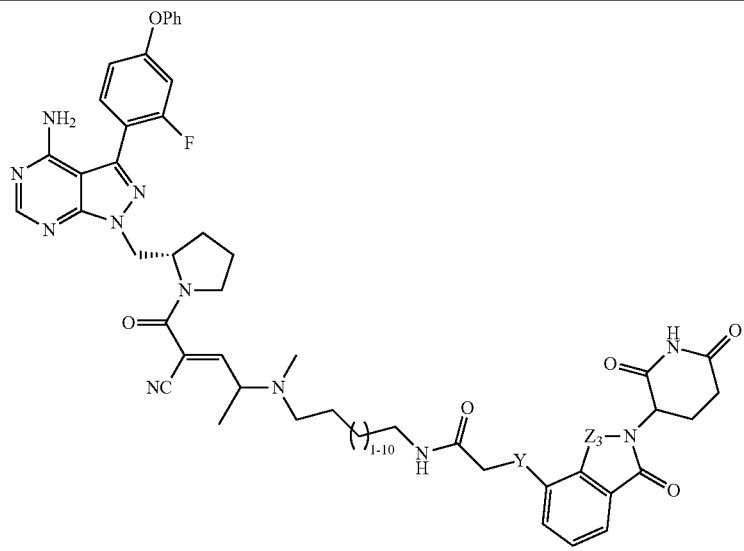
Z₃ = CH₂, C═O
Y = O, NH
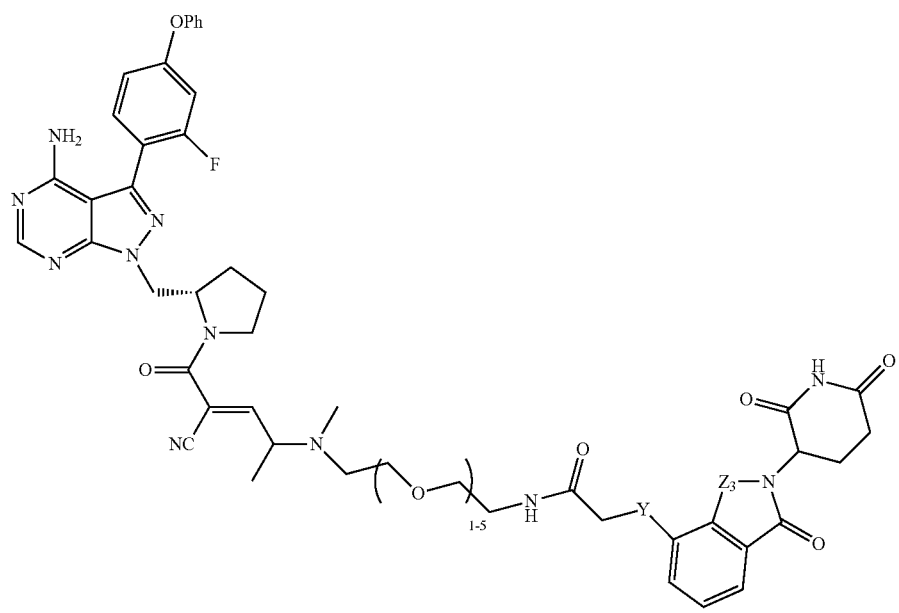
Y = O, NH
Z₃ = CH₂, C═O TABLE B-continued
Structure
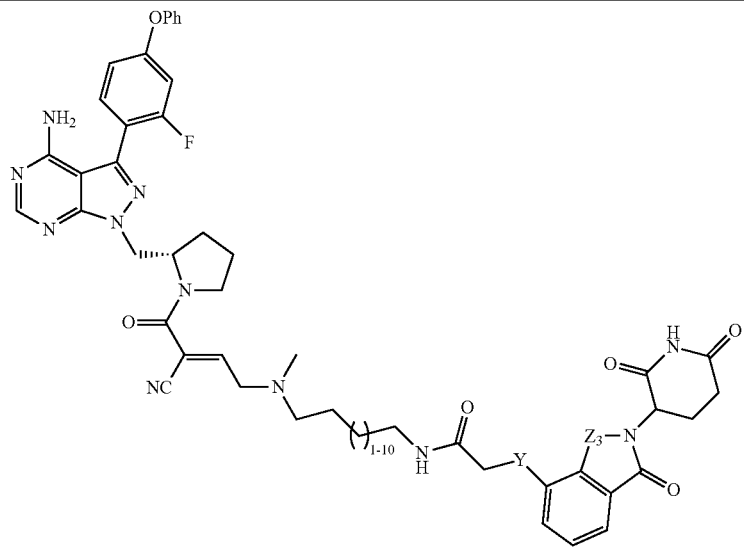
Z₃ = CH₂, C═O
Y = O, NH
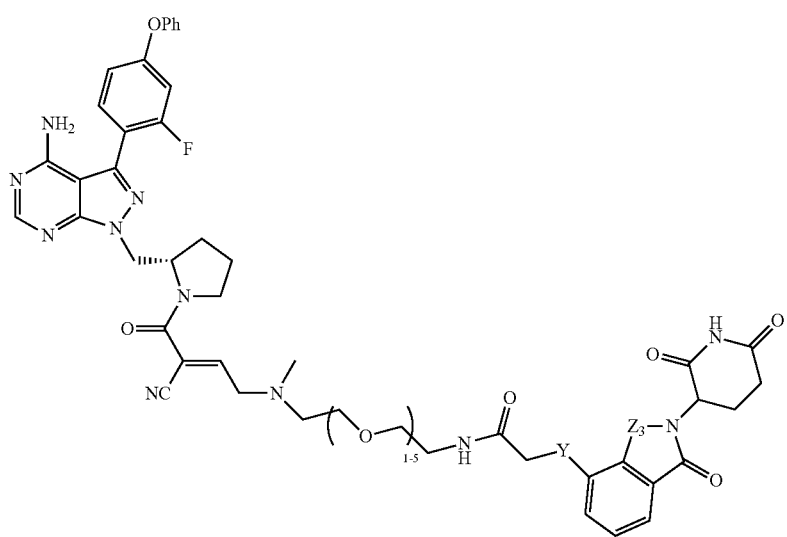
Y = O, NH
Z₃ = CH₂, C═O TABLE B-continued
Structure
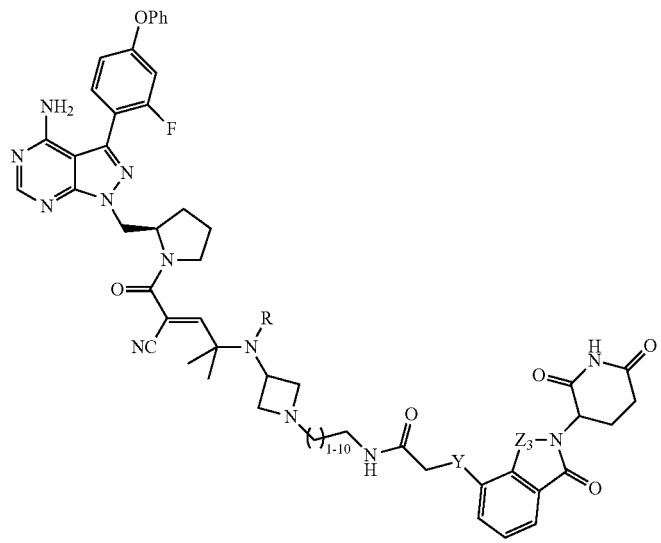
R = H, Me, Et
Y = O, NH
$Z_3$ = $CH_2$, C=O
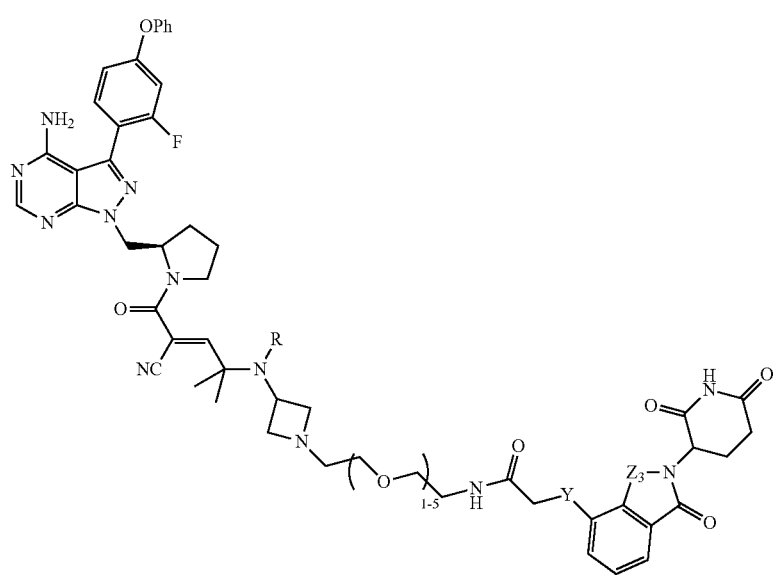
R = H, Me, Et
$Z_3$ = $CH_2$, C=O
Y = O, NH TABLE B-continued
Structure
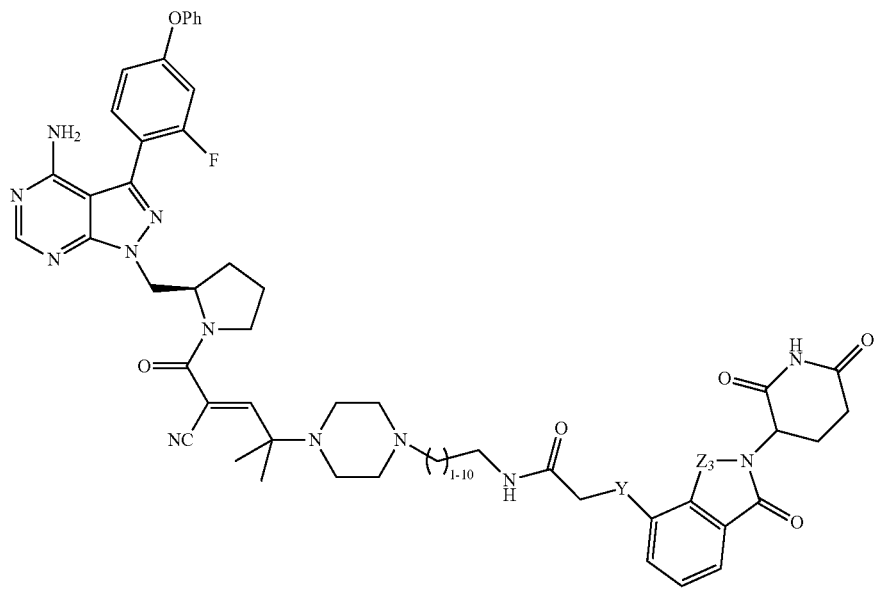
Z₃ = CH₂, C=O
Y = O, NH
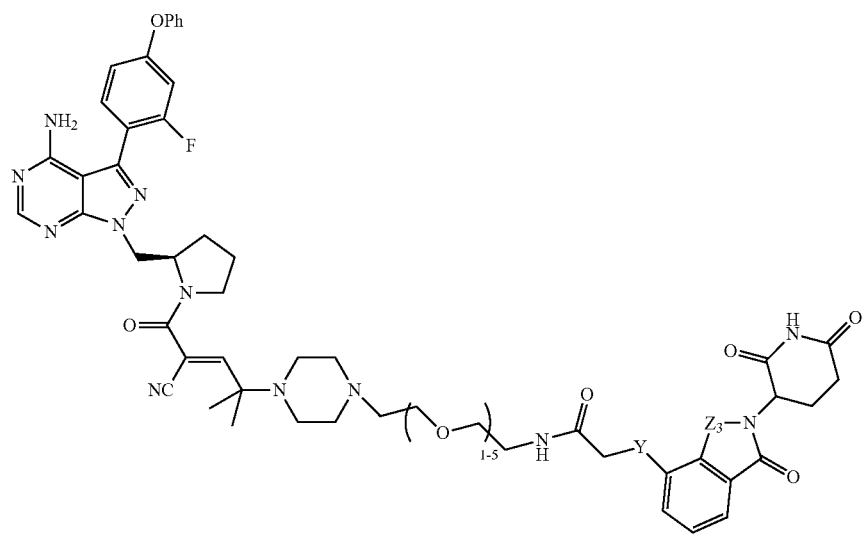
Z₃ = CH₂, C=O
Y = O, NH TABLE B-continued
Structure
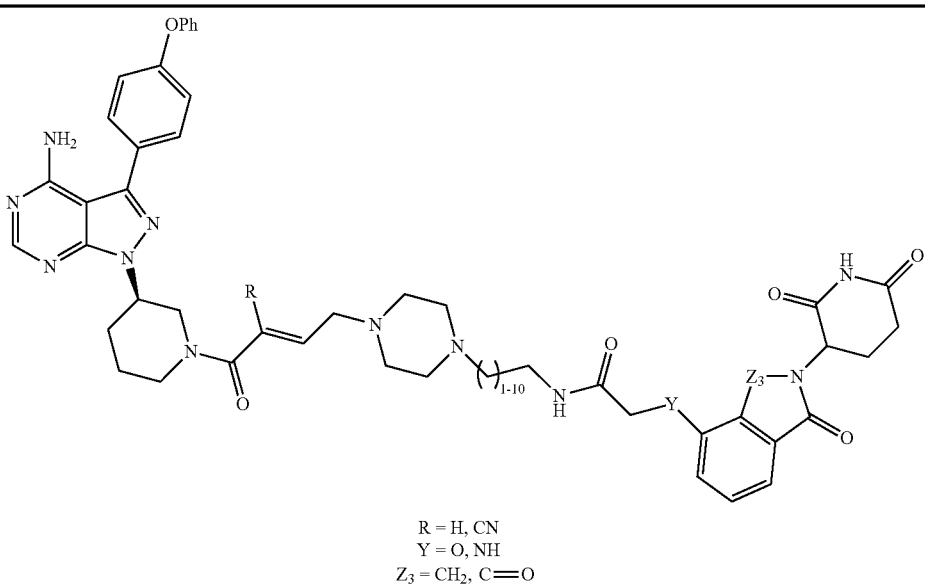
R = H, CN
Y = O, NH
$Z_3$ = $CH_2$, C=O
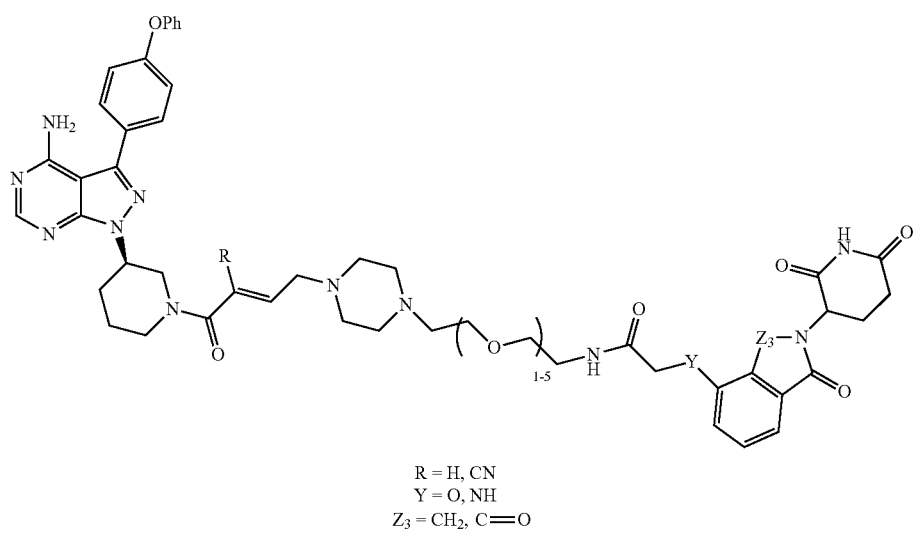
R = H, CN
Y = O, NH
$Z_3$ = $CH_2$, C=O
TABLE B1
Structure
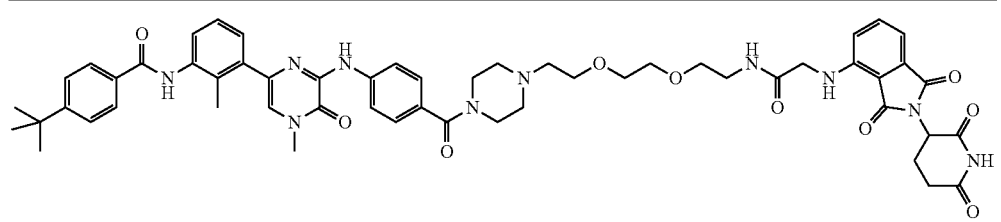
(II-0)

TABLE B1-continued
Structure
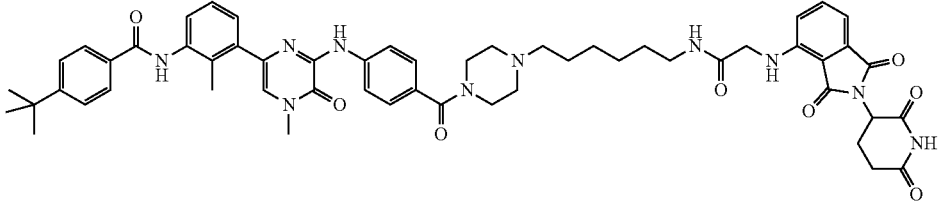 [SMILES: Cc1c(NC(=O)c2ccc(C(C)(C)C)cc2)cccc1-c1cn(C)c(=O)c(Nc2ccc(C(=O)N3CCN(CCCCCCNC(=O)CNc4cccc5c4C(=O)N(C4CCC(=O)NC4=O)C5=O)CC3)cc2)n1]
(II-1)
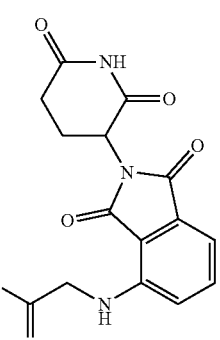
(II-2)
| TABLE C |
|---|
| Structure |
|  |
| 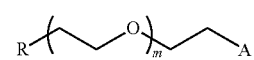 |
|  |
|  |
|  |
| 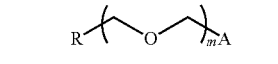 |
| 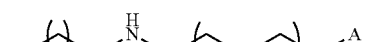 |
| TABLE C-continued |
|---|
| Structure |
|  |
|  |
| 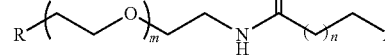 |
|  |
| 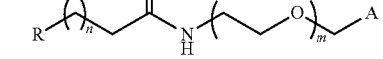 |

TABLE C-continued

Structure

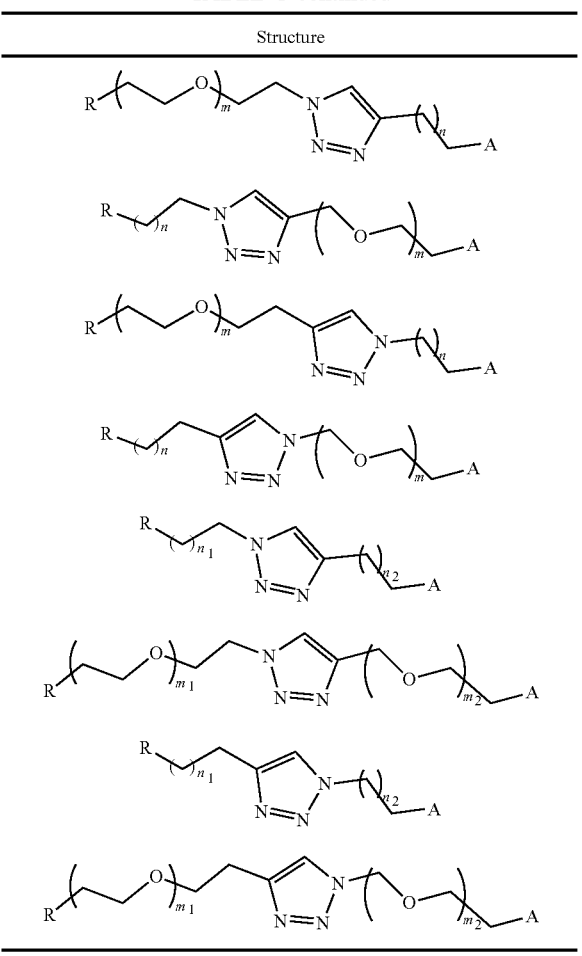

R = Targeting Ligand
A = Degron
n, n1, n2 = 0-20
m, m1, m2 = 1-10

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application relates to compounds that target proteins, such as BTK for degradation, which have numerous advantages over inhibitors of protein function (e.g., protein activity) and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity (e.g., protein activity) can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Some embodiments relate to the loss of 50-100% of the target protein. Other embodiments relate to the loss of 75-95% of the targeted protein.

A bifunctional compound of the present application (e.g., a bifunctional compound of any of the formulae described herein, or selected from any bifunctional compounds described herein) is capable of modulating (e.g., decreasing) the amount of a targeted protein (e.g., BTK). A bifunctional compound of the present application (e.g., a bifunctional compound of any of the formulae described herein, or selected from any bifunctional compounds described herein) is also capable of degrading a targeted protein (e.g., BTK) through the UPP pathway. Accordingly, a bifunctional compound of the present application (e.g., a bifunctional compound of any of the formulae described herein, or selected from any bifunctional compounds described herein) is capable of treating or preventing a disease or disorder in which BTK plays a role. A bifunctional compound of the present application (e.g., a bifunctional compound of any of the formulae described herein, or selected from any bifunctional compounds described herein) is also capable of treating or preventing a disease or disorder in which BTK plays a role or in which BTK is deregulated (e.g., overexpressed).

Modulation of BTK through UPP-mediated degradation by a bifunctional compound of the application, such as those described herein, provides a novel approach to the treatment, prevention, or amelioration of diseases or disorders in which BTK plays a role including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy. Further, modulation of BTK through UPP-mediated degradation by a bifunctional compound of the application, such as those described herein, also provides a new paradigm for treating, preventing, or ameliorating diseases or disorders in which BTK is deregulated.

In one embodiment, a bifunctional compound of the present application (e.g., a bifunctional compound of any of the formulae described herein, or selected from any bifunctional compounds described herein) is more efficacious in treating a disease or condition (e.g., cancer) than, or is capable of treating a disease or condition resistant to, the Targeting Ligand, when the Targeting Ligand is administered alone (i.e., not bonded to a Linker and a Degron). In one embodiment, a bifunctional compound of the present application (e.g., a bifunctional compound of any of the formulae described herein, or selected from any bifunctional compounds described herein) is capable of modulating (e.g., decreasing) the amount of BTK, and thus is useful in treating a disease or condition (e.g., cancer) in which BTK plays a role.

In one embodiment, the bifunctional compound of the present application that is more efficacious in treating a disease or condition than, or is capable of treating a disease or condition resistant to, the Targeting Ligand, when the Targeting Ligand is administered alone (i.e., not bonded to a Linker and a Degron), is more potent in inhibiting the growth of cells (e.g., cancer cells) or decreasing the viability of cells (e.g., cancer cells), than the Targeting Ligand, when the Targeting Ligand is administered alone (i.e., not bonded to a Linker and a Degron). In one embodiment, the bifunctional compound inhibits the growth of cells (e.g., cancer cells) or decreases the viability of cells (e.g., cancer cells) at an $IC_{50}$ that is lower than the $IC_{50}$ of the Targeting Ligand (when the Targeting Ligand is administered alone (i.e., not bonded to a Linker and a Degron)) for inhibiting the growth or decreasing the viability of the cells. In one embodiment, the $IC_{50}$ of the bifunctional compound is at most 90%, 80%, 70%, 60%, 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 1%, 0.8%, 0.5%, 0.4%, 0.3%, 0.2%, or 0.1% of the $IC_{50}$ of the Targeting Ligand. In one embodiment, the bifunctional compound inhibits the growth of cells (e.g., cancer cells) or decreases the viability of cells (e.g., cancer cells) at an $E_{max}$ that is lower than the $E_{max}$ of the Targeting Ligand (when the Targeting Ligand is administered alone (i.e., not bonded to a Linker and a Degron)) for inhibiting the growth or decreasing the viability of the cells. In one embodiment, the $E_{max}$ of the bifunctional compound is at most 90%, 80%, 70%, 60%, 50%, 40%, 30%, 20%, 10%, 8%, 5%, 4%, 3%, 2, or 1% of the $E_{max}$ of the Targeting Ligand. In one embodiment, the $E_{max}$ of the bifunctional compound is at most 50%, 40%, 30%, 20%, 10%, 8%, 5%, 4% 3%, 2%, or 1% of the $E_{max}$ of the Targeting Ligand. In one embodiment, the $E_{max}$ of the bifunctional compound is at most 90%, 80%, 70%, 60%, 50%, 40%, 30%, 20%, or 10% of the $E_{max}$ of the Targeting Ligand.

In some embodiments, the inhibition of BTK activity is measured by $IC_{50}$.

In some embodiments, the inhibition of BTK activity is measured by $EC_{50}$.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining a BTK-dependent cell proliferation, in vitro or in vivo (e.g., in cells expressing BTK).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a BTK-dependent cell proliferation, in vitro or in vivo (e.g., in cells expressing BTK).

In one embodiment, the bifunctional compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

A "selective BTK inhibitor," can be identified, for example, by comparing the ability of a compound to inhibit BTK kinase activity to its ability to inhibit other kinases. For example, a substance may be assayed for its ability to inhibit BTK kinase activity, as well as another kinase. In some embodiments, the selectivity can be identified by measuring the $EC_{50}$ or $IC_{50}$ of the compounds.

Definitions

Listed below are definitions of various terms used in this application. These definitions apply to the terms as they are used throughout this specification and claims, unless otherwise limited in specific instances, either individually or as part of a larger group.

The term "alkyl" as used herein, refers to saturated, straight or branched-chain hydrocarbon radicals containing, in certain embodiments, between one and six carbon atoms. For example $C_1$-$C_3$ alkyl includes methyl, ethyl, n-propyl, and isopropyl. Examples of $C_1$-$C_6$ alkyl radicals include, but are not limited to, methyl, ethyl, propyl, isopropyl, n-butyl, tert-butyl, neopentyl, and n-hexyl radicals.

The term "alkylenyl" or "alkylene," as used herein, refers to a divalent group derived from a saturated, straight or branched hydrocarbon chain of from 1 to 32 carbon atoms. The term "$C_1$-$C_4$ alkylenyl" means those alkylenyl or alkylene groups having from 1 to 4 carbon atoms. Representative examples of alkylenyl groups include, but are not limited to, —$CH_2$—, —$CH(CH_3)$—, —$CH(C_2H_5)$—, —$CH(CH(CH_3)(C_2H_5))$—, —$C(H)(CH_3)CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—. Alkylenyl groups may be unsubstituted or substituted by one or more suitable substituents, as defined herein.

The term "alkenylenyl" or "alkenylene," as used herein, refers to a divalent group derived from a straight or branched chain hydrocarbon of 2 to 32 carbon atoms, which contains at least one carbon-carbon double bond. Representative examples of alkenylenyl groups include, but are not limited to, —$C(H)=C(H)$—, —$C(H)=C(H)$—$CH_2$—, —$C(H)=C(H)$—$CH_2$—$CH_2$—, —$CH_2$—$C(H)=C(H)$—$CH_2$—, —$C(H)=C(H)$—$CH(CH_3)$—, and —$CH_2$—$C(H)=C(H)$—$CH(CH_2CH_3)$—. Alkenylenyl groups may be unsubstituted or substituted by one or more suitable substituents, as defined herein.

The term "alkoxy" refers to an —O-alkyl radical. For example $C_1$-$C_3$ alkoxy includes methoxy, ethoxy, n-propoxy, and isopropoxy. Examples of $C_1$-$C_6$ alkyl radicals include, but are not limited to, methoxy, ethoxy, propoxy, isopropoxy, n-butoxy, tert-butoxy, neopentoxy, and n-hexoxy radicals.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with this application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_2$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_2$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_2$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_2$-alkenyl, —OCONH—$C_2$-$C_2$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_2$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_2$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-Cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC (NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_2$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "BTK" herein refers to Bruton's tyrosine kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The term "targeted protein(s)" is used interchangeably with "target protein(s)", unless the context clearly dictates otherwise. In one embodiment, a "targeted protein" is BTK.

The term "disease(s)", "disorder(s)", and "condition(s)" are used interchangeably, unless the context clearly dictates otherwise.

The term "therapeutically effective amount" of a bifunctional compound or pharmaceutical composition of the application, as used herein, means a sufficient amount of the bifunctional compound or pharmaceutical composition so as to decrease the symptoms of a disorder in a subject. As is well understood in the medical arts a therapeutically effective amount of a bifunctional compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the bifunctional compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the bifunctional compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of bifunctional compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a bifunctional compound of the application, or an enantiomer, diastereomer, stereoisomer, or pharmaceutically acceptable salt thereof, and a pharmaceutically acceptable carrier.

In another aspect, the application provides a kit comprising a bifunctional compound capable of inhibiting BTK activity selected from one or more compounds disclosed herein, or a pharmaceutically acceptable salt, hydrate, solvate, prodrug, stereoisomer, or tautomer thereof, optionally in combination with a second agent and instructions for use in treating cancer.

In another aspect, the application provides a method of synthesizing a bifunctional compound disclosed herein.

The synthesis of the bifunctional compounds of the application can be found herein and in the Examples below.

Other embodiments are a method of making a bifunctional compound of any of the formulae herein using any one, or combination of, reactions delineated herein. The method can include the use of one or more intermediates or chemical reagents delineated herein.

Another aspect is an isotopically labeled bifunctional compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the bifunctional compound. Such compounds are useful for drug metabolism studies and diagnostics, as well as therapeutic applications.

A bifunctional compound of the application can be prepared as a pharmaceutically acceptable acid addition salt by reacting the free base form of the compound with a pharmaceutically acceptable inorganic or organic acid. Alternatively, a pharmaceutically acceptable base addition salt of a bifunctional compound of the application can be prepared by reacting the free acid form of the bifunctional compound with a pharmaceutically acceptable inorganic or organic base.

Alternatively, the salt forms of the bifunctional compounds of the application can be prepared using salts of the starting materials or intermediates.

The free acid or free base forms of the bifunctional compounds of the application can be prepared from the corresponding base addition salt or acid addition salt from, respectively. For example, a bifunctional compound of the application in an acid addition salt form can be converted to the corresponding free base by treating with a suitable base (e.g., ammonium hydroxide solution, sodium hydroxide, and the like). A bifunctional compound of the application in a base addition salt form can be converted to the corresponding free acid by treating with a suitable acid (e.g., hydrochloric acid, etc.).

Prodrugs of the bifunctional compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized bifunctional compound of the application with a suitable carbamylating agent (e.g., 1,1-acyloxyalkylcarbanochloridate, para-nitrophenyl carbonate, or the like).

Protected derivatives of the bifunctional compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared or formed during the process of the application, as solvates (e.g., hydrates). Hydrates of bifunctional compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_{14}$) occurs more than one time in any constituent or formula for a compound, its definition at each occurrence is independent of its definition at every other occurrence. Thus, for example, if a group is shown to be substituted with one or more $R_{14}$ moieties, then $R_{14}$ at each occurrence is selected independently from the definition of $R_{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chrial isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the bifunctional compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the bifunctional compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized bifunctional compounds can be separated from a reaction mixture and further purified by a method such as column chromatography, high pressure liquid chromatography, or recrystallization. As can be appreciated by the skilled artisan, further methods of synthesizing the bifunctional compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{th}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Scheme 1 and 2 which comprise different sequences of assembling intermediates. Starting materials are either commercially available or made by known procedures in the reported literature as illustrated.

General Scheme 1 Synthesis of Thalidomide-based Degraders

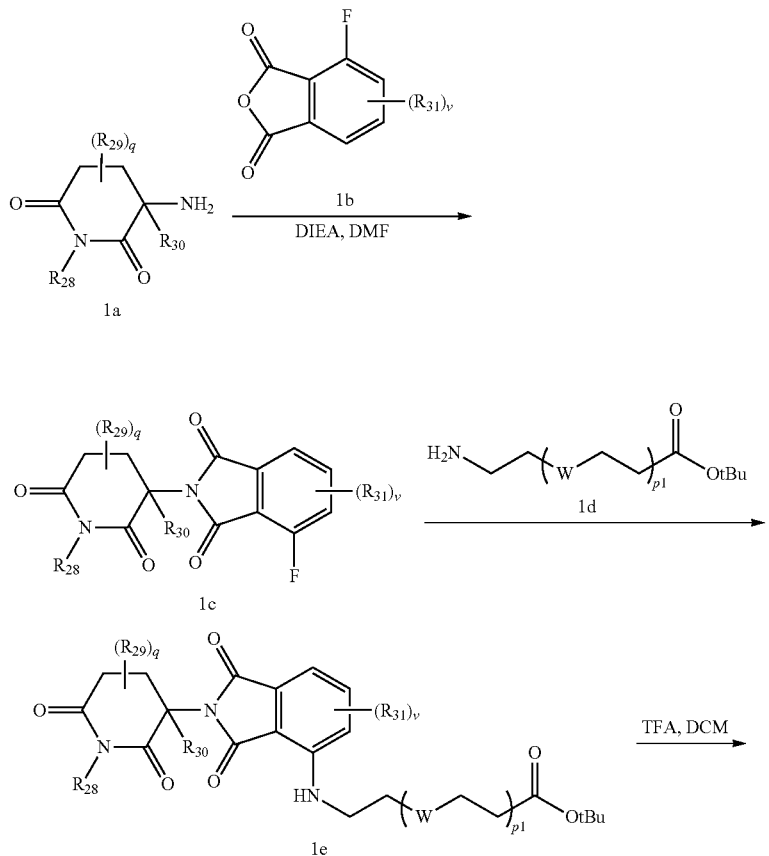

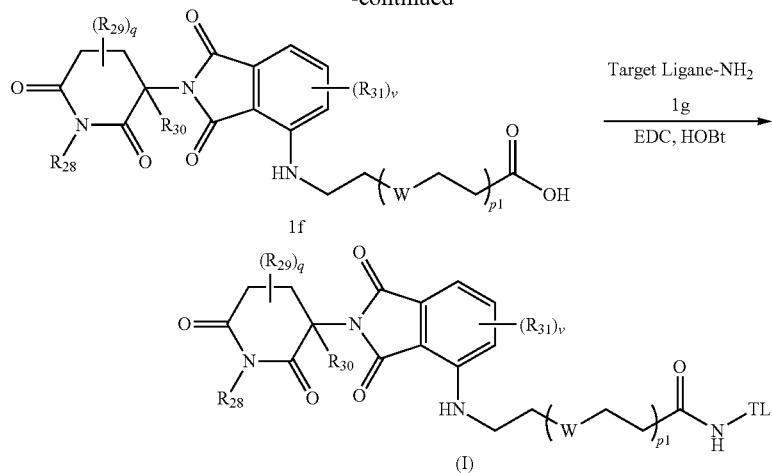

wherein $R_{28}$, $R_{29}$, $R_{30}$, $R_{31}$, W, p1, q, and v are as defined herein above.

The general way of preparing representative compounds of the present application (i.e., Compounds of formula (I) shown above) using intermediates 1a, 1b, 1c, 1d, 1e, 1f, and 1g is outlined in General Scheme 1. Reaction of 1a with 1b in the presence of a base, i.e., diisopropylethylamine (DIPEA), and in a solvent, dimethylformamide (DMF), provides intermediate 1c. Reaction of 1d with fluoride 1c provides intermediate 1e. Deprotection of the 1e in the presence of TEA in a solvent, i.e., dichloromethane (DCM) or methanol (MeOH), provides 1f. Coupling of 1f and Target Ligand (TL) 1g under standard coupling conditions using a coupling reagent, i.e., 1-ethyl-3-(3-dimethylaminopropyl) carbodiimide (EDCI) and hydroxybenzotriazole, in a solvent, i.e., DCM or DMF, provides bifunctional compound of formula (I).

General Scheme 2 Synthesis of VHL-based Degraders

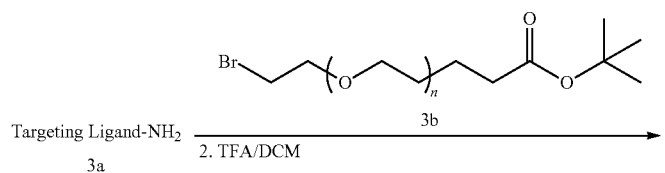

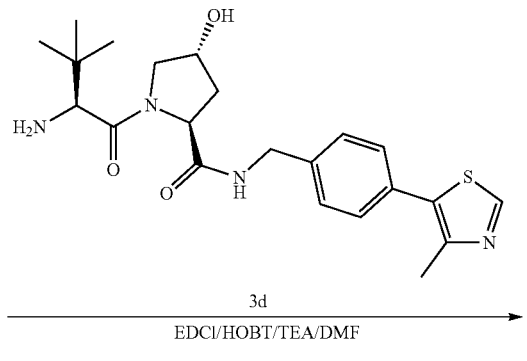

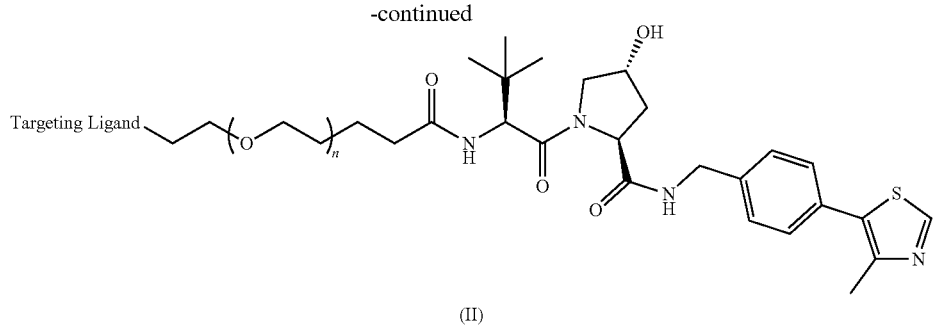

(II)

The general way of preparing representative compounds of the present application (i.e., Compound of formula (II) shown above) using intermediates 3a, 3b, 3c, and 3d is outlined in General Scheme 2. Reaction of 3a with 3b in the presence of potassium iodide (KI), a base, i.e., potassium carbonate ($K_2CO_3$), and in a solvent, i.e., acetone), followed by Boc deprotection in the presence of strong acid (i.e., hydrochloric acid (HCl) or trifluoroacetic acid (TFA)) in a solvent, i.e., dichloromethane (DCM) or methanol (MeOH) provides intermediate 3c. Coupling of amine 3d and Target Ligand 3c under standard coupling conditions using a coupling reagent, i.e., 1-ethyl-3-(3-dimethylaminopropyl) carbodiimide (EDCI) and hydroxybenzotriazole (HOBt), and a base (i.e., triethylamine (TEA)) in a solvent, i.e., DCM or DMF, provides bifunctional compound of formula (II) in shown in General Scheme 2.

Biological Assays
Cell Viability Assay

Wild-type of cereblon null cells are treated with various concentrations of a bifunctional compound of the application and allowed to grow. Cells are then assayed to determine cell viability by measuring the amount of ATP present, which is an indicator of cell metabolic activity. Results are graphed as relative luminescent values.

Methods of the Application

In another aspect, the application provides a method of modulating a kinase, comprising contacting the kinase with a bifunctional compound disclosed herein, or an enantiomer, diastereomer, or stereoisomer thereof, or pharmaceutically acceptable salt, hydrate, solvate, or prodrug thereof, or with a pharmaceutical composition disclosed herein. In some embodiments, the kinase is BTK.

In another aspect, the application provides a method of inhibiting a kinase, comprising contacting the kinase with a bifunctional compound disclosed herein, or an enantiomer, diastereomer, or stereoisomer thereof, or pharmaceutically acceptable salt, hydrate, solvate, or prodrug thereof or with a pharmaceutical composition disclosed herein. In some embodiments, the kinase is BTK.

In still another aspect, the application provides a method of inhibiting BTK, the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof.

In still another aspect, the application provides a method of inhibiting BTK, the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

Another aspect of the application provides a method of treating or preventing a disease, the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof. In some embodiments, the disease is mediated by a kinase. In further embodiments, the kinase is BTK.

Another aspect of the application provides a method of treating or preventing a disease, the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier. In some embodiments, the disease is mediated by a kinase. In further embodiments, the kinase is BTK.

In some embodiments, the disease is mediated by BTK (e.g., BTK plays a role in the initiation or development of the disease).

In certain embodiments, the disease or disorder is cancer or a proliferation disease.

In further embodiments, the disease or disorder is lung cancer, colon cancer, breast cancer, prostate cancer, liver cancer, pancreatic cancer, brain cancer, kidney cancer, ovarian cancer, stomach cancer, skin cancer, bone cancer, gastric cancer, glioma, glioblastoma, hepatocellular carcinoma, papillary renal carcinoma, head and neck squamous cell carcinoma, leukemias, lymphomas, myelomas, or solid tumors.

In further embodiments, the disease or disorder is sarcoma. In further embodiments, the disease or disorder is sarcoma of the bones, muscles, tendons, cartilage, nerves, fat, or blood vessels. In further embodiments, the disease or disorder is soft tissue sarcoma, bone sarcoma, or osteosarcoma. In further embodiments, the disease or disorder is angiosarcoma, fibrosarcoma, liposarcoma, leiomyosarcoma, Karposi's sarcoma, osteosarcoma, gastrointestinal stromal tumor, Synovial sarcoma, Pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In further embodiments, the disease or disorder is multiple myeloma.

In other embodiments, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease or disorder is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

Another aspect of the application provides a method of treating a kinase mediated disorder, the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof. In some embodiments, the bifunctional compound is an inhibitor of BTK. In other embodiments, the subject is administered an additional therapeutic agent. In other embodiments, the bifunctional compound and the additional therapeutic agent are administered simultaneously or sequentially.

Another aspect of the application provides a method of treating a kinase mediated disorder, the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier. In some embodiments, the bifunctional compound is an inhibitor of BTK. In other embodiments, the subject is administered an additional therapeutic agent. In other embodiments, the pharmaceutical composition comprising a bifunctional compound and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreatic cancer, brain cancer, kidney cancer, ovarian cancer, stomach cancer, skin cancer, bone cancer, gastric cancer, glioma, glioblastoma, hepatocellular carcinoma, papillary renal carcinoma, head and neck squamous cell carcinoma, leukemias, lymphomas, myelomas, or solid tumors.

Another aspect of the present application relates to a method of treating or preventing a proliferative disease. The method comprises administering to a subject in need thereof an effective amount of a bifunctional compound of the application, or an enantiomer, diastereomer, or stereoisomer thereof, or pharmaceutically acceptable salt, hydrate, solvate, or prodrug thereof.

Another aspect of the present application relates to a method of treating or preventing a proliferative disease. The method comprises administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In another aspect, the application provides a method of treating or preventing cancer, wherein the cancer cell comprises activated BTK, comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof.

In another aspect, the application provides a method of treating or preventing cancer, wherein the cancer cell comprises activated BTK, comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In certain embodiments, the BTK activation is selected from mutation of BTK, amplification of BTK, expression of BTK, and ligand mediated activation of BTK.

Another aspect of the application provides a method of treating or preventing cancer in a subject, wherein the subject is identified as being in need of BTK inhibition for the treatment of cancer, comprising administering to the subject an effective amount of a bifunctional compound disclosed herein, or an enantiomer, diastereomer, or stereoisomer thereof, or pharmaceutically acceptable salt, hydrate, solvate, or prodrug thereof.

Another aspect of the application provides a method of treating or preventing cancer in a subject, wherein the subject is identified as being in need of BTK inhibition for the treatment of cancer, comprising administering to the subject an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In certain embodiments, the application provides a method of treating any of the disorders described herein, wherein the subject is a human. In certain embodiments, the application provides a method of preventing any of the disorders described herein, wherein the subject is a human.

In another aspect, the application provides a bifunctional compound disclosed herein, or an enantiomer, diastereomer, or stereoisomer thereof, or pharmaceutically acceptable salt, hydrate, solvate, or prodrug thereof, for use in the manufacture of a medicament for treating or preventing a disease in which BTK plays a role.

In still another aspect, the application provides a bifunctional compound of the application, or an enantiomer, diastereomer, or stereoisomer thereof, or pharmaceutically acceptable salt, hydrate, solvate, or prodrug thereof for use in treating or preventing a disease in which BTK plays a role.

In another aspect, the application provides a pharmaceutical composition comprising a bifunctional compound disclosed herein, or an enantiomer, diastereomer, or stereoisomer thereof, or pharmaceutically acceptable salt, hydrate, solvate, or prodrug thereof f and a pharmaceutically acceptable carrier, for use in the manufacture of a medicament for treating or preventing a disease in which BTK plays a role.

In still another aspect, the application provides a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier, for use in treating or preventing a disease in which BTK plays a role.

As inhibitors of BTK, the bifunctional compounds and compositions of this application are particularly useful for treating or lessening the severity of a disease, condition, or disorder where a protein kinase is implicated in the disease, condition, or disorder. In one aspect, the present application provides a method for treating or lessening the severity of a disease, condition, or disorder where a protein kinase is implicated in the disease state. In another aspect, the present application provides a method for treating or lessening the severity of a protein kinase mediated disease, condition, or disorder where inhibition of enzymatic activity is implicated in the treatment of the disease. In another aspect, this application provides a method for treating or lessening the severity of a disease, condition, or disorder with bifunctional compounds that inhibit enzymatic activity by binding to the protein kinase. Another aspect provides a method for treating or lessening the severity of a protein kinase mediated disease, condition, or disorder by inhibiting enzymatic activity of the protein kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this application provides bifunctional compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject bifunctional compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the bifunctional compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more bifunctional compounds of the application in the manufacture of a medicament for the treatment of cancer, including without limitation the various types of cancer disclosed herein.

In some embodiments, the bifunctional compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the bifunctional compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject bifunctional compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Another aspect of this application provides a method for the treatment or lessening the severity of a disease selected from a proliferative or hyperproliferative disease, or a neurodegenerative disease, comprising administering an effective amount of a bifunctional compound, or a pharmaceutically acceptable composition comprising a bifunctional compound, to a subject in need thereof.

As inhibitors of BTK kinase, the compounds and compositions of this application are also useful in biological samples. One aspect of the application relates to inhibiting protein kinase activity in a biological sample, which method comprises contacting said biological sample with a bifunctional compound of the application or a composition comprising said bifunctional compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this application relates to the study of BTK kinase in biological and pathological phenomena; the study or intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present application as BTK inhibitors may be assayed in vitro, in vivo, or in a cell line. In vitro assays include assays that determine inhibition of either the enzyme activity or ATPase activity of the activated kinase. Alternate in vitro assays quantitate the ability of the inhibitor to bind to the protein kinase and may be measured either by radio labelling the inhibitor prior to binding, isolating the inhibitor/BTK complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application further provides a method for preventing or treating any of the diseases or disorders described above in a subject in need of such treatment, which method comprises administering to said subject a therapeutically effective amount of a bifunctional compound of the application, or an enantiomer, diastereomer, or stereoisomer thereof, or pharmaceutically acceptable salt, hydrate, solvate, or prodrug thereof. For any of the above uses, the required dosage will vary depending on the mode of administration, the particular condition to be treated and the effect desired.

Pharmaceutical Compositions

In another aspect, the application provides a pharmaceutical composition comprising a therapeutically effective amount of a bifunctional compound of the present application or an enantiomer, diastereomer, or stereoisomer thereof, or pharmaceutically acceapatable salt, hydrate, solvate, or prodrug thereof, and a pharmaceutically acceptable carrier.

Bifunctional compounds of the application can be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preseravatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinatorial therapy with one or more therapeutic agents (pharmaceutical combinations) or modalities, e.g., an antiproliferative, anti-cancer, immunomodulatory or anti-inflammatory agent. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinatorial therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients (such as, but not limited to, a second BTK inhibitor, a second and different antineoplastic agent, a kinase inhibitor and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In another aspect of the application, the compounds may be administered in combination with one or more separate pharmaceutical agents, e.g., a chemotherapeutic agent, an immunotherapeutic agent, or an adjunctive therapeutic agent.

EXAMPLES

Analytical Methods, Materials, and Instrumentation

All reactions are monitored on a Waters Acquity UPLC/MS system (Waters PDA ex Detector, QDa Detector, Sample manager—FL, Binary Solvent Manager) using Acquity UPLC® BEH C18 column (2.1×50 mm, 1.7 µm particle size): solvent gradient=90% A at 0 min, 1% A at 1.8 min; solvent A=0.1% formic acid in Water; solvent B=0.1% formic acid in Acetonitrile; flow rate: 0.6 mL/min. Reaction products are purified by flash column chromatography using CombiFlash® Rf with Teledyne Isco RediSep® Rf High Performance Gold or Silicycle SiliaSep™ High Performance columns (4 g, 12 g, 24 g, 40 g, or 80 g), Waters HPLC system using SunFire™ Prep C18 column (19×100 mm, 5 µm particle size): solvent gradient=80% A at 0 min, 5% A at 25 min; solvent A=0.035% TFA in Water; solvent B=0.035% TFA in MeOH; flow rate: 25 mL/min (Method A), and Waters Acquity UPLC/MS system (Waters PDA eλ Detector, QDa Detector, Sample manager—FL, Binary Solvent Manager) using Acquity UPLC® BEH C18 column (2.1×50 mm, 1.7 □m particle size): solvent gradient=800% A at 0 min, 5% A at 2 min; solvent A=0.1% formic acid in Water; solvent B=0.1% formic acid in Acetonitrile; flow rate: 0.6 mL/min (method B). The purity of all compounds is over 95% and is analyzed with Waters LC/MS system. $^1$H NMR is obtained using a 500 MHz Bruker Avance III. Chemical shifts are reported relative to dimethyl sulfoxide (δ=2.50) for $^1$H NMR. Data are reported as (br=broad, s=singlet, d=doublet, t=triplet, q=quartet, m=multiplet).

Abbreviations used in the following examples and elsewhere herein are:

br broad

DCM dichloromethane

DMF N,N-dimethylformamide

EDCI 1-ethyl-3-(3-dimethylaminopropyl) carbodiimide

ESI electrospray ionization

EtOAc ethyl acetate

HCl hydrochloric acid h hour(s)

HPLC high-performance liquid chromatography

LCMS liquid chromatography-mass spectrometry m multiplet

MeOH methanol

MHz megahertz min minutes

MS mass spectrometry

NMR nuclear magnetic resonance

Pd(PPh$_3$)$_4$ tetrakis(triphenylphosphine)dipalladium(0)

ppm parts per million

TFA trifluoracetic acetic acid

Example 1: Synthesis of 4-(tert-butyl)-N-(2-methyl-3-(4-methyl-5-oxo-6-((4-(piperazine-1-carbonyl)phenyl)amino)-4,5-dihydropyrazin-2-yl)phenyl)benzamide trifluoroacetic Acid Salt (Intermediate 2-1)
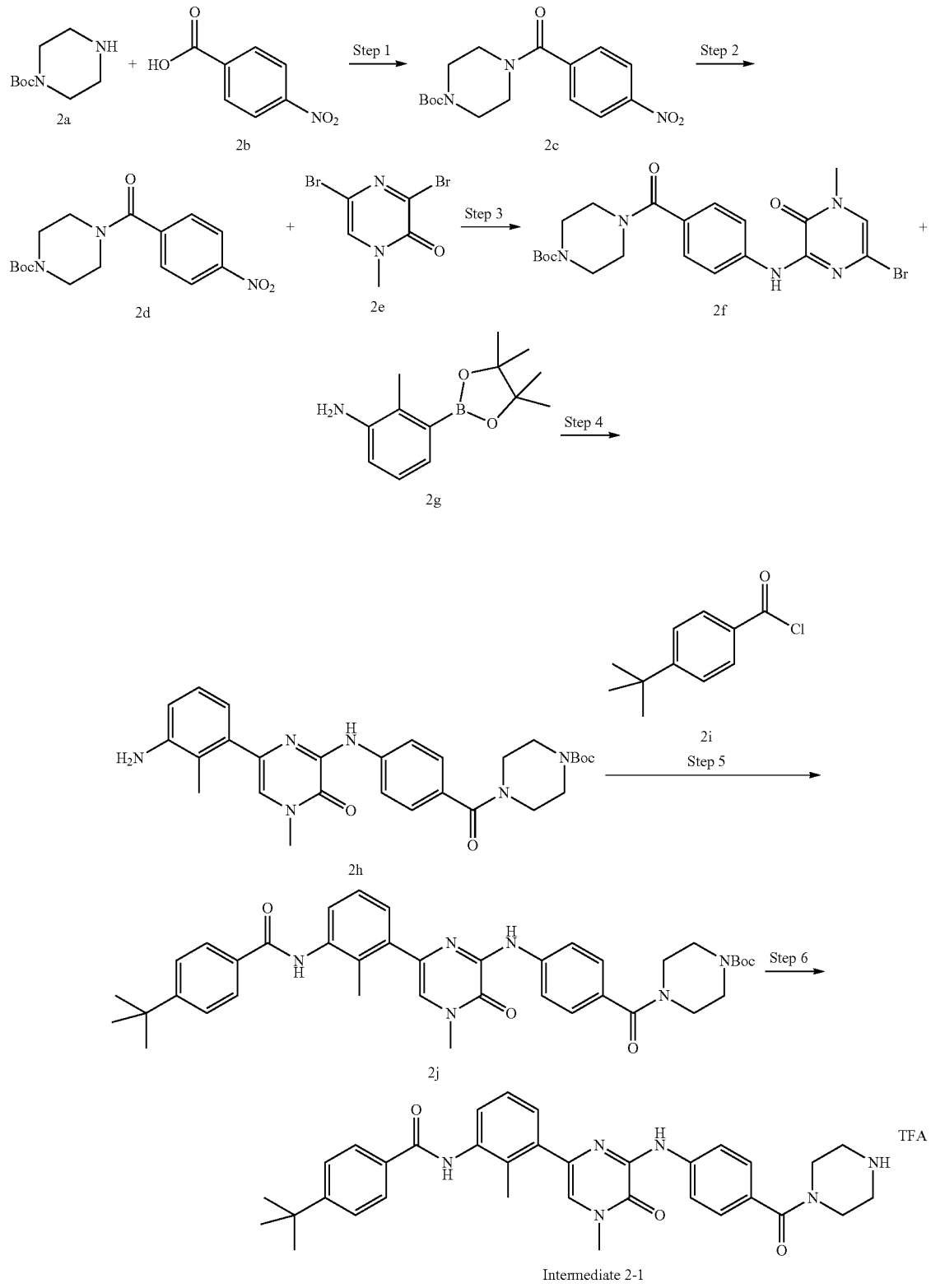

Step 1. tert-butyl 4-(4-nitrobenzoyl)piperazine-1-carboxylate (2c)

To a solution of tert-butyl piperazine-1-carboxylate (2a, 3.1 g, 16.6 mmol, 1 equiv.), 4-nitrobenzoic acid (2b, 2.8 g, 16.6. mmol, 1 equiv.), N,N-diisopropylethylamine (5.8 mL, 33.2 mmol, 2 equiv.), and hydroxybenzotriazole (2.2 g, 16.6 mmol, 1 equiv.) in anhydrous DCM (40 mL) was added N-(3-dimethylaminopropyl)-N'-ethylcarbodiimide hydrochloride (3.8 g, 20.0 mmol, 1.2 equiv.) at 0° C. The resulting solution was warmed to room temperature and then stirred for 24 h. Water was added and the mixture was extracted three times with DCM. The combined organic layers were dried with $Na_2SO_4$, filtered, and concentrated. The resulting crude product was then purified via silica gel column chromatography to obtain the product 2c as a yellow solid (4.6 g, 13.7 mmol, 82% yield).

Step 2. tert-butyl 4-(4-aminobenzoyl)piperazine-1-carboxylate (2d)

To a degassed solution of tert-butyl 4-(4-nitrobenzoyl)piperazine-1-carboxylate (2c, 4.1 g, 12.3 mmol, 1 equiv.) in anhydrous MeOH (40 mL) was added Pd/C (10% wt., dry; 600 mg). The reaction was sealed, fitted with a $H_2$ balloon and then stirred for 3 h at room temperature. The reaction mixture was filtered through Celite and then concentrated to obtain the product 2d as a white foam (3.7 g, 12 mmol, 98% yield).

Step 3. tert-butyl 4-(4-((6-bromo-4-methyl-3-oxo-3,4-dihydropyrazin-2-yl)amino)benzoyl)piperazine-1-carboxylate (2f)

A solution of tert-butyl 4-(4-aminobenzoyl)piperazine-1-carboxylate (2d, 1.7 g, 5.7 mmol, 1 equiv.), 3,5-dibromo-1-methylpyrazin-2(1H)-one (2e, 1.8 g, 6.8 mmol, 1.2 equiv.) and N,N-diisopropylethylamine (1.48 mL, 8.5 mmol, 1.5 equiv.) in N,N-dimethylacetamide (5 mL) was stirred in a sealed vial at 105° C. for 30 h. The reaction was cooled to room temperature and EtOAc (20 mL) was then added. The solid precipitate was filtered and dried on high vacuum overnight to provide tert-butyl 4-(4-((6-bromo-4-methyl-3-oxo-3,4-dihydropyrazin-2-yl)amino)benzoyl)piperazine-1-carboxylate 2f. The product was carried onto the next step without further purification.

Step 4. tert-butyl 4-(4-((6-(3-amino-2-methylphenyl)-4-methyl-3-oxo-3,4-dihydropyrazin-2-yl)amino)benzoyl)piperazine-1-carboxylate (2h)

tert-butyl 4-(4-((6-bromo-4-methyl-3-oxo-3,4-dihydropyrazin-2-yl)amino)benzoyl)piperazine-1-carboxylate (2f, 1 g, 2.0 mmol, 1 equiv.) was dissolved in anhydrous 1,4-dioxane (6 mL) and $Na_2CO_3$ (323 mg, 3.0 mmol, 1.5 equiv.) and $H_2O$ (1.2 mL) was added. The mixture was degassed by bubbling $N_2$ gas through the reaction solution for 10 min. $Pd(PPh_3)_4$ (328 mg, 0.28 mmol, 0.14 equiv.) was then added and the vial was sealed and then stirred at 105° C. for 16 h. The resulting mixture was cooled to r.t. and filtered through Celite. The filtrate was concentrated, the resulting residue was redissolved in EtOAc, and the organic layer was washed with saturated $NaHCO_3$(aq). The organic layer was dried with $Na_2SO_4$, filtered, and concentrated in vacuo. The residue was purified via silica gel column chromatography to provide the product 2h as a white solid (244 mg, 0.47 mmol, 27% yield).

Step 5. 4-(tert-butyl)-N-(2-methyl-3-(4-methyl-5-oxo-6-((4-(piperazine-1-carbonyl)phenyl)amino)-4,5-dihydropyrazin-2-yl)phenyl)benzamide trifluoroacetic Acid Salt (2j)

To a solution of tert-butyl 4-(4-((6-(3-amino-2-methylphenyl)-4-methyl-3-oxo-3,4-dihydropyrazin-2-yl)amino)benzoyl)piperazine-1-carboxylate (2h, 238 mg, 0.46 mmol, 1 equiv.) in anhydrous DCM (4 mL) was added anhydrous pyridine (56 μL, 0.68 mmol, 1.5 equiv.) and 4-tert-butyl benzoyl chloride (107 μL, 0.55 mmol, 1.2 equiv.). After stirring at room temperature for 1 h, the reaction mixture was concentrated to provide 2j as crude solid, which was carried onto next step directly without further purification.

Step 6. 4-(tert-butyl)-N-(2-methyl-3-(4-methyl-5-oxo-6-((4-(piperazine-1-carbonyl)phenyl)amino)-4,5-dihydropyrazin-2-yl)phenyl)benzamide trifluoroacetic Acid Salt (2-1)

4-(tert-butyl)-N-(2-methyl-3-(4-methyl-5-oxo-6-((4-(piperazine-1-carbonyl)phenyl) amino)-4,5-dihydropyrazin-2-yl)phenyl)benzamide trifluoroacetic acid salt (2j) was dissolved in anhydrous DCM (3 mL) and trifluoroacetic acid (3 mL) was added. After stirring for 2 h, the reaction mixture was concentrated. The resulting crude product was dissolved in DMSO and purified using a HPLC chromatography on a reverse phase C18 column to afford intermediate 2-1 as a white solid (154 mg, 0.22 mmol, 48% yield over two steps). $^1H$ NMR (500 MHz, DMSO) δ 9.90 (s, 1H), 9.50 (s, 1H), 8.85 (s, 2H), 8.11 (d, J=8.7 Hz, 2H), 7.95 (d, J=8.4 Hz, 2H), 7.55 (d, J=8.5 Hz, 2H), 7.42-7.34 (m, 3H), 7.33-7.27 (m, 3H), 3.67 (bs, 4H), 3.57 (s, 3H), 3.17 (bs, 4H), 2.28 (s, 3H), 1.33 (s, 9H).

Example 2: Synthesis of 4-(tert-butyl)-N-(3-(6-((4-(4-(2-(2-(2-(2-((2-(2,6-dioxopiperidin-3-yl)-1,3-dioxoisoindolin-4-yl)amino)acetamido)ethoxy)ethoxy)ethyl)piperazine-1-carbonyl)phenyl)amino)-4-methyl-5-oxo-4,5-dihydropyrazin-2-yl)-2-methylphenyl)benzamide (I-1)

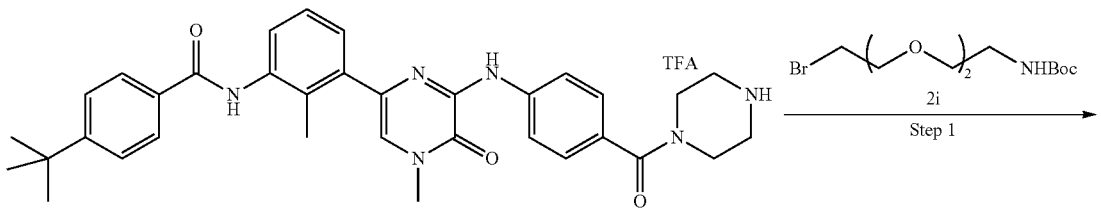

2-1

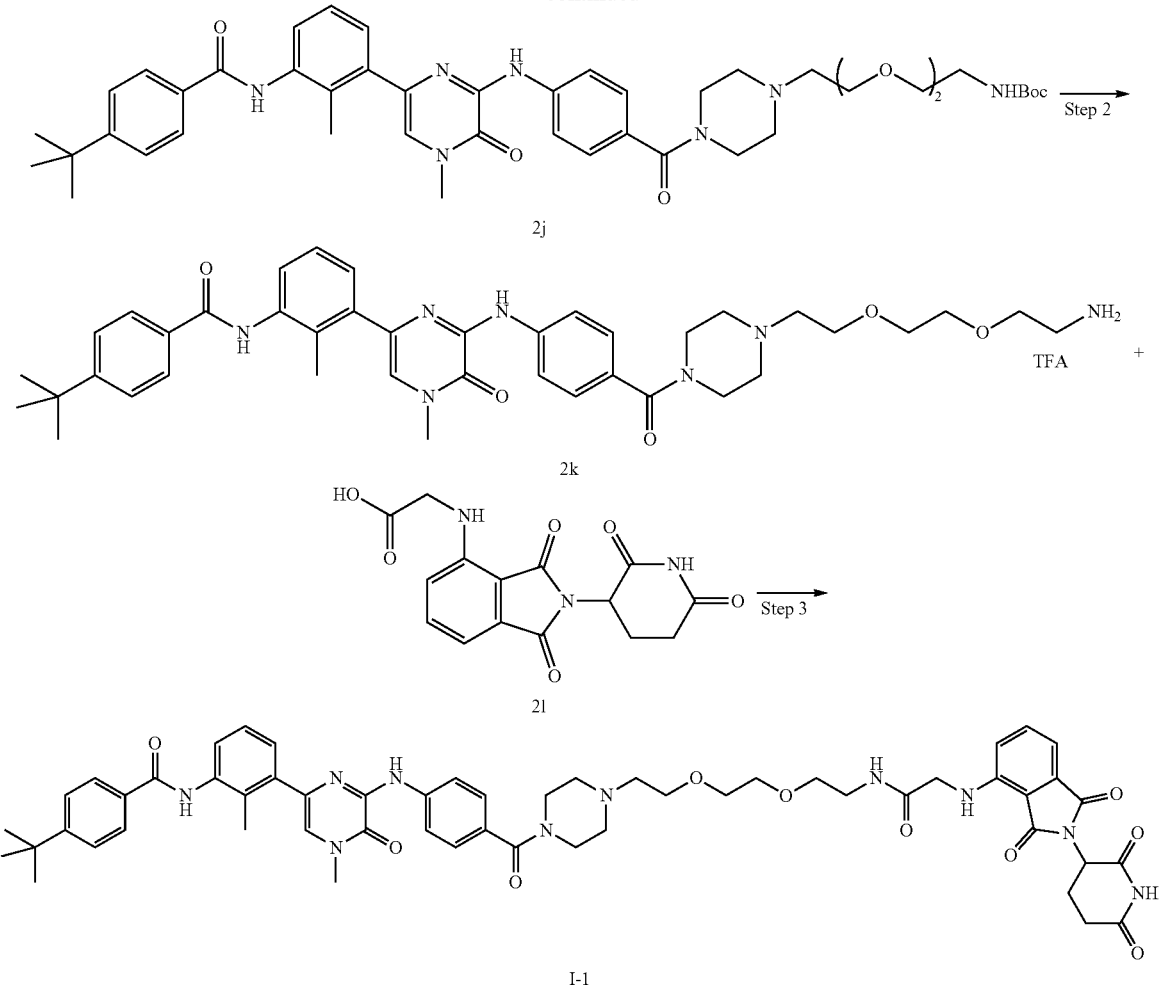

Step 1. tert-butyl (2-(2-(4-(4-((6(3-(4-(tert-buty) benzamido)-2-methylphenyl)-4-methyl-3-oxo-3,4-dihydropyrazin-2-yl)amino)benzoyl)piperazin-1-yl) ethoxy)ethyl)carbamate (2j)

4-(tert-butyl)-N-(2-methyl-3-(4-methyl-5-oxo-6-((4-(piperazine-1-carbonyl)phenyl)amino)-4,5-dihydropyrazin-2-yl)phenyl)benzamide trifluoroacetic acid salt (2-1, 112 mg, 0.163 mmol, 1 equiv.), tert-butyl (2-(2-(2-bromoethoxy)ethoxy)ethyl)carbamate (2i, 111 mg, 0.356 mmol, 2 equiv.), and K₂CO₃ (113 mg, 0.815 mmol, 5 equiv.) were dissolved in anhydrous DMF (2 mL) and then stirred at 80° C. in a sealed vial for 8h. The reaction mixture was cooled to room temperature and water (3 mL) was added. The resulting mixture was extracted with EtOAc (4×10 mL). The combined organic layers were washed with H₂O (2×3 mL) and brine (1×3 mL), dried with Na₂SO₄, filtered, and concentrated to afford 2j as an oil which was carried onto the next step without further purification.

Step 2. N-(3-(6-((4-(4-(2-(2-(2-aminoethoxy) ethoxy)ethyl)piperazine-1-carbonyl)phenyl)amino)-4-methyl-5-oxo-4,5-dihydropyrazin-2-yl)-2-methylphenyl)-4-(tert-butyl)benzamide Trifluoroacetic Acid Salt (2k)

tert-butyl (2-(2-(4-(4-((6-(3-(4-(tert-butyl)benzamido)-2-methylphenyl)-4-methyl-3-oxo-3,4-dihydropyrazin-2-yl) amino)benzoyl)piperazin-1-yl)ethoxy)ethyl)carbamate (2j) was dissolved in anhydrous DCM (2 mL), and trifluoroacetic acid (2 mL) was added. The reaction mixture was stirred for 20 min. The resulting solution was concentrated and purified using HPLC on a reverse phase C18 column to afford 2k as a white solid (16 mg, 0.02 mmol, 12% yield over two steps). ¹H NMR (500 MHz, DMSO) δ 9.91 (s, J=8.0 Hz, 1H), 9.51 (s, J=18.5 Hz, 1H), 8.12 (d, J 8.7 Hz, 2H), 7.95 (d, J=8.5 Hz, 2H), 7.84 (s, J=18.4 Hz, 3H), 7.58-7.51 (m, 2H), 7.43-7.33 (m, 3H), 7.33-7.23 (m, 3H), 3.82-3.68 (m, 2H), 3.65-3.52 (m, 10H), 3.40-3.23 (m, 7H), 3.19-3.04 (m, 2H), 3.04-2.87 (m, 2H), 2.29 (s, 3H), 1.33 (s, 9H).

Step 3. 4-(tert-butyl)-N-(3-(6-((4-(4-(2-(2-(2-(2-((2-(2,6-dioxopiperidin-3-yl)-1,3-dioxoisoindolin-4-yl) amino)acetamido)ethoxy)ethoxy)ethyl)piperazine-1-carbonyl)phenyl)amino)-4-methyl-5-oxo-4,5-dihydropyrazin-2-yl)-2-methylphenyl)benzamide (I-1)

To a solution of N-(3-(6-((4-(4-(2-(2-(2-aminoethoxy) ethoxy)ethyl)piperazine-1-carbonyl)phenyl)amino)-4-methyl-5-oxo-4,5-dihydropyrazin-2-yl)-2-methylphenyl)-4-(tert-butyl)benzamide trifluoroacetic acid salt (2k, 8 mg, 0.0815 mmol), (2-(2,6-dioxopiperidin-3-yl)-1,3-dioxoisoindolin-4-yl)glycine (21, 40 mg, 0.122 mmol, 1.5 equiv.), and diisopropylethylamine (43 µL, 0.244 mmol, 3 equiv.) in anhydrous DMF (1 mL), was added 1-[Bis(dimethylamino)methylene]-1H-1,2,3-triazolo[4,5-b]pyridinium 3-oxid hexafluorophosphate (50 mg, 0.130 mmol, 1.6 equiv.) and the resulting mixture was stirred at r.t. for 1 h. The reaction mixture was purified using HPLC on a reverse phase C18 column followed by further purification via silica gel column to provide I-1 as a yellow solid (9.4 mg, 0.0092 mmol, 11% yield). $^1$H NMR (500 MHz, DMSO) δ 11.09 (s, 1H), 9.88 (s, 1H), 9.44 (s, 1H), 8.14 (t, J=5.4 Hz, 1H), 8.07 (d, J=8.3 Hz, 2H), 7.94 (d, J=8.4 Hz, 2H), 7.56 (dd, J=18.7, 8.0 Hz, 3H), 7.42-7.20 (m, 6H), 7.06 (d, J=7.0 Hz, 1H), 6.94 (t, J=5.6 Hz, 1H), 6.85 (d, J=8.5 Hz, 1H), 5.07 (dd, J=12.7, 5.3 Hz, 1H), 3.92 (d, J=5.5 Hz, 2H), 3.69-3.36 (m, 16H), 3.28-3.19 (m, 2H), 2.89 (dd, J=21.4, 9.5 Hz, 1H), 2.56 (dd, J=26.9, 13.2 Hz, 3H), 2.41 (s, 4H), 2.28 (s, 3H), 2.09-1.96 (m, 1H), 1.32 (s, 9H).

Example 3: BTK Degradation

MOLM14 cells were treated with DMSO or with 40 nM, 200 nM, or 1 µM of a BTK bifunctional degrader compound of the disclosure for 4 hours, followed by protein lysate harvest and Western blotting analysis of BTK, PTK2B, AURKA, CDK7, and GAPDH levels. Cells treated with Compound I-0 showed BTK degradation. (FIG. 1).

Figure 3:
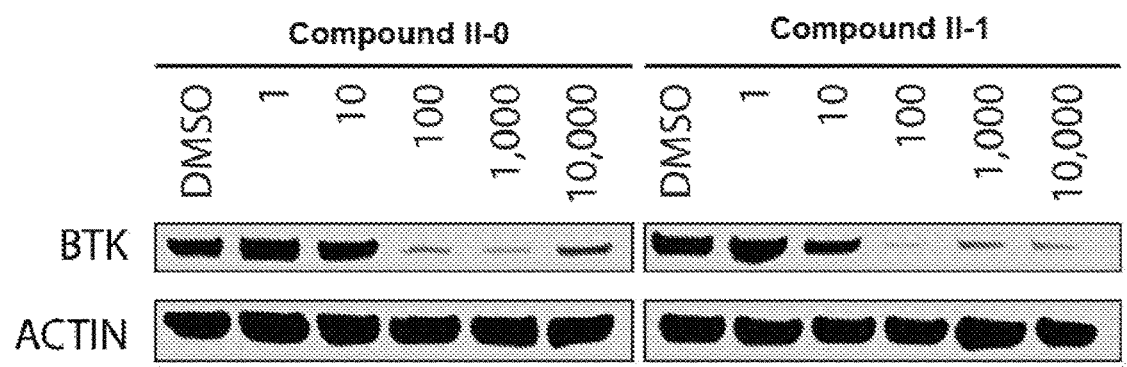
FIG. 3 is a Western blot showing the levels of BTK and Actin in Ramos B cells treated for 4 hours with DMSO or 1 nM, 10 nM, 100 nM, 1,000 nM, or 10,000 nM of Compound II-0 or Compound II-1.
Figure 4:
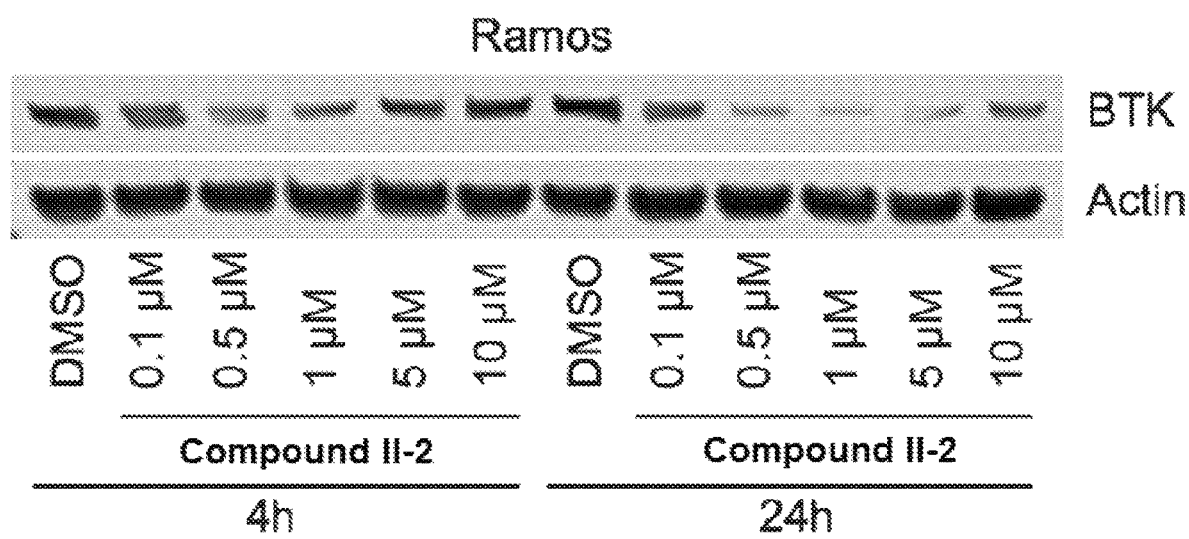
FIG. 4 is a Western blot showing the levels of BTK and Actin in Ramos B cells treated for 4 hours and 24 hours with DMSO or 0.1 µM, 0.5 µM, 1.0 µM, 5 µM, or 10 µM of Compound II-2.

Similar results were seen for Compound II-0, Compound II-1, and Compound II-2 with Ramos B cells (FIG. 3 and FIG. 4).

Western Blotting

Cells were lysed using RPA buffer supplemented with protease inhibitor cocktail (Roche) and PhosSTOP phosphatase inhibitor cocktail (Roche) on ice for at least 30 minutes. The lysates were spun at 20,000×g for 10 minutes at 4° C. Protein concentration was determined using BCA assay (Pierce). Lysate concentrations were normalized, mixed with 4× NuPAGE LDS sample buffer (supplemented with 10% fresh 2-mercaptoethanol, Thermo Fisher Scientific), and denatured at 95° C. for 10 minutes. Equal amount of proteins (20-40 mg) was resolved by Bolt 4-12% Bis-Tris Plus gels, and then transferred onto a nitrocellulose membrane. The membrane was blocked with 5% non-fat milk in TBS-T (TBS with 0.2% Tween-20), followed by incubation with primary antibodies at 4° C. overnight. Next day, after washing with TBS-T, the membrane was incubated with fluorophore-conjugated secondary antibodies for 1 hour at room temperature. The membrane was then washed and scanned with an Odyssey Infrared scanner (Li-Cor Biosciences, Lincoln, Nebr.).

Example 4: Inhibition of Cell Proliferation

Figure 2:
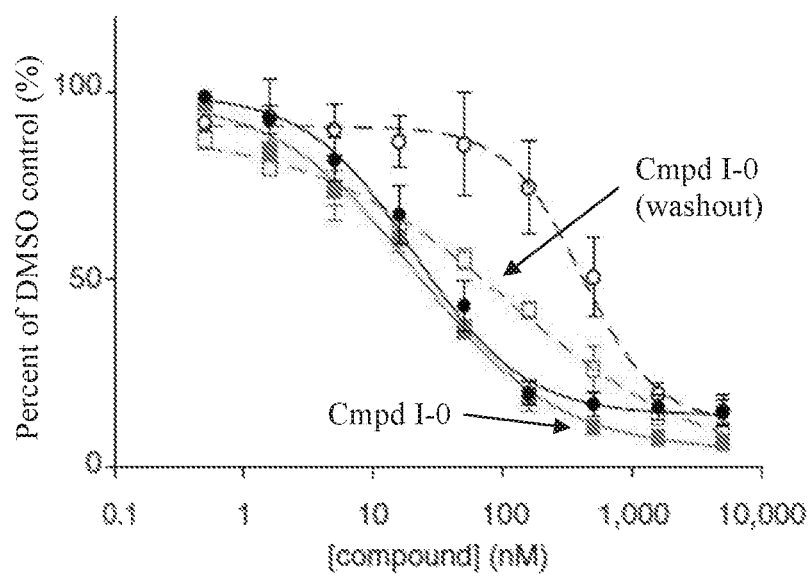
FIG. 2 is a plot showing the percentage of proliferation of TMD8 cells treated with Compound I-0 at the indicated concentrations, with or without washout following 6 hours of treatment, relative to TMD8 cells treated with DMSO.

TMD8 cells, a diffuse large B cell lymphoma line highly dependent on BTK activity, were treated with various concentrations of a BTK bifunctional degrader compound of the disclosure for 3 days. The proliferation of TMD8 cells was determined as a percentage of TMD8 cells treated with DMSO. Cells treated with Compound I-0 showed inhibition of proliferation. (FIG. 2).

Cellular Proliferation Assay

100 µL of 5×10$^5$ cells/mL TMD8 cells were seeded per 96-well and treated with compounds at indicated concentrations (5 mM to 0.5 nM in triplicates) for 3 days. Washout assays were performed in the same way, except that after 6 hours of treatment, cells were washed 3 times with culture medium without drugs, and allowed to grow in culture medium without drugs for the remaining time. Relative cell numbers were assessed using CellTiter-Glo assay kits (Promega, G7571) as described in product manual by luminescence measurements on an Envision plate reader (PerkinElmer). IC$_{50}$ values were determined using GraphPad Prism v6 nonlinear regression curve fit.

Patient-Derived Xenograft MCL Mouse Model

Figure 5:
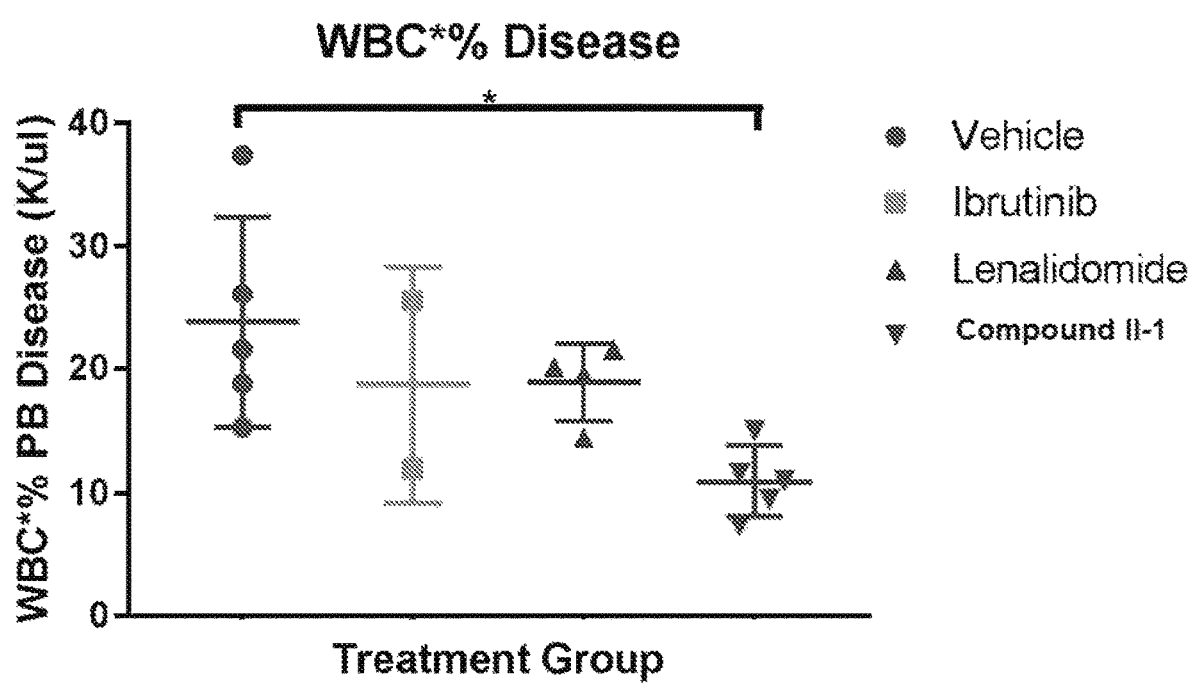
FIG. 5 is a plot showing efficacy of the BTK degrader Compound II-1 in a patient-derived xenograft MCL mouse model.

NSG Mice were grafted with patient-derived mantle cell lymphoma (MCL) cells (DFBL-96069). Once burden of disease reached ~2%, treatment began with indicated compounds: vehicle (IP, BID), Compound I-1 (IP, QD, 50 mg/kg), lenalidomide (IP, QD, 50 mg/kg), and ibrutinib (PO, QD, 30 mg/kg). Mice were treated for two weeks and 4-6 hours after the last dose, peripheral blood was taken and quantified for disease burden via flow cytometry. Mice treated with Compound II-1 showed efficacy (FIG. 5).

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:
1. A bifunctional compound of Formula X:

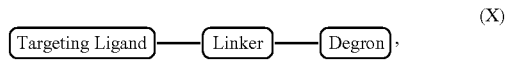

wherein:
the Targeting Ligand is capable of binding to BTK;
the Linker is a group that covalently binds to the Targeting Ligand and the Degron; and
the Degron is capable of binding to a ubiquitin ligase, wherein the Targeting Ligand is of Formula TL-I:

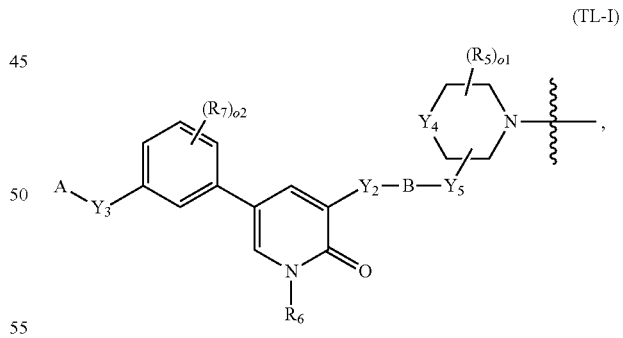

or a stereoisomer or pharmaceutically acceptable salt thereof,
wherein:
A is phenyl or 5- or 6-membered heteroaryl containing 1 or 2 heteroatoms selected from N and S, wherein the phenyl or heteroaryl is optionally substituted with 1 to 3 R$_8$;
B is phenyl or 5- or 6-membered heteroaryl containing 1 or 2 heteroatoms selected from N and S, wherein the phenyl or heteroaryl is optionally substituted with 1 to 3 R$_9$;

$Y_2$ is $NR_{10a}$ or O;
$Y_3$ is $C(O)NR_{10b}$ or $NR_{10b}C(O)$;
$Y_4$ is $NR_5'$ or, when B is bonded to $Y_4$, N, or, when $Y_5$ is bonded to $Y_4$, N;
$Y_5$ is absent, C(O), or $CH_2$;
$R_5'$ is H, $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen;
each $R_5$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, or oxo;
$R_6$ is H, $(C_1\text{-}C_4)$ alkyl, or $(C_1\text{-}C_4)$ haloalkyl;
each $R_7$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, $(C_1\text{-}C_4)$ hydroxyalkyl, halogen, OH, or $NH_2$;
each $R_8$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, $NH_2$, or $(C_3\text{-}C_6)$ cycloalkyl; or two $R_8$ together with the atoms to which they are attached form a $(C_5\text{-}C_7)$ cycloalkyl ring; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;
each $R_9$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen;
$R_{10a}$ and $R_{10b}$ are each independently H, $(C_1\text{-}C_4)$ alkyl, or $(C_1\text{-}C_4)$ haloalkyl; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;
each $R_{11}$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, oxo, OH, or $NH_2$; and
o1 and o2 are each independently 0, 1, 2, or 3, or the Targeting Ligand is of Formula TL-II:

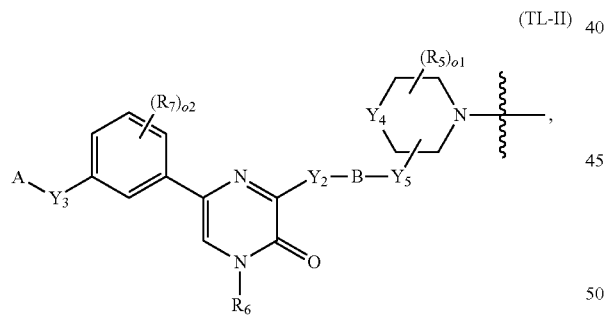

(TL-II)

or a stereoisomer or pharmaceutically acceptable salt thereof,
wherein:
A is phenyl or 5- or 6-membered heteroaryl containing 1 or 2 heteroatoms selected from N and S, wherein the phenyl or heteroaryl is optionally substituted with 1 to 3 $R_8$;
B is phenyl or 5- or 6-membered heteroaryl containing 1 or 2 heteroatoms selected from N and S, wherein the phenyl or heteroaryl is optionally substituted with 1 to 3 $R_9$;
$Y_2$ is $NR_{10a}$ or O;
$Y_3$ is $C(O)NR_{10b}$ or $NR_{10b}C(O)$;
$Y_4$ is $NR_5'$ or, when B is bonded to $Y_4$, N, or, when $Y_5$ is bonded to $Y_4$, N;
$Y_5$ is $CH_2$;
$R_5'$ is H, $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen;
each $R_5$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, or oxo;
$R_6$ is H, $(C_1\text{-}C_4)$ alkyl, or $(C_1\text{-}C_4)$ haloalkyl;
each $R_7$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, $(C_1\text{-}C_4)$ hydroxyalkyl, halogen, OH, or $NH_2$;
each $R_8$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, $NH_2$, or $(C_3\text{-}C_6)$ cycloalkyl; or two $R_8$ together with the atoms to which they are attached form a $(C_5\text{-}C_7)$ cycloalkyl ring; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;
each $R_9$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen;
$R_{10a}$ and $R_{10b}$ are each independently H, $(C_1\text{-}C_4)$ alkyl, or $(C_1\text{-}C_4)$ haloalkyl; or at least one $R_8$ and $R_{10b}$ together with the atoms to which they are attached form a 5- or 6-membered heterocycloalkyl or heteroaryl containing 1 or 2 heteroatoms selected from N, O, and S and optionally substituted with 1 to 3 $R_{11}$;
each $R_{11}$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, oxo, OH, or $NH_2$; and
o1 and o2 are each independently 0, 1, 2, or 3,
wherein the Targeting Ligand is bonded to the Linker via the

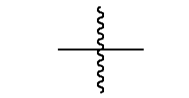

next to

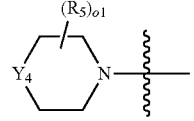

in TL-I and

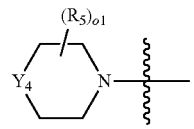

in TL-II.

2. The bifunctional compound of claim 1, wherein the Targeting Ligand is of Formula TL-I.

3. The bifunctional compound of claim 2, wherein $R_6$ is $(C_1\text{-}C_4)$ alkyl.

4. The bifunctional compound of claim 2, wherein B is phenyl or pyridinyl.

5. The bifunctional compound claim 2, wherein the Targeting Ligand is of Formula TL-Ia:

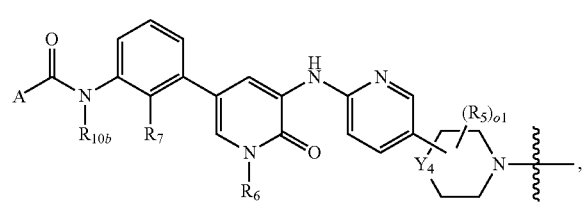

(TL-Ia)

or a stereoisomer or pharmaceutically acceptable salt thereof.

6. The bifunctional compound of claim 1, wherein the Targeting Ligand is of Formula TL-II.

7. The bifunctional compound of claim 6, wherein $R_6$ is $(C_1-C_4)$ alkyl.

8. The bifunctional compound of claim 6, wherein B is phenyl or pyridinyl.

9. The bifunctional compound claim 6, wherein the Targeting Ligand is of Formula TL-IIa:

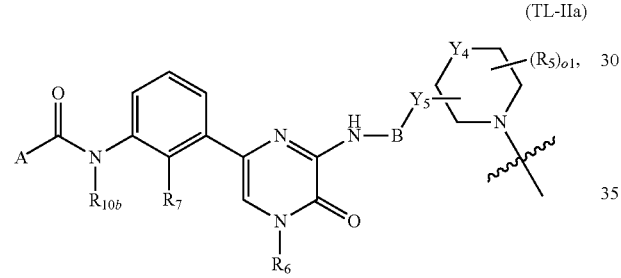

(TL-IIa)

or a stereoisomer or pharmaceutically acceptable salt thereof.

10. The bifunctional compound of claim 1, wherein the Linker is of Formula L1 or L2:

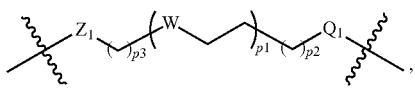

(L1)

or a stereoisomer thereof, wherein
p1 is an integer selected from 0 to 12;
p2 is an integer selected from 0 to 12;
p3 is an integer selected from 1 to 6;
each W is independently absent, $CH_2$, O, S, or $NR_{24}$;
$Z_1$ is absent, C(O), $CH_2$, O, $(CH_2)_jNR_{24}$, $O(CH_2)_jC(O)NR_{24}$, $C(O)NR_{24}$, $(CH_2)_jC(O)NR_{24}$, $NR_{24}C(O)$, $(CH_2)_jNR_{24}C(O)$, $(CH_2)_kNR_{24}(CH_2)_jC(O)NR_{24}$, or $NR_{24}(CH_2)_jC(O)NR_{24}$;
each $R_{24}$ is independently H or $C_1-C_3$ alkyl;
j is 1, 2, or 3;
k is 1, 2, or 3; and
$Q_1$ is absent, C(O), $NHC(O)CH_2$, $OCH_2C(O)$, or $O(CH_2)_{1-2}$;

wherein the Linker is covalently bonded to a Degron via the

next to $Q_1$, and covalently bonded to a Targeting Ligand via the

next to $Z_1$, or the Linker is covalently bonded to a Degron via the

next to $Z_1$, and covalently bonded to a Targeting Ligand via the

next to $Q_1$; or

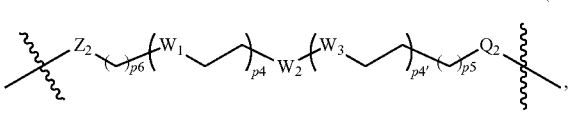

(L2)

or a stereoisomer thereof, wherein
p4 and p4' are each independently an integer selected from 0 to 12;
p5 is an integer selected from 0 to 12;
p6 is an integer selected from 1 to 6;
each $W_1$ is independently absent, $CH_2$, O, S, or $NR_{25}$;
$W_2$ is $NR_{25}C(O)(CH_2)_{0-2}$ or

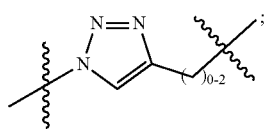

each $W_3$ is independently absent, $CH_2$, O, S, or $NR_{25}$;
$Z_2$ is absent, C(O), $CH_2$, O, $(CH_2)_{j1}NR_{25}$, $O(CH_2)_{j1}C(O)NR_{25}$, $C(O)NR_{25}$, $(CH_2)_{j1}C(O)NR_{25}$, $NR_{25}C(O)$, $(CH_2)_{j1}NR_{25}C(O)$, $(CH_2)_{k1}NR_{25}(CH_2)_{j1}C(O)NR_{25}$, or $NR_{25}(CH_2)_{j1}C(O)NR_{25}$;
each $R_{25}$ is independently H or $C_1-C_3$ alkyl;
j1 is 1, 2, or 3;

k1 is 1, 2, or 3; and $Q_2$ is absent, $C(O)$, $NHC(O)CH_2$, or $O(CH_2)_{1-2}$;

wherein the Linker is covalently bonded to a Degron via the

next to $Q_2$, and covalently bonded to a Targeting Ligand via the

next to $Z_2$, or the Linker is covalently bonded to a Degron via the

next to $Z_2$, and covalently bonded to a Targeting Ligand via the

next to $Q_2$.

11. The bifunctional compound of claim 10, wherein the Linker is selected from:

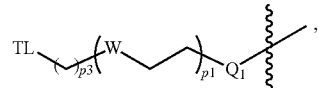 (L1a)

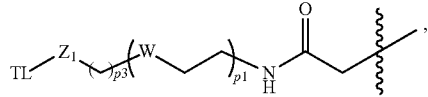 (L1b)

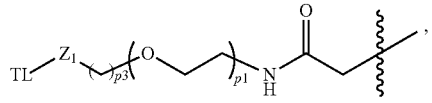 (L1c)

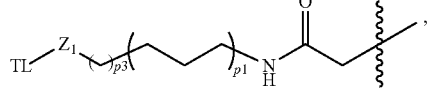 (L1d)

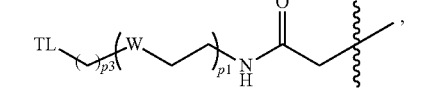 (L1e)

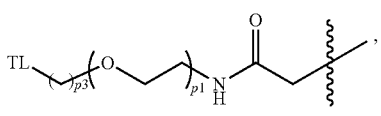 (L1f)

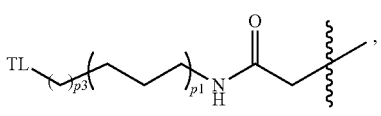 (L1g)

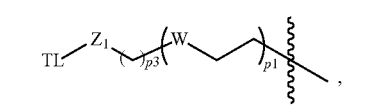 (L1h)

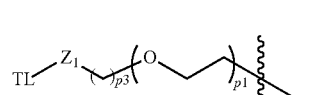 (L1i)

 (L1j)

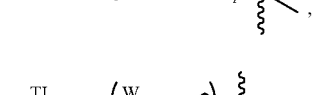 (L1k)

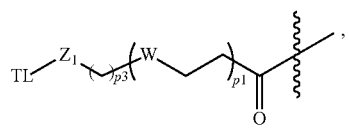 (L1l)

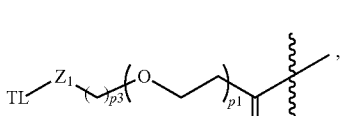 (L1m)

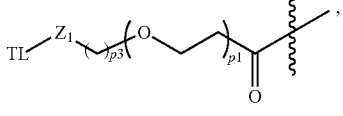 (L1n)

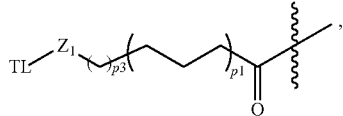 (L1o)

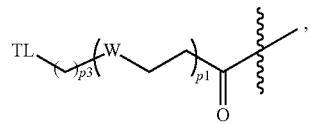 (L2a)

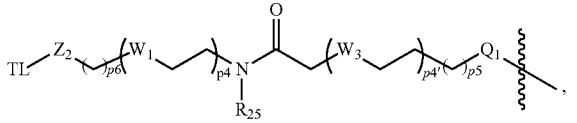 (L2b)

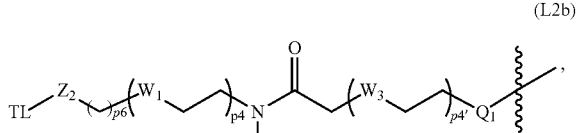

(L2c)
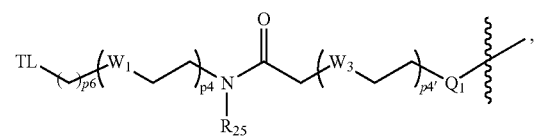
(L2d)
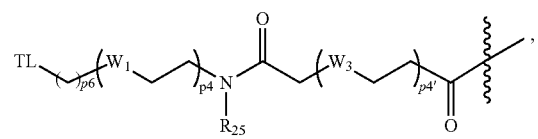
(L2e)
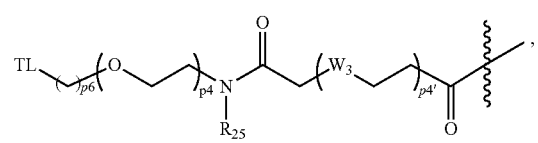
(L2f)
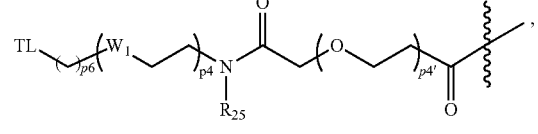
(L2g)
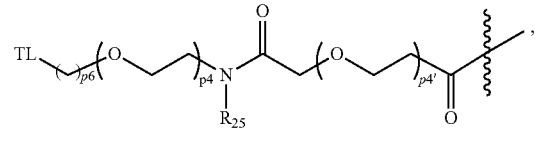
(L2h)
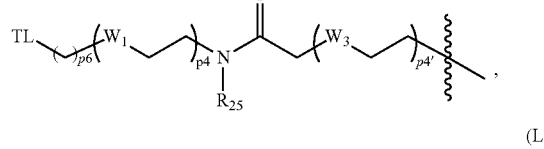
(L2i)
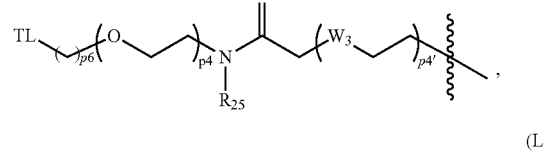
(L2j)
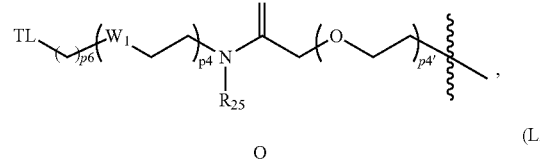
(L2k)
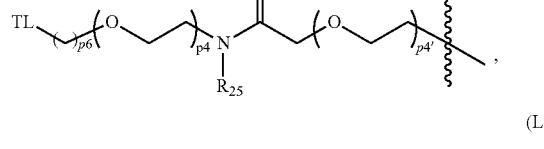
(L2l)
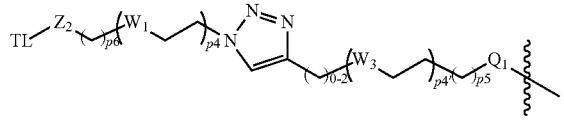
(L2m)
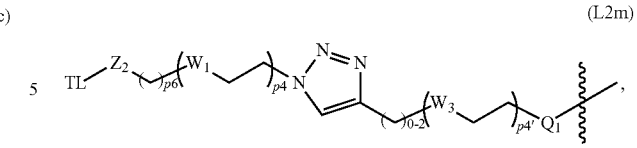
(L2n)
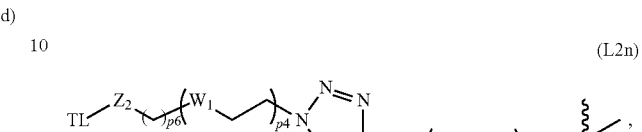
(L2o)
(L2p)
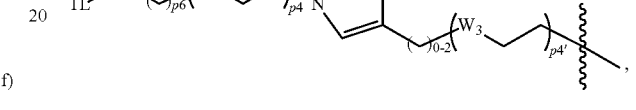
(L2q)
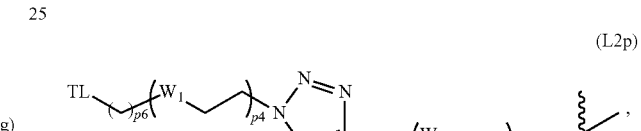
(L2r)
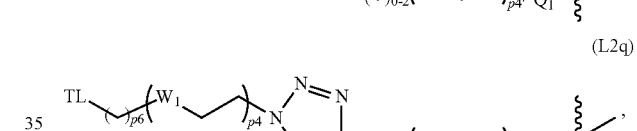
(L2s)
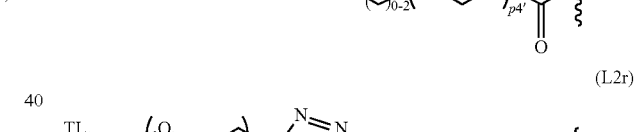
(L2t)
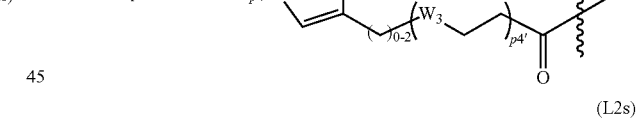
(L2u)
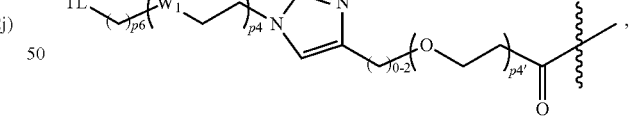
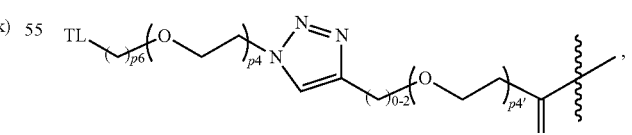
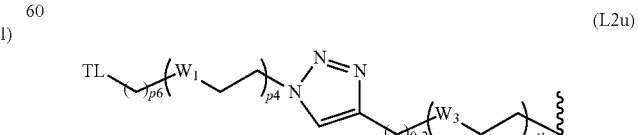
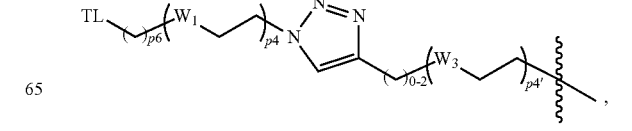

(L2v)

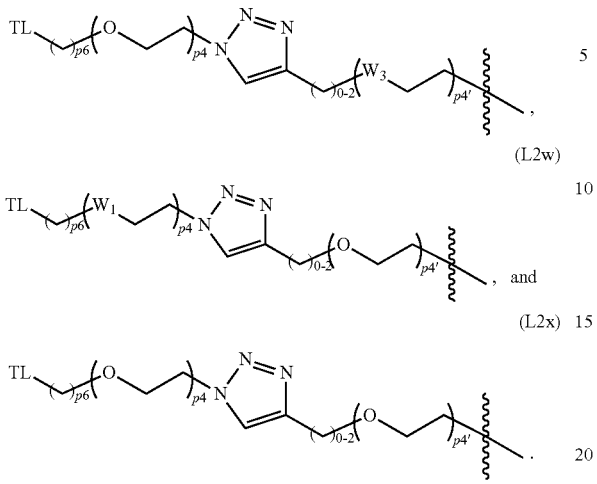

(L2w)

(L2x)

12. The bifunctional compound of claim 1, wherein the Degron is of Formula D0, D1, D2, D3, or D4:

(D0)

or a stereoisomer thereof, wherein:
Y is a bond, $(CH_2)_{1-6}$, $(CH_2)_{0-6}$—O, $(CH_2)_{0-6}$—C(O)NR$_{26}$, $(CH_2)_{0-6}$—NR$_{26}$C(O), $(CH_2)_{0-6}$—NH, or $(CH_2)_{0-6}$—NR$_{27}$;
$Z_4$ is N or CR$_{36}$;
$R_{26}$ is H or $C_1$-$C_6$ alkyl;
$R_{27}$ is $C_1$-$C_6$ alkyl or C(O)—$C_1$-$C_6$ alkyl;
$R_{28}$ is H or $C_1$-$C_3$ alkyl;
each $R_{29}$ is independently $C_1$-$C_3$ alkyl;
$R_{30}$ is H, deuterium, $C_1$-$C_3$ alkyl, F, or Cl;
each $R_{31}$ is independently halogen, OH, $C_1$-$C_6$ alkyl, or $C_1$-$C_6$ alkoxy; or at least one $R_{31}$ and at least one $R_{37}$ together with the atoms to which they are attached form a 5- or 6-membered cycloalkyl, aryl, heterocycloalky containing 1 or 2 heteroatoms selected from N, O, and S, or heteroaryl containing 1 or 2 heteroatoms selected from N, O, and S, each optionally substituted with 1 to 3 $R_{37}$';
$R_{35}$ is H, $(C_1$-$C_4)$ alkyl, $(C_1$-$C_4)$ haloalkyl; or $R_{35}$ and $R_{36}$ together with the atoms to which they are attached form a 5- or 6-membered heterocycloalkyl or heteroaryl containing 1 or 2 heteroatoms selected from N, O, and S and optionally substituted with 1 to 3 $R_{37}$;
$R_{36}$ is H or $C_1$-$C_3$ alkyl; or $R_{36}$ and $R_{35}$ together with the atoms to which they are attached form a 5- or 6-membered heterocycloalkyl or heteroaryl containing 1 or 2 heteroatoms selected from N, O, and S and optionally substituted with 1 to 3 $R_{37}$;
each $R_{37}$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, oxo, OH, or NH$_2$; or at least one $R_{37}$ and at least one $R_{31}$ together with the atoms to which they are attached form a 5- or 6-membered cycloalkyl, aryl, heterocycloalkyl containing 1 or 2 heteroatoms selected from N, O, and S, or heteroaryl containing 1 or 2 heteroatoms selected from N, O, and S, each optionally substituted with 1 to 3 $R_{37}$';
each $R_{37}$' is independently $(C_1$-$C_4)$ alkyl, $(C_1$-$C_4)$ haloalkyl, $(C_1$-$C_4)$ alkoxy, $(C_1$-$C_4)$ haloalkoxy, halogen, oxo, OH, or NH$_2$;
q is 0, 1, or 2; and
v is 0, 1, 2, or 3, or (D1)

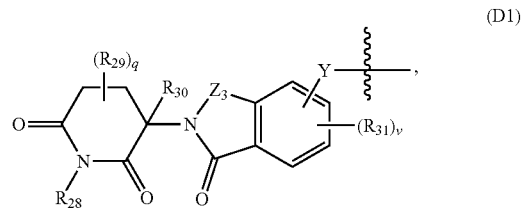

or a stereoisomer thereof, wherein:
$Z_3$ is C(O) or C(R$_{38}$)$_2$; and
each $R_{38}$ is independently H or $C_1$-$C_3$ alkyl, or (D2)

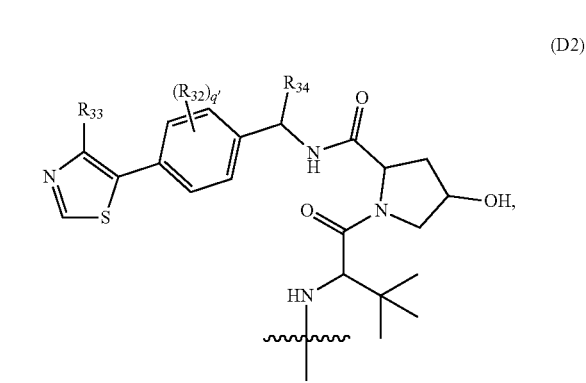

or a stereoisomer thereof, wherein:
each $R_{32}$ is independently $C_1$-$C_3$ alkyl;
q' is 0, 1, 2, 3 or 4;
$R_{33}$ is H or $C_1$-$C_3$ alkyl; and
$R_{34}$ is H or $C_1$-$C_3$ alkyl, or (D3)

or a stereoisomer thereof, wherein:
$Y_1$ is a bond, $(CH_2)_{1-6}$, $(CH_2)_{0-6}$—O, $(CH_2)_{0-6}$—C(O)NR$_{43}$, $(CH_2)_{0-6}$—NR$_{43}$C(O), $(CH_2)_{0-6}$—NH, or $(CH_2)_{0-6}$—NR$_{44}$;
$Z_5$ is a bond, $(CH_2)_{0-6}$—C(O)NR$_{43}$, NR$_{43}$C(O)—$(CH_2)_{0-6}$, $(CH_2)_{0-6}$—S(O)$_{0-2}$NR$_{43}$, NR$_{43}$S(O)$_{0-2}$—

(CH$_2$)$_{0-6}$, (CH$_2$)$_{0-6}$—NR$_{43}$C(O), C(O)NR$_{43}$—(CH$_2$)$_{0-6}$, (CH$_2$)$_{0-6}$—NR$_{43}$S(O)$_{0-2}$, or S(O)$_{0-2}$NR$_{43}$—(CH$_2$)$_{0-6}$;

R$_{43}$ is H or C$_1$-C$_6$ alkyl;

R$_{44}$ is C$_1$-C$_6$ alkyl, S(O)$_{0-2}$—C$_1$-C$_6$ alkyl, or C(O)—C$_1$-C$_6$ alkyl;

R$_{39}$ is H or C$_1$-C$_3$ alkyl;

each R$_{40}$ is independently halogen, CN, OH, C$_1$-C$_6$ alkyl, or C$_1$-C$_6$ alkoxy;

each R$_{41}$ is independently halogen, CN, or C$_1$-C$_6$ alkyl;

each R$_{42}$ is independently halogen, CN, OH, C$_1$-C$_6$ alkyl, or C$_1$-C$_6$ alkoxy;

v1 is 0, 1, 2, 3 or 4;

v2 is 0, 1, or 2; and v3 is 0, 1, 2 or 3, or (D4)

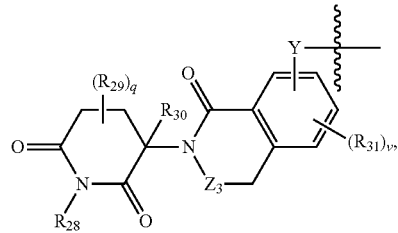

or a stereoisomer thereof, wherein:

Z$_3$ is C(O) or C(R$_{38}$)$_2$; and each R$_{38}$ is independently H or C$_1$-C$_3$ alkyl, wherein the Degron is covalently bonded to the Linker via

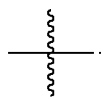

13. The bifunctional compound of claim 12, wherein the Degron is of Formula D0a, D0b, D0c, D0d, D1a, D1b, D1c, D1d, D1e, D1f, D1g, D1h, D1i, D1j, D1k, D1l, D2a, D2a', D2b, D2b', D2c, D2c', D2d, or D2d', D3a, D3b, D3c, D4a, or D4b:

(D0a)

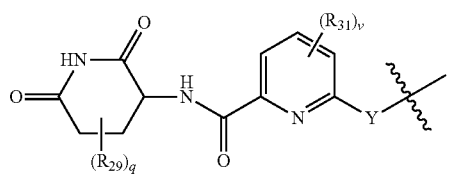

(D0b)

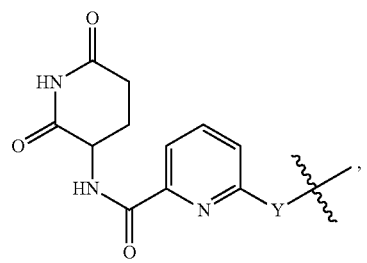

(D0c)

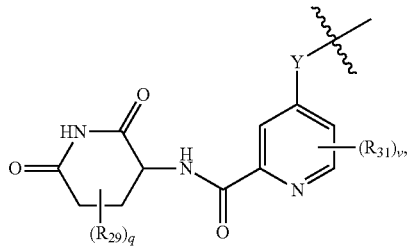

(D0d)

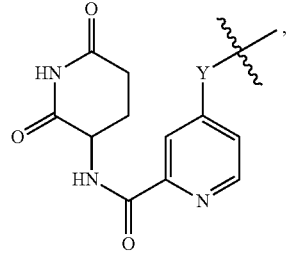

(D1a)

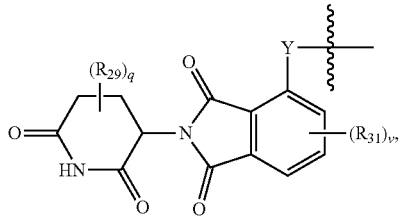

(D1b)

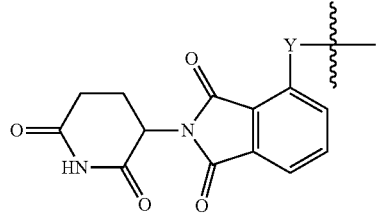

(D1c)

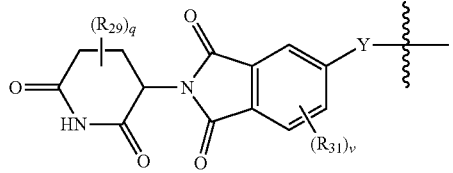

(D1d)

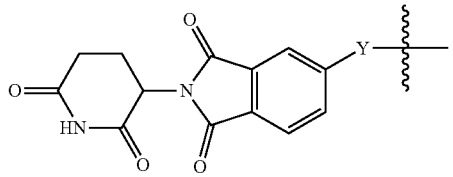

(D1e)

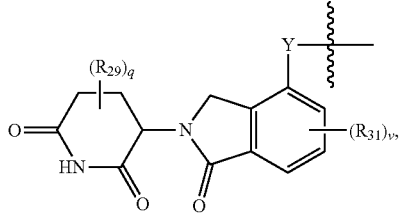

(D1f)
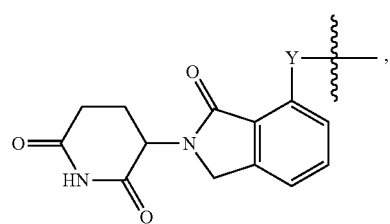
(D1g)
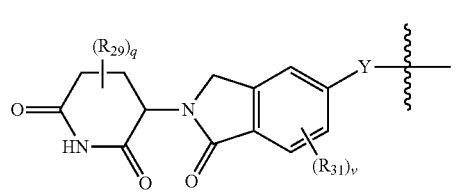
(D1h)
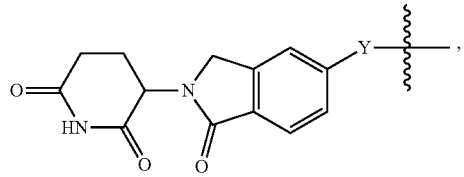
(D1i)
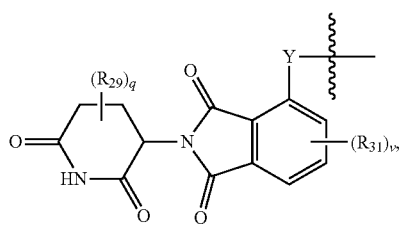
(D1j)
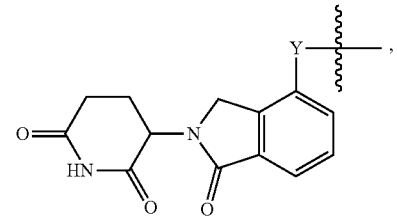
(D1k)
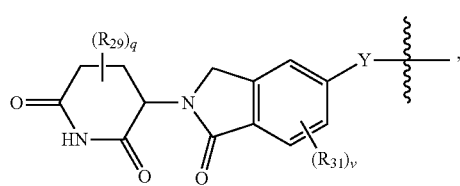
(D1l)
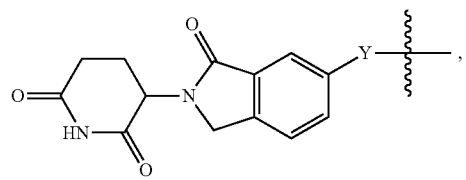
(D2a)
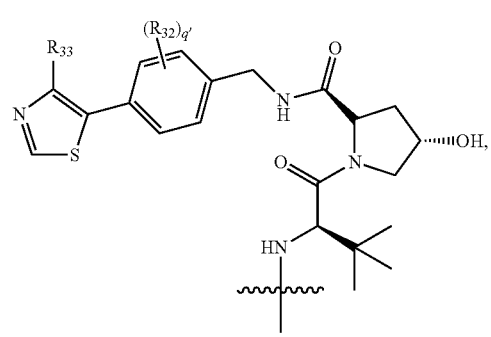
(D2a')
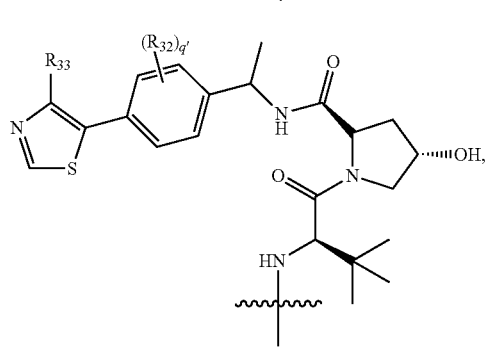
(D2b)
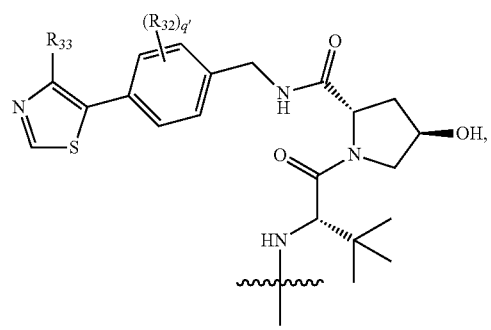
(D2b')
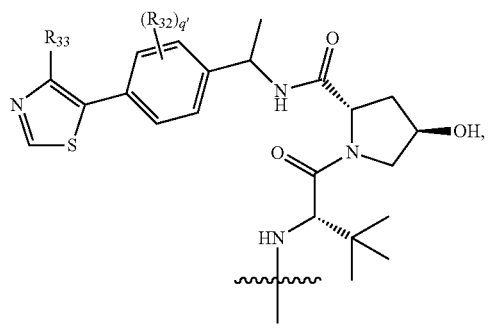

223
-continued (D2c)
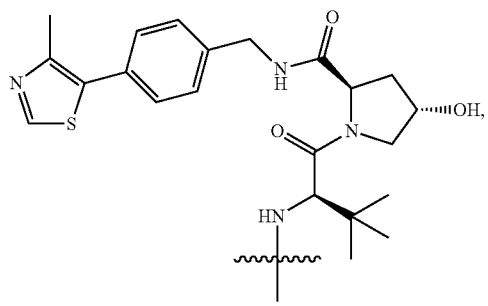

(D2c')
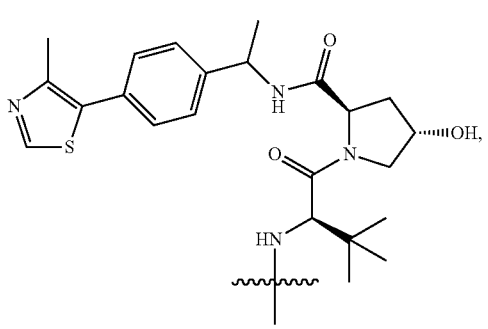

(D2d)
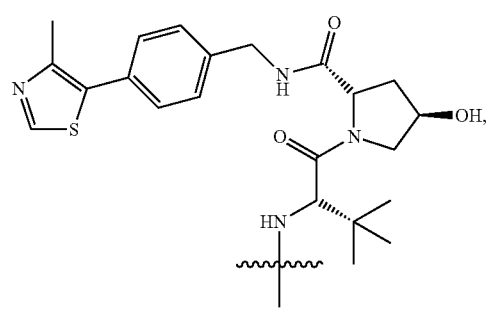

(D2d')
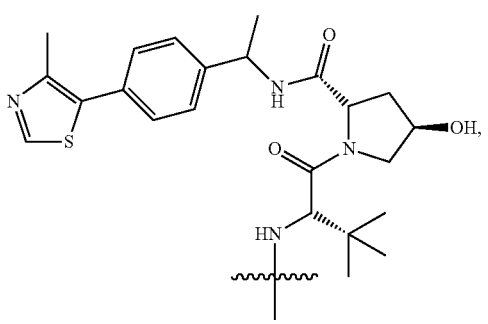

(D3a)
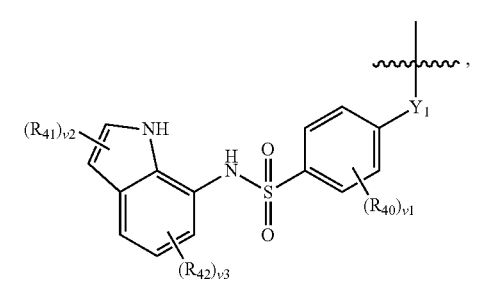

224
-continued (D3b)
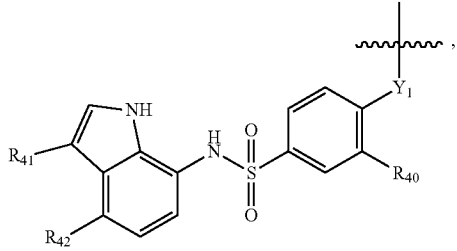

(D3c)
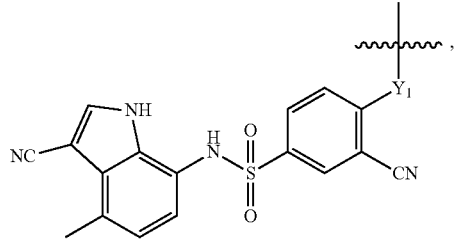

(D4a)
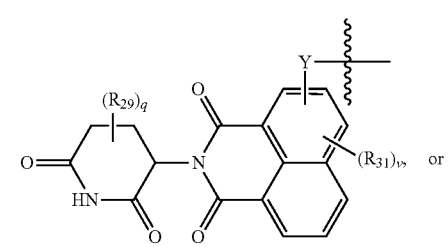

(D4b)
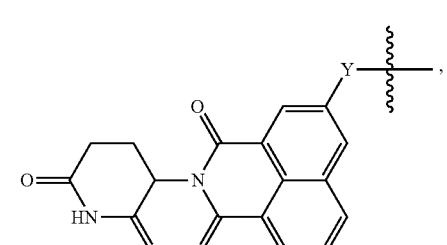

or a stereoisomer thereof.

14. A pharmaceutical composition comprising a therapeutically effective amount of the bifunctional compound of claim 1, or a stereoisomer or pharmaceutically acceptable salt thereof, and a pharmaceutically acceptable carrier.

15. A method of inhibiting or modulating the amount of Burton's tyrosine kinase (BTK), comprising administering to a subject in need thereof an effective amount of a compound of claim 1.

16. The bifunctional compound of claim 1, which is:
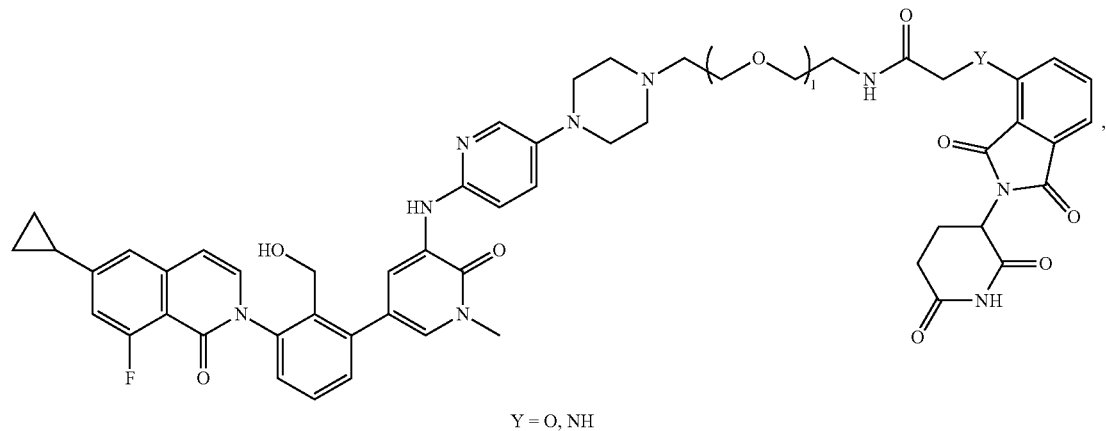
Y = O, NH
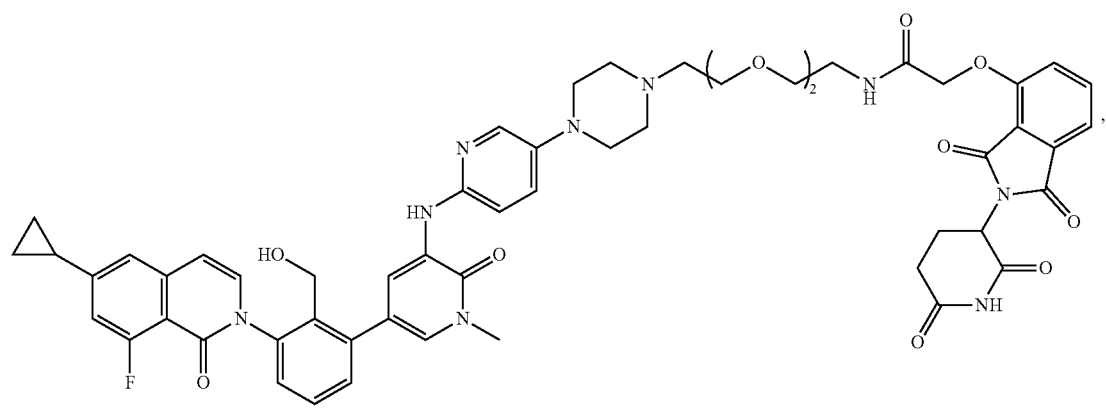
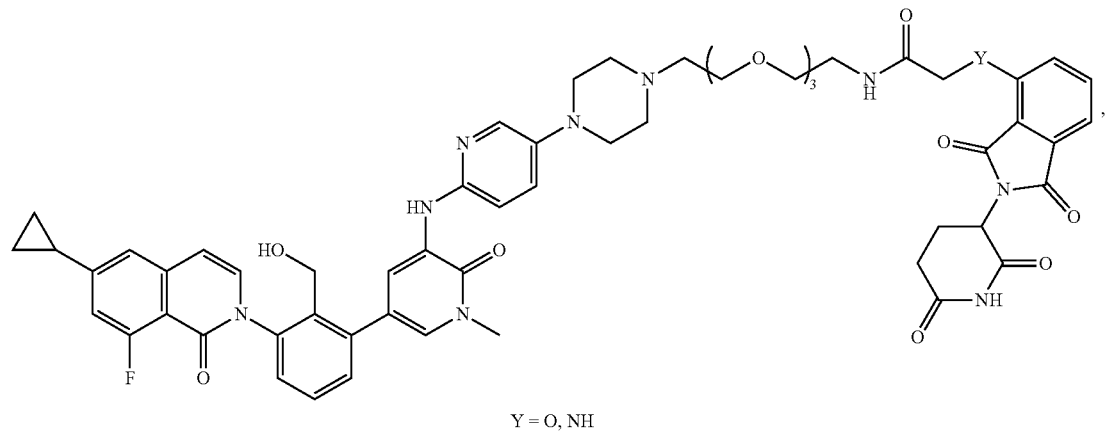
Y = O, NH -continued
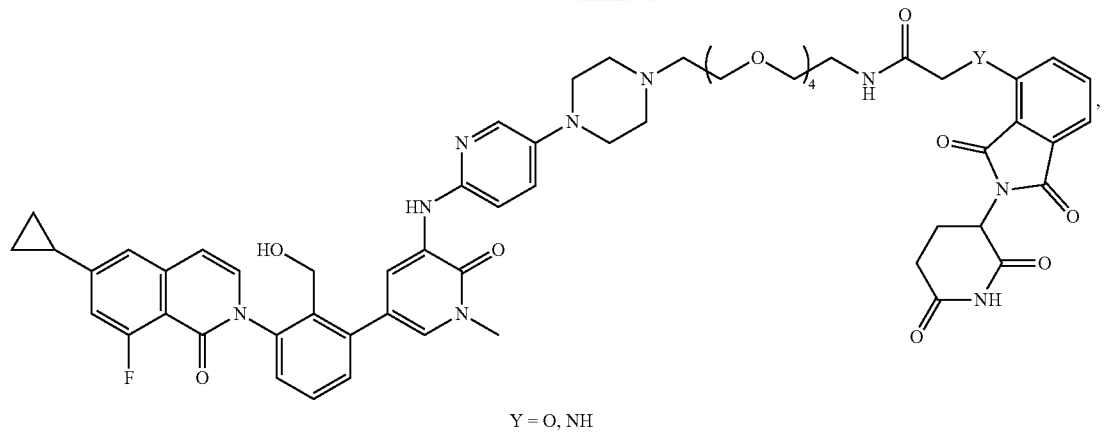
Y = O, NH
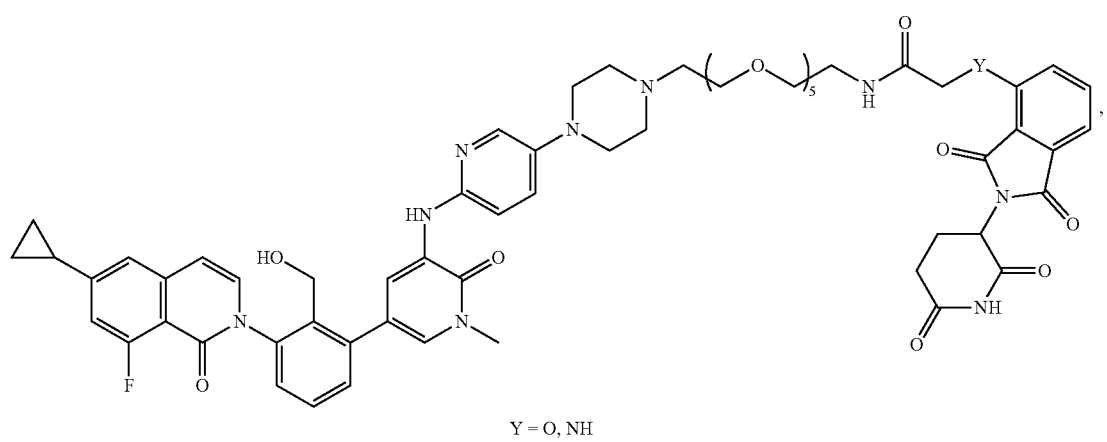
Y = O, NH
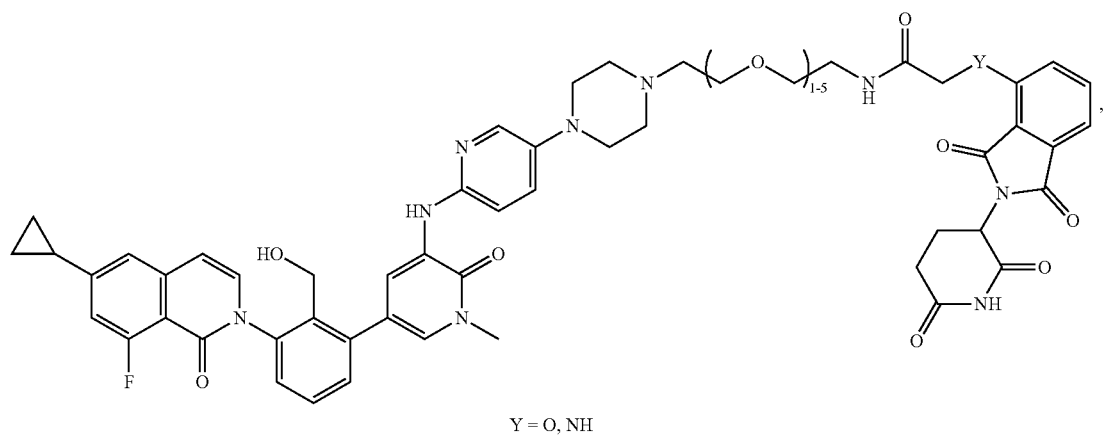
Y = O, NH

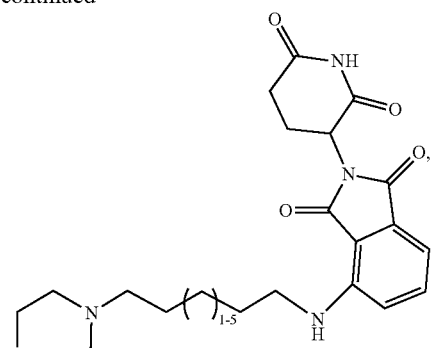
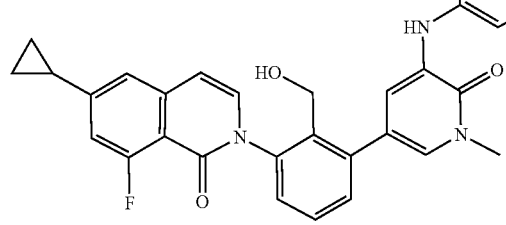
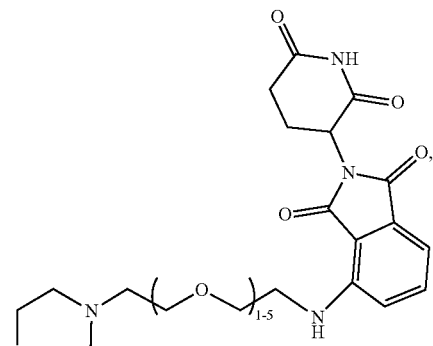
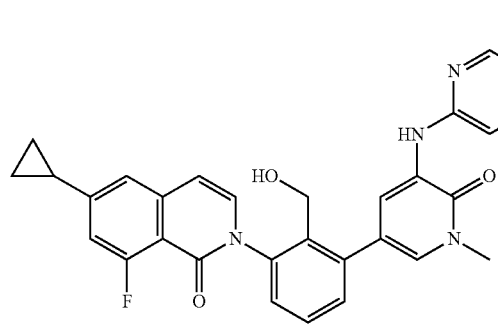
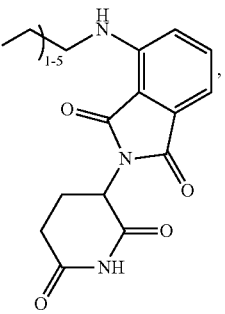

231    232
-continued
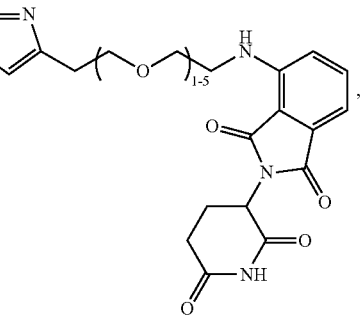
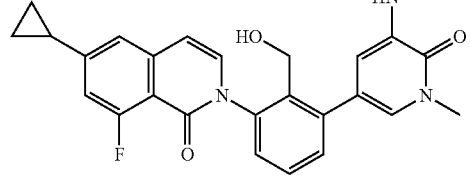
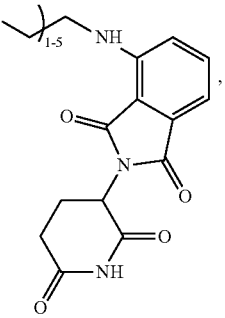
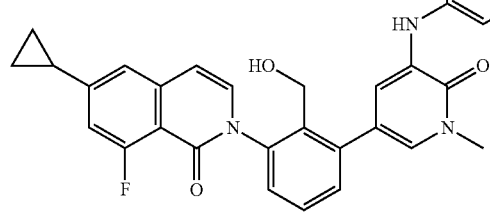
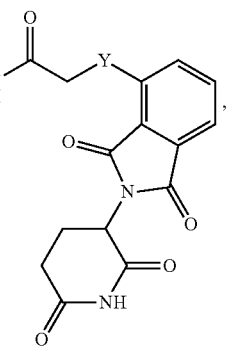
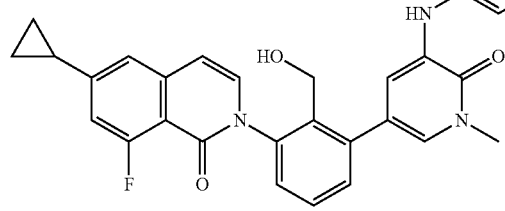
Y = O, NH
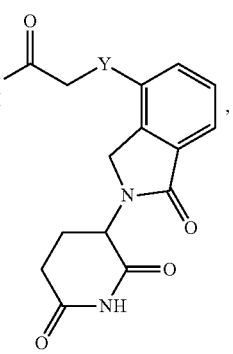
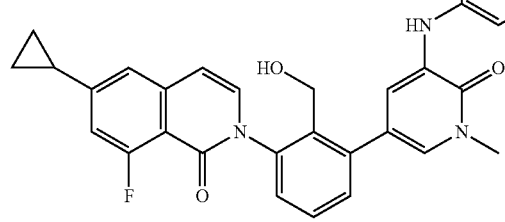
Y = O, NH 233
234
-continued
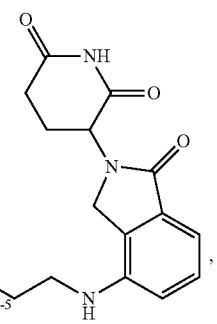
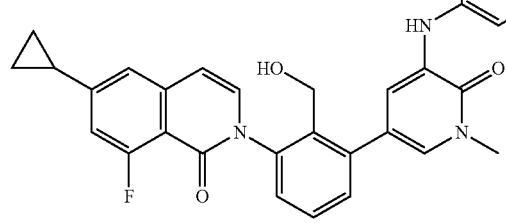
,
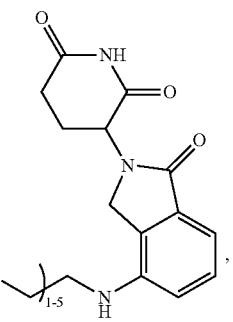
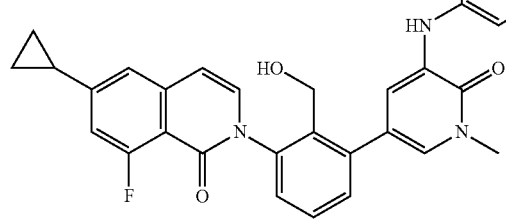
,
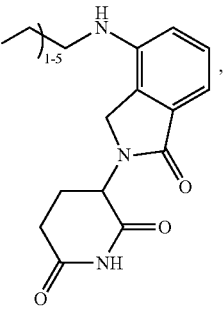
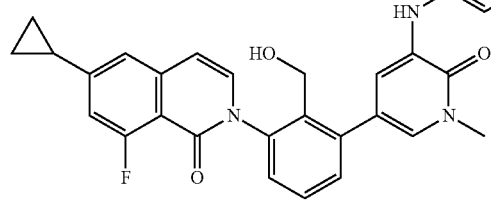
, -continued
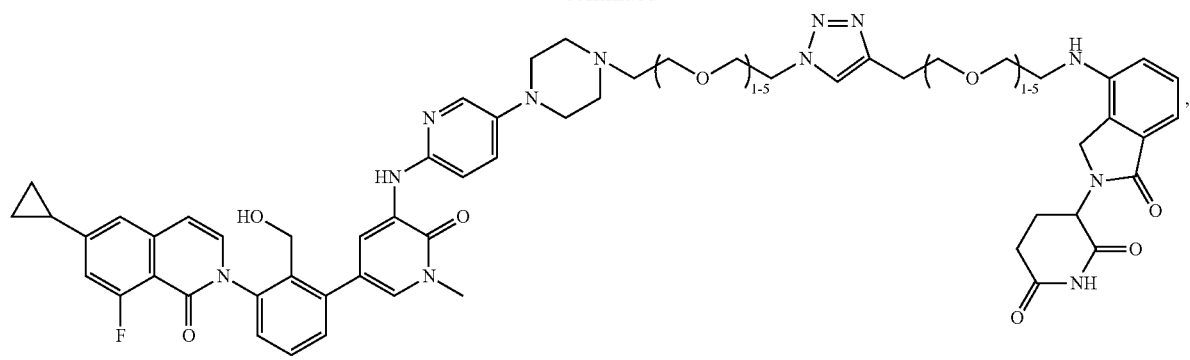
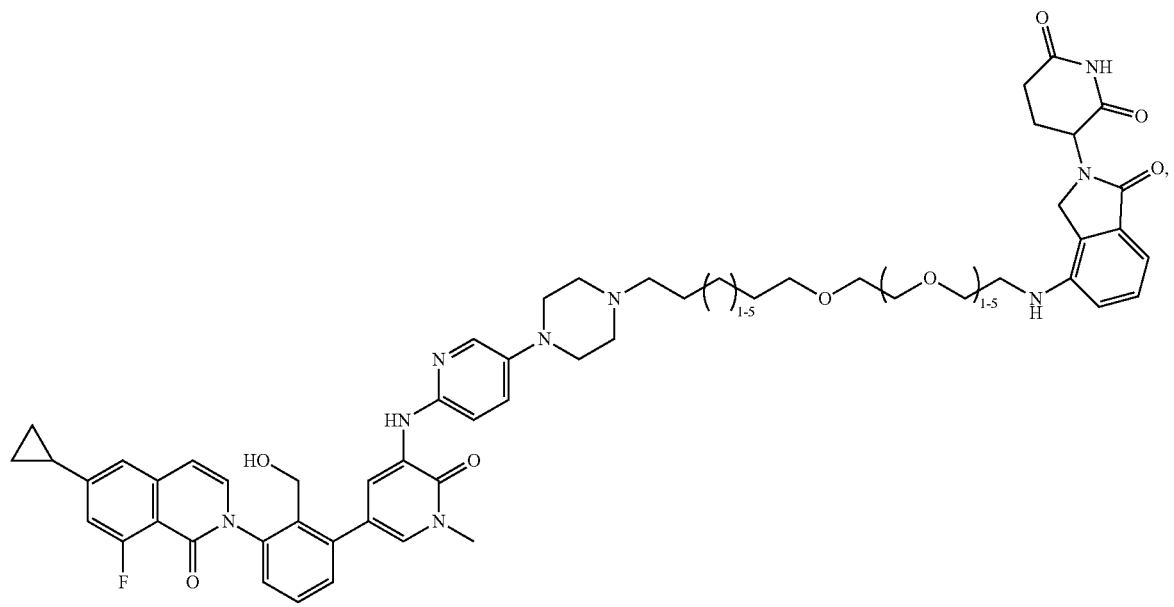
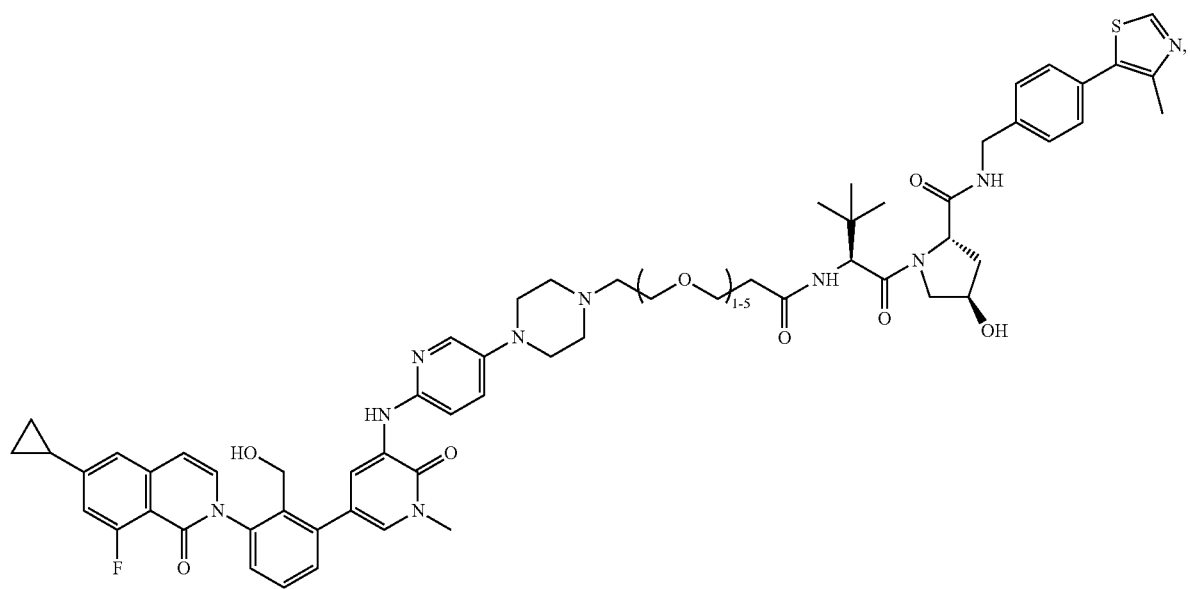

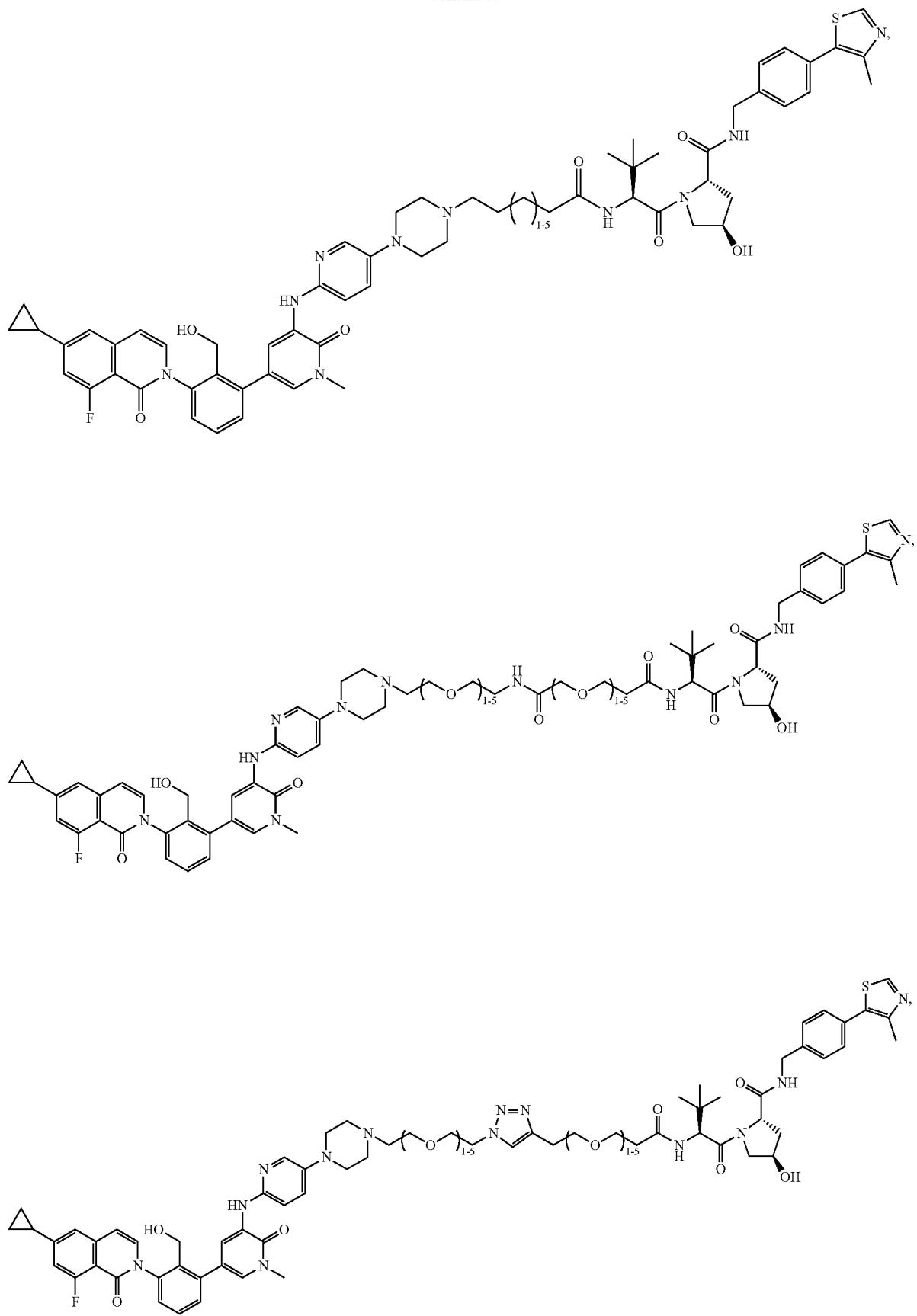

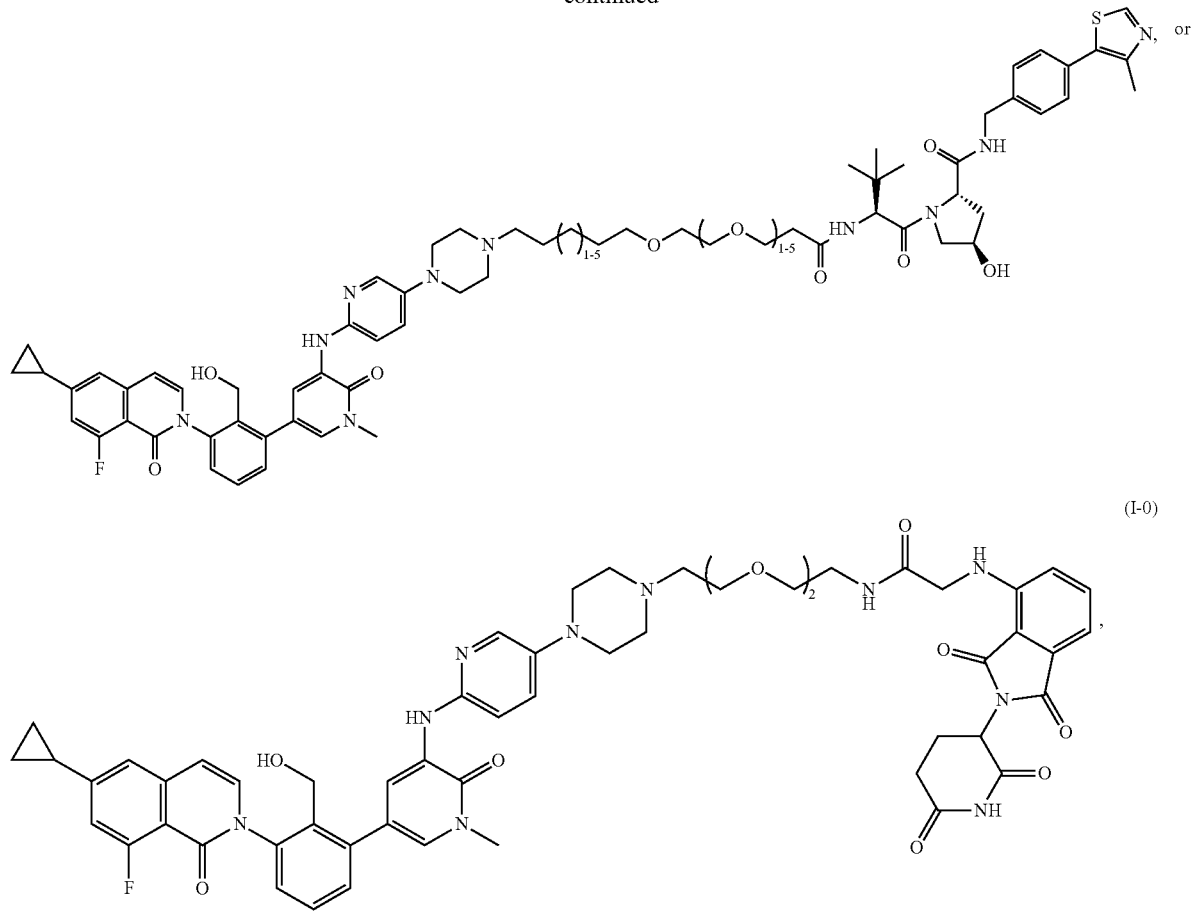

or a stereoisomer or pharmaceutically acceptable salt thereof.

17. The bifunctional compound claim 5, wherein the Targeting Ligand is of Formula TL-Ib:

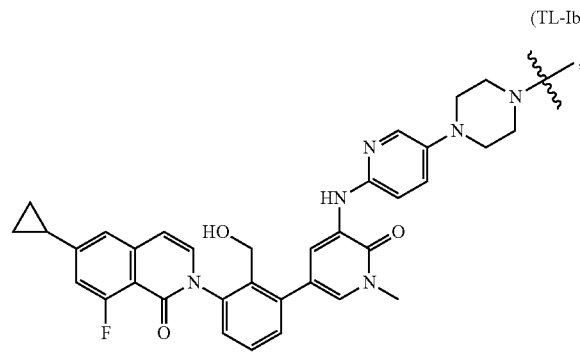

or a stereoisomer or pharmaceutically acceptable salt thereof.

18. A method of treating a hematological cancer by decreasing the amount of Bruton's tyrosine kinase (BTK), comprising administering to a subject in need thereof an effective amount of bifunctional compound or pharmaceutically acceptable salt or stereoisomer of claim 1.

19. The method of claim 18, wherein the hematological cancer is leukemia.

20. The method of claim 18, wherein the hematological cancer is lymphoma.

* * * * *